US006770740B1

(12) United States Patent
Rice et al.

(10) Patent No.: US 6,770,740 B1
(45) Date of Patent: Aug. 3, 2004

(54) CROSSLINKED DNA CONDESATE COMPOSITIONS AND GENE DELIVERY METHODS

(75) Inventors: Kevin G. Rice, Ann Arbor, MI (US); Roger C. Adami, Noank, CT (US); Donald L. McKenzie, Ypsilanti, MI (US); Wendy T. Collard, Saline, MI (US); Kai Y. Kwok, Ann Arbor, MI (US); Youmie Park, Ann Arbor, MI (US); Yongsheng Yang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/615,153

(22) Filed: Jul. 13, 2000

Related U.S. Application Data

(60) Provisional application No. 60/157,761, filed on Oct. 5, 1999, and provisional application No. 60/143,600, filed on Jul. 13, 1999.

(51) Int. Cl.$^7$ .......................... C07K 5/00; C07K 16/00
(52) U.S. Cl. ..................................... 530/300; 530/332
(58) Field of Search .................... 514/44; 435/320.1; 530/300

(56) References Cited

U.S. PATENT DOCUMENTS

| | | | |
|---|---|---|---|
| 5,166,320 A | 11/1992 | Wu et al. .................... 530/395 |
| 5,171,678 A | 12/1992 | Behr et al. .................. 435/458 |
| 5,270,300 A | 12/1993 | Hunziker ..................... 514/12 |
| 5,298,422 A | 3/1994 | Schwartz et al. ......... 435/320.1 |
| 5,304,121 A | 4/1994 | Sahatjian ..................... 604/53 |
| 5,324,775 A | 6/1994 | Rhee et al. ................. 525/54.2 |
| 5,354,844 A | 10/1994 | Beug et al. .................. 530/345 |
| 5,460,831 A | 10/1995 | Kossovsky et al. ......... 424/493 |
| 5,464,650 A | 11/1995 | Berg et al. .................... 427/2.3 |
| 5,470,829 A | 11/1995 | Prisell et al. .................. 514/12 |
| 5,476,962 A | 12/1995 | Behr et al. .................... 360/168 |
| 5,545,135 A | 8/1996 | Iacob et al. .................... 604/96 |
| 5,580,859 A | 12/1996 | Felgner et al. ................ 514/44 |
| 5,593,974 A | 1/1997 | Rosenberg et al. ........... 514/44 |
| 5,616,745 A | 4/1997 | Behr et al. .................... 554/56 |
| 5,635,383 A | 6/1997 | Wu et al. .................... 435/458 |
| 5,635,487 A | 6/1997 | Wolff et al. .................... 514/44 |
| 5,674,192 A | 10/1997 | Sahatjian et al. ............. 604/28 |
| 5,674,703 A | 10/1997 | Woo et al. .................. 435/69.1 |
| 5,693,622 A | 12/1997 | Wolff et al. .................... 514/44 |
| 5,698,531 A | 12/1997 | Nabel et al. .................... 514/44 |
| 5,707,969 A | 1/1998 | Nabel et al. .................... 514/44 |
| 5,723,119 A | 3/1998 | Schwartz et al. .......... 424/85.2 |
| 5,736,392 A | 4/1998 | Hawley-Nelson et al. ....................... 435/320.1 |
| 5,744,335 A | 4/1998 | Wolff et al. .................. 435/458 |
| 5,763,416 A | 6/1998 | Bonadio et al. .............. 514/44 |
| 5,770,580 A | 6/1998 | Ledley et al. ................. 514/44 |
| 5,844,107 A | 12/1998 | Hanson et al. ............. 536/23.1 |
| 5,846,947 A | 12/1998 | Behr et al. .................... 514/44 |
| 5,874,297 A | 2/1999 | Wu et al. ................. 435/320.1 |
| 5,877,302 A | 3/1999 | Hanson et al. ............. 536/23.1 |
| 5,879,713 A | 3/1999 | Roth et al. ................... 424/489 |
| 5,942,496 A | 8/1999 | Bonadio et al. .............. 514/44 |
| 5,965,434 A | 10/1999 | Wolff et al. .............. 435/320.1 |
| 6,008,336 A | 12/1999 | Hanson et al. ............. 536/23.1 |
| 6,077,835 A | 6/2000 | Hanson et al. ................ 514/44 |
| 6,387,700 B1 * | 5/2002 | Rice et al. ................... 435/455 |

FOREIGN PATENT DOCUMENTS

| | | |
|---|---|---|
| EP | 0 190 833 | 8/1986 |
| WO | WO 90/11092 | 10/1990 |
| WO | WO9 3/21969 | 11/1993 |
| WO | WO 95/02397 | 1/1995 |
| WO | WO 95/24929 | 9/1995 |
| WO | WO 95/29184 | 11/1995 |
| WO | WO 96/02655 | 2/1996 |
| WO | WO 96/20698 | 7/1996 |
| WO | WO 97/38729 | 10/1997 |
| WO | WO 97/46100 | 12/1997 |
| WO | WO 97/47254 | 12/1997 |
| WO | WO 98/19711 | 5/1998 |
| WO | WO 98/29541 | 6/1998 |
| WO | WO 99/29349 | 6/1999 |
| WO | WO 99/53961 | 10/1999 |

OTHER PUBLICATIONS

Midoux et al., Efficient gene transfer by histidylated polylysine/pDNA complexes, 1999, Bioconjugate Chemistry, vol. 10, pp. 406–411.*

1998 AAPS Annual Meeting, PHARMSCI., vol. 1, pp. S–286–287.*

Wadhwa et al., Peptide–mediated gene delivery: influence of peptide structure on gene expression, 1997, Bioconjugate Chemistry, vol. 8, pp. 81–88.*

Choi et al., Lactose–poly(ethylene Glycol)–grafted poly–L–lysine as hepatoma cell–targeted gene carrier, 1998, Bioconjugate Chemistry, vol. 9, pp. 708–718.*

Gottschalk et al., "A Novel DNA–Peptide Complex for Efficient Gene Transfer and Expression in Mammalian Cells," *Gene Therapy*, 3:448,457, 1996.

Langer and Folkman, "Polymers for the Sustained Release of Proteins and Other Macromolecules," *Nature*, 263:797–799, 1976.

(List continued on next page.)

*Primary Examiner*—Anne-Marie Falk
*Assistant Examiner*—Celine Qian
(74) *Attorney, Agent, or Firm*—Williams, Morgan and Amerson

(57) ABSTRACT

Disclosed are improved compositions and methods for use in gene delivery and expression. A range of surprisingly effective cross-linking agents and peptides are provided, as are peptide-DNA carrier compositions and condensed particles with reduced toxicity and increased stability. Advantageous methods of using such compositions in gene delivery and gene expression are further disclosed, which may be used in combination with biocompatible matrices, carriers and/or targeting agents.

35 Claims, 90 Drawing Sheets

OTHER PUBLICATIONS

Ledley, "Somatic Gene Therapy for Human Disease: Background and Prospects," *J. Pediatrics*, 110:1–8, 1987.

Midoux et al., "Specific Gene Transfer Mediated by Lactosylated Poly–L–Lysine Into Hepatoma Cells," *Nucleic Acids Res.*, 21(4):871–878, 1993.

Nicolau et al., "In Vivo Expression of Rat Insulin After Intravenous Administration of the Liposome–Entrapped Gene for Rat Insulin I," *Proc. Natl. Acad. Sci. USA*, 80:1068–1072, 1983.

Wasan et al., "Plasmid DNA is Protected Against Ultrasonic Cavitation–Induced Damage when Complexed to Cationic Liposomes," *J. Pharm. Sci.*, 85(4):427–433, 1996.

Wolfert et al., "Characterization of Vectors for Gene Therapy Formed by Self–Assembly Of DNA with Synthetic Block Co–Polymers," *Human Gene Therapy*, 7(10):2123–2133, 1996.

Co–pending application Ser. No. 09/668,624, filed Sep. 22, 2000.

Duguid et al., "A Physicochemical Approach for Predicting the Effectiveness of Peptide–Based Gene Delivery Systems for Use in Plasmid–Based Gene Therapy," *Biophys, J.*, 74:2802–2814, 1998.

Choi et al., "Lactose–Poly(ethylene Glycol)–Grafted Poly–L–Lysine at Hepatoma Cell–Targeted Gene Carrier," *Bioconjugate Chem.*, 9:708–718, 1998.

Katayose and Kataoka, "Water Soluble Polyion Complex between DNA and Peg–Poly (L–Lysine) Block Copolymer for Novel Gene Vector," *Proceed. Intern. Symp. Control. Rel. Bioact. Mater.*, 23:899–900, 1996.

Merwin et al., "Targeted Delivery of DNA Using YEE(Gal-NAcAH)$_3$, a Synthetic Glycopeptide Ligand for the Asialogycoprotein Receptor," *Bioconjugate Chem.*, 5(6):612–620, 1994.

Smith et al., "Synthetic Peptide–Based DNA Complexes for Nonviral Gene Delivery," *Advanced Drug Delivery Reviews*, 30:115–131, 1998.

Wadhwa and Rice, "Glycopeptide Carriers for Site–Targeted, Receptor–Mediated Gene Delivery," *Pharm. Res.*, 12(9):S79, also *Biotec 2002*, 579, 1995.

International Search Report for PCT/US00/19164, mailed Apr. 25, 2001.

Adami and Rice, "Metabolic stability of glutaraldehyde cross–linked peptide DNA condensates," *J. Pharm. Sci.*, 88(8):739–746, 1999.

Adami and Rice, "Metabolically stabilized peptide/DNA formulations for enhanced gene expression," *PharmSci*, 1(1):S286–S287, 1998.

Adami et al., "Stability of peptide–condensed plasmid DNA formulations," *J. Pharm. Sci.*, 87(6):678–683, 1998.

Blessing, Remy and Behr, "Monomolecular collapse of plasmid DNA into stable virus–like particles," *Proc. Natl. Acad. Sci. USA*, 95:1427–1431, 1998.

Collard et al., "Biodistribution, metabolism and in vivo gene expression of low molecular weight glycopeptide polyethylene glycol peptide DNA co–condensates," *J. Pharm. Sci.*, 89(4):499–512, 2000.

Collard et al., "Synthesis of homogeneous glycopeptides and their utility as DNA condensing agents," *Carbohydrate Res.*, 323:176–184, 2000.

Fang et al., "Stimulation of new bone formation by direct transfer of osteogenic plasmid genes," *Proc. Natl. Acad. Sci. USA*, 93:5753–5758. 1996.

Kwok et al., "Formulation of highly soluble poly(ethylene glycol)–peptide DNA condensates," *J. Pharm. Sci.*, 88(10):996–1003, 1999.

Kwok et al., "Strategies for maintaining the particle size of peptide DNA condensates following freeze–drying," *Int. J. Pharm.*, 203(1–2):81–88, 2000.

Laurent et al., "Uptake by rat liver and intracellular fate of plasmid DNA complexed with poly–L–lysine or poly–D–lysine," *FEBS Lett.*, 443(1):61–65, 1999.

McKenzie, Kwok and Rice, "A potent new class of reductively activated peptide gene delivery agents," *J. Biol. Chem.*, 275(14):9970–9977, 2000.

McKenzie, Kwok and Rice, "Self–cross–linking peptides: Potent new agents for gene delivery," *219th American Chemical Society National Meeting*, San Francisco, California, Mar. 26–30, 2000.

Ogris et al., "PEGylated DNA/transferrin–PEI complexes: Reduced interaction with blood components, extended circulation in blood and potential for systemic gene delivery," *Gene Ther.*, 6:595–605, 1999.

Trubetskoy et al., "Caged DNA does not aggregate in high ionic strength solutions," *Bioconj. Chem.*, 10(4):624–628, 1999.

Trubetskoy et al., "Layer–by–layer deposition of oppositely charged polyelectrolytes on the surface of condensed DNA particles," *Nucl. Acids Res.*, 27(15):3090–3095, 1999.

Trubetskoy et al., "Quantitative assessment of DNA condensation," *Anal. Biochem.*, 267(2):309–313, 1999.

Trubetskoy et al., "Self–assembly of DNA–polymer complexes using template polymerization," *Nucl. Acids Res.*, 26(18):4178–4185, 1998.

Wadhwa et al., "Peptide–mediated gene delivery: Influence of peptide structure on gene expression," *Bioconjug. Chem.*, 8(1):81–88, 1997.

Wadhwa et al., "Targeted gene delivery with a low molecular weight glycopeptide carrier," *Bioconjug. Chem.*, 6(3):283–291, 1995.

Co–pending U.S. patent application Ser. No. 09/050,811; filed: Mar. 30, 1998; Entitled: "Peptides for Gene Delivery," by Kevin G. Rice and Manpreet S. Wadhwa, which claims priority to U.S. patent application Ser. No. 08/961,625; filed: Oct. 31, 1997; Entitled: "Peptides for Gene Delivery," by Kevin G. Rice and Manpreet S. Wadhwa, now abandoned, which claims priority to U.S. patent application Ser. No. 08/743,269; filed: Nov. 4, 1996; Entitled: "Peptides for Gene Delivery," by Kevin G. Rice, now abandoned.

Co–pending U.S. patent application Ser. No. 09/469,523; filed: Dec. 22, 1999; Entitled: "Methods and Compositions for Increasing Gene Transfection Efficiencies," by Jeffery Bonadio et al.

\* cited by examiner

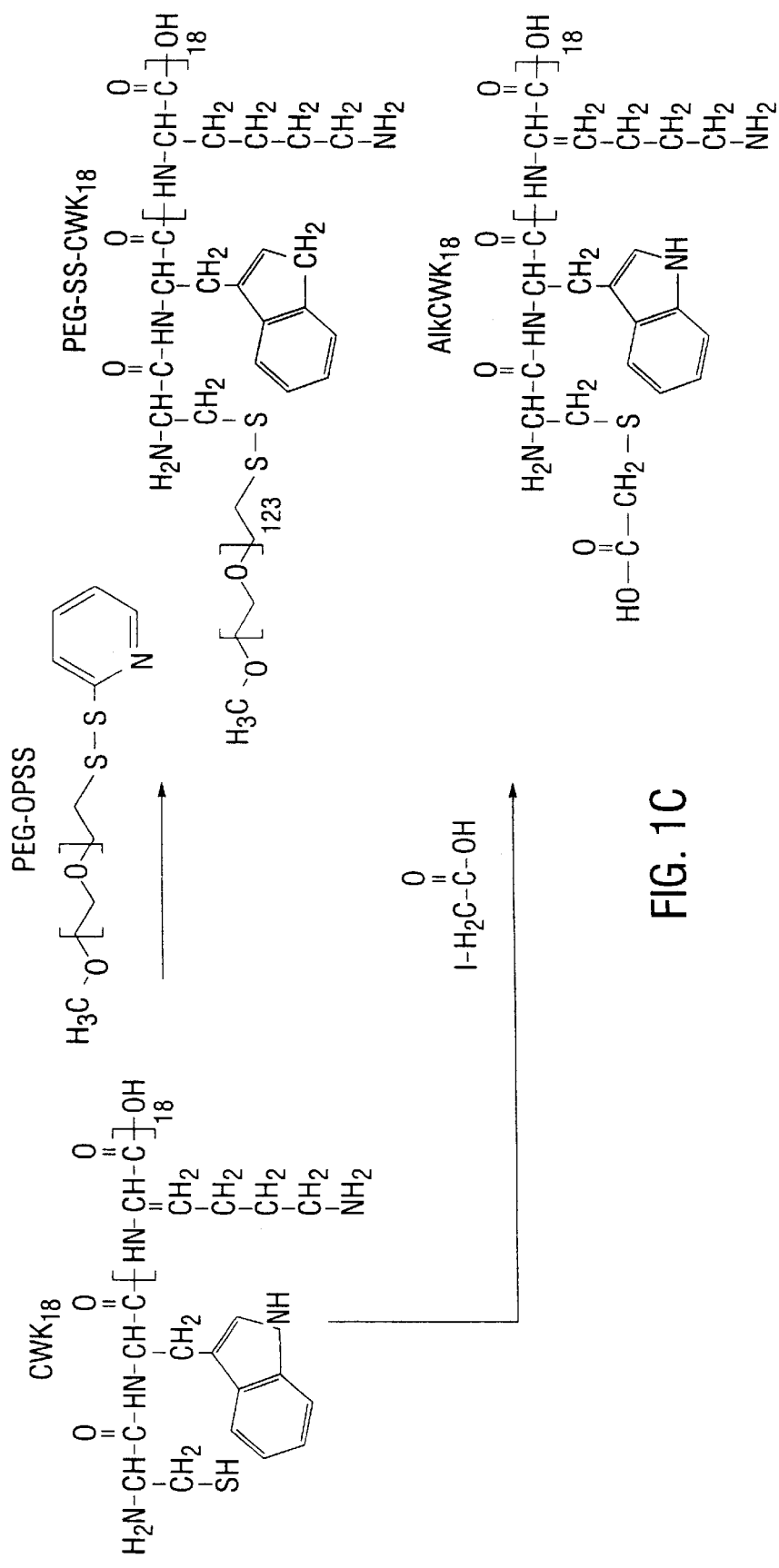

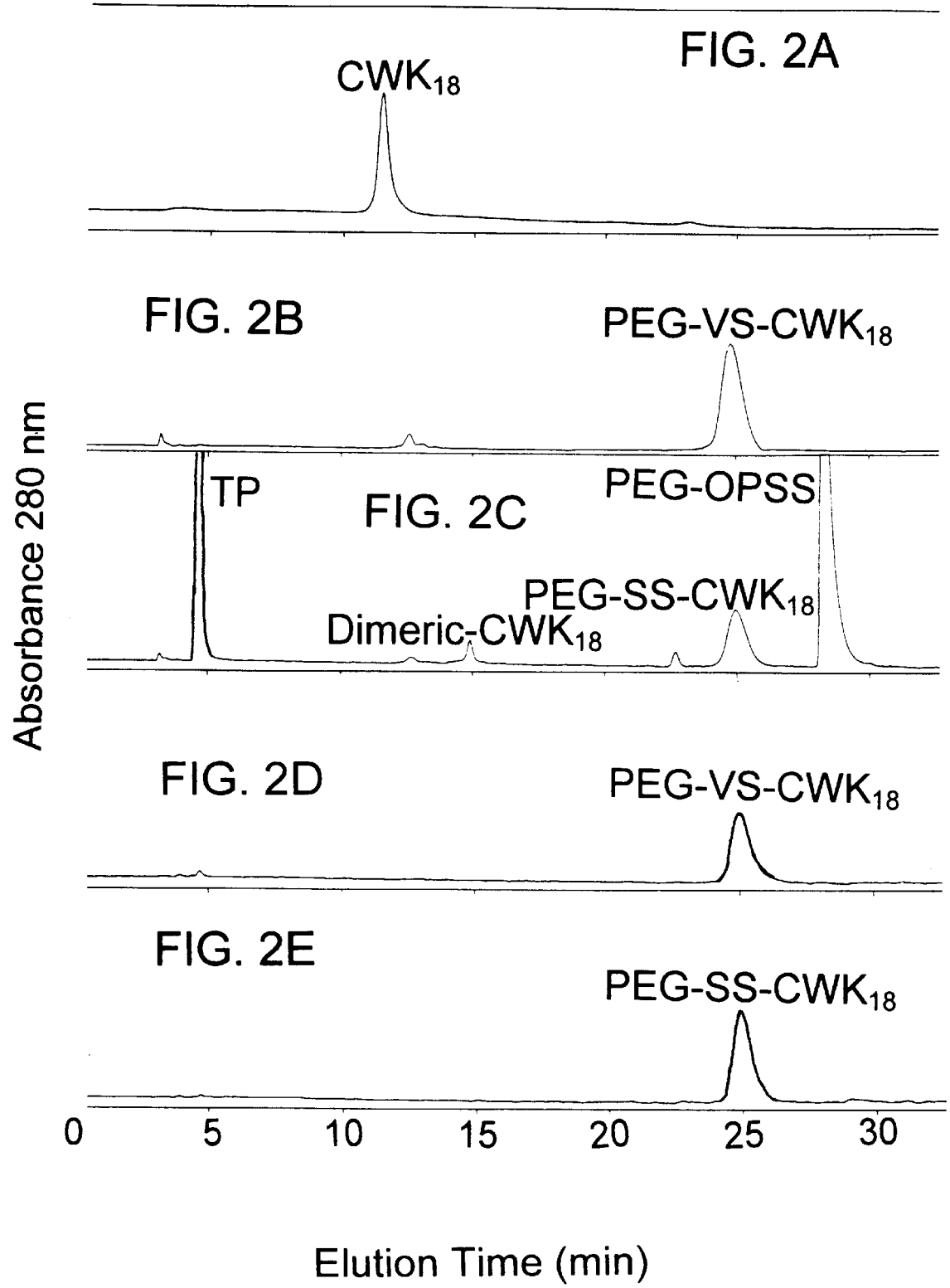

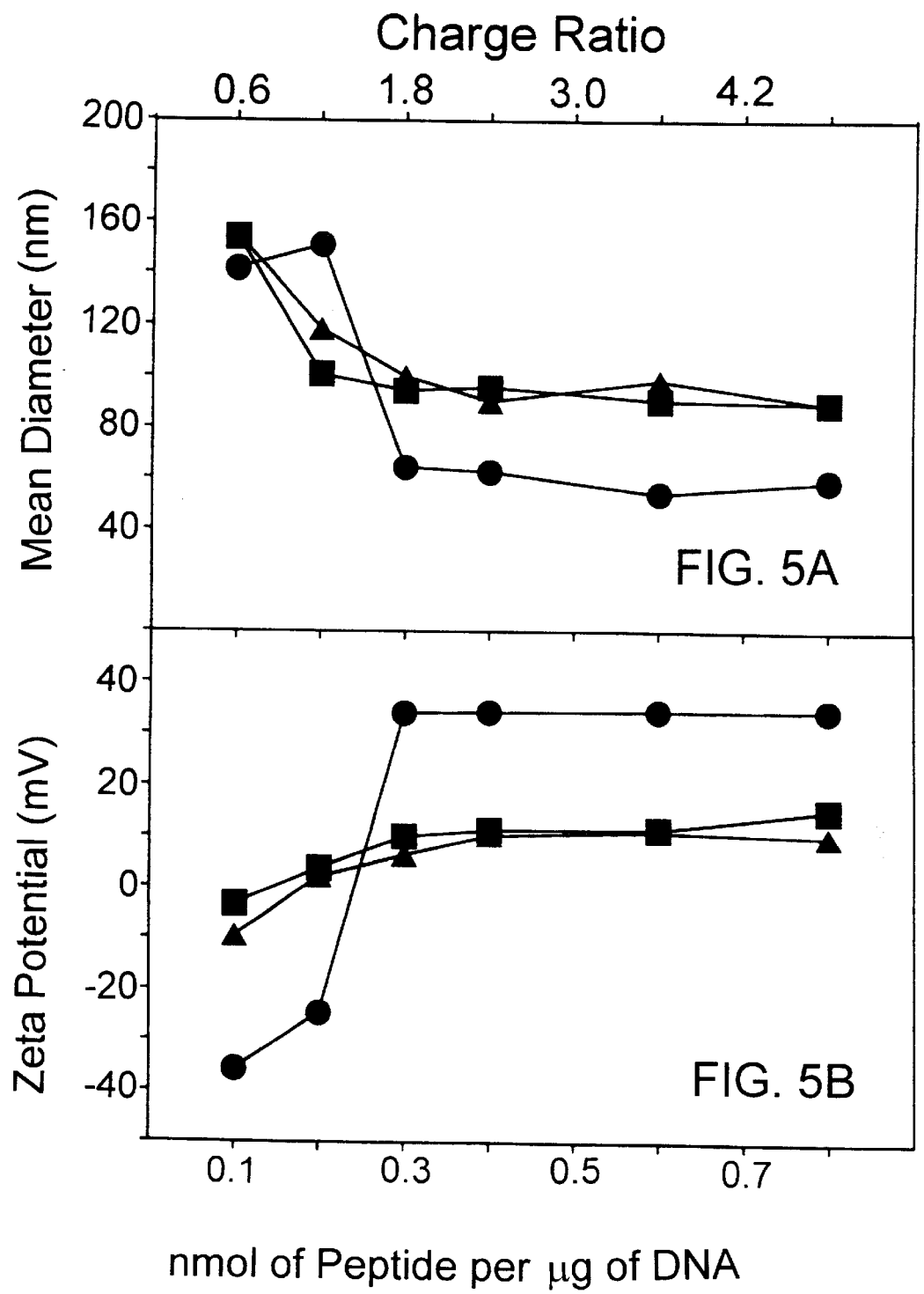

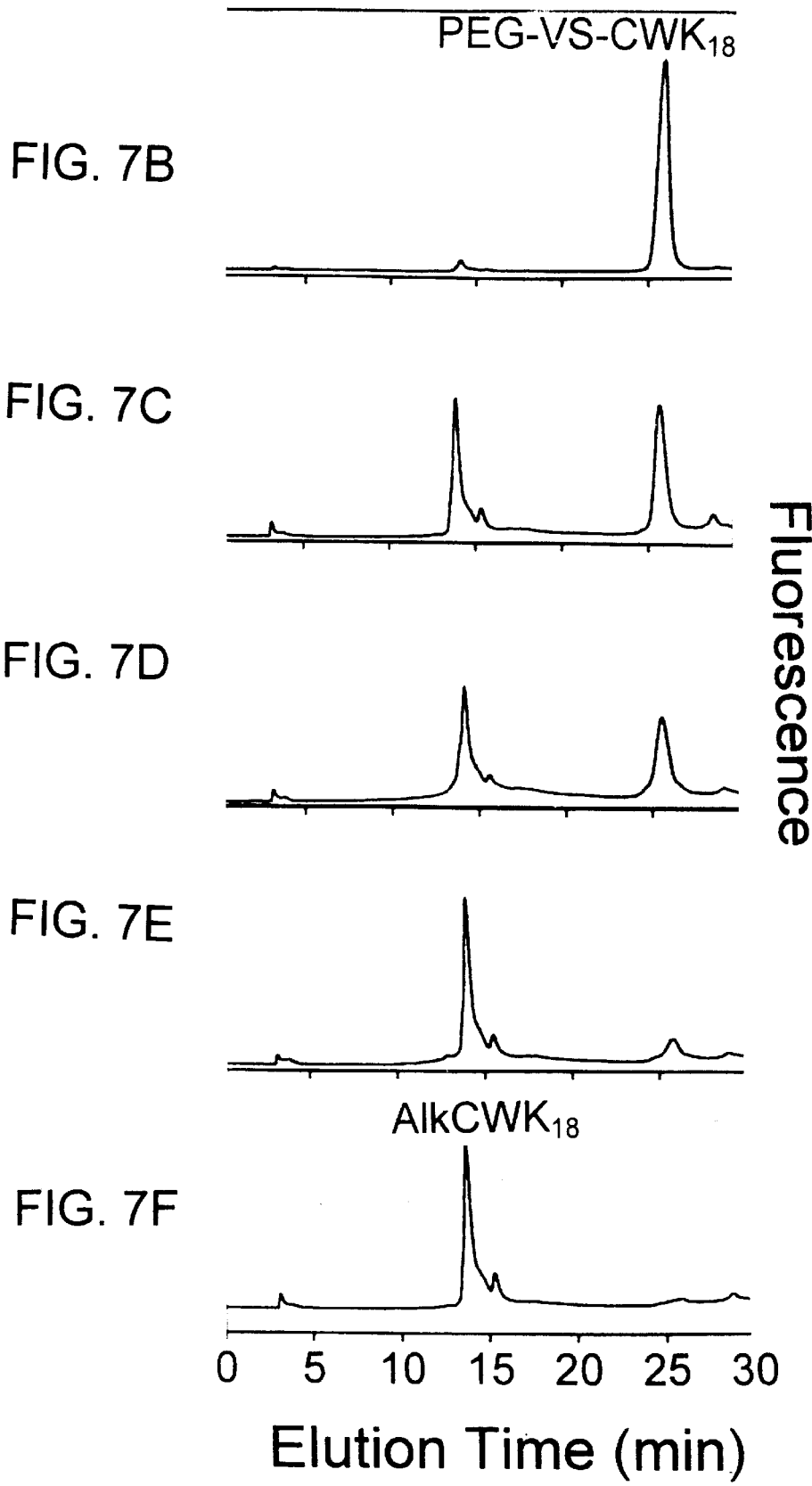

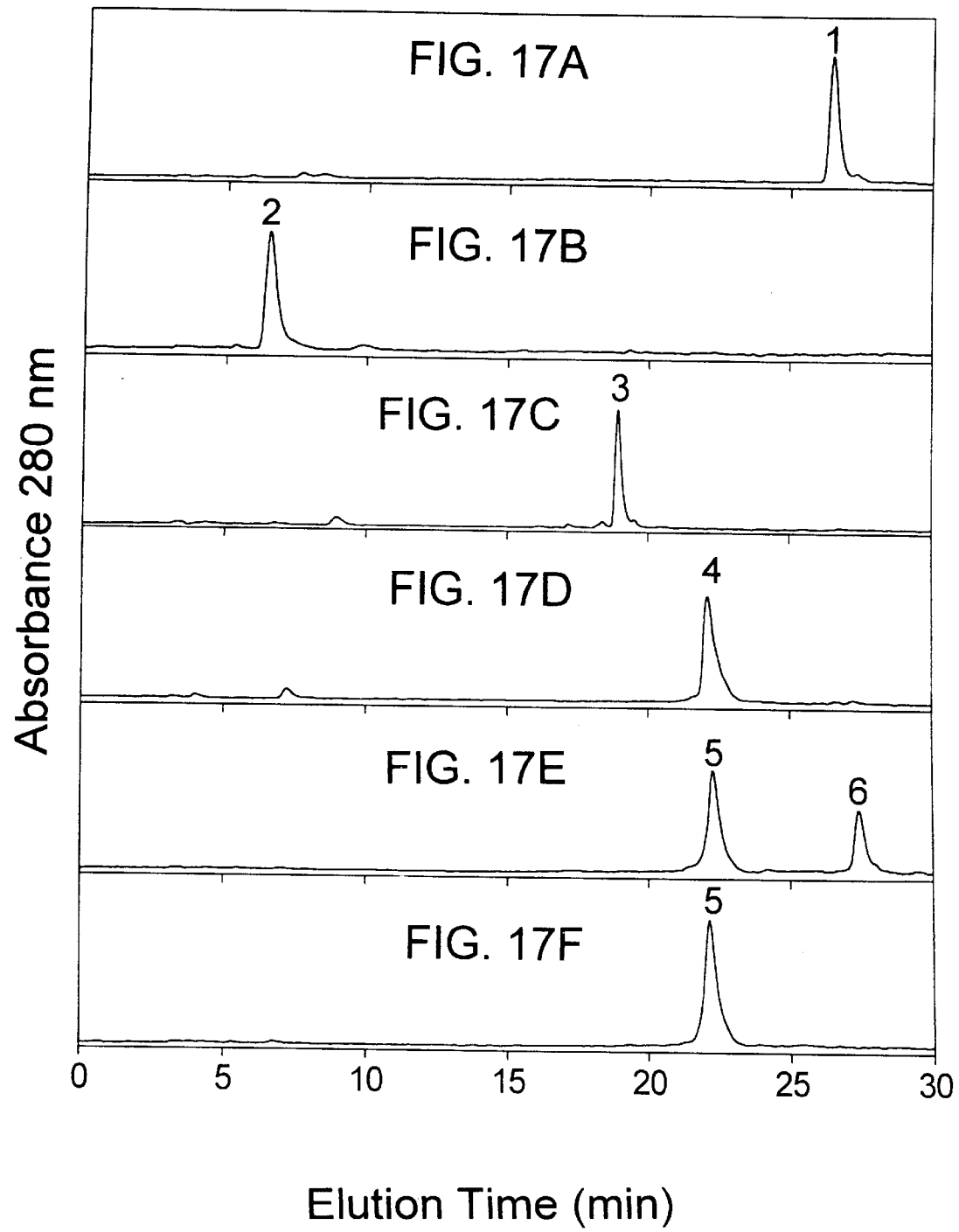

Man9-CWK$_{18}$

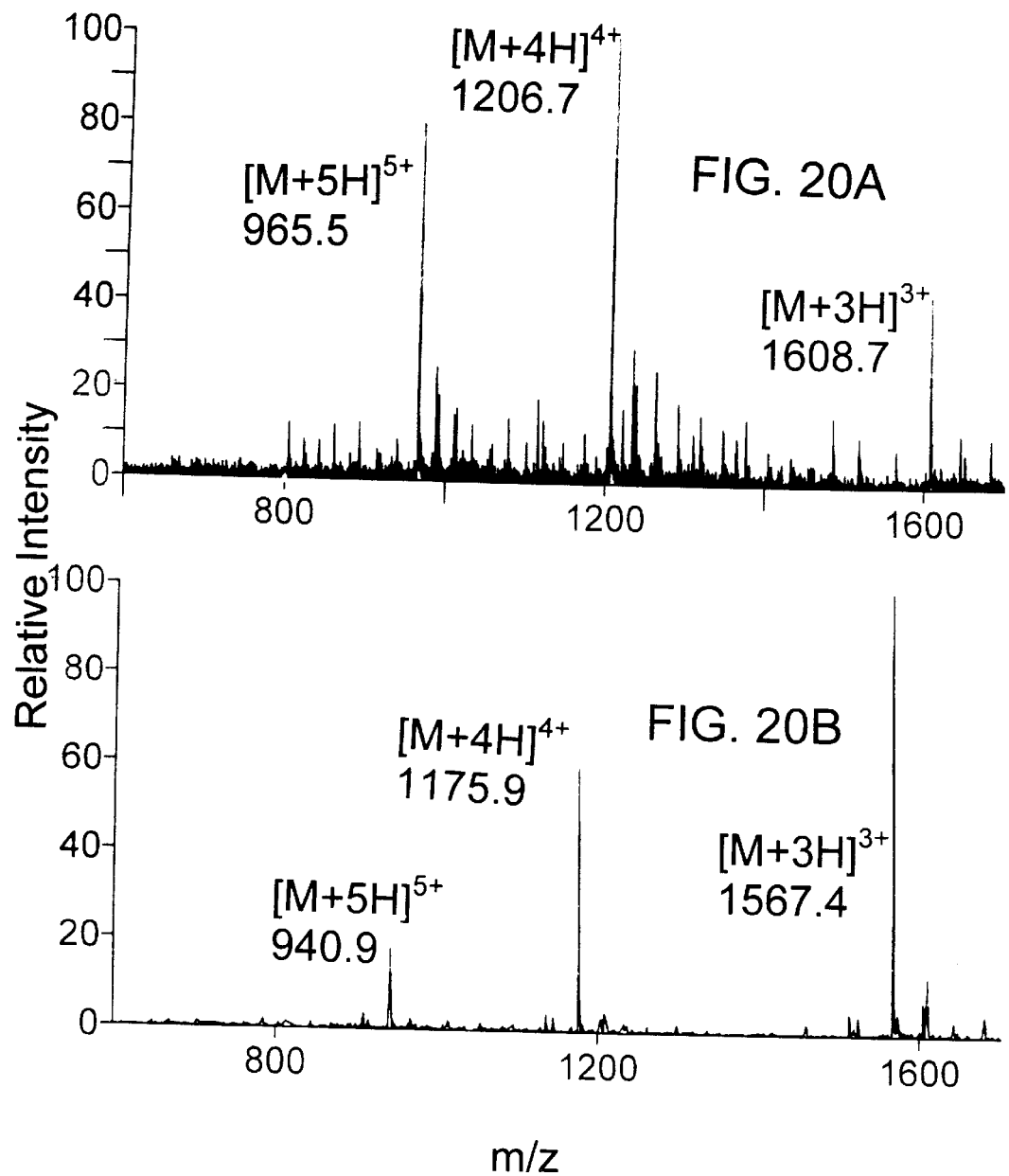

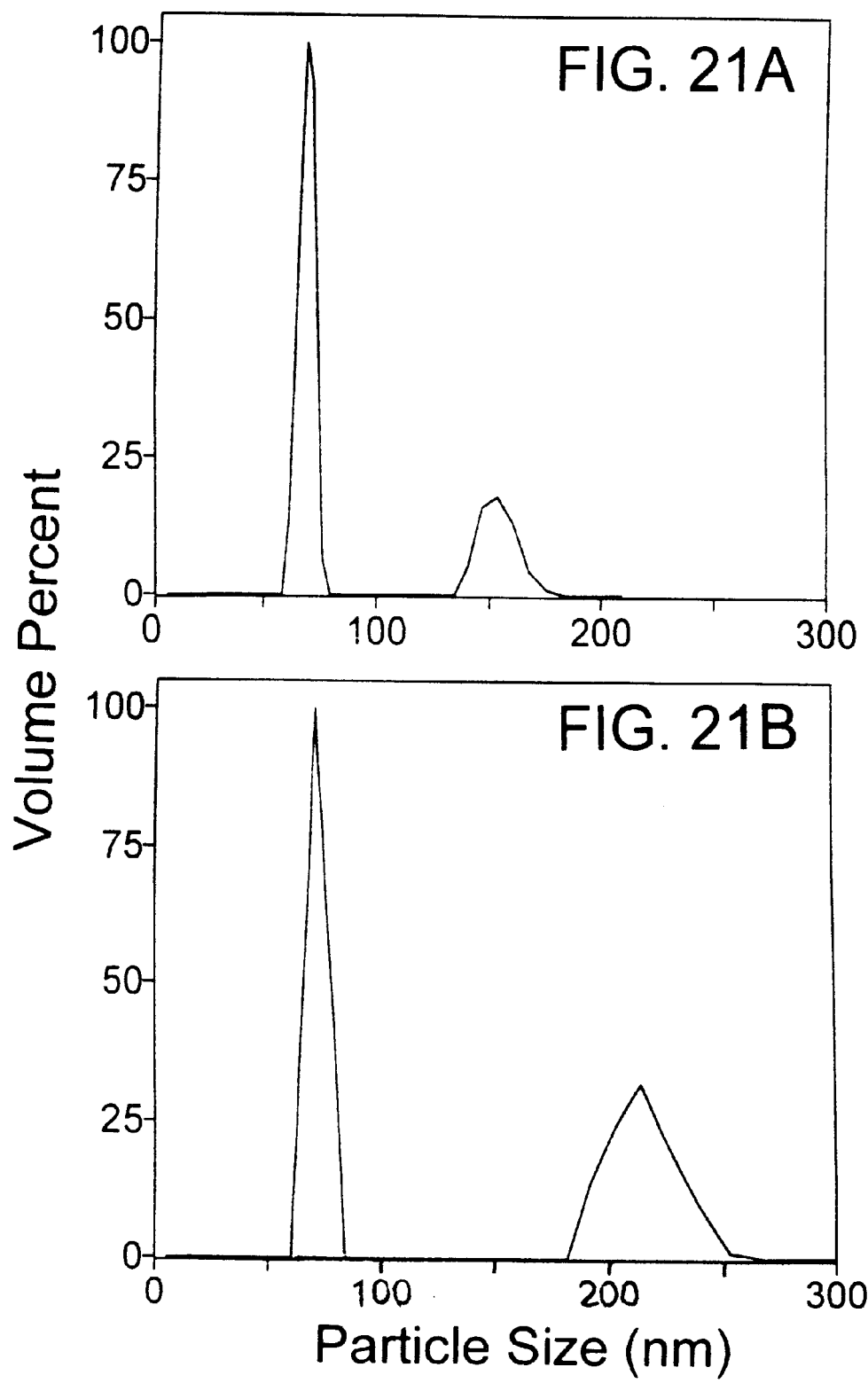

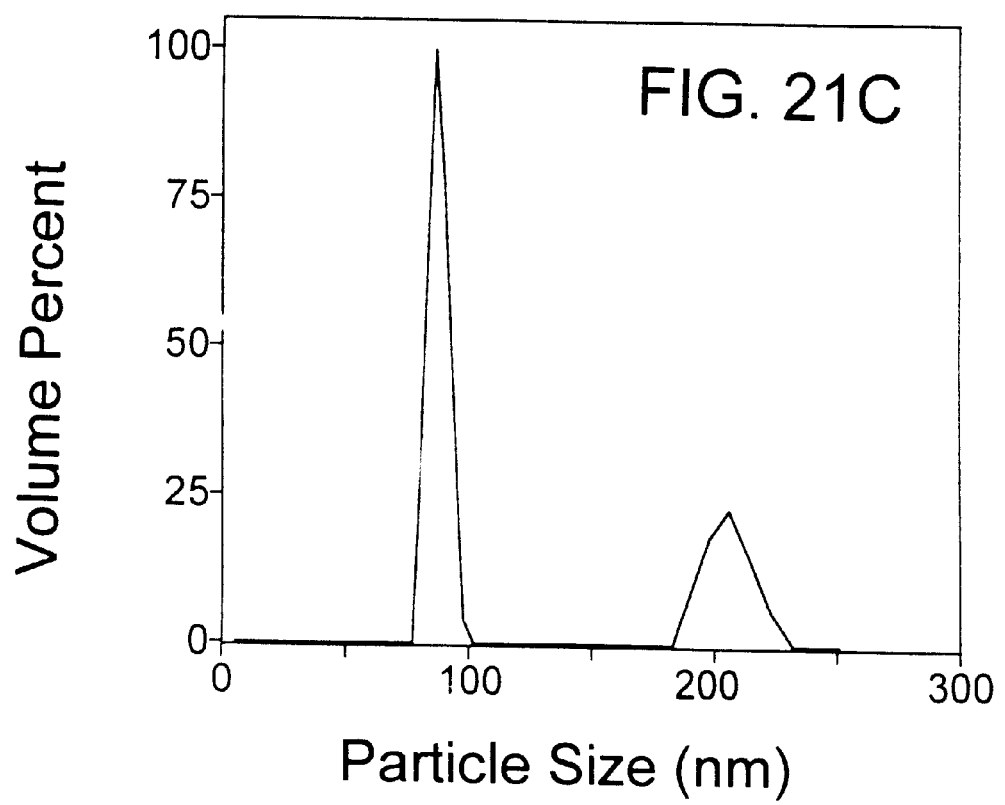

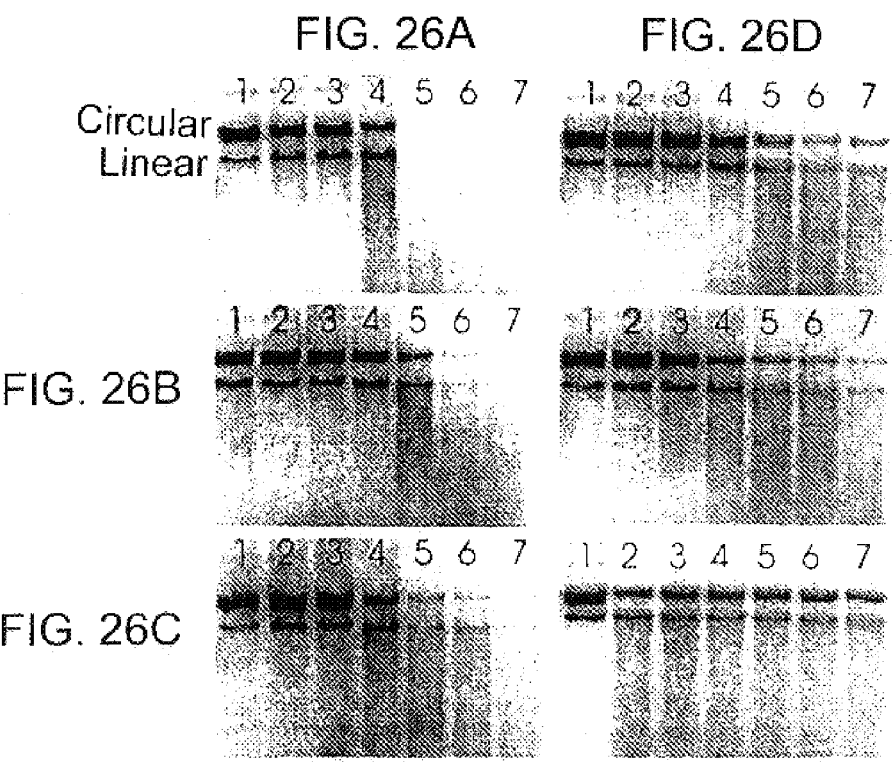

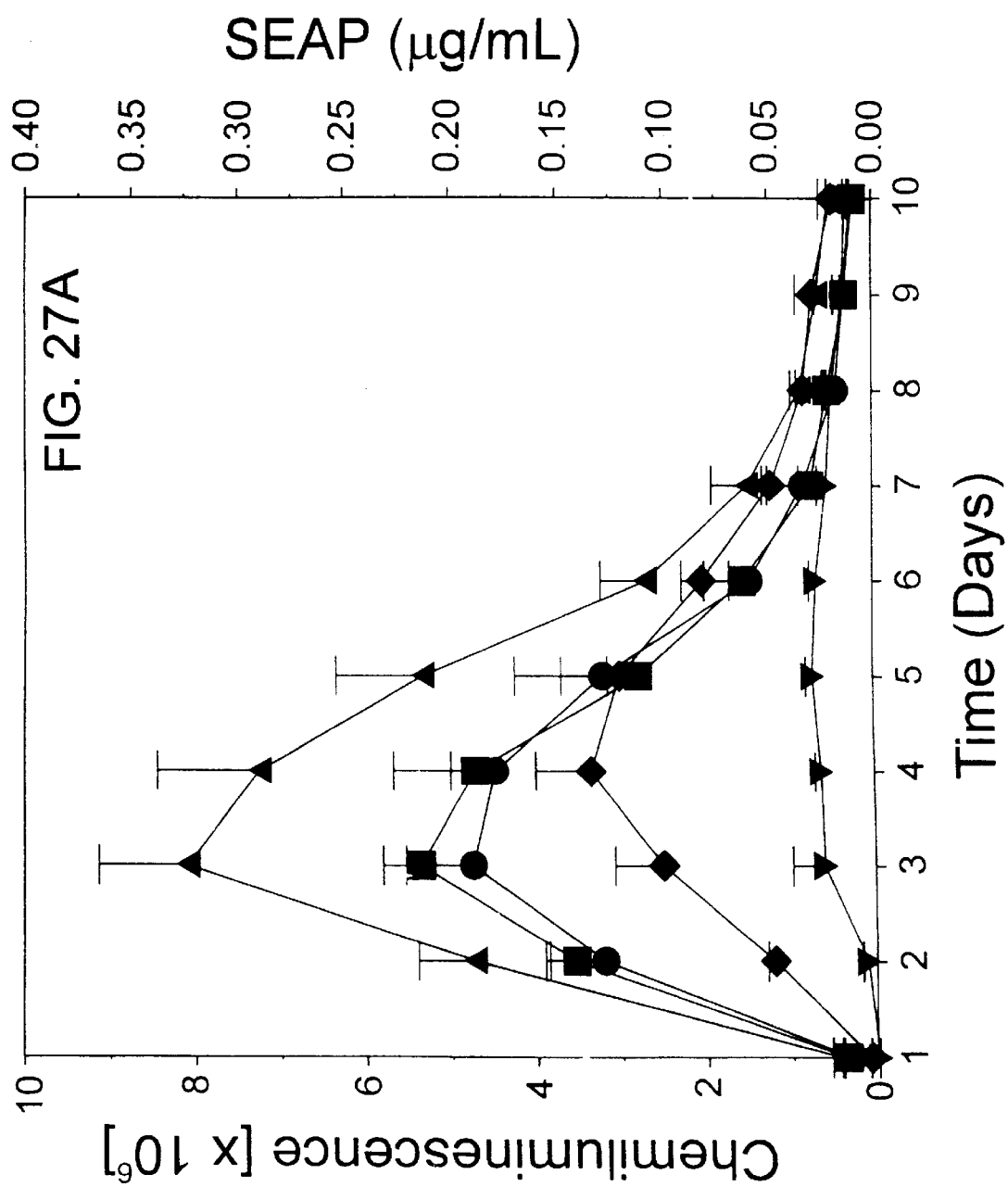

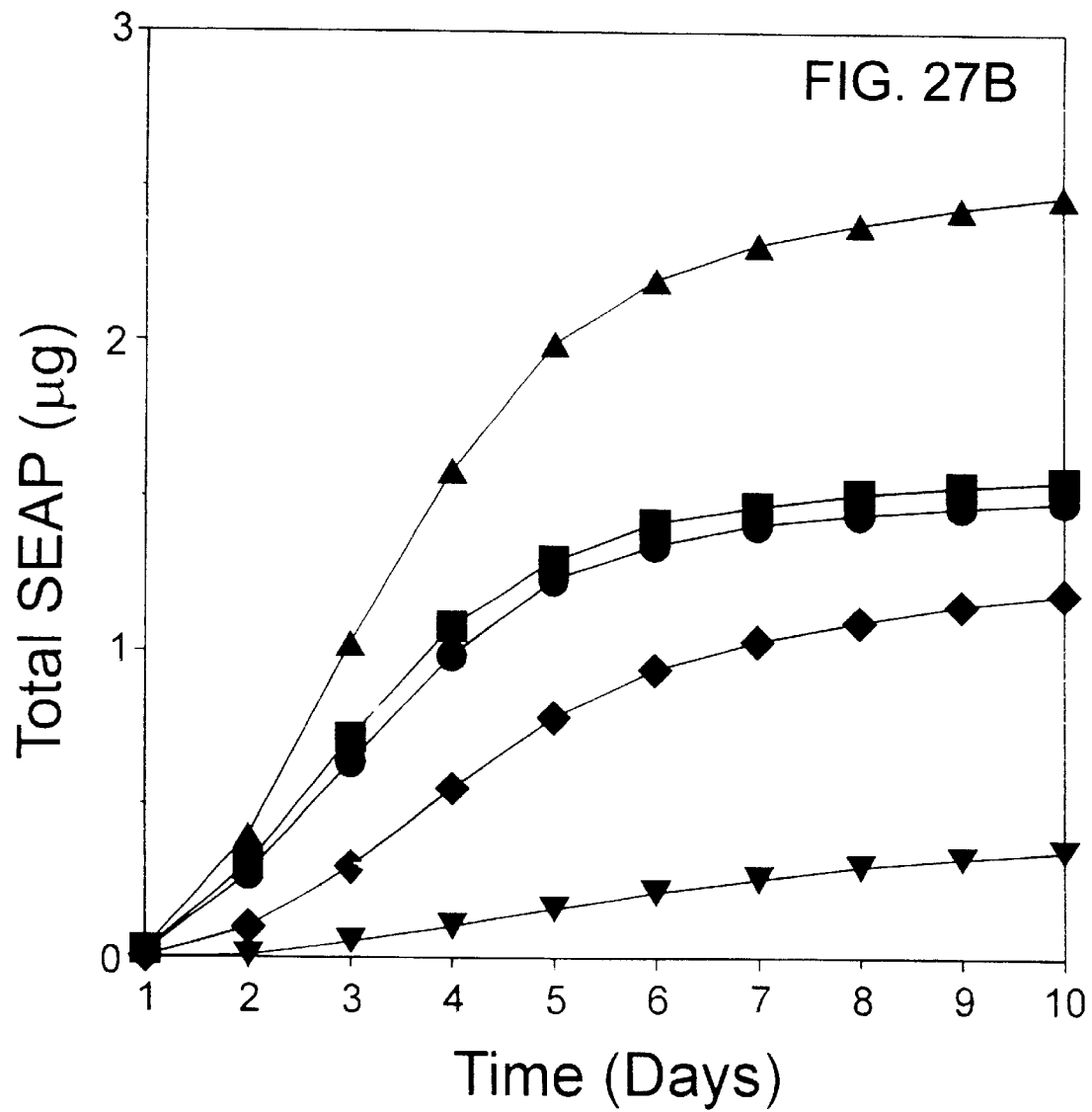

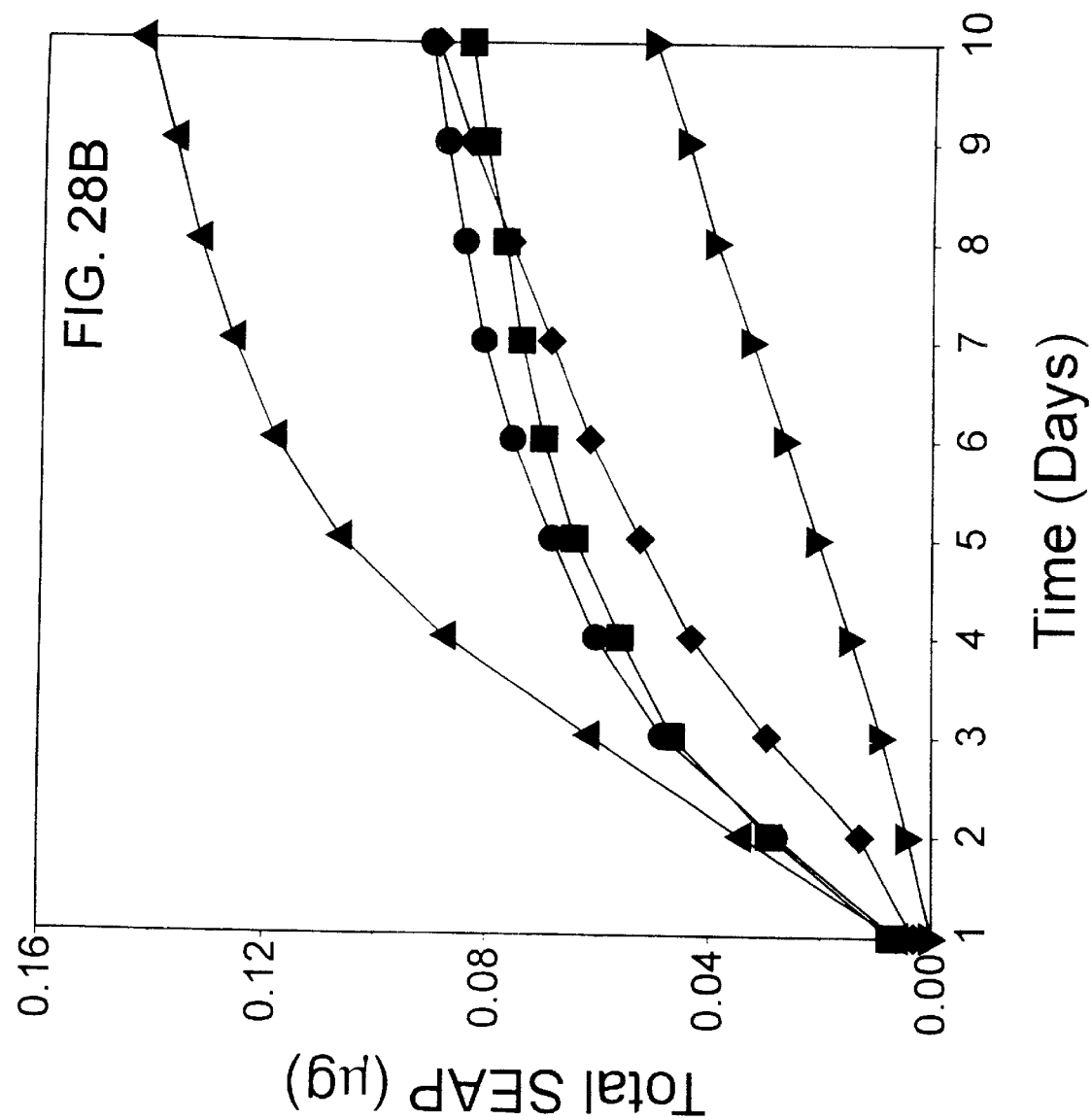

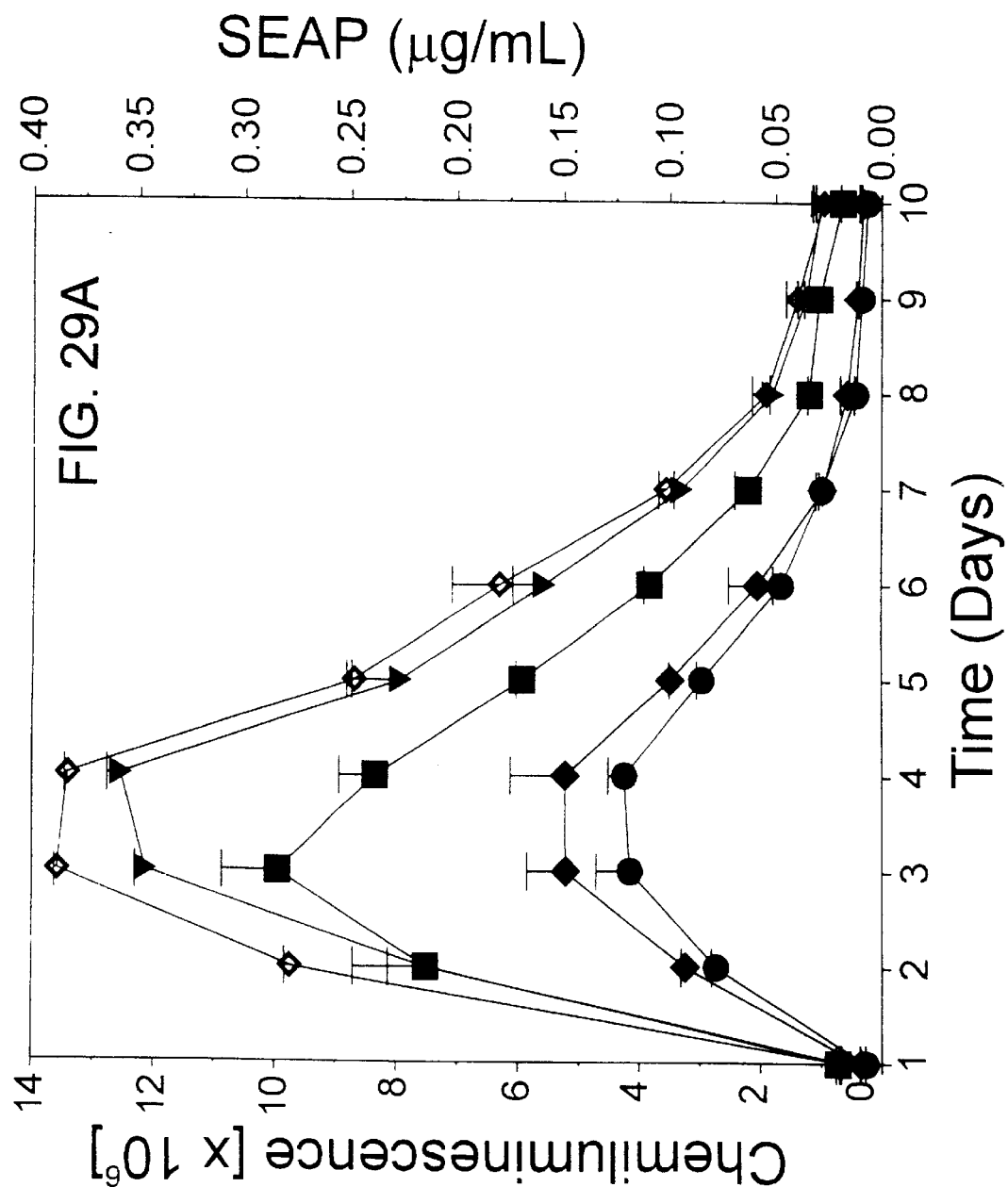

Cross-linking Peptide V

Cross-linking Peptide 5

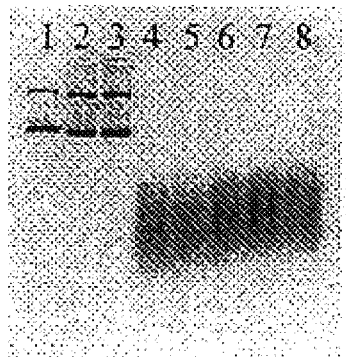
FIG. 34A
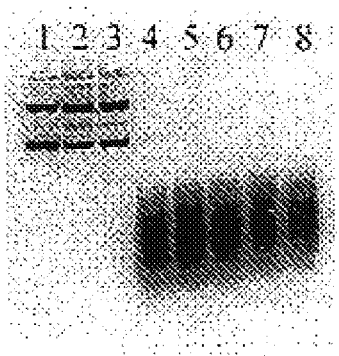
FIG. 34B
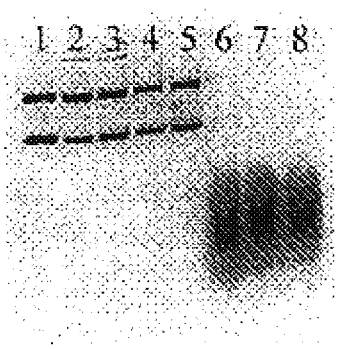
FIG. 34C
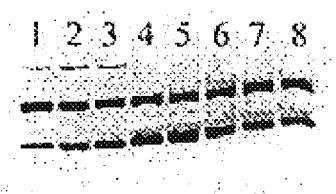
FIG. 34D
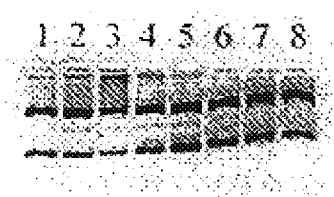
FIG. 34E
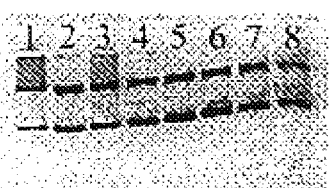
FIG. 34F
FIG. 34G
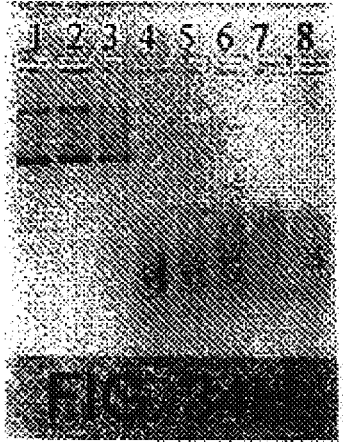
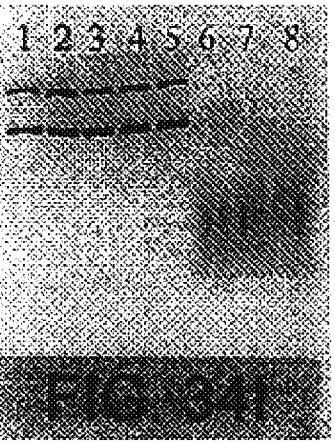

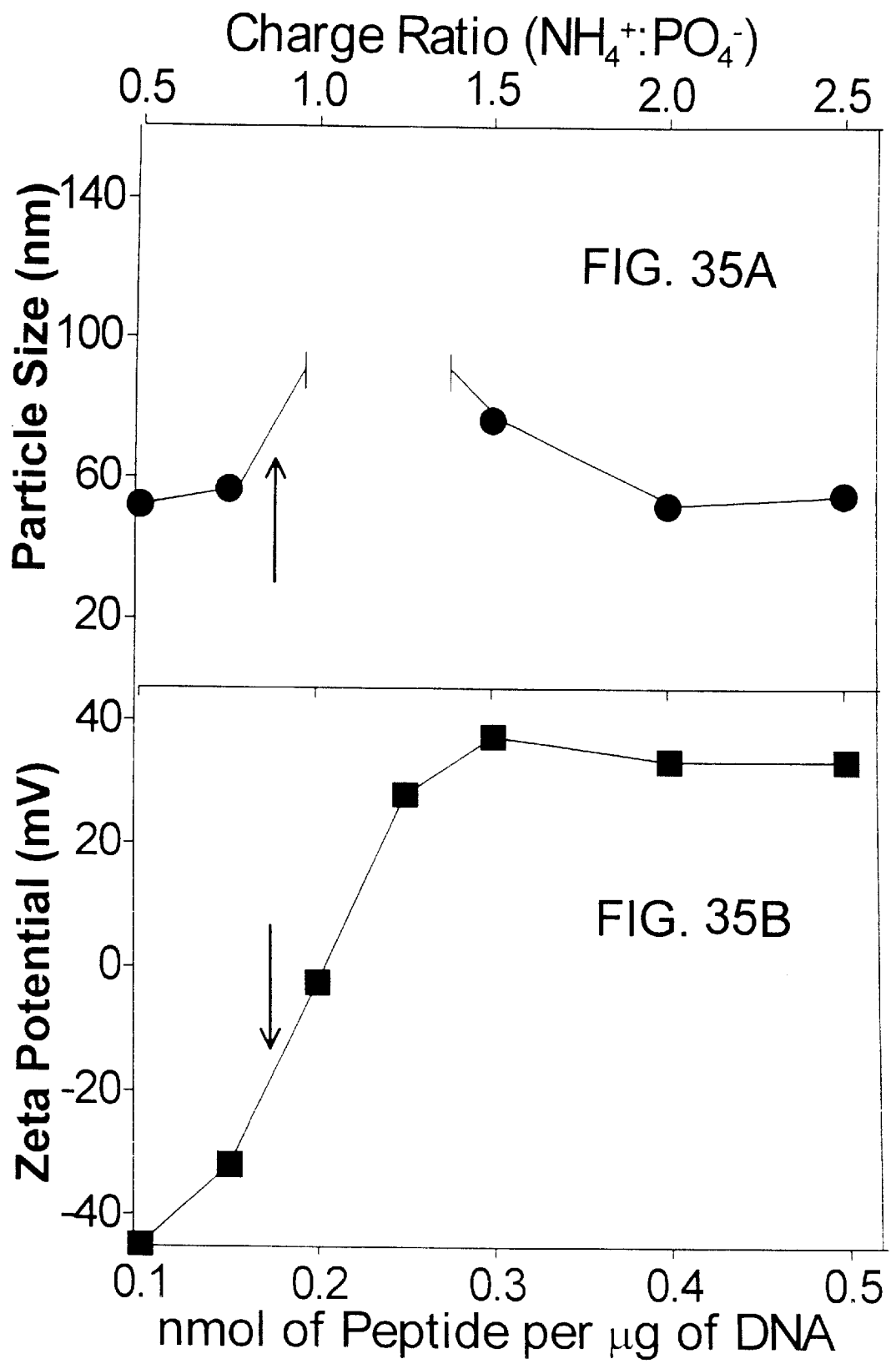

 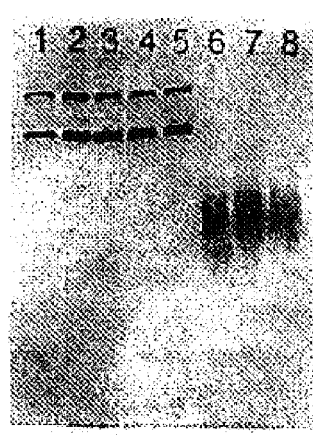 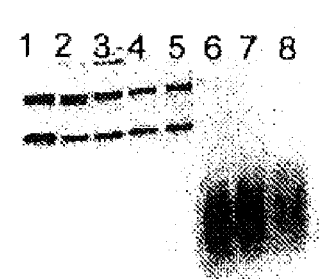
A  FIG. 42A  FIG. 42B  C  FIG. 42C 1 2 3 4 5 6 7 8    1 2 3 4 5 6 7 8    1 2 3 4 5 6 7 8
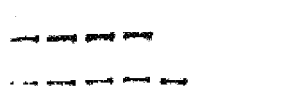
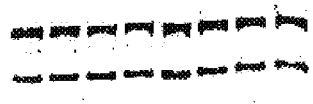
D          E          F
FIG. 42D     FIG. 42E     FIG. 42F

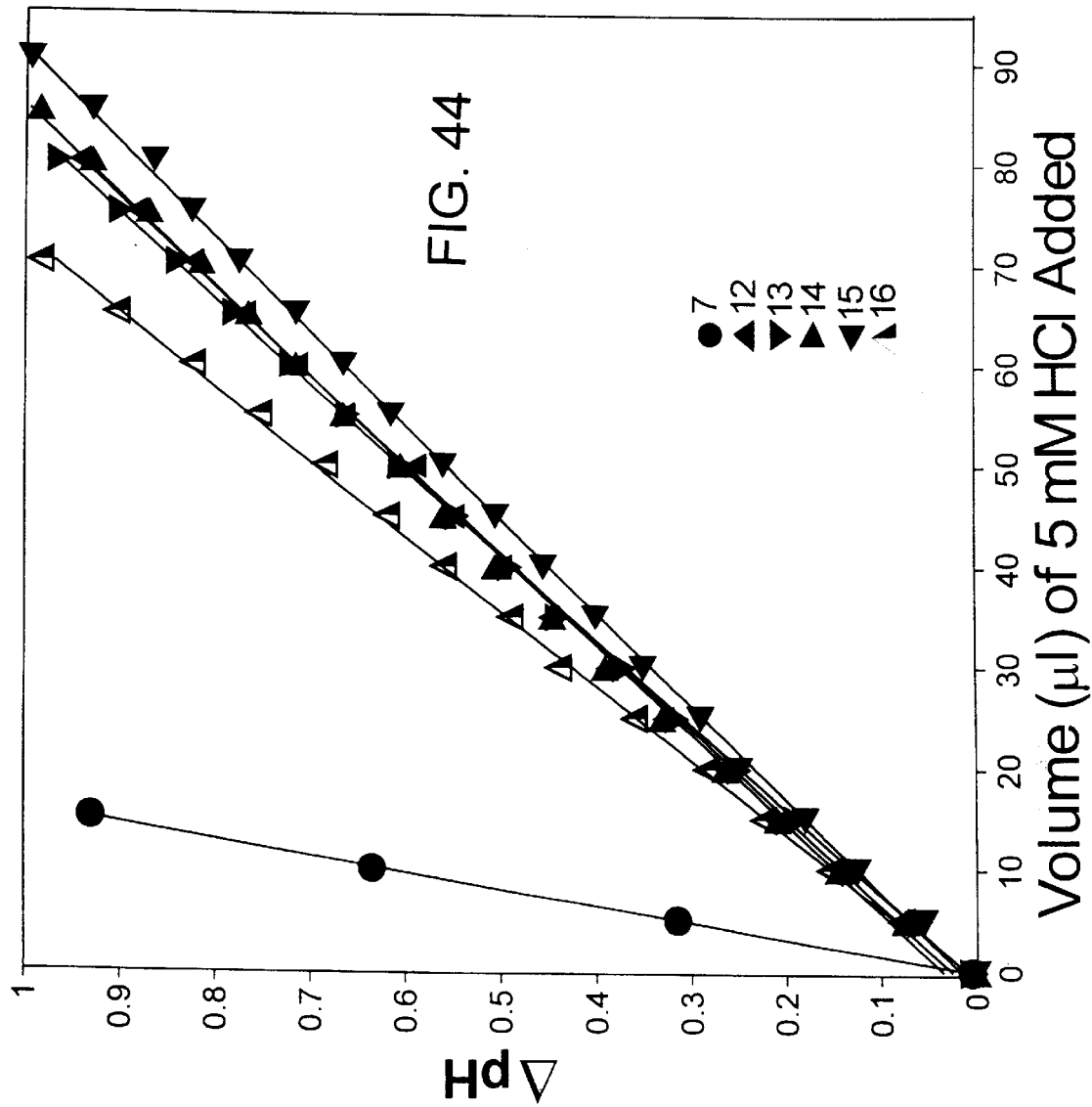

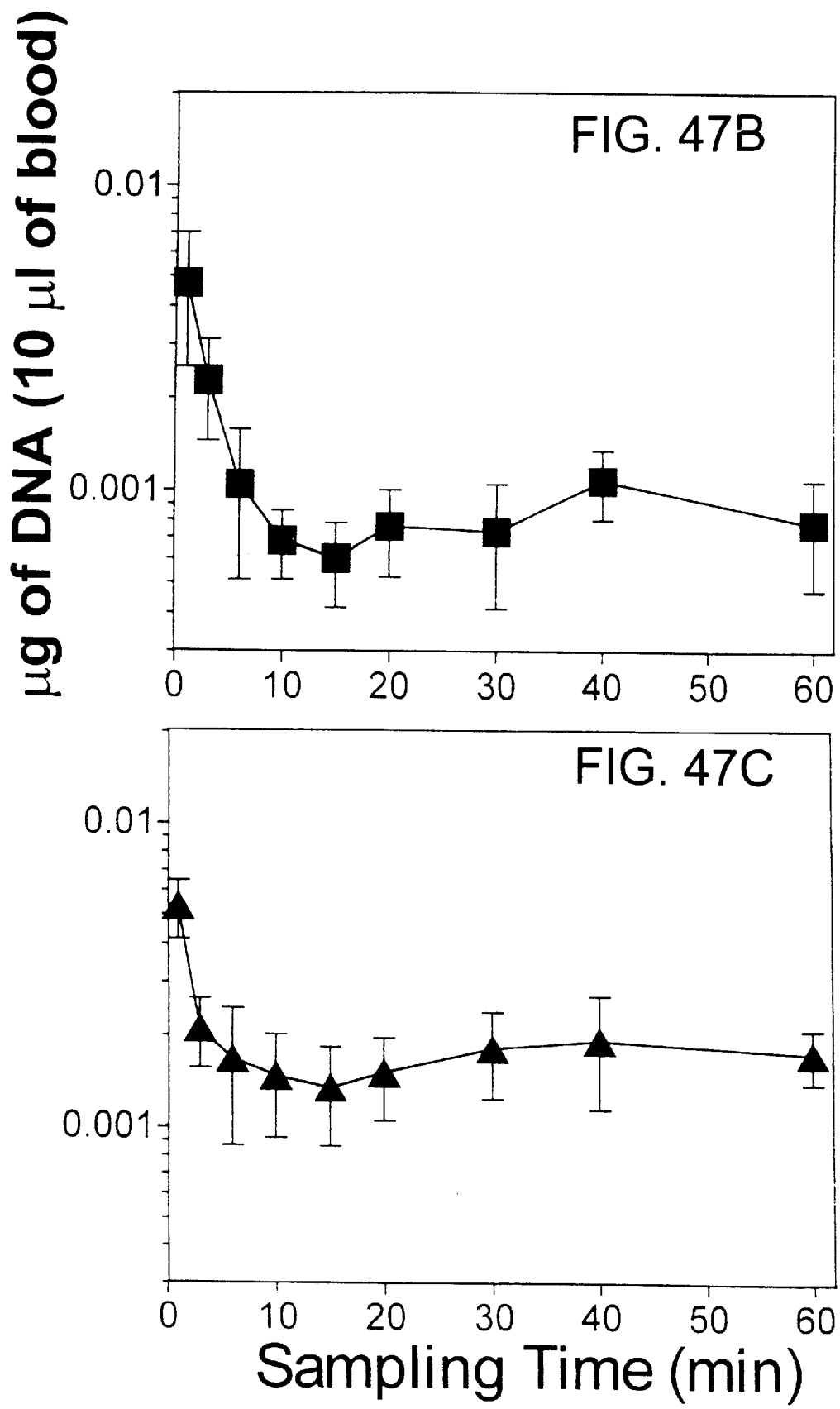

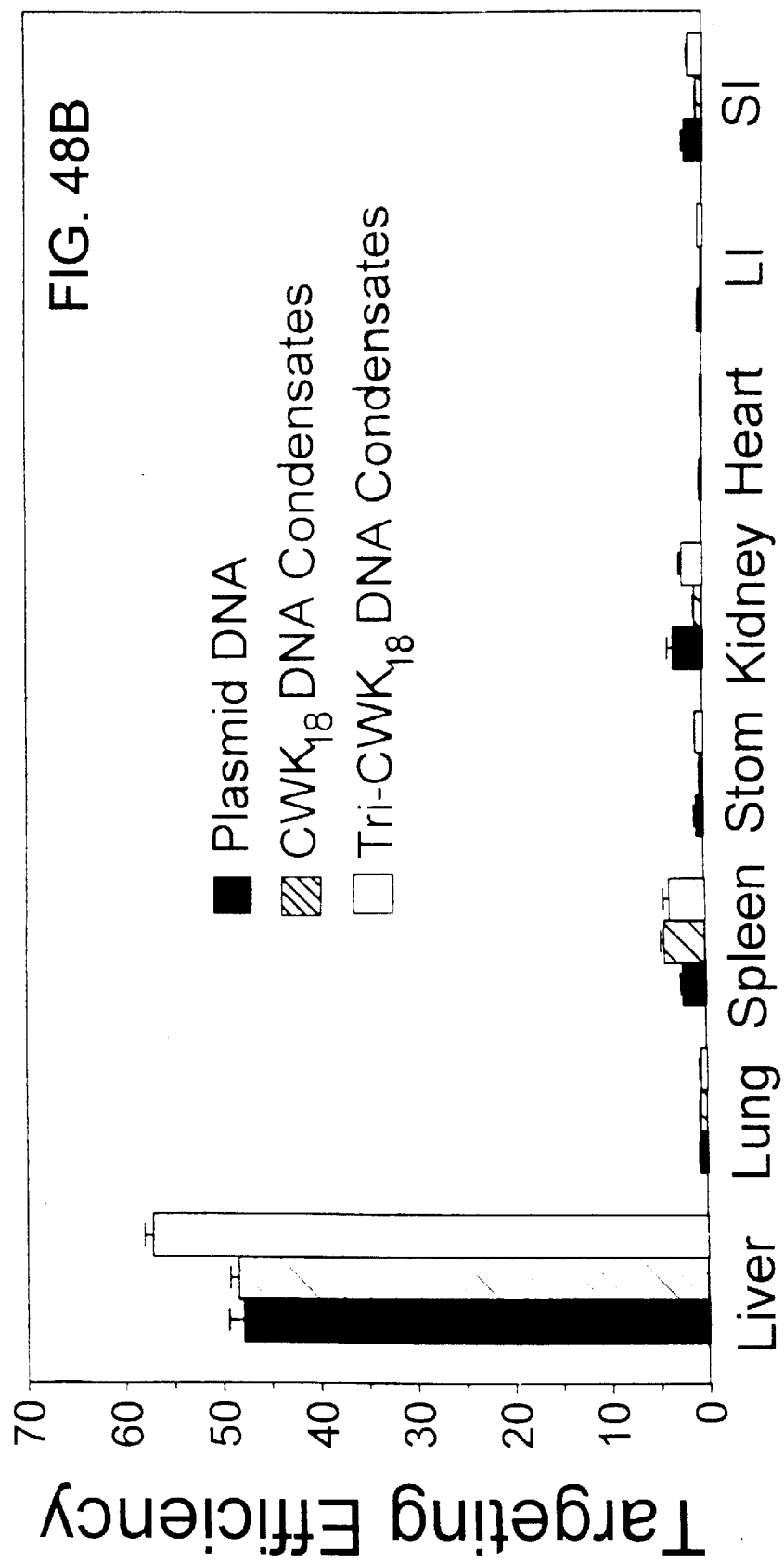

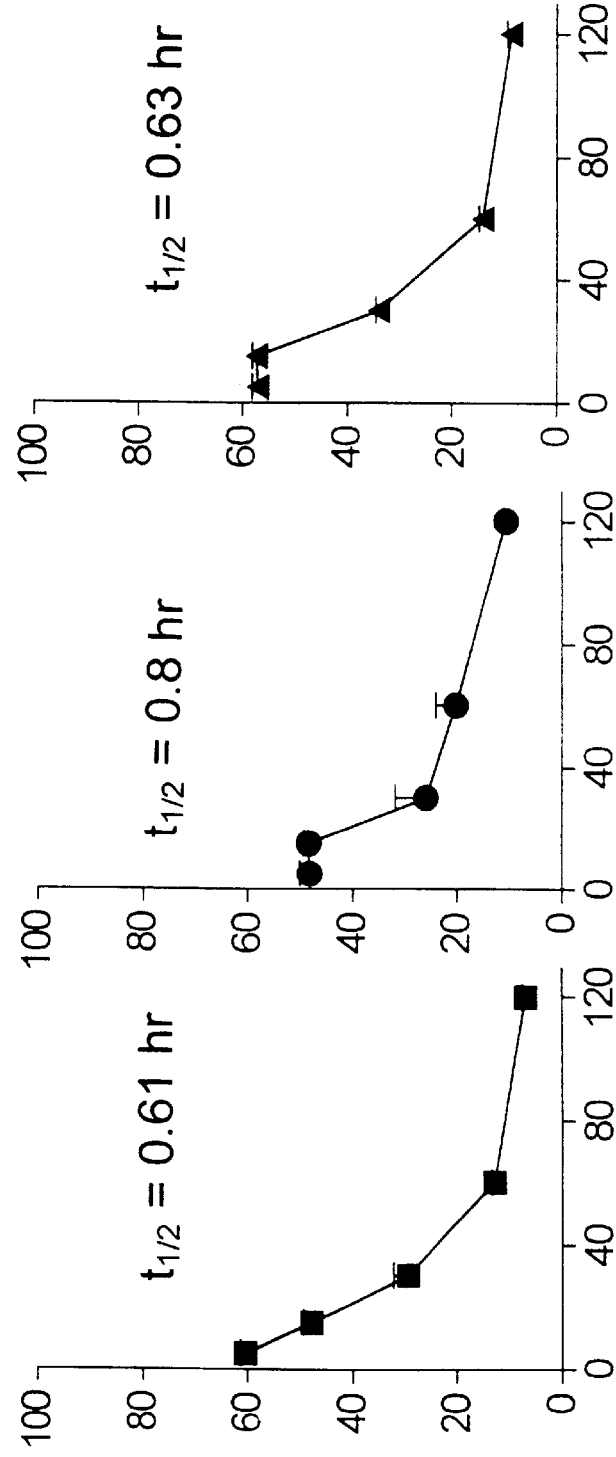
FIG. 49A  $t_{1/2} = 0.61$ hr
FIG. 49B  $t_{1/2} = 0.8$ hr
FIG. 49C  $t_{1/2} = 0.63$ hr

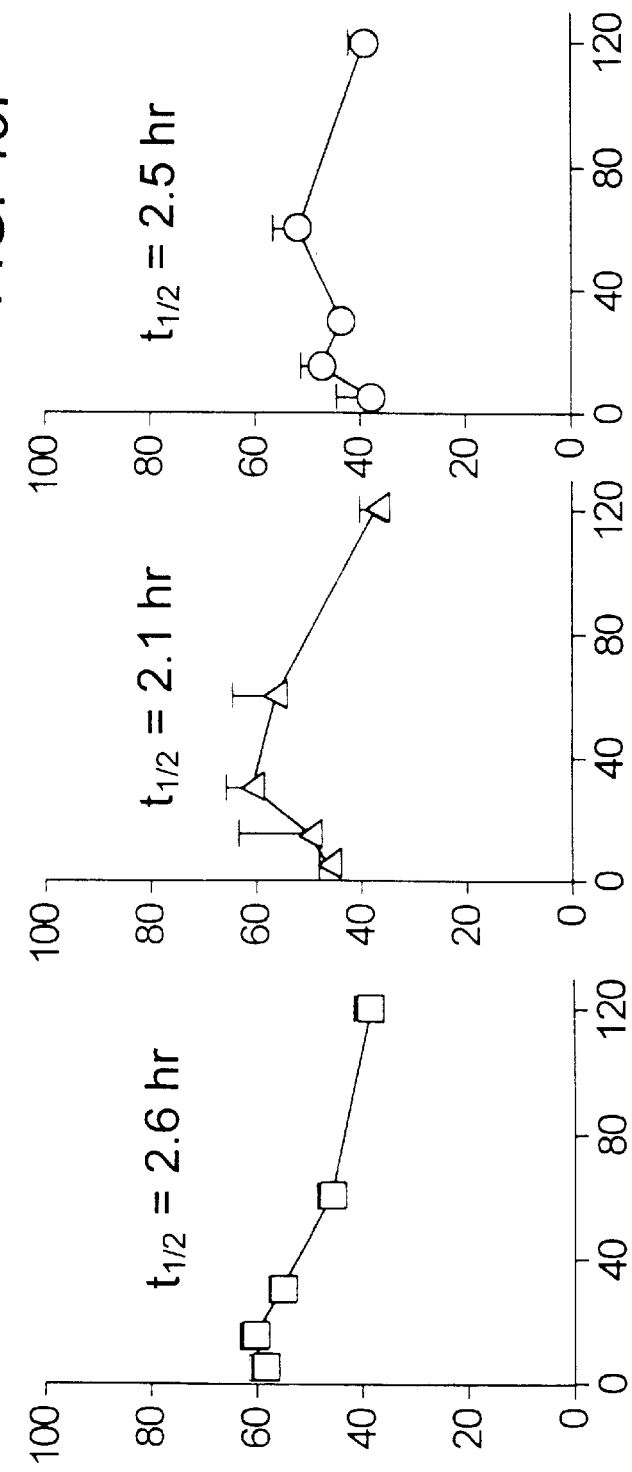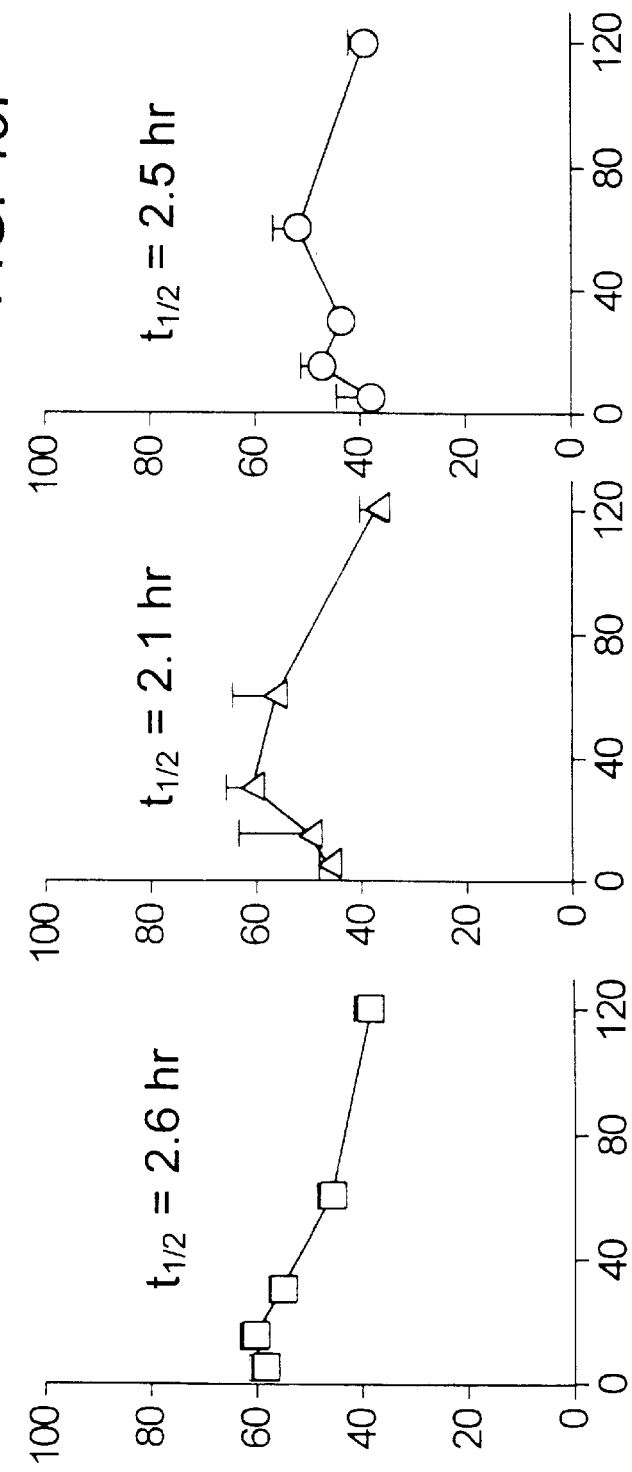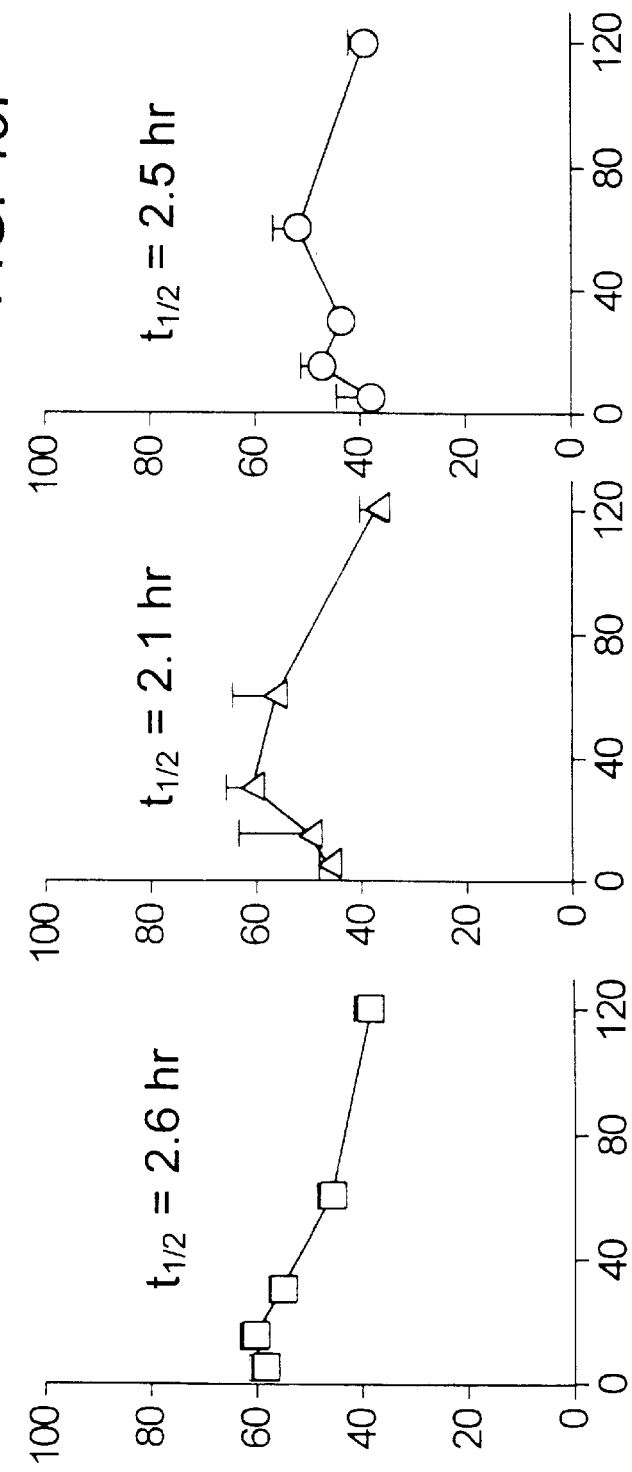

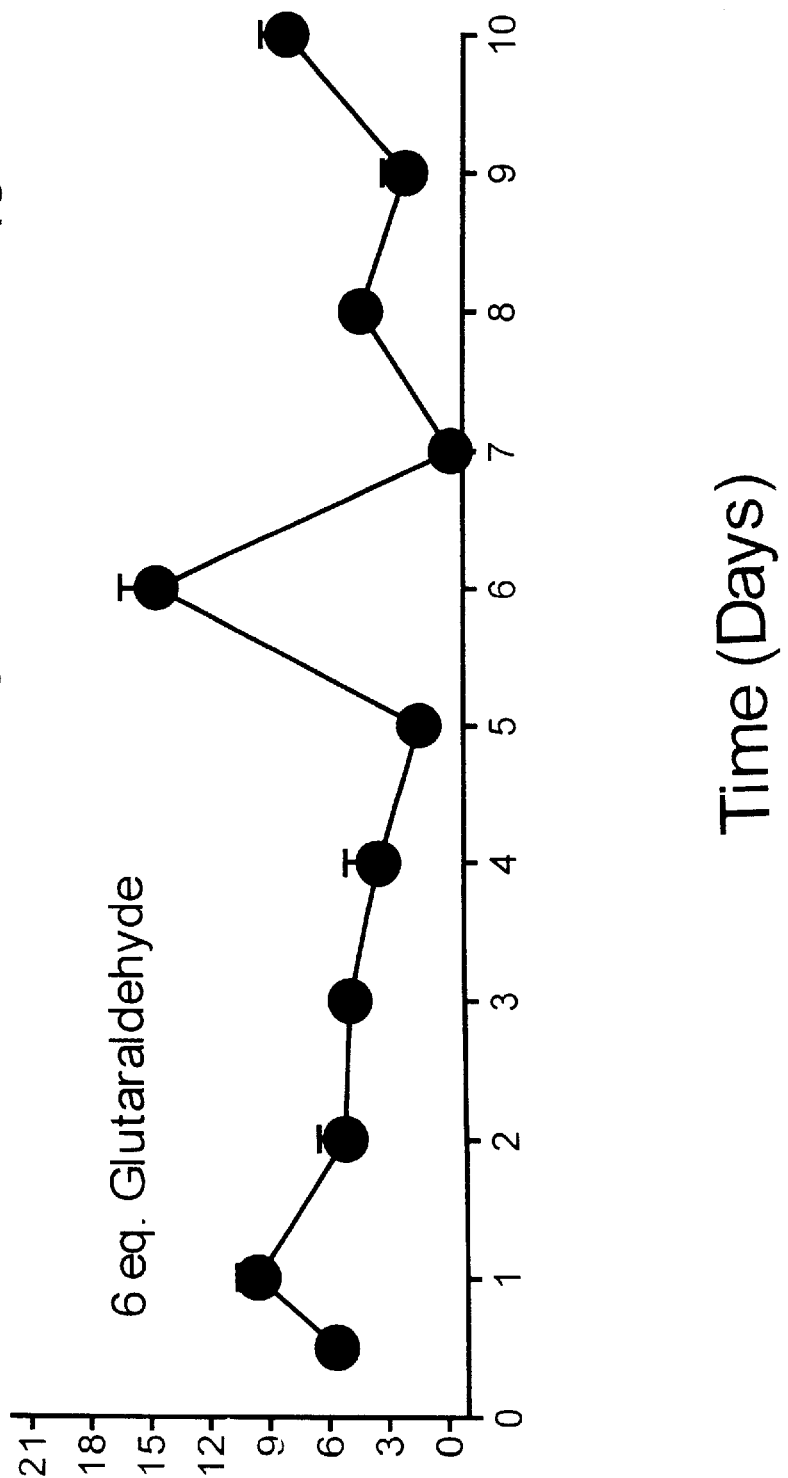

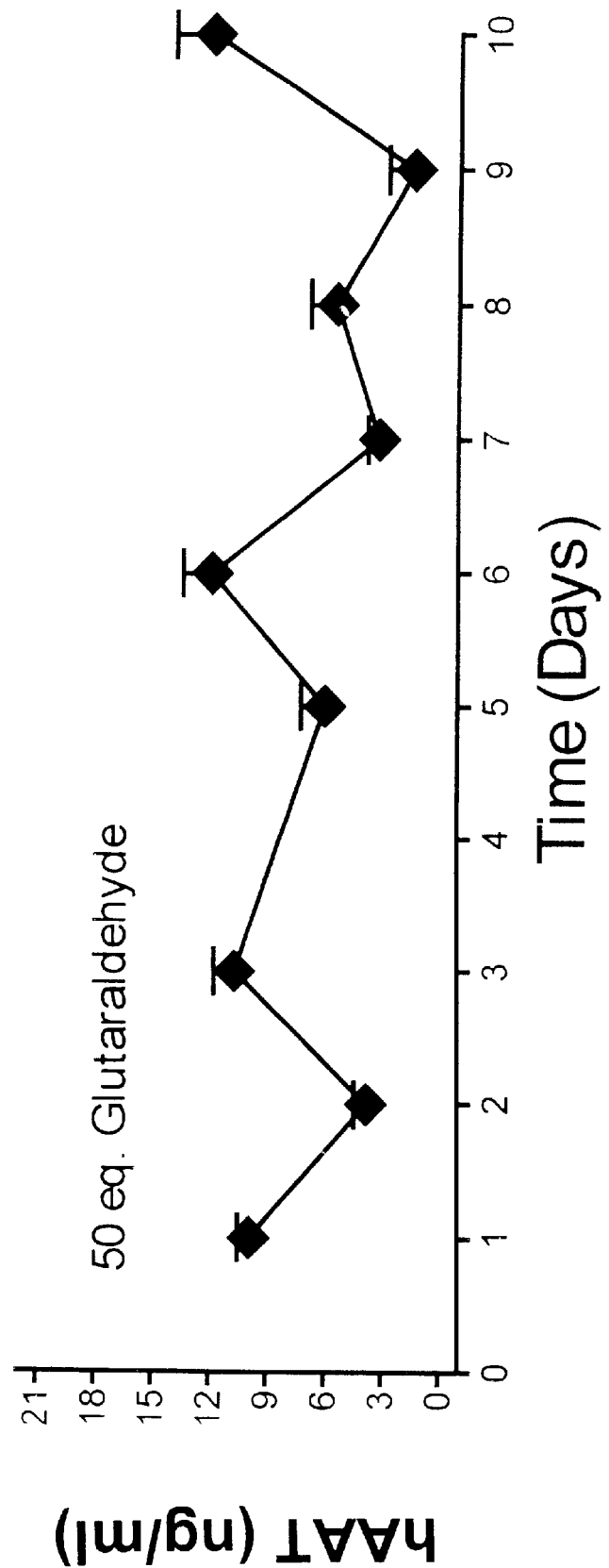

CROSSLINKED DNA CONDESATE COMPOSITIONS AND GENE DELIVERY METHODS

The present application claims priority to first provisional application Serial No. 60/143,600, filed Jul. 13, 1999, and to second provisional application Serial No. 60/157,761, filed Oct. 5, 1999, the entire text and figures of which are incorporated herein by reference without disclaimer.

The United States Government has certain rights in the present invention pursuant to Grants GMS 035973, GM07767, GM48049 and DE13004 from the National Institutes of Health.

BACKGROUND OF THE INVENTION

1. Field of the Invention

The present invention relates generally to the fields of chemical cross-linkers, peptide chemistry and DNA carriers. More particularly, the invention provides surprisingly effective cross-linking peptides and peptide-DNA compositions with increased stability and reduced toxicity. Methods of using the peptide-DNA condensates in gene delivery and gene expression are also provided, optionally in combination with matrices, carriers and/or targeting agents.

2. Description of Related Art

Gene therapy is a growing field with far-reaching medical implications. Gene therapy can be used to replace specific genes, as in the correction of a heritable defect, and/or to deliver functionally active therapeutic genes into target cells. Other clinically applicable aspects of nucleic acid delivery involve the application of inhibitory nucleic acids, such as antisense constructs and/or ribozymes, to inhibit aberrant gene products, as in the treatment of cancer.

Initial efforts towards somatic gene therapy relied on indirect means of introducing genes into tissues, i.e., ex vivo gene therapy. In such embodiments, cells are removed from the body, transfected or infected with vectors carrying recombinant genes in vitro, and re-implanted into the body ("autologous cell transfer"). As an alternative, viral-mediated gene delivery is efficient, but is associated with drawbacks that limit its clinical application.

A variety of nonviral gene delivery carriers have been developed and tested as in vitro transfection agents, used to transiently express foreign DNA in cells in culture. Cationic lipids (Zhang et al., 1997), polylysine peptides (Wagner et al., 1990; Wyman et al., 1997; Morris et al., 1997) and cationic polymers such as polyethylenamine (Ogris et al., 1998; Boussif et al., 1995), bind electrostatically to the phosphate backbone of DNA to form complexes that mediate cellular uptake in culture.

Nonviral gene delivery using various carrier molecules has also been proposed for in vivo use (Wu and Wu, 1988; Wu et al., 1989; Wagner et al., 1990; Tang et al., 1996; Hara et al., 1997; Ogris et al., 1998). As opposed to their success in vitro, the attempted in vivo use of these agents to delivery DNA has revealed many complications. Notable downsides include those related to toxicity (Wolfert and Seymour, 1996), antigenicity (Stankovics et al., 1994), complement activation (Plank et al., 1996), solubility (Toncheva et al., 1998), blood compatibility (Yang and Huang, 1997), and stability (Kwoh et al., 1999). These complications relate to the size and charge of DNA carrier complexes and ultimately to the molecular characteristics of the carrier itself.

The high molecular weight (HMW) of most DNA carrier polymers increases the likelihood of activating the complement system (Plank et al., 1996), eliciting antigenicity (Stankovics et al., 1994), and being cytotoxic (Wolfert and Seymour, 1996). The size and heterogeneity of such polymers also significantly complicates regio-specific derivatization with ligands or polyethylene glycol (Wolfert et al., 1996) to arrive at optimized well-characterized DNA carriers that mediate efficient gene transfer in vivo.

In an attempt to circumvent the problems of HMW carriers, several low molecular weight (LMW) carrier peptides have been developed. Certain of these even mediate in vitro gene transfer as efficiently as their HMW counterparts (Wadhwa et al., 1997; Plank et al., 1999). These offer the advantage of controlled synthesis and defined purity, which then allows for a strategy of systematic optimization to increase expression levels and eliminate side effects.

However, when tested for in vivo efficacy, LMW carriers have been shown to lack sufficient stability to remain intact during circulation and thereby do not significantly protect DNA from premature metabolism in tissue (Kwoh et al., 1999). Recently, certain crosslinking agents have been applied to form caged DNA condensates by template polymerization, but thus far, these have not been shown to be transfection competent (Trubetskoy et al, 1998; 1999). The use of carriers with different isomeric forms is also being investigated (Laurent et al., 1999). In seeking a solution to the relative instability of LMW carriers, increased stability should not be over-emphasized to the detriment of gene transfer efficiency and/or gene expression.

Therefore, despite increasing attention in this field, the development of effective, low toxicity carriers for DNA delivery still constitutes a major challenge. The generation of low toxicity carriers with sufficient stability to mediate in vivo delivery and yet still provide efficient gene expression in target tissues would be a significant advance.

SUMMARY OF THE INVENTION

The present invention overcomes these and other drawbacks inherent in the prior art by providing a range of DNA carrier compositions for use in improved gene transfer methods. The invention particularly provides low molecular weight carriers that are minimal in size, reduce toxicity, function to condense DNA into small particles, have increased stability, mediate gene expression and, preferably, provide surprisingly effective gene expression levels.

The compositions and methods of the invention achieve high affinity binding to DNA using only low molecular weight (LMW) carriers. The invention is thus broadly based upon providing temporary, but sufficient, stability through molecular crosslinking of LMW carriers to DNA condensates.

Certain aspects of the invention exploit unpaired amines to provide effectively crosslinked peptide DNA condensates. Increasing the stability of peptide DNA condensates is thus achieved by introducing dialdehyde groups, such as glutaraldehyde, to crosslink surface amine groups on the peptides. LMW peptides cross-linked in this manner condense DNA into small condensates with improved stability, as demonstrated by increased resistance to shear stress induced fragmentation. Glutaraldehyde-crosslinked condensates are also significantly more resistant to in vitro metabolism by serum endonucleases and still mediate steady-state gene expression.

Important embodiments of the present invention concern LMW peptide DNA condensates with metabolic stability and reversibility, which provide high level gene expression. The LMW peptide portions of the DNA condensates incorporate multiple cysteine residues that allow the peptides to undergo oxidation to form interpeptide disulfide bonds while bound to DNA. Once in a target cell, the disulfide cross-links are reduced, releasing DNA for efficient gene expression. The reducing environment of the endosome is believed to mediate disulfide reduction and DNA release.

In preferred embodiments, the cross-linking peptides of the invention are prepared by replacing lysine residues with cysteine residues to provide low molecular weight DNA condensing peptides that spontaneously cross-link, after binding to DNA, by forming interpeptide disulfide bonds. The peptides thus contain multiple sulfhydryl groups designed to spontaneously polymerize and cross-link when bound to DNA. The stability of cross-linked peptide DNA condensates is dependent, at least in part, on the number of cysteines incorporated into the peptide. Disulfide bond formation in this manner decreases DNA condensates particle size, relative to control peptide DNA condensates, and prevents dissociation of peptide DNA condensates.

Importantly, the gene expression mediated by the cross-linked DNA condensates of the invention is not only maintained, but is actually increased 5 to 60-fold over uncrosslinked DNA condensates, depending on the number of cysteine residues. The cross-linking peptides caused elevated gene expression without increasing DNA uptake by cells, indicating a mechanism involving intracellular release of DNA triggered by disulfide bond reduction.

The invention provides panels and an admixtures of low molecular weight, synthetic cross-linking peptides (of generally less than twenty amino acids) that not only form small, stabilized DNA condensates, but mediate efficient gene expression. The "self cross-linking" peptides and resultant DNA condensates of the invention are thus highly efficient DNA delivery agents that represent a breakthrough in gene therapy technology. The peptide-DNA condensates of the invention provide their own multicomponent peptide condensed DNA formulations and can be further combined with other gene therapy agents, such as matrices, carriers and targeting agents, for even more effective in vivo therapies.

Exemplary combined compositions and methods of using the present invention include the formulation of DNA-peptide condensates with matrices that allow cells to migrate into the matrix to encounter and take up the DNA; formulation of DNA-peptide condensates with targeting agents for cellular or sub-cellular delivery; and combination with stealthing agents, such as polyethylene glycol (PEG), to reduce non-specific cellular uptake and/or interaction with blood components, thereby enhancing systemic gene delivery (Ogris et al., 1999).

The cross-linking peptides themselves may be covalently derivatized with polyethylene glycol (PEG). PEG-peptides form a steric layer on the surface of DNA condensates that block optimization, mask DNA condensate recognition by the reticuloendothelial system and increase DNA condensate solubility by blocking the formation of aggregates.

In still further embodiments, the self-cross-linking peptides of the invention may be converted into cross-linking and targeting peptides by the addition of targeting units. For example, target specificity is achieved by derivatizing a cross-linking peptide with a single N-glycan resulting in glycopeptides that direct targeting to either the asialoglycoprotein receptor on hepatocytes or the mannose receptor on liver Kupffer cells.

DNA co-condensates can thus be prepared using systematically determined admix ratios of cross-linking glycopeptide and PEG-peptide. The backbone of cross-linking peptides are chemically modifiable by reduction of the amide linkages to install secondary amines designed to buffer endosomes and allow DNA condensates to release into the cytosol of target cells. Once in the cytosol, cross-linked DNA condensates slowly release plasmid DNA following disulfide reduction. Decreasing DNA metabolism by increasing DNA condensate stability prolongs the liver half-life of DNA and produces a longer duration and higher level of gene expression in vivo. The present invention thus overcomes various limitations of current nonviral gene delivery systems.

The dialdehyde aspects of the present invention provide nucleic acid condensates, comprising a nucleic acid and at least two nucleic acid-binding peptides that are crosslinked via a low molecular weight dialdehyde; nucleic acid condensates, comprising a nucleic acid and at least two nucleic acid-binding peptides that are crosslinked via glutaraldehyde; nucleic acid condensates, comprising a nucleic acid and at least two positively-charged, low molecular weight peptides that are crosslinked via glutaraldehyde; and nucleic acid condensates, comprising a nucleic acid and at least two nucleic acid-binding peptides; wherein the peptides are crosslinked by glutaraldehyde.

Further nucleic acid condensates are those comprising a nucleic acid and at least two low molecular weight peptides with sufficient positive charge to bind to a nucleic acid, the peptides being linked via a glutaraldehyde crosslinker; and comprising a nucleic acid and an amount of glutaraldehyde-crosslinked, nucleic acid-binding peptides that form a non-covalently linked peptide-nucleic acid condensate.

Stable nucleic acid condensates are provided, comprising nucleic acids and an amount of glutaraldehyde-crosslinked, nucleic acid-binding peptides effective to stabilize the nucleic acid. Nucleic acid condensates with in vivo stability comprise a nucleic acid and an amount of glutaraldehyde-crosslinked, nucleic acid-binding peptides effective to stabilize the nucleic acid under in vivo conditions.

Methods of stabilizing a nucleic acid-peptide condensate comprise crosslinking nucleic acid-binding peptides within the condensate with at least a first glutaraldehyde crosslinker; whereas methods of protecting a nucleic acid from degradation comprise preparing a nucleic acid-peptide condensate and crosslinking at least a portion of the peptides within the condensate using a glutaraldehyde crosslinker.

Methods of stabilizing a nucleic acid-peptide condensate comprise crosslinking nucleic acid-binding peptides within the condensate with at least a first glutaraldehyde crosslinker; whereas methods of protecting a nucleic acid from degradation comprise preparing a nucleic acid-peptide condensate and crosslinking at least a portion of the peptides within the condensate using a glutaraldehyde crosslinker.

The self-crosslinking aspects of the invention provide a cationic linker comprising sufficient positive charge to bind to a nucleic acid and at least two thiol groups; a low molecular weight cationic linker comprising sufficient positive charge to bind to a nucleic acid and at least two thiol groups; and cationic linkers wherein the linker comprises a positively-charged peptide, a cationic polymer, or a cationic lipid with sufficient positively-charged amine groups to bind to a nucleic acid.

Nucleic acid condensing agents are provided comprising a low molecular weight cationic linker with sufficient positive charge to bind to a nucleic acid and sufficient thiol groups to form a self-crosslinked construct that induces a bound nucleic acid to condense.

Further provide are peptides comprising sufficient positively-charged residues to bind to a nucleic acid and capable of forming a disulfide-bonded peptide; and peptides comprising sufficient positively-charged residues to bind to a nucleic acid and at least two thiol groups.

The peptides are between about 3 and about 50 amino acids in length; between about 4 and about 50 amino acids in length; between about 5 and about 50 amino acids in length; between about 10 and about 50 amino acids in length; between about 5 and about 40 amino acids in length; between about 5 and about 30 amino acids in length; between about 5 and about 20 amino acids in length; between about 5 and about 10 amino acids in length; between about 25 and about 30 amino acids in length; between about 20 and about 25 amino acids in length; between about 15 and about 20 amino acids in length; and between about 10 and about 15 amino acids in length.

The peptides are further about 3, 4, 5, 6, 7, 8, 9, 10, 11, 12, 13, 14, 15, 16, 17, 18, 19, 20, 21, 22, 23, 24, 25, 25, 27, 28, 29, 30, 31, 32, 33, 34, 35, 36, 37, 38, 39, 40, 41, 42, 43, 44, 45, 46, 47, 48, 49 or 50 or so amino acids in length.

The peptides may comprise between about 2 and about 45 positively-charged residues; between about 3 and about 45 positively-charged residues; between about 4 and about 45 positively-charged residues; between about 5 and about 45 positively-charged residues; between about 10 and about 45 positively-charged residues; between about 15 and about 45 positively-charged residues; between about 20 and about 45 positively-charged residues; between about 25 and about 45 positively-charged residues; between about 30 and about 45 positively-charged residues; between about 35 and about 45 positively-charged residues; between about 40 and about 45 positively-charged residues.

This can be achieved by comprising between about 2 and about 45 positively-charged lysine residues; between about 3 and about 45 positively-charged lysine residues; between about 4 and about 45 positively-charged lysine residues; between about 5 and about 45 positively-charged lysine residues; between about 10 and about 45 positively-charged lysine residues; between about 15 and about 45 positively-charged lysine residues; between about 20 and about 45 positively-charged lysine residues; between about 25 and about 45 positively-charged lysine residues; between about 30 and about 45 positively-charged lysine residues; between about 35 and about 45 positively-charged lysine residues; between about 40 and about 45 positively-charged lysine residues.

The peptides may be thiolylated substantially polylysine peptides. They may comprise at least 3, 4, 5, 6, 7, 8 or so thiol groups or may have only two thiol groups.

At least one, two, three, four, five, six, seven, eight or so cysteine residue may provide at least one of the thiol groups. Two cysteine residues are suitable examples. The peptides may be alkylated, wherein it may be that the at least a first cysteine residue is alkylated. D-amino acid residues may be employed if desired.

The peptides may be dispersed within a pharmaceutically acceptable medium, bound to a nucleic acid, associated with a matrix, associated with a carrier or a targeting ligand, covalently linked to a targeting ligand, covalently linked to at least a first glycosyl unit, thereby forming a glycopeptide targeting ligand, covalently linked to at least a first oligosaccharide unit to form a glycopeptide targeting ligand, or may be both bound to a nucleic acid and associated with a matrix, carrier or a targeting ligand.

The peptides may thus be summarized as being between about 3 and about 50 amino acids in length, comprising sufficient positively-charged residues to bind to a nucleic acid and at least two thiol groups, such as two cysteine residues. The peptides may comprise sufficient positively-charged residues to bind to a nucleic acid and a number of thiol groups sufficient to form a reversibly-linked nucleic acid-peptide composition that dissociates under endosomal conditions.

Nucleic-acid cross-linking peptides may comprise an amount of positively-charged residues effective to bind nucleic acid and at least two thiol groups effective to form spontaneous peptide-crosslinks sufficient to produce ionic-crosslinked nucleic acids upon contact, optionally with at least a first glycosyl unit.

Exemplary nucleic acid condensates are those comprising a nucleic acid and a nucleic acid-binding peptide that comprises a plurality of positively-charged residues and at least two thiol groups and those comprising a nucleic acid condensate that comprises a nucleic acid and a nucleic acid-binding peptide that comprises a plurality of positively-charged residues and at least two thiol groups.

Peptide-linked nucleic acid condensates may comprise nucleic acids and an amount of positively-charged, double-thiol-containing nucleic acid-binding peptides effective to form a non-covalently linked peptide-nucleic acid condensate; or nucleic acids and an amount of positively-charged, double-thiol-containing nucleic acid-binding peptides effective to form interpeptide disulfide bonds, thereby condensing nucleic acids in non-covalent contact with the disulfide-bonded peptides; or a nucleic acid and nucleic acid-binding peptides, wherein the peptides each comprise a plurality of positively-charged residues and at least two thiol groups and form a condensed nucleic acid particle of between about 10 nm and about 20 nm in diameter upon contact with nucleic acids.

Stable nucleic acid condensates are those comprising a nucleic acid and at least two positively-charged nucleic acid-binding peptides that comprise an amount of thiol groups effective to stabilize the nucleic acid; nucleic acid condensates with in vivo stability comprise a nucleic acid and at least two positively-charged nucleic acid-binding peptides that comprise an amount of thiol groups effective to stabilize the nucleic acid under in vivo conditions.

Reversibly-bound nucleic acid-peptide condensates comprise nucleic acids and an amount of positively-charged nucleic acid-binding peptides with an amount of thiol groups effective to form a nucleic acid-peptide condensate that is substantially stable in an extracellular biological environment and that releases nucleic acids upon contact with an intracellular endosome.

Gene delivery complexes of the invention comprise a carrier and a nucleic acid condensate of nucleic acids and positively-charged nucleic acid-binding peptides that comprise an amount of thiol groups effective to condense and stabilize the nucleic acids. The carrier may be a polyethyleneglycol carrier.

Targeted gene delivery complexes comprise a targeting ligand and a nucleic acid condensate of nucleic acids and positively-charged nucleic acid-binding peptides that comprise an amount of thiol groups effective to condense and stabilize the nucleic acids.

Multimolecular complexes of the present invention comprise a carrier, a targeting ligand and a nucleic acid condensate of nucleic acids and positively-charged nucleic acid-binding peptides that comprise an amount of thiol groups effective to condense and stabilize the nucleic acids. The multimolecular complexes may further comprise a biocompatible matrix.

Gene-matrix formulations may comprise a biocompatible matrix and a nucleic acid condensate comprising a nucleic acid and positively-charged nucleic acid-binding peptides that comprise an amount of thiol groups effective to stabilize and condense the nucleic acids.

Stealthed gene-delivery compositions may comprise a stealthing agent and a nucleic acid condensate comprising nucleic acids and positively-charged peptides that bind to nucleic acid and comprise an amount of thiol groups effective to stabilize and condense the nucleic acids.

The unified concepts of the invention thus provide nucleic acid condensates, comprising a nucleic acid and at least a first and second low molecular weight cationic linker bound to the nucleic acid; wherein:

the first and second cationic linker are crosslinked to each other by reaction with a low molecular weight dialdehyde; or the first and second cationic linker each comprise at least two thiol groups and wherein the cationic linkers are crosslinked to each other by reaction of the thiol groups.

Nucleic acid condensates with a particle size of between about 10 nm and about 100 nm in diameter; between about 10 nm and about 50 nm in diameter; and between about 10 nm and about 20 nm in diameter are included, but are not limiting of the invention.

Preferred cationic linkers are first and second low molecular weight peptides, preferably of between about 6 and about 20 amino acids in length or between about 6 and about 10 amino acids in length or between about 10 and about 20 amino acids in length.

The first and second peptides each preferably comprise between about four and about eight Lysine residues that mediate binding of the peptides to the nucleic acid; and at least two, three or four thiol groups and wherein the peptides are crosslinked to each other by reaction of the thiol groups.

In addition to Cysteine residues, preferred first and second peptides each comprise at least two Penicillamine (Pen) residues that provide the thiol groups. The at least two Cysteine or Penicillamine (Pen) residues are preferably each located at, or proximal to, the termini of the peptides.

At least one of the first or second peptides preferably comprises at least one, two, three, four, five, or six or so secondary or tertiary amine residue that mediates endosomal buffering of the peptide upon uptake into a cell. Histidine residues are suitable examples for endosomal buffering.

Certain preferred peptides have the amino sequence of CWK$_{17}$C (SEQ ID NO:3), CK$_4$C (SEQ ID NO:9), CK$_8$C (SEQ ID NO:11), CHK$_6$HC (SEQ ID NO:17), PenWK$_5$PenK$_5$PenK$_5$Pen (SEQ ID NO:21) or PenHK$_4$CK$_4$HPen (SEQ IS NO:22).

The purified low molecular weight synthetic peptides themselves form aspects of the present invention, wherein the peptide comprises sufficient positive charge to bind to a nucleic acid and sufficient thiol groups to form disulfide-crosslinked peptides that induce nucleic acids to condense upon contact with a population of the peptides.

A population of purified nucleic-acid condensing peptides is provided, wherein the peptides are synthetic peptides of between about 6 and about 20 amino acids in length, comprise an amount of positively-charged residues effective to bind nucleic acid, comprise at least two thiol groups effective to spontaneously crosslink peptides within the population and comprises an amount of secondary or tertiary amines effective to promote dissociation under endosomal conditions; wherein the population of peptides is effective to form a nucleic acid-peptide condensate that is substantially stable in an extracellular biological environment and that releases nucleic acids intracellularly in a manner effective for gene expression.

Operative associated with at least a first stealthing agent, targeting agent or biocompatible matrix is preferred. The peptides themselves provide for such operative attachment to at least a first stealthing or targeting agent, thereby associating the stealthing or targeting agent with the nucleic acid condensate. Preferred examples are wherein at least one of the first or second peptides comprises a thiol group at each terminus and wherein at least a first stealthing or targeting agent is operatively attached to the peptide at a site distal from each terminus.

Polyethyleneglycol (PEG) stealthing agents, antibody, growth factor and carbohydrate targeting agents are preferred.

Co-condensates are particular preferred, such as those comprising at least a first peptide operatively attached to at least a first stealthing agent and at least a second peptide operatively attached to at least a first targeting agent. Exemplary co-condensates are those comprising a population of peptides; wherein between about 5% and 20% of the peptides are operatively attached to PEG; between about 5% and 20% of the peptides are operatively attached to a glycosyl targeting unit; and the remainder of the peptides comprise about four Histidine or secondary or tertiary amine residues.

The nucleic acids may be single-stranded nucleic acids, double-stranded nucleic acids, degradation-resistant nucleic acids, DNA, plasmid DNA, RNA, and DNA-RNA chimera, an antisense nucleic acid, a ribozyme or an expression vector. Preferably, the nucleic acids express at least a therapeutic product upon provision to a cell.

These include antigenic or immunogenic proteins or polypeptides that stimulate an immune response when expressed by a cell of the immune system; cytotoxic or apoptosis-inducing proteins or polypeptides that induce cell death upon expression in a target cell; a transcription or elongation factor, cell cycle control protein, kinase, phosphatase, DNA repair protein, oncogene, tumor suppressor, angiogenic protein, anti-angiogenic protein, immune response stimulating protein, cell surface receptor, accessory signaling molecule, transport protein, enzyme, anti-bacterial or anti-viral protein or polypeptide.

Further examples are nucleic acids that encode a hormone, neurotransmitter, growth factor, growth factor receptor, interferon, interleukin, chemokine, cytokine, colony stimulating factor or chemotactic factor protein or polypeptide; such as growth hormone (GH), a fibroblast growth factor (FGF), a granulocyte/macrophage colony stimulating factor (GMCSF), an epidermal growth factor (EGF), a platelet derived growth factor (PDGF), an insulin-like growth factor (IGF), a leukemia inhibitory factor (LIF) or an activin/inhibin protein or polypeptide.

At least two distinct nucleic acids, up to and including plurality of nucleic acids may be included.

Kits of the invention comprising, in at least a first container:

a plurality of low molecular weight peptides with sufficient positive charge to bind to a nucleic acid and an amount of glutaraldehyde effective to cross-link at least a portion of the peptides; or a plurality of low molecular weight peptides that each comprise at least two thiol groups and have sufficient positive charge to bind to nucleic acids, the peptides spontaneously forming intermolecular disulfide-crosslinks.

Methods of preparing a nucleic acid-peptide condensate comprise contacting a nucleic acid with at least two nucleic acid-binding peptides that have sufficient positive charge to bind to a nucleic acid; wherein:

the nucleic acid-binding peptides are cross-linked with glutaraldehyde, thereby condensing the nucleic acid in contact with the crosslinked peptides; or wherein the nucleic acid-binding peptides each comprise a thiol capacity sufficient to spontaneously form interpeptide crosslinks, thereby condensing the nucleic acid in contact with the crosslinked peptides.

Method of expressing a nucleic acid in a cell comprise contact a cell with an effective amount of a nucleic acid condensate that comprises a nucleic acid having bound thereto at least two low molecular weight nucleic acid-binding peptides; wherein:

the nucleic acid-binding peptides are cross-linked with glutaraldehyde; or wherein the nucleic acid-binding peptides each comprise at least two thiol groups and spontaneously form disulfide cross-links.

The cell may be located within an animal, wherein the nucleic acid condensate is administered to the animal.

Methods for providing a nucleic acid to an animal comprise providing to the animal an effective amount of a nucleic acid condensate that comprises the nucleic acid in functional association with a population of low molecular weight nucleic acid-binding peptides; wherein:

the nucleic acid-binding peptides are cross-linked with glutaraldehyde in a manner effective to stabilize the nucleic acid under in vivo conditions; or wherein the nucleic acid-binding peptides each comprise at least two thiol groups and spontaneously form disulfide cross-links in a manner effective to stabilize the nucleic acid under in vivo conditions.

Method for expressing a nucleic acid in target cells of an animal comprise providing to the animal an effective amount of a nucleic acid condensate comprising a nucleic acid that is non-covalently attached to an amount of low molecular weight nucleic acid-binding peptides; wherein:

the nucleic acid-binding peptides are cross-linked with glutaraldehyde in a manner effective to stabilize the nucleic acid under in vivo conditions for a time sufficient to allow delivery of the nucleic acid to the target cells within the animal; or wherein the nucleic acid-binding peptides each comprise at least two thiol groups and spontaneously form disulfide cross-links in a manner effective to stabilize the nucleic acid under in vivo conditions for a time sufficient to allow delivery of the nucleic acid to the target cells within the animal.

The invention further provides compositions in accordance with the present invention for use in therapy or diagnosis, including in gene therapy and human gene therapy.

Uses of the compositions in accordance with the present invention in the manufacture of medicaments for use in expressing nucleic acids in animals and humans and for use in gene therapy and human gene therapy are further encompassed.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, FIG. 1B and FIG. 1C. Reaction Schemes for the Synthesis of PEG-CWK$_{18}$ Conjugates. FIG. 1A: TCEP was used to reduce dimeric-CWK$_{18}$ to generate CWK$_{18}$. This was reacted in situ with PEG-VS to form PEG-VS-CWK$_{18}$. FIG. 1B: The reaction of CWK$_{18}$ with PEG-OPSS to form PEG-SS-CWK$_{18}$. FIG. 1C: AlkCWK$_{18}$ was produced by reacting CWK$_{18}$ with iodoacetic acid. The $\alpha,\beta,\gamma,\delta$ and $\epsilon$ protons of Lys of PEG-SS-CWK$_{18}$ illustrate the nomenclature used for assigning PEG-peptides in FIG. 3.

FIG. 2A, FIG. 2B, FIG. 2C, FIG. 2D and FIG. 2E. Analytical RP-HPLC Analysis of PEG-CWK$_{18}$ Conjugates. FIG. 2A: Reduced CWK$_{18}$. FIG. 2B: The reaction of dimeric-CWK$_{18}$ with TCEP and PEG-VS formed a single major product. FIG. 2C: Reduced CWK$_{18}$ reacted with PEG-OPSS to produce PEG-SS-CWK$_{18}$, dimeric-CWK$_{18}$, thiol-pyridine (TP), and unreacted PEG-OPSS. FIG. 2D: Purified PEG-VS-CWK$_{18}$ eluted as a single peak. FIG. 2E: Purified PEG-SS-CWK$_{18}$ eluted as a single peak.

FIG. 5A and FIG. 5B. QELS Particle Size and Zeta Potential Analysis of PEG-CWK$_{18}$ DNA Condensates. FIG. 5A: The mean particle size of AlkCWK$_{18}$ (●), PEG-SS-CWK$_{18}$ (■), and PEG-VS-CWK$_{18}$ ($\pi$) DNA condensates as a function of peptide:DNA stoichiometry. FIG. 5B: The mean zeta potential for each DNA condensate. An indistinguishable particle size and zeta potential was determined for each PEG-CWK$_{18}$ conjugate. However, a significant decrease in the zeta potential for PEG-CWK$_{18}$ DNA condensates (+10 mV) vs. AlkCWK$_{18}$ DNA condensates (±35 mV) provided evidence of the formation of a steric barrier.

FIG. 6A: Particle size analysis was used to characterize peptide DNA co-condensates prepared at 50 $\mu$g/ml of DNA and varying mol % of AlkCWK$_{18}$ and PEG-VS-CWK$_{18}$. FIG. 6B: The zeta potential of DNA co-condensates. The mean particle size changes from 65 to 80 nm whereas the zeta potential of DNA co-condensates decreases from +35 to +10 mV with increasing mol % of PEG-VS-CWK$_{18}$.

FIG. 7A, FIG. 7B, FIG. 7C, FIG. 7D, FIG. 7E and FIG. 7F. RP-HPLC Analysis of Peptide DNA Co-Condensates. FIG. 7A: The time course of dialysis of free AlkCWK$_{18}$ (●), free PEG-VS-CWK$_{18}$ (■), AlkCWK$_{18}$ DNA condensates ($\theta$), PEG-VS-CWK$_{18}$ DNA ($\pi$), and co-condensates of 25:75 (♦), 50:50 (○), 75:25 (◇) mol % of AlkCWK$_{18}$:PEG-VS-CWK$_{18}$ bound to DNA determined by tryptophan fluorescence in the retentate. After 75 h of dialysis, peptide DNA condensates in the retentate were dissociated with sodium chloride and directly chromatographed on RP-HPLC. FIG. 7B through FIG. 7F: Chromatograms resulting from 100 mol % PEG-VS-CWK$_{18}$ DNA condensates (FIG. 7B), DNA co-condensates prepared with 75:25 (FIG. 7C), 50:50 (FIG. 7D), 25:75 (FIG. 7E) PEG-VS-CWK$_{18}$:AlkCWK$_{18}$, and 100 mol % AlkCWK$_{18}$ DNA condensates (FIG. 7F).

FIG. 17A, FIG. 17B, FIG. 17C, FIG. 17D, FIG. 17E and FIG. 17F. RP-HPLC Analysis of Man9-CWK$_{18}$ Synthesis. An example of RP-HPLC monitoring of glycopeptide synthesis is illustrated. Peaks are labeled according to numbering in FIG. 16.

FIG. 18A: triantennary-CWK$_{18}$. FIG. 18B: Man9-CWK$_{18}$. Nomenclature used in assigning NMR spectra are shown.

FIG. 19A: 500-MHz $^1$H NMR spectrum of triantennary-CWK$_{18}$. FIG. 19B: 500-MHz $^1$H NMR spectrum of Man9-CWK$_{18}$. The α,β,γ,δ and ε lysine resonances are assigned along with the anomeric and N-acetyl resonances of the oligosaccharide using the nomenclature presented in FIG. 18A and FIG. 18B.

FIG. 20A and FIG. 20B. ESIMS Analysis of Triantennary-CWK$_{18}$ and Man9-CWK$_{18}$. FIG. 20A: Positive ion ESIMS analysis of triantennary-CWK$_{18}$. FIG. 20B: Positive ion ESIMS analysis of Man9-CWK$_{18}$.

FIG. 21A, FIG. 21B and FIG. 21C. Particle Size Analysis of Glycopeptide DNA Condensates. The particle size of triantennary-CWK$_{18}$ (FIG. 21A), Man9-CWK$_{18}$ (FIG. 21B) and AlkCWK$_{18}$ DNA condensates (FIG. 21C) are compared by QELS analysis.

FIG. 24A: $CWK_{18}$ DNA condensates crosslinked with 0–5 mol equivalents of glutaraldehyde exhibit particle sizes between 50–70 nm. At concentrations of 10 and 50 mol equivalents of glutaraldehyde the particle size increases by one and two-orders of magnitude. FIG. 24B: Condensates prepared at 0–4 mol equivalents glutaraldehyde have a zeta potential between +34–38 mV.

FIG. 26A, FIG. 26B, FIG. 26C, FIG. 26D, FIG. 26E and FIG. 26F. Serum Stability of Crosslinked Condensates. The serum stability of DNA condensates crosslinked with 0 (FIG. 26A) 1 (FIG. 26B), 2 (FIG. 26C), 3 (FIG. 26D) and 4 (FIG. 26E) mol equivalents of glutaraldehyde are compared to polylysine$_{1007}$ DNA condensates (FIG. 26F) using gel electrophoresis. Lanes 1 through 7 correspond to 0, 15, 30, 60, 90, 120, and 180 min digestion period. Metabolism was evident from the disappearance of bands after 60 min in uncrosslinked DNA condensates (FIG. 26A, lane 4). DNA condensates prepared with 1 mol equivalent of glutaraldehyde were delayed in metabolism until 90 min (FIG. 26B, lane 5). DNA Condensates prepared with 2, 3 and 4 mol equivalents of glutaraldehyde were significantly more protected from metabolism during the 180 min digestion, exhibiting only a decrease in the band intensity for circular and linear DNA (FIG. 26C and FIG. 26D, lanes 5–7). Likewise, polylysine$_{1007}$ was equivalent or better to crosslinked condensates at protecting DNA throughout the 180 min digestion (FIG. 26F).

FIG. 27A and FIG. 27B. Transient Gene Expression Profiles for Crosslinked DNA Condensates in the Presence of Chloroquine. FIG. 27A: The 10-day HepG2 SEAP expression profiles for crosslinked DNA condensates when including chloroquine in the transfection. The data represents the mean and standard deviation when using uncrosslinked (■), 1 mol equivalent crosslinked (●), 2 mol equivalent (π), 3 mol equivalent (♦), and 4 mol equivalent crosslinked DNA condensates (θ). FIG. 27B: The cumulative SEAP production for each DNA condensate. The slope of the day 7–10 cumulative expression was 28.3 ng/mL ■, 26.8 ng/mL ●, 52.8 ng/mL π, and 52.9 ng/mL ♦ with $r^2 \geq 0.965$ for each.

FIG. 28A and FIG. 28B. Transient Gene Expression Profiles for Crosslinked DNA Condensates in the Absence of Chloroquine. FIG. 28A: The 10-day HepG2 SEAP expression profile mediated for crosslinked DNA condensates when chloroquine from the transfection. The data represents the mean and standard deviations when using uncrosslinked (■), 1 mol equivalent crosslinked (●), 2 mol equivalent (π), 3 mol equivalent (♦), and 4 mol equivalent crosslinked DNA condensates (θ). FIG. 28B: The cumulative SEAP production for each DNA condensate. The slope of the day 7–10 cumulative expression was 3.3 ng/mL ■, 3.4 ng/mL ●, 5.2 ng/mL π, and 7.1 ng/mL ♦ with $r^2 \geq 0.996$ for each.

FIG. 29A and FIG. 29B. Transient Gene Expression Profiles for HMW Polylysine DNA Condensates. FIG. 29A: The 10-day HepG2 SEAP expression profiles are compared for $CWK_{18}$ (■) and dimeric-$CWK_{18}$ (♦) polylysine$_{99}$ (●), polylysine$_{476}$ (θ), and polylysine$_{1007}$ (π) DNA condensates when including chloroquine in the transfection. FIG. 29B: The cumulative SEAP production for each DNA condensate. The slope of the day 7–10 cumulative expression was 25.5 ng/mL ■, 32.7 ng/mL ♦, 74.7 ng/mL ●, 103.7 ng/mL θ, and 109.3 ng/mL π with $r^2 \geq 0.978$ for each.

FIG. 32A: The fluorescence intensity of intercalated SYBR-Gold continuously monitored over time during the formation of peptide DNA condensates prepared with AlkCWK$_{18}$ (), CWK$_{18}$ (▼), II (♦), III (▲), IV (■), V (●) and polylysine$_{1007}$ (). The results indicate a decrease in fluorescence over time for cross-linking peptides but not for AlkCWK$_{18}$ and polylysine$_{1007}$ which are not able to form cross-links. FIG. 32B: The influence of increasing peptide IV stoichiometry (0.4 ■, 0.8 ●, and 1.2 ρ nmol per μg of DNA) on the apparent rate of the cross-linking reaction.

FIG. 34A, FIG. 34B, FIG. 34C, FIG. 34D, FIG. 34E, FIG. 34F, FIG. 34G, FIG. 34H and FIG. 34I. Shear Stress Stability of Cross-linked Peptide DNA Condensates. The stability of cross-linked DNA condensates were measured by gel electrophoresis following a 30 sec sonication in the presence of increasing sodium chloride concentration. Peptide DNA condensates were formed using AlkCWK$_{18}$ (FIG. 34A), CWK$_{18}$ (FIG. 34B), II (FIG. 34C), III (FIG. 34D), IV (FIG. 34E), V (FIG. 34F), pre-oxidized V (FIG. 34G), V in the presence of TCEP (FIG. 34H), and polylysine$_{1007}$ (FIG. 34I). Lanes 1 through 8 represent 0, 0.2, 0.4, 0.8, 1.0, 1.5, 2.0, and 2.5 M sodium chloride in the sonication solutions. The results show an increased stability of cross-linked peptide DNA condensates with increasing number of cysteine residues.

FIG. 35A and FIG. 35B. Shear Stress Stability of Electronegative Cross-linked Peptide DNA Condensates. FIG. 35A: The particle size of peptide IV DNA condensates as a function of peptide DNA stoichiometry. FIG. 35B. The zeta potential of the same condensates. DNA condensates prepared at a charge ratio of 0.9 (arrows) formed small (62 nm) electronegative (−18 mV) DNA condensates that were stable to sonication shear stress in 2.5 M sodium chloride indicating the formation of disulfide bonds. The broken line in FIG. 35A indicates that neutrally charged cross-linking peptide DNA condensates possess a large (>1 µm) particle size.

FIG. 40A: Condensates formed with peptides 4–7; FIG. 40B: Condensates formed with peptides 8–11; and FIG. 40C: Condensates formed with peptides 12–16. See Table 5 for peptide structures.

FIG. 42A, FIG. 42B, FIG. 42C, FIG. 42D, FIG. 42E and FIG. 42F. Shear Stress Stability of Peptide DNA Condensates. The stability of peptide DNA condensates were analyzed by gel electrophoresis following 30 sec sonication in the presence of increasing concentrations of sodium chloride. DNA condensates were formed using peptide 1 (FIG. 42A), 3 (FIG. 42B), polylysine$_{1007}$ (FIG. 42C), 7 (FIG. 42D), 11 (FIG. 42E), and 12 (FIG. 42F). Lanes 1 through 8 represent sodium chloride concentrations of 0, 0.2, 0.4, 0.8, 1.0, 1.5, 2.0, and 2.5 M sodium chloride, respectively. The results establish DNA condensates prepared with peptides 3, 7 and 12 are nearly as stable polylysine$_{1007}$ DNA condensates whereas peptide 11 DNA condensates are completely stable in 2.5 M sodium chloride.

FIG. 44. Peptide Buffering Capacity. The change in pH was monitored for peptides 7 and 12–16 by titrating 5 µl alliquots of 5 mM hydrochloric acid into 100 µl of a 0.5 mM peptide solution in 150 mM sodium chloride.

FIG. 47A, FIG. 47B, FIG. 47C, FIG. 47D, FIG. 47E and FIG. 47F. Pharmacokinetic Analysis of $^{125}$I-DNA and $^{125}$I-DNA Condensates. Plasmid DNA (FIG. 47A), AlkCWK$_{18}$ DNA (FIG. 47B), and Tri-CWK$_{18}$ DNA condensates (FIG. 47C) (5 µg) were dosed i.v. in triplicate mice and 10 µL blood samples were drawn at times ranging from 1 to 60 min. Direct γ-counting of blood time points resulted in the pharmacokinetic profiles plotted as the mean±standard deviation vs. sampling time in FIG. 47A, FIG. 47B and FIG. 47C. Following extraction from blood time points, DNA samples were resolved by agarose gel electrophoresis and detected by autoradiography to establish the DNA morphology as supercoiled (sc), circular (cir), or fragmented as illustrated in FIG. 47D, FIG. 47E, and FIG. 47F. The results indicate that plasmid DNA and condensed DNA is quickly cleared from the circulation and metabolized into DNA fragments within 6 min following i.v. dosing.

FIG. 48A, FIG. 48B and FIG. 48C. Biodistribution of $^{125}$I-DNA and $^{125}$I-DNA Condensates in Mice. Quantitative biodistribution was performed by direct γ-counting of dissected tissues at 5 (FIG. 48A), 15 (FIG. 48B), and 30 min (FIG. 48C) following jugular vein dosing in triplicate mice. The targeting efficiency (percent of dose in the organ) was determined for plasmid $^{125}$I-DNA, AlkCWK$_{18}$, and Tri-CWK$_{18}$ $^{125}$I-DNA condensates (2.5 µg dose) in the tissues indicated. The data represent the mean and standard deviation of triplicate mice.

FIG. 49A, FIG. 49B, FIG. 49C, FIG. 49D, FIG. 49E, FIG. 49F, FIG. 49G, FIG. 49H and FIG. 49I. Liver Targeting Efficiency and Elimination of $^{125}$I-DNA and $^{125}$I-DNA Condensates. The radioactivity in the liver was determined by γ-counting as a function of time after dosing plasmid $^{125}$I-DNA (FIG. 49A), AlkCWK$_{18}$ $^{125}$I-DNA condensates (FIG. 48B), Tri-CWK$_{18}$ $^{125}$I-DNA condensates (FIG. 49C), cross-linked (6 mol eq) Tri-CWK$_{18}$ $^{125}$I-DNA condensates (FIG. 49D), cross-linked (15 mol eq.) Tri-CWK$_{18}$/PEG-CWK$_{18}$ (50:50) $^{125}$I-DNA condensates (FIG. 49E), cross-linked (15 mol eq.) agalactosyl-Tri-CWK$_{18}$PEG-CWK$_{18}$ (50:50) $^{125}$I-DNA condensates (FIG. 49F), cross-linked (15 mol eq.) Tri-CWK$_{18}$PEG-CWK$_{18}$ (10:90) $^{125}$I-DNA condensates (FIG. 49G), and cross-linked (15 mol eq.) agalactosyl-Tri-CWK$_{18}$/PEG-CWK$_{18}$ (10:90) $^{125}$I-DNA condensates (FIG. 49H), cross-linked PEG-CWK$_{18}$ (15 mol eq.) $^{125}$I-DNA condensates (FIG. 49I). The data represents the mean and standard deviation for 3 mice at each time point.

FIG. 53A: Compares the apparent parmacokinetic half-life for formulations with and without Man9CWK$_{18}$. A small difference in circulation time was detected when using 6 eq of glutaraldehyde to cross-link DNA condensates. FIG. 53B: In contrast, illustrates that 50 eq glutaraldehyde cross-linking results in a long circulatory half-life for AlkCWK$_{18}$PEG-CWK$_{18}$ DNA co-condensates and short half-life for Man9CWK$_{18}$/PEG-CWK$_{18}$ DNA co-condensates.

FIG. 54A, FIG. 54B and FIG. 54C. In vivo transient gene expression for differentially cross-linked DNA formulation. The transient gene expression profiles for mice dosed with 50 μg of DNA formulated with Man9CWK$_{18}$/PEG-CWK$_{18}$ and cross-linked with 6 eq (FIG. 54A), 15 eq (FIG. 54B) and 50 eq (FIG. 54C) of glutaraldehyde are illustrated.

FIG. 55B: Solid phase peptide synthesis is used to generate an ACM protected peptide with a single exposed sulfhydryl group. FIG. 55A: Conjugation of an iodoacetamide triantennary glycopeptide followed by removal of the ACM groups results in a sulfhydryl cross-linking glycopeptide (FIG. 55C). An identical strategy is used to prepare the sulfhydryl cross-linking PEG-peptide.

FIG. 57A: The chemical reduction of the amide backbone of a Pen sulfhydryl cross-linking peptide. FIG. 57B: The chemical reduction of the amide backbone of a Pen sulfhydryl cross-linking peptide to possess secondary amines.

DESCRIPTION OF ILLUSTRATIVE EMBODIMENTS

Figure 1A:
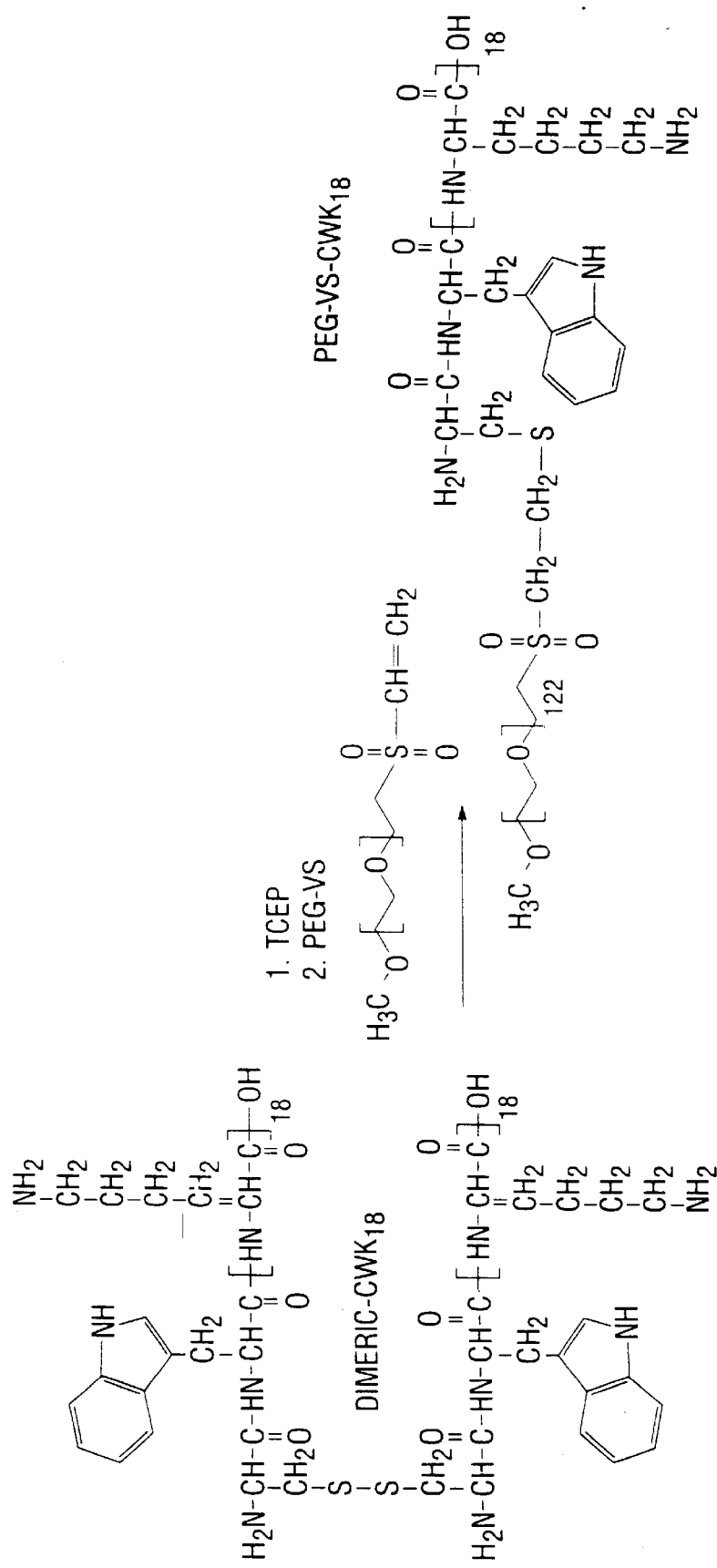

To achieve optimal and prolonged gene expression, carrier molecules are used to protect plasmid DNA from metabolism while en route, and once inside the target cell. Strategies to enhance non-viral DNA delivery have involved the use of cationic carriers such as lipids, peptides and polymers that bind DNA through ionic interaction (Duguid et al., 1998; Niidome et al., 1997; Pouton et al., 1998; Perales et al., 1997; Wagner et al., 1991a). In each case, ion pairing leads to varying degrees of DNA condensation, resulting in cationic particles that internalize into cells and mediate transient gene expression (Kabanov and Kabanov, 1995).

To be effective in delivering DNA, carrier molecules should have low toxicity, exhibit low levels of antigenicity or complement activation, and protect DNA from degradation (Ledley, 1996). Simultaneously addressing each of these problems has been one of the major impediments to developing sufficiently effective in vivo gene delivery formulations (Duguid et al., 1998; Niidome et al., 1997; Pouton et al., 1998; Perales et al., 1997; Wagner et al., 1991a; Kabanov and Kabanov, 1995; Ledley, 1996; Mahato et al., 1997).

Dissociation of a carrier molecule from DNA in serum exposes the DNA to metabolizing endonucleases, leading to premature degradation (Yang and Huang, 1997). The inventors reasoned that the stability of DNA condensates in serum is dependent on the nature and affinity of a carrier molecule for binding DNA, the ionic strength, the concentration of endonuclease, and the presence of molecules that compete for carrier binding.

Only a few studies have addressed the issue of DNA metabolism, despite the relationship to the level and duration of gene expression (Yang and Huang, 1997; Escriou et al., 1998; Katayose and Kataoka, 1998; Liu and Liu, 1996; Chiou et al., 1994). HMW polylysines$_{38-1007}$ offer the advantage of binding to DNA with higher affinity, resulting in a greater protection of DNA to metabolism. Early studies by Wu and coworkers concluded that high molecular weight (HMW) polylysines could protect DNA from rapid metabolism in vitro for up to 1.5 h (Chiou et al., 1994).

However, there are significant drawbacks in using HMW polylysine to create carriers for gene delivery. For example, the polydispersity of HMW polylysine results in batch to batch variation (McKenzie et al., 1999a). The derivatization of HMW polylysine with ligands or polyethylene glycol is achieved by random coupling reactions that cannot control the conjugation site along the polylysine chain, creating further heterogeneity in the carrier molecule (Wagner et al., 1991b; Haensler and Szoka Jr., 1993; Batra et al., 1994).

More significant problems involve the known cytotoxicity, complement activation and inflammation mediated by HMW polylysine (Plank et al., 1996). Therefore, despite the ability of HMW polylysines to retard metabolism, the associated toxicity of these polymers has prompted the search for low molecular weight (LMW) carriers for use in vivo (Gottschalk et al., 1996). The present inventors have therefore focused their efforts on developing LMW DNA carriers that are homogenous, condense DNA into small condensates, can be selectively derivatized, and that are minimal in size to reduce toxicity.

Subsequent studies by the inventors and colleagues determined that a twenty amino acid peptide ($CWK_{18}$) was sufficient to stabilize DNA condensates from in vitro metabolism (Adami et al., 1998). Such LMW carriers therefore have the potential for further development as gene delivery agents. However, realizing that further improvements should be sought, the inventors contemplated that increasing the stability of LMW carrier binding to DNA would likely yield DNA condensates with improved characteristics.

The inventors therefore developed various strategies to achieve high affinity binding using LMW carriers. These strategies are based upon providing temporary stability through molecular crosslinking of carriers on DNA condensates. The inventors reasoned that unpaired amines on the surface of peptide DNA condensates could be crosslinked with a variety of agents, and have developed effective crosslinking compositions based upon this observation.

Even though peptide DNA condensates are more resistant to metabolism than naked plasmid DNA (Katayose and Kataoka, 1998) or cationic lipid DNA condensates (Escriou et al., 1998; Thierry et al., 1997), the in vitro stability determined by incubating condensates in serum may not be predictive of the in vivo stability, wherein carrier molecules dissociate and are removed under sink conditions. This is exemplified by earlier studies by Wu and coworkers, which showed the prolonged stability of DNA condensates in vitro (Chiou et al., 1994) but a more limited stability in vivo (Chowdhury et al., 1993).

To overcome the limited stability afforded by LMW DNA carriers, the present invention provides various means to introduce inter-chain crosslinks to preformed DNA condensates to further improve their stability. One advantage of this invention is the ability to vary the degree of crosslinking to create condensates that possess the required stability for different gene therapy applications. Also, a variety of crosslinking agents can be used alone or in combination to create a controlled release of the DNA upon hydrolysis and dissociation of the crosslinker and a carrier. The control over these events afforded by the present invention provides for delayed or prolonged transgene expression, as required in gene therapy.

I. GLUTARALDEHYDE CROSSLINKING

The stability of a DNA formulation is fundamental to its successful application in vivo since metabolism results in the generation of fragmented DNA that no longer mediates gene expression (Adami et al., 1998). The present invention provides DNA formulations with increased stability without increased toxicity. Basically, high affinity binding is providing using LMW carriers.

One aspect of the invention provides temporary stability through molecular crosslinking of carriers on DNA condensates using aldehyde groups. Glutaraldehyde is a five carbon dialdehyde that has been used as a reagent to increase the tensile strength of transplanted pig heart valves and to develop controlled release microspheres for drug delivery (Jayakrishnan and Jameela, 1996; Jones et al., 1989; Gupta and Hung, 1989).

The chemical crosslinking of albumin lysines with glutaraldehyde leads to particles with controlled drug release properties (Lin et al., 1994; Royer and Lee, 1983). The degree of crosslinking directly affects the particle size, biodegradation, and release properties of drugs encapsulated in glutaraldehyde crosslinked microspheres (Jones et al., 1989; Gupta and Hung, 1989; Leong et al., 1998). Glutaraldehyde has not previously been connected with nucleic acid stability or delivery.

In the present invention, glutaraldehyde is used to crosslink DNA condensates to improve their metabolic stability and alter the resulting transient gene expression profiles in vitro. This crosslinking enhances the stability of LMW peptide DNA condensates and leads to steady-state transient gene expression.

As an example, the surface amine groups on $CWK_{18}$ DNA condensates were crosslinked using glutaraldehyde. The inventors chose glutaraldehyde because the Schiffs-base that forms is theoretically reversible (Jayakrishnan and Jameela, 1996; Ege, 1994). Also, although not previously connected with nucleic stability or delivery, glutaraldehyde has a good safety record when used in a variety of prostheses (Gratzer et al., 1996) and has been used in diverse biomedical fields, particularly for developing crosslinked albumin microspheres for parenteral applications (Royer and Lee, 1983).

The results indicate that $CWK_{18}$ DNA condensates undergo crosslinking over a 4–5 h period when very low concentrations of glutaraldehyde (1–4 mol equivalents relative to $CWK_{18}$) are added. This amount of glutaraldehyde is far below the amounts needed to observe toxicity in cells grown in culture. Likewise, the maximum amount of glutaraldehyde used (4 mol equivalents) can theoretically crosslink 20% of the amines present, assuming glutaraldehyde distributes equally throughout the DNA condensates. At this low level, the particle size is maintained, the zeta potential of the DNA condensates is unaffected, and trypsin can still be used to enzymatically remove $CWK_{18}$ to quantitatively release the DNA. However, spontaneous reversal of glutaraldehyde crosslinked DNA condensates has yet to be demonstrated on prolonged dialysis in the presence of protein.

One measure that establishes the relative stability of peptide DNA condensates is the ability of DNA to resist fragmentation during a 30 s 100 W sonication in a dissociating concentration of sodium chloride. Crosslinked DNA condensates were increasingly stable to sonicative fragmentation at crosslinking levels ranging from 1–4 mol equivalents of glutaraldehyde and were even found to be more stable than HMW $polysine_{99-1007}$ DNA condensates. This result indicates that inter-chain peptide crosslinks, and not linear polymerization of $CWK_{18}$, are responsible for the observed stabilization.

A similar correlation was observed from in vitro metabolism studies that indicated that 4 mol equivalent crosslinked DNA condensates were significantly stabilized (although inferior to $polylysine_{1007}$ in their ability to protect DNA from accelerated metabolism). Interestingly, DNA condensates with and without crosslinking appeared to be directly metabolized into fragments without going through the linear form. This is in contrast to the catabolism of naked DNA, which is converted completely into linear DNA prior to the formation of fragments (Adami et al., 1998). It is also evident that intracellular proteolysis must somehow be involved in the release of DNA from crosslinked condensates since it less likely that the spontaneous reversal of Shiffs-base is the major route of DNA release prior to gene expression.

The ability of crosslinked DNA condensates to mediate gene expression is a measure of their ability to be most useful in gene therapy applications. Since crosslinking could delay the release of DNA inside cells, it was important to study the transient gene expression as opposed to a single 24 or 48 h expression level. However, this was also technically challenging due to the doubling rate of cells in culture, which slows as they reach confluence. At an optimal seeding density, cell cultures could be maintained for 10-days and the gene expression occurring each day was determined using secreted alkaline phosphatase.

The most significant effect of crosslinking DNA condensates, in addition to stabilization to metabolism, was an apparent flattening of the expression profile such that 4 mol equivalent crosslinking of DNA condensates resulted in a low level of steady-state expression over the 10-day transfection which could not be extended in cell culture. Omitting chloroquine more closely models in vivo conditions and further confirmed that crosslinking could produce a steady-state rate of expression. Analysis of the transient gene expression profile for HMW polylysine$_{38-1007}$ DNA condensates indicated a correlation between the cumulative gene expression and the degree of polymerization.

The results from glutaraldehyde crosslinking at least partially validate the hypothesis that increasing the DNA condensate stability will result in greater gene expression. However, this data also led the inventors to analyze other means of crosslinking to stabilize peptide DNA condensates from metabolism and to prolong gene expression in vivo. In particular, DNA condensates with more than one LMW carrier would endow a gene delivery system with specific targeting properties.

II. Self-Crosslinking Peptides

Following i.v. delivery of a nonviral gene formulation, the duration of transient gene expression in the target tissue generally depends on how long the DNA can survive metabolism (Chiou et al., 1994). One of the functions of polylysine and other polymers used as carriers for gene delivery is to protect DNA from premature metabolism (Adami et al., 1998). Polylysine DNA condensates prepared at a charge ratio of 2:1 or greater are electropositive and resist endonuclease digestion. The degree of metabolic protection afforded to DNA by polylysine is proportional to its molecular weight, since longer polylysines bind to DNA with higher affinity and create more stable peptide DNA condensates.

HMW polylysine also enhances in vitro gene transfer efficiency several fold relative to LMW peptides, due to differences in both protection and release of DNA. Studies that utilize HMW polylysine conjugates for in vivo gene delivery have tried to control the stoichiometry of polylysine to DNA to create partially condensed DNA that has a neutral or negative charge (Kwoh et al., 1999). This is necessary since i.v. dosing of electropositive DNA condensates leads to rapid opsonization and non-specific biodistribution to lung and liver.

LWM DNA carriers are attractive as drug candidates due to their reduced toxicity (Wolfert and Seymour, 1996), ease of synthesis, selective derivatization and characterization (Kwok et al., 1999; Collard et al., 1999) relative to HWM polylysine conjugates. However, even though LMW carriers such as AlkCWK$_{18}$ bind with sufficient affinity to form small DNA condensates, these are not stable during circulation and fail to provide any metabolic protection in the target tissue (Kwoh et al., 1999). In fact, LMW peptides are rapidly stripped from DNA condensates during circulation, at all charge ratios, due to their lower DNA binding affinity relative to HMW polylysine.

Thus, there is a difference in the metabolic stability required of formulations designed for in vitro versus in vivo gene delivery. There remains a need for low molecular weight in vivo gene transfer agents, but their design needs to be improved so that they form small (<100 nm diameter) metabolically stable DNA condensates with the desired surface charge (Duguid et al., 1998).

The present inventors have previously evaluated the relationship between LMW polylysine chain length, DNA condensate particle size and in vitro gene transfer efficiency (Wadhwa et al., 1997). These studies revealed that peptides possessing 18 lysines (CWK$_{18}$) were sufficient to form small (<100 nm) DNA condensates that were efficient in mediating non-specific in vitro gene transfer. Whereas shorter peptides formed large DNA condensates, longer peptides were equivalent in gene transfer to CWK$_{18}$ (Wadhwa et al., 1997). Commercially available polylysine$_{19}$ has now been shown to be inferior to CWK$_{18}$ due to its heterogeneity and lower molecular weight (McKenzie et al., 1999a; incorporated herein by reference).

Although the tryptophan in CWK$_{18}$ was originally proposed to contribute to the DNA binding affinity, the inventors' subsequent studies established that a homogeneous polylysine (K$_{20}$) was equivalent to CWK$_{18}$ (McKenzie et al., 1999a; incorporated herein by reference). The single cysteine residue in CWK$_{18}$ was still thought useful as a conjugation site, and the inventors have prepared polyethylene glycol-CWK$_{18}$ and triantennary N-glycan CWK$_{18}$, both of which have been used in DNA formulation for in vivo gene delivery Prior to the present invention, notable improvements were not being made in the stability of LMW peptide DNA condensates for use in vivo. One solution to this is to chemically cross-link DNA condensates to stabilize carrier molecules from dissociation. The use of glutaraldehyde as a cross-linking agent significantly improved the in vitro and in vivo stability of LMW peptide DNA condensates (Example 4; Adami and Rice, 1999). However, the slow reversal of the resulting Schiffs-bases resulted in sub-optimal gene expression. Other reversible cross-linking agents have been proposed in an attempt to stabilize LMW carrier DNA condensates (Trubetskoy et al., 1998; 1999), but these require careful control over stoichiometry and have yet to be proven transfection competent.

The inventors thus sought other innovative solutions to balance the stability-expression problem. As endocytosed macromolecules must pass through the reducing environment of the endosomal compartment (Mellman et al., 1986; Feener et al., 1990), the inventors envisioned that disulfide bonds could be used to transiently stabilize a LMW peptide-DNA condensate outside the cell and yet allow release of DNA intracellularly. This led to the second aspect of the overall invention, namely self-crosslinking peptides.

Cysteine residues were thus substituted for lysine residues in DNA binding peptides and the physical and gene transfer properties of the resulting cross-linked peptide DNA condensates were studied. Although the cysteine residue had never before been contemplated for use outside of conjugation, the present inventors realized that CWK$_{18}$ was an appropriate starting point for the generation of cross-linked peptide and DNA condensates. Further cysteines were thus introduced in CWK$_{18}$ and like peptides, based on the inventive concept of producing a self-crosslinked entity, rather than simply a peptide that could be further chemically conjugated to another agent, such as polyethylene glycol (PEG).

The results indicated that disulfide bond formation occurs rapidly during a 30 min. incubation at pH7.4. The cross-linking occurs at approximately the same rate when the peptide is either free in solution or bound to DNA. DNA condensate stability increased coincidentally with the number of cysteine residues, as revealed by both the indirect fluorescence assay (FIG. 32A and FIG. 32B) and by the salt sonication electrophoresis assay (FIG. 34A, FIG. 34B, FIG. 34C, FIG. 34D, FIG. 34E, FIG. 34F, FIG. 34G, FIG. 34H and FIG. 34I).

The upper limit of shear stress stability afforded to DNA condensates by cross-linking peptides III–V could not be ascertained since these remained intact in 2.5 M sodium chloride and even in saturated 4 M sodium chloride. Thus, a LMW peptide (20 mer) with as few as three cysteine residues produced DNA condensates that far exceeded the stability afforded by polylysine$_{1007}$. Although the shear stress stability of DNA condensates afforded by peptide II was equivalent to polylysine$_{1007}$ the former were surprisingly enhanced in mediating gene expression, as discussed below.

To reach full stability, inter-peptide disulfide bonds must form after the peptide binds to DNA since pre-oxidized peptide V formed primarily intra-molecular disulfide bonds as established by mass spectral analysis and shear stress stability studies. Ionic binding of peptides to the DNA backbone may inhibit peptide folding and could promote the desired inter-peptide disulfide bond formation (Trubetskoy et al., 1998).

Formation of inter-peptide disulfide bonds also appears to decrease the size of peptide II-V DNA condensates resulting in mean particle diameters of 40–50 nm compared to 70–100 nm determined for AlkCWK$_{18}$, DiCWK$_{18}$, or polylysine$_{1007}$ DNA condensates (Table 3). The inventors hypothesize that DNA condensates compact when DNA loops within the condensate collide and tether together disulfide bond formation. Consequently, reduction of disulfide bonds within cross-linked DNA condensates would release the DNA loops and cause an increase in particle size. QELS analysis of TCEP-reduced peptide II-V DNA condensates supported this hypothesis by revealing a large population of DNA condensates.

The time-dependent increase in the particle size of cross-linked DNA condensates prepared in normal saline agrees with previous observations for LMW peptide DNA condensates (Plank et al., 1999) even though it was expected that these would resist aggregation as observed when using other cross-linking strategies (Trubetskoy et al., 1999). However, this does not pose a problem since the use of cross-linking peptides in vivo gene delivery will likely involve attaching PEG to the peptide which dramatically improves DNA condensate solubility (Example 1, Kwok et al., 1999) and inhibits salt induced aggregation (Example 2).

It is also apparent that disulfide bond formation is not restricted to electropositive DNA condensates (FIG. 35A and FIG. 35B). The ability to form small (62 nm), electronegative (−18 mV) and highly stable DNA condensates is an important prerequisite to using these as carriers for in vivo gene delivery.

The level of gene expression mediated by CWK$_{18}$ and peptides II-V was well above that determined for AlkCWK$_{18}$ DNA condensates. The increase in gene expression mediated by CWK$_{18}$ over AlkCWK$_{18}$ is likely due to the formation of DiCWK$_{18}$ within the DNA condensate. Both CWK$_{18}$ and DiCWK$_{18}$ were still 5-fold inferior to polylysine$_{1007}$ as a DNA carrier, in agreement with previous correlations established between polylysine length and in vitro gene transfer efficiency (Adami and Rice, 1999). Cross-linking peptide III mediated a comparable level of gene expression as polylysine$_{1007}$ whereas less expression resulted when using peptide IV, which was partially regained when using peptide V as a condensing peptide. Most surprisingly, the gene expression mediated by peptide II in HepG2 cells was 60-fold greater than AlkCWK$_{18}$ DNA condensates and nearly 5-fold greater than polylysine$_{1007}$ DNA condensates. The increase in gene expression mediated by II-V was less dramatic in COS 7 cells, but still significantly improved over AlkCWK$_{18}$ as a carrier molecule.

The enhanced expression mediated by peptide II DNA condensates is probably not related to their small particle size (42 nm) since CWK$_{18}$ DNA condensates were also small (51 nm) but mediated similar level of expression as DiCWK$_{18}$ DNA condensates (68 nm). It also appears that the increase in DNA stability afforded by peptides III-V inversely correlates with the gene transfer efficiency. Presently, the addition of more than two cysteine residues seemingly exceeds the number of disulfide bonds that can be most efficiently reduced in the cell.

The results of luciferase expression, NTβGal transfection, and radiolabeled DNA uptake studies collectively support a probable mechanism involving enhanced transduction mediated by peptide II. Even though the DNA uptake mediated by AlkCWK$_{18}$ was the same as peptide II in HepG2 cells (FIG. 38), the number of cells reporting positive for nuclear targeted β-galactosidase was 9-fold higher (FIG. 37) and the magnitude of the luciferase reporter gene expression was 60-fold higher (FIG. 36A and FIG. 36B) when using peptide II.

A possible explanation for these results is the intracellular stability afforded to DNA condensates when using peptide II, resulting in a longer residence time of the internalized DNA relative to AlkCWK$_{18}$ DNA condensates. The ability of peptide II DNA condensates to undergo reduction provides a release mechanism for DNA relative to polylysine$_{1007}$ DNA condensates. Upon reduction, peptide II would rapidly convert to a weaker binding peptide that could dissociate and release the DNA intracellularly whereas the dissociation of polylysine$_{1007}$ from DNA would presumably occur more slowly. The finding that chloroquine enhanced the expression of peptide II DNA condensates more than AlkCWK$_{18}$ DNA condensates may relate to a previously reported pH dependence of reduction within cells (Feener et al., 1990).

The present invention thus provides highly efficient non-viral gene delivery agents using cross-linking peptides that improve on the concept of LMW peptide DNA condensates. The cross-linking peptides mediate efficient gene transfer. They can be further derivatized with polyethylene glycol (Kwok et al., 1999) and targeting ligands (Collard et al., 1999) in order to produce an optimal in vivo gene therapy agent.

III. Self-Crosslinking, Endosomal Buffering Peptides

In addition to stabilizing peptide DNA condensates, a delivery system should facilitate the escape from lyosomal trafficking and delivery of DNA to the cytosol. Several groups have reported attempts to facilitate endosomal escape of DNA condensates by the addition of chloroquinone or fusogenic peptides to the transfecting media (Wagner, 1998; Midoux et al., 1998), but only recently has this been tried extended in in vivo (Nishikawa et al., 2000). PEI, dendrimers and other agents containing secondary and tertiary amines can apparently serve to buffer the endosomal compartment, resulting in osmotic lysis (Pouton and Seymour, 1998; Midoux and Monsigny, 1999).

In Example 6, a panel of peptides containing two to eight Lys, one to five His and either two to three Cys residues were synthesized and evaluated for DNA binding and gene transfer efficiency to incorporate endosomal buffering capacity. The successful results further advanced the concept of LMW cross-linking peptides as novel gene transfer agents.

Based on the results of the Cys-containing peptides, the present inventors reasoned that cross-linking peptides could potentially overcome the stability, particle size and gene transfer limitations even for very short polylysine peptides. The results in Example 6 demonstrate peptide 5 as a minimal structure possessing four Lys and two terminal Cys residues that rapidly cross-links on DNA to form small condensates that are stable in 0.4 M salt and mediate gene expression equivalent to peptide 3 DNA condensates in two of the three cell lines tested (FIG. 40A, FIG. 40B, FIG. 40C, FIG. 41, FIG. FIG. 42A, FIG. 42B, FIG. 42C, FIG. 42D, FIG. 42F, FIG. 42F, FIG. 43A, FIG. 43B and FIG. 43C). Peptide 4, with only two Lys residues, lacked appreciable affinity for DNA and had a greater propensity to undergo internal disulfide bond formation vs. template polymerization, and was thereby unable to condense DNA.

Decreasing the overall length of the peptide from twenty down to ten residues had little effect on the stability of the cross-linking peptide DNA condensates. Peptide 7 DNA condensates, consisting of eight Lys and two terminal Cys residues, possesses the same stability as peptide 3 and polylysine$_{1007}$ DNA condensates (FIG. 42A, FIG. 42B, FIG. 42C, FIG. 42D, FIG. 42F and FIG. 42F). As demonstrated in Example 5, adding an internal Cys to peptide 3 allows for interpeptide cross-linking in addition to linear polymerization, which further increases the stability of DNA condensates to above 2.5 M sodium chloride (McKenzie et al., 2000).

Similarly, peptide 9–11 DNA condensates were found to be improved in stability, although the particle size was much larger. This cannot be the result of too few Lys residues since the particle size of DNA condensates prepared with peptide 5 possessing four Lys residues was 10-fold smaller than the determined for those prepared with peptide 11 possessing eight Lys residues. It is more likely that the internal Cys in peptides 9–11 contributes both to interpeptide as well as interparticle cross-linking which occurs rapidly since the particle size determined for peptide 7 to 11 DNA condensates did not change appreciably between 30 min and 24 h.

Taken collectively, the data suggest that a small DNA condensate particle size can be achieved with a short, six to ten amino acid peptide, possessing two terminal Cys residues. Within this size range, additional Cys residues improve stability but increase particle size and thereby decrease in vitro gene expression. Including multiple Cys residues into a twenty amino acid peptide circumvents the problem of increasing particle size (Example 5; McKenzie et al., 2000). This information is fundamental to the design of a variety of gene delivery systems. However, in applications to the design of i.v. dosed targeted gene delivery systems, the relationships described for LMW cross-linking peptides binding to DNA may need to be optimized when these are derivatized with polyethylene glycol and targeting moieties such as N-glycans (Example 1, Kowk et al., 1999; Example 3; Collard et al., 2000a; Example 7; Collard et al., 2000b).

Figure 45A:
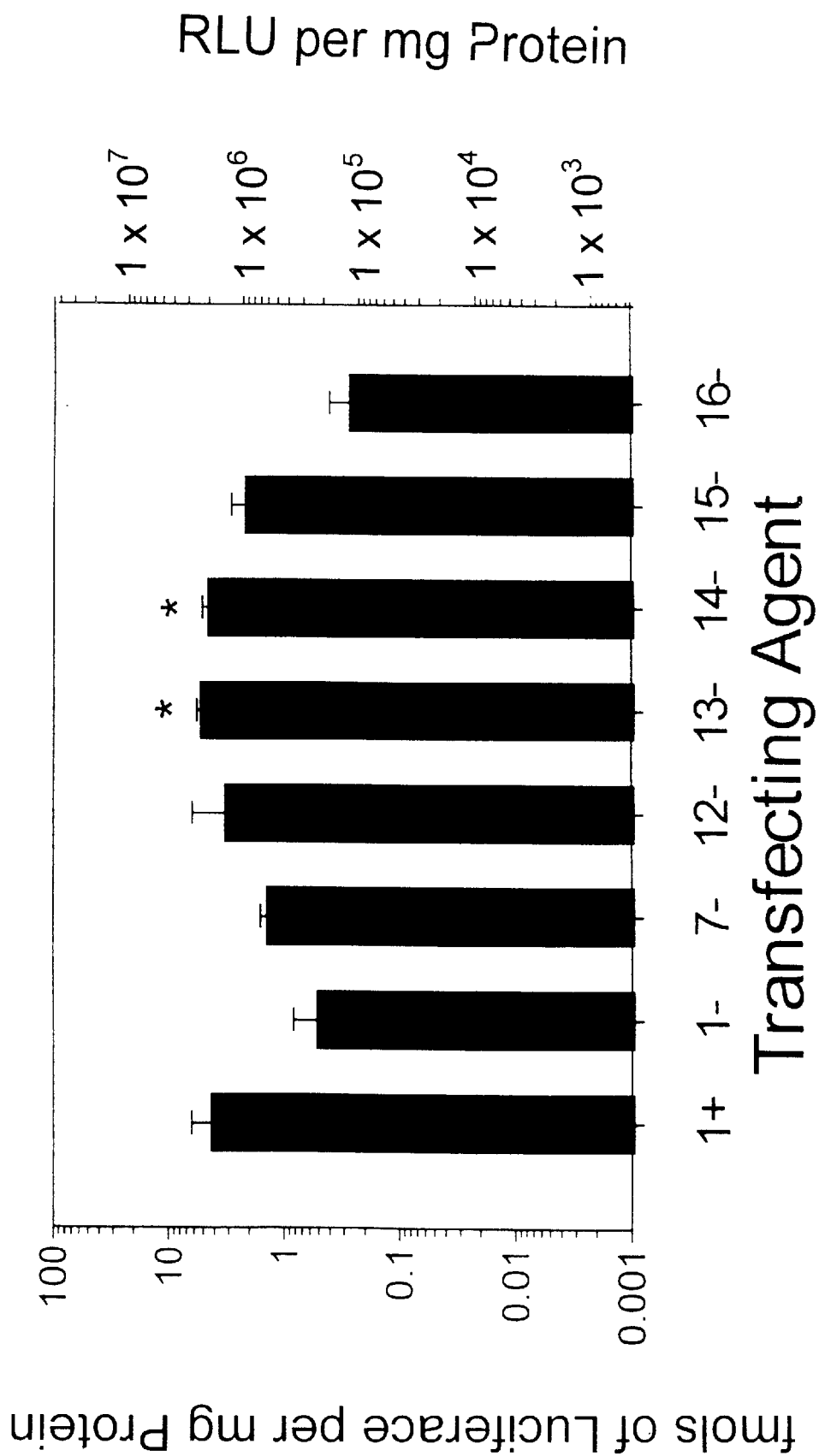
FIG. 45A, FIG. 45B and FIG. 45C. Luciferace Expression of Endosomal Buffered DNA Condensates. The luciferace reporter gene expression for peptide DNA condensates in the presence (+) or absence of chloroquine (−) were compared in HepG2 (FIG. 45A), COS 7 (FIG. 45B) and CHO cells (FIG. 45C). Each experimental result represents the mean and standard deviation of three determinations. The * indicates a p<0.05 relative to peptide 7. See Table 5 for peptide structures. L represents LipofectAce™.
Figure 45B:
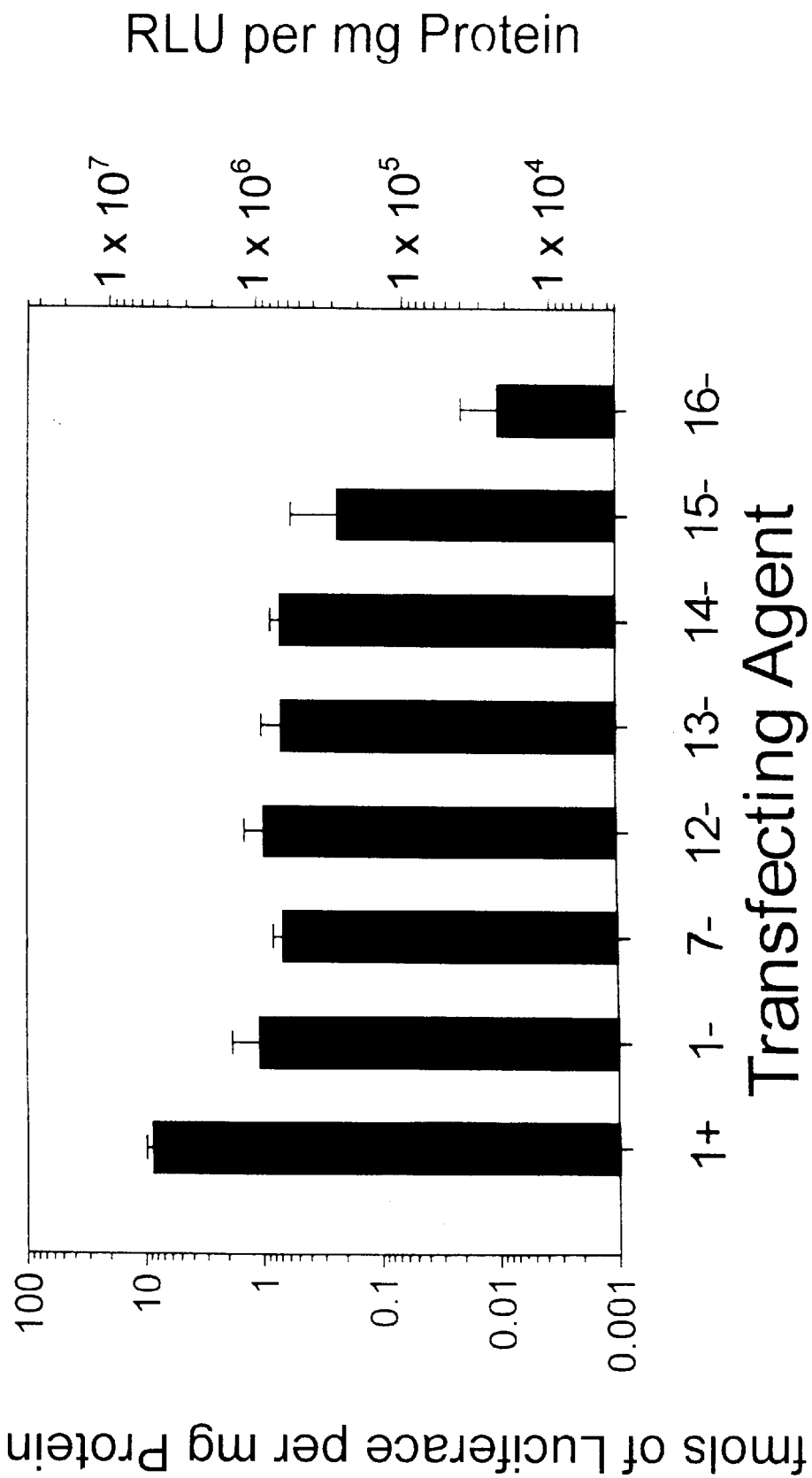
Figure 45C:
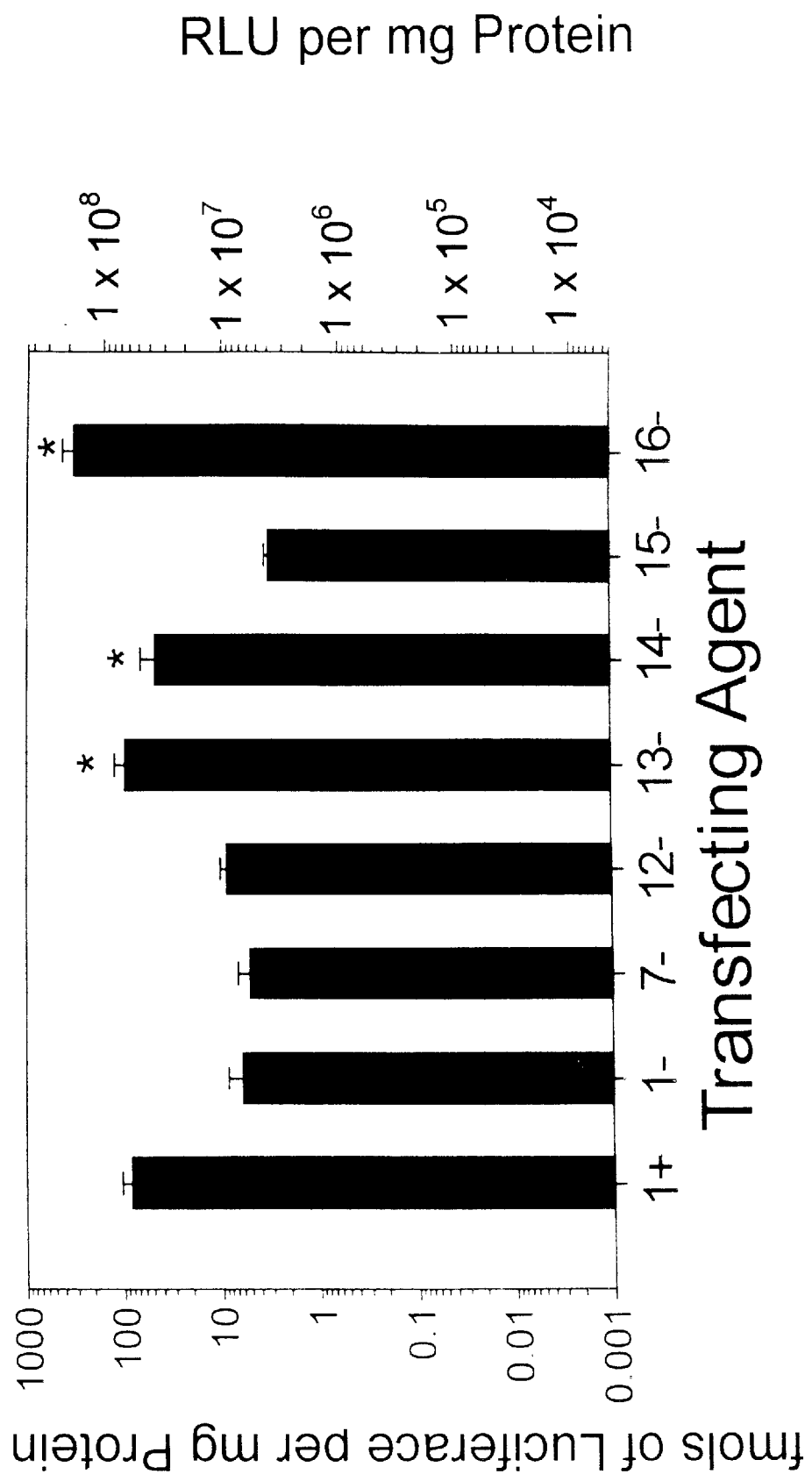
Figure 46A:
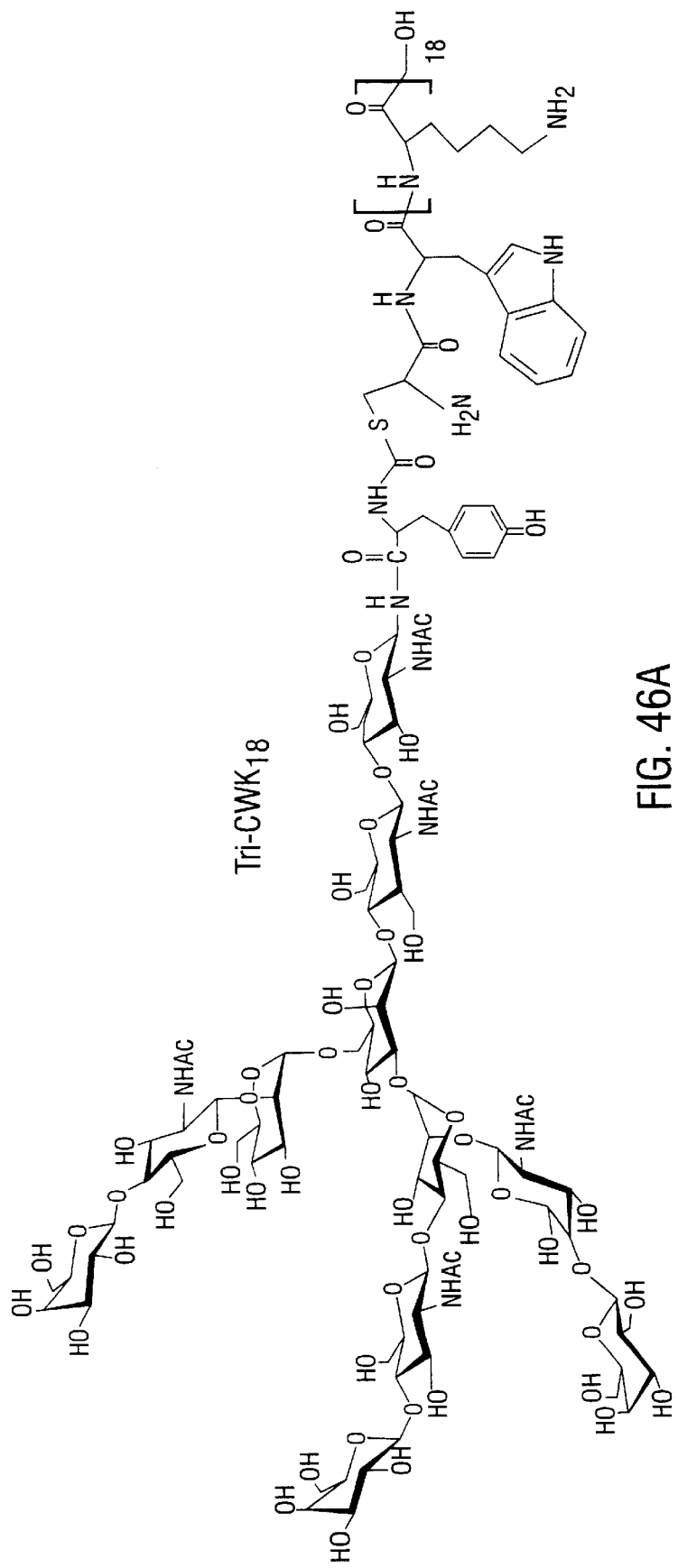
FIG. 46A, FIG. 46B, FIG. 46C and FIG. 46D. Structure of Tri-CWK$_{18}$ (FIG. 46A), Agalactosyl-Tri-CWK$_{18}$ (FIG. 46B), PEG-CWK$_{18}$ (FIG. 46C), and AlkCWK$_{18}$ (FIG. 46D). The chemical structure of each LMW DNA carrier used in illustrated. Each carrier shares a common 20 amino acid peptide (CWK$_{18}$) but differs in the structure attached to the systeine residue.
Figure 46B:
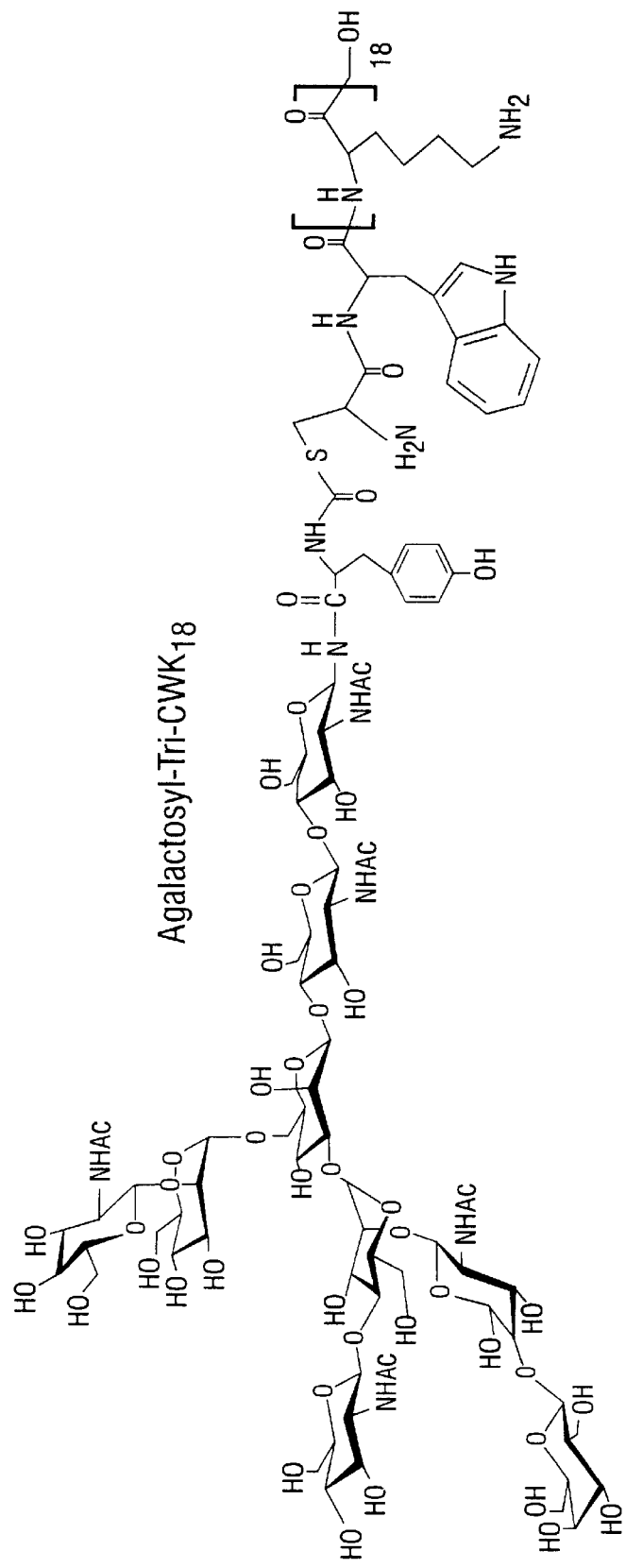
Figure 46D:
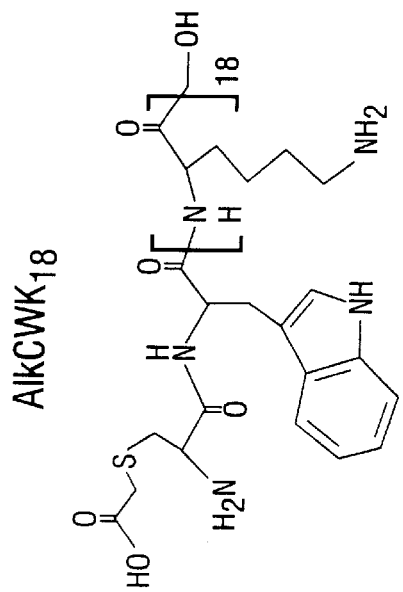
Figure 46C:
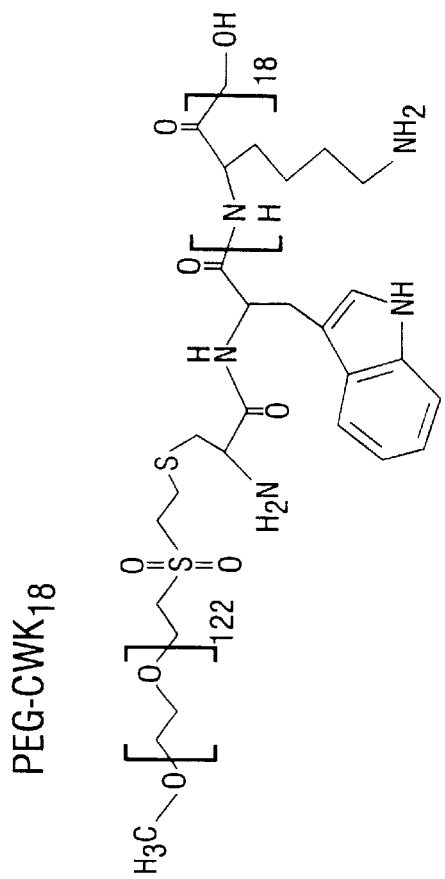

Peptide 7 was selected to determine whether substitution of one to five His residues could further enhance expression. The results establish that peptide 13– and 14– DNA condensates possessed 4 to 10-fold enhanced gene expression relative to peptide 7–, dependent on cell type (FIG. 45A, FIG. 45B and FIG. 45C). Likewise, the gene expression mediated by peptide 1+ to 13– DNA condensate in HepG2 and CHO cells were equivalent (FIG. 45A, FIG. 45B and FIG. 45C). These results show that a mechanism of endosomal buffering for His derivatized polylysine peptides, demonstrating that LMW cross-linking peptides can serve to buffer endosomes and enhance gene expression.

Example 6 thus extends the concept of LMW cross-linking peptides by identifying the minimal Cys and Lys peptide that polymerizes while bound to DNA leading to enhanced gene expression. The concept of endosomal buffering has been extended by determining the number of His residues in a LMW cross-linking peptide needed to enhance gene expression. These LMW cross-linking peptides thus represent the latest stage in the development of agent to systemically increase the level of gene expression in vivo.

IV. Gene Delivery Formulations

Nonviral gene delivery relies on the use of carrier molecules to bind plasma DNA and mediate cell-specific uptake of the DNA carrier complex (Wu and Wu, 1988; Wu et al., 1989; Wagner et al., 1990; Tang et al., 1996; Hara et al., 1997; Ogris et al., 1998). The efficiency of an i.v. dosed nonviral gene delivery dosage form is dependent on the DNA carrier complex to overcome obstacles that prevent it from arriving at the target cell. Depending on the size and charge of a DNA complex, it may be opsonized and entrapped in the capillary beds of the lung or may be phagocytosed by liver Kupffer cells or spleen macrophages (Pouton and Seymour et al., 1998).

The DNA carrier complex should possess sufficient serum stability to remain intact during circulation since premature dissociation exposes unprotected DNA resulting in rapid metabolism by serum endonucleases (Kawabata et al., 1995). Once endocytosed by target cells, the DNA carrier complex must also escape degradative pathways and target the nucleus (Pouton and Seymour et al., 1998).

In the absence of a carrier molecule, 60–70% of i.v. dosed plasmid DNA is taken up by scavenger receptors on liver Kupffer cells (Kawabata et al., 1995; Lew et al., 1995). To facilitate selective targeting to hepatocytes, ligands for the asialoglycoprotein receptor (ASGP-R) have been incorporated into carrier molecules (Wu and Wu, 1988; 1989; Wu et al., 1991; Stankovics et al., 1994; Chowdhury et al., 1993; Midoux et al., 1993; Perales et al., 1994; Nishikawa et al., 1998; Hashida et al., 1998; Wadhwa et al., 1995; Merwin et al., 1994).

One of the first carriers was a conjugate of high molecular weight (HMW) polylysine$_{440}$ covalently linked to asialoorosomucoid (ASOR) (Stankovics et al., 1994), a glycoprotein possessing terminal galactose residues on its N-glycans. Following i.v. dosing, ASOR-polylysine DNA condensates were also rapidly taken up by liver and then slowly eliminated with $t_{1/2}$ of 1.3 h due to the metabolic protection provided on polylysine (Stankovics et al., 1994). To further extend the liver half-life of DNA and the duration of gene expression, Chowdhury et al. (1993) performed partial hepatectomy following the delivery of ASOR-polylysine DNA condensates to rats. Since lysosomal trafficking is dramatically decreased following partial hepatectomy, the rate of DNA metabolism was also decreased, resulting in the recovery of 9% of the dose in the liver after 24 h.

Refinements in carrier design have resulted in the replacement of ASOR-polylysine with lactosylated and galactosylated polylysine (Midoux et al., 1993; Perales et al., 1994). Perales et al. (1994) examined the ability of a galactosylated polylysine$_{100}$ to mediate liver targeting and reported the PCR™ detection of DNA in the liver for 32 days, but did not attempt to determine cell-type specific targeting. Recent studies by H ashida and colleagues utilized galactosylated polylysine$_{100}$ as a carrier to establish that 70% of the liver targeted DNA resides in hepatocytes (Nishikawa et al., 1998; Hashida et al., 1998). Opsonization of the DNA carrier complex could be minimized by controlling the polylysine DNA stoichiometry to create electronegative DNA complexes; however, this approach is unlikely to allow DNA targeting to peripheral sites since electronegative DNA condensates are also taken up non-specifically by liver Kupffer cells (Nishikawa et al., 1998; Hashida et al., 1998).

An alternative approach to increase the resistance of polylysine DNA condensates to opsonization is to incorporate polyethylene glycol (PEG)-polylysine to shield the surface charge of DNA condensates (Wolfert et al., 1996; Katoyose and Kataoka 1997; Choi et al., 1999). Thus far, only one study has examined the utility of PEGylated ASOR-polylysine$_{100}$ as a DNA carrier for i.v. dosed formulations and found that PEG decreased the aggregation of DNA condensates but failed to influence the in vivo biodistribution (Kwoh et al., 1999).

It is becoming recognized that optimizing a gene delivery formulation will require deriving correlations between the physio-chemical properties of the DNA carrier complex and in vivo parameters such as biodistribution, cell-type targeting specificity, metabolism and elimination, and gene expression. The present inventors realized that to analyze such correlations, and prepare an effective gene delivery vehicle, one requires complete synthetic control over the design of carrier molecules. They further realized that such control can only be achieved effectively by reducing the molecular weight of the carriers.

Consequently, the inventors believe that the use of derivatized HMW polylysine as a condensing agent to optimize gene expression is inadequate since it leads to increased heterogeneity and does not allow precise control over the location or stoichiometry of ligand or PEG attachment. It was therefore an object of the invention to properly design LMW DNA carriers that will not only eliminate heterogeneity, but can also be systematically optimized to reduce or eliminate toxicity.

These objectives have been achieved by the provision of low molecular weight carriers of minimal size and reduced toxicity that nonetheless function to condense DNA into small particles with increased stability and maintained or even improved gene expression levels. The low molecular carriers of the invention can thus be used to replace HMW polylysine conjugates as i.v. dosed nonviral gene delivery system. For optimal in vivo use, the inventors propose that the low molecular carriers be used in combination with agents that provide targeting specificity, such as ligands that bind to specific cell surface receptors, and/or with agents that reduce non-specific cellular interactions, such as components that mask the surface charge of DNA condensates.

Example 7 shows the systematic optimization of LMW carries using both targeting ligands and PEG. The LMW carriers used toe exemplify the specific targeting and surface charge masking embodiments are based upon the synthetic peptide, Cys-Trp-Lys$_{18}$ (CWK$_{18}$), which forms small (<100 nm) DNA condensates capable of mediating efficient non-specific gene transfer to cells in culture (Wadhwa et al., 1997; Adami et al., 1998; McKenzie et al., 1999a). The methodology disclosed can now be used to advantage in combination with the preferred self-crosslinking peptide aspects if the overall invention.

To endow a delivery system with targeting specificity, a natural triantennary N-glycan ligand can be incorporated into the DNA delivery formulation. For example, it can be covalently attached to a protein or peptide, including attachment to the peptides that form the peptidyl component of a peptide-DNA condensate. In one example, a triantennary N-glycan ligand is attached to the side chain of cysteine in CWK$_{18}$ resulting in a triantennary glycopeptide (Tri-CWK$_{18}$) that binds to the ASGP-R with a nM dissociation constant (Collard et al., 1999; Rice et al., 1990).

For increased stability of LMW peptide DNA condensates, glutaraldehyde may be used as a cross-linking agent that both slows DNA metabolism and alters the in vitro transient gene expression profile (Example 4; Adami and Rice, 1999). The present inventors have also prepared formulations of PEG-CWK$_{18}$ DNA condensates that mask the surface charge of DNA condensates and reduce non-specific interactions with cells (Kwok et al., 1999).

Aspects of the present disclosure concern the in vivo analysis of glutaraldehyde cross-linked DNA co-condensates prepared with Tri-CWK$_{18}$ and PEG-CWK$_{18}$ to systematically optimize DNA targeting to hepatocytes via the ASGP-R (Example 7). Optimal targeting to hepatocytes was achieved by the combined use of the triantennary glycopeptide and PEG-CWK$_{18}$, to mediate specific recognition by the asialoglycoprotein receptor and to reduce non-specific uptake by Kupffer cells.

The results in Example 7 suggest that all LMW carriers, by themselves, are not sufficient to mediate effective gene targeting of an i.v. dosed DNA formulation. This is not immediately evident from a preliminary investigation, since 58% of Tri-CWK$_{18}$ DNA condensates targeted the liver after 5 min of biodistribution. However, when evaluated in light of control studies demonstrating that plasmid DNA and AlkCWK$_{18}$ DNA condensates also target the liver with similar efficiency, it becomes clear that plasmid DNA is released upon dissociation of LMW carriers during circulation.

Also, cross-linked Tri-CWK$_{18}$ DNA condensates are not sufficient to achieve maximum hepatocyte targeting even though the oligosaccharide used is a potent ligand for the ASGP-R, possessing a million-fold greater affinity than galactose (Rice et al., 1990). Despite the presence of approximately 700 copies of the triantennary ligand per 6.9 kb plasmid, the electropositive charge of cross-linked Tri-CWK$_{18}$ DNA condensates is apparently still detected by Kupffer cells. It is also interesting to note that cross-linked Tri-CWK$_{18}$ DNA condensates did have significantly altered biodistribution in comparison to HMW polylysine and cross-linked AlkCWK$_{18}$ DNA condensates of comparable size and charge. The presence of the triantennary N-glycan allowed these DNA condensates to avoid lung targeting, presumably by blocking opsonization in the serum.

By incorporating both PEG-CWK$_{18}$ and Tri-CWK$_{18}$ into DNA condensates, specific recognition by hepatocytes can be achieved. Specific hepatocyte targeting closely correlated with a decreased zeta potential, indicating that PEG functioned to block Kupffer cell recognition by masking the surface charge of Tri-CWK$_{18}$ DNA condensates. The masking was equally efficient with either 50, 90, or 98 mol % PEG-CWK$_{18}$, as indicated by the hepatocyte targeting efficiency. Moreover, this data indicates that attachment of as few as 14 copies (2 mol %) of the triantennary oligosaccharide to a plasmid is sufficient to mediate specific recognition by the ASGP-R and that the surface bound PEG does not sterically block ASGP-R recognition of Tri-CWK$_{18}$. Using this high affinity ligand, the ASGP-R was able to bind DNA co-condensates in the dosing range of 2.5–50 μg delivered via tail vein without a significant reduction in target selectivity for hepatocytes (Table 6).

Central aspects of the present invention concern the use of LMW carriers in combination with cross-linking agents to stabilize the resultant DNA carrier condensates. The advantages of this approach are that LMW carriers can be synthesized, purified and structurally characterized, eliminating uncertainty over the stoichiometry or attachment site of ligands to the backbone peptide. Two or more LMW carriers can then be combined and used to condense DNA to form co-condensates. Since each LMW carrier contains an identical cationic peptide they incorporate into DNA co-condensates according to their admix ratio (Kwok et al., 1999), allowing systematic optimization of the amount of ligand or PEG bound to DNA condensates.

The use of certain molecular cross-linking mechanisms, such as glutaraldehyde, to stabilize DNA condensates to metabolism can result in an overall lower level of in vitro gene expression, which appears also to be true of in vivo expression. Likewise, certain cross-linked LMW carriers may resemble HMW carriers once they are released inside the cell and exhibit similar toxicity. The preferred self-crosslinking peptides of the present invention circumvent these problems by providing transiently stabilized LMW DNA carrier condensates with enhanced gene expression levels (Example II; McKenzie et al., 1999b).

Example 7 provides proof of principle for specific targeting of DNA to hepatocytes using cross-linked DNA-peptide condensates with targeting agents and PEG. The metabolic stabilization afforded by cross-linking is apparent by comparison of the liver $t_{1/2}$ of uncross-linked and cross-linked Tri-CWK$_{18}$ DNA condensates (FIG. 49A through FIG. 49I). Since retention of DNA in the target site is an important prerequisite to sustaining transient gene expression, the degree of cross-linking can be used as an adjustable parameter to control the time of onset or duration of gene expression.

Incorporating PEG-CWK$_{18}$ into DNA condensates resulted in a large of 40–60 min in the peak accumulation of $^{125}$I-DNA in the liver (FIG. 49E, FIG. 49F, FIG. 49G, FIG. 49H, FIG. 49I). Since this lag is not apparent when using uncross-linked DNA condensates (FIG. 49A, FIG. 49B, FIG. 49C), it is unlikely the result of re-distribution and uptake of metabolized $^{125}$I-DNA. It is more likely due to a slower recognition of the DNA condensate by either the asialoglycoprotein receptor when incorporating Tri-CWK$_{18}$ or by the Kupffer cell scavenger receptor when substituted with agalactosyl-Tri-CWK$_{18}$.

Comparison of the transient gene expression of optimized LMW dosage forms with and without ligand established a dependency on galactose. The maximal gene expression occurring at day-7 is mostly likely due to the slow release of cross-linked DNA co-condensates. Although the serum levels of the hAAT are lower than hepatic portal vein dosed viral vector delivery systems (Kay et al., 1995), there is no reference data regarding the levels of liver expression of hAAT following i.v. dosing of a viral delivery systems.

In conclusion, the results of Example 7 demonstrate that it is possible to use a combination of LMW carrier molecules to achieve cell-type specific gene delivery and transient gene expression in vivo. The liver targeting information of Example 7 also provides a foundation for DNA targeting to other organs. The choice of specific targeting ligand and receptor combinations will be straightforward to those of skill in the art in light of the present disclosure.

Applying the techniques of Example 7 to the self cross-linking strategies of Example 5 and Example 6 can also be readily achieved, thus further optimizing the use of LMW carriers in gene expression. In so doing, the relationships between the physiochemical properties and the biodistribution of gene delivery compositions will be equated to provide optimized formulations for selective gene targeting and expression in vivo.

The following examples are included to demonstrate various embodiments of the invention. It will be appreciated by those of skill in the art that the techniques disclosed in the examples that follow represent techniques discovered by the inventors to function in the practice of the invention. Certain preferred modes for practicing the invention are provided therein. However, those of skill in the art will, in light of the present disclosure, appreciate that many changes can be made in the specific embodiments disclosed and still obtain a like or similar result without departing from the spirit and scope of the invention.

TABLE A

Peptide Identification

| Name | EXAMPLE 5 | Example 6 | SEQ ID NO: |
|---|---|---|---|
| CWK$_{18}$ | I | 1 | No. 1 |
| Alk-CWK$_{18}$ | | | Alk-No. 1 |
| DiCWK$_{18}$ | | | No. 2 |
| | II | 3 | No. 3 |
| | III | | No. 4 |
| | IV | | No. 5 |
| | V | | No. 6 |
| | | 2 | Alk-No. 7 |
| | | 4 | No. 8 |
| | | 5 | No. 9 |
| | | 6 | No. 10 |
| | | 7 | No. 11 |
| | | 8 | No. 12 |
| | | 9 | No. 13 |
| | | 10 | No. 14 |
| | | 11 | No. 15 |
| | | 12 | No. 16 |
| | | 13 | No. 17 |
| | | 14 | No. 18 |
| | | 15 | No. 19 |
| | | 16 | No. 20 |
| Exemplary PenPeptide | | | No. 21 |

*** - FUS - INSERT HERE

EXAMPLE 1

PEG-Peptide DNA Condensates

The present example concerns the ability of poly(ethylene glycol) (PEG)-peptides to bind to plasmid DNA and form soluble DNA condensates with reduced spontaneous gene expression. PEG-vinylsulfone or PEG-orthopyridyl-disulfide was reacted with the sulfhydryl of Cys-Trp-Lys$_{18}$ (CWK$_{18}$) (Cys-Typ-Lys$_{18}$; SEQ ID NO:1) resulting in the formation of non-reducible (PEG-VS-CWK$_{18}$) and reducible (PEG-SS-CWK$_{18}$) PEG-peptides. Both PEG-peptides were prepared on a $\mu$mol scale, purified by RP-HPLC in >80% yield, and characterized by (Zhang et al., 1997) H-NMR and MALDI-TOF. PEG-peptides bound to plasmid DNA with an apparent affinity that was equivalent to alkylated (Alk)CWK$_{18}$, resulting in DNA condensates with mean diameter of 80–90 nm and zeta potential of +10 mV. The particle size of PEG-peptide DNA condensates was constant throughout the DNA concentration range of p0.05–2 mg/ml, indicating these to be approximately 20-fold more soluble than AlkCWK$_{18}$ DNA condensates.

The spontaneous gene transfer of HepG2 cells mediated by PEG-VS-CWK$_{18}$ DNA condensates was over two-orders of magnitude lower than PEG-SS-CWK$_{18}$ DNA condensates and three-orders of magnitude lower than AlkCWK$_{18}$ DNA condensates. PEG-VS-CWK$_{18}$ efficiently blocked in vitro gene transfer by reducing cell uptake. The results indicate that PEG loaded on DNA, preferably at a high loading, is able to achieve highly soluble DNA condensates that reduce spontaneous in vitro gene transfer (as exemplified by blocking non-specific uptake by HepG2 cells). These two properties are important for developing targeted gene delivery systems to be used in vivo.

A. Introduction

A variety of macromolecules including cationic lipids (Zhang et al., 1997), polylysine (Wu and Wu, 1988), polyethyleneimine (Ogris et al., 1998), and dendrimers (Tang et al., 1996) have been used as carriers to negatively charged plasmid DNA and facilitate spontaneous gene transfer in cell culture as a result of charge interaction between the DNA carrier complex and the cell surface. Unfortunately, the performance of these nonviral gene delivery carriers is far less efficient in vivo due in part to the rapid pharmacokinetics and clearance of DNA complexes (Niven et al., 1996; Nishikawa et al., 1998). This relates to both the particle size and surface charge of the delivery system (Kwhoh et al., 1999). For example, cationic liquids form large DNA complexes that are trapped in the capillary beds of the lung (Niven et al., 1996), whereas smaller (<100 nm) peptide DNA condensates are scavenged by mononuclear phagocytic system (MPS) cells of the liver (Nishikawa et al., 1998), limiting the development of DNA delivery systems that target peripheral tissues.

The intravenous dosing of most colloids leads to opsonization and MPS cell uptake in the lung, liver, and spleen (Woodle, 1998). In the case of liposomes, this limitation has been largely overcome by simultaneously reducing the particle size to <100 nm and modifying the surface with PEG (Torchilin et al., 1994) since this polymer possesses the ideal hydration and flexibility to crate a steric layer that allows liposomes to avoid opsonization and detection by MPS cells (Torchilin, 1998).

Several studies have described the synthesis of PEG-containing polymers designed to create a steric layer on the surface of DNA condensates (Kwhoh et al., 1999; Wolfert et al., 1996; Toncheva et al., 1998; Choi et al., 1998; 1999; Harada and Kataoka, 1995; Katayose and Kataoka, 1997; 1998), with the aim of improving their solubility and in vivo performance. An early study by Wolfert et al. described the synthesis of grafted co-polymers of PEG (5 or 12 kDa) and polylysine$_{100}$ prepared by carbodiimide coupling 5–10 mol % of succinylated-PEG onto the side chains of polylysine (Wolfert et al., 1996; Toncheva et al., 1998). The resulting PEG-peptides were less toxic to cells in culture compared to polylysine$_{100}$, formed DNA condensates possessing a reduced effective surface charge, and had slightly improved solubility over control polylysine DNA condensates but, surprisingly, were unable to reduce spontaneous gene transfer in HepG2 cells (Tonchev et al., 1988) in vitro suggesting they would not be able to block non-specific interactions with cells in vivo.

Subsequently, Choi et al. derivatized the side chains of polylysine$_{120}$ with 5–25 mol % low molecular weight PEG of 550 Da (Choi et al., 1998). The resulting PEG-peptide DNA condensates were also less toxic to cells than polylysine$_{120}$ DNA condensates but were similar to Wolfert's PEG-peptide in their ability to reduce spontaneous gene transfer in HepG2 cells, indicating that low molecular weight PEG was no more effective than high molecular weight PEG. Using a similar approach, PEG polylysine dendrimer copolymers were recently reported by the same group and used to form DNA condensates that were more nuclease resistant than polylysine DNA condensates but which were not examined for gene transfer (Choi et al., 1999).

In addition, Katayose et al. synthesized PEG-polylysine block copolymers to incorporate 5 kDa PEG into polylysine by random polymerization of N-carboxyanhydride ε-Benzyloxycarbonyl-Lysine with amino-PEG, resulting in a polymer with a lysine to PEG ratio of approximately 18:1 (Harada and Kataoka, 1995; Katayose and Kataoka, 1997) representing approximately 5 mol % PEG. These PEG-polylysine DNA condensates were also reportedly much more resistant to endonuclease than uncondensed DNA but were not examined for solubility or gene transfer (Katayose and Kataoka, 1997; 1998).

To date, there are no reports of a PEG-peptide DNA condensing agents that significantly increase the solubility of the DNA condensates and/or reduce spontaneous gene transfer to HepG2 cells. These are both significant problems since the poor solubility of peptide DNA condensates of approximately 50–100 μg/ml limits the dosing volume and precludes dose escalation during in vivo gene transfer. Likewise, reducing the level of spontaneous gene transfer in vitro in a first step toward developing DNA formulations that avoid non-specific gene transfer to cell in vivo, allowing the development of DNA formulations that target to peripheral sites.

The present example describes the synthesis and formulation properties of PEG-peptides that significantly improve DNA condensate solubility, one of which dramatically reduces spontaneous gene transfer of DNA condensates in vitro. The results suggest that these two properties are closely linked to the loading level of PEG on peptide DNA condensates.

B. Materials and Methods

1. Materials

PEG-orthopyridyl-disulfide (PEG-OPSS, 5 kDa) and PEG-vinylsulfone (PEG-VS, 5 kDa) were purchased from Shewarwater Inc. (Huntsville, Ala.) and Fluka (Ronkonkoma, N.Y.), respectively. Fetal calf serum and LipofectAce™ were obtained from Gibco BRL (Gaithersburg, Md.). Minimum essential media (MEM) and CM Sephadex™ C50 were purchased from Sigma (St. Louis, Mo.). TCEP (tris(2-carboxyethyl) phosphine hydrochloride) was purchased from Aldrich, (Milwaukee, Wis.). D-luciferin and luciferase from *Photinus pyralis* were from Boehringer Mannheim (Indianapolis, Ind.).

The 5.6 kb plasmid (pCMVL) encoding the reporter gene luciferase under the control of the cytomegalovirus promoter was obtained from Dr. M. A. Hickman at the University of California, Davis (Plank et al., 1992). pCMVL was produced in *E. coli* and purified using a Quiagen Ultrapure™-100 kit (Santa Clarita, Calif.). Bradford reagent was purchased from Bio-Rad (Hercules, Calif.). Preparative and analytical C18 reverse phase HPLC columns were purchased from Vydac (Hesperia, Calif.). HPLC was performed using a computer-interfaced HPLC and fraction collector from ISCO (Lincoln, Neb.).

2. Synthesis of PEG-VS-CWK18 and PEG-SS-CWK18

CWK$_{18}$ (Cys-Trp-Lys$_{18}$) and dimeric-CWK$_{18}$ were synthesized and characterized as described previously (Wadhwa et al., 1997; specifically incorporated herein by reference). The Cys residue on CWK$_{18}$ was alkylated with iodoacetic acid resulting in AlkCWK$_{18}$ as reported (Wadhwa et al., 1997). The synthesis of PEG-VS-CWK$_{18}$ utilized dimeric-CWK$_{18}$ (0.5 μmol), which was reduced to form 1 μmol of CWK$_{18}$ by reaction with 25 μmol of TCEP (Burns et al., 1991) in 0.5 ml of 0.1 M sodium phosphate pH 7 for 4° h at RT.

PEG-VS-CWK$_{18}$ was formed by reacting 1 μmol of reduced CWK$_{18}$ with 30 μmol of PEG-VS in a total volume of 1.2 ml of 0.1 M sodium phosphate pH 7 at RT for 12 h. The progress of the reaction was monitored by analytical RP-HPLC eluted at 1 ml/min with 0.1% TFA and a gradient of acetonitrile (5–65% over 30 min) while detecting by $A_{280\,nm}$. The reaction mixture was applied to a CMP Sephadex™ C50 cation-exchange column (0.7×15 cm) eluted with 60 ml of water to remove free PEG-VS as the unbound fraction, then with 15 ml of 1.5 M sodium chloride while collecting 5 ml fractions.

PEG-VS-CWK$_{18}$ and CWK$_{18}$ were detected by $A_{280\,nm}$ and were pooled and desalted by 5 h dialysis against 4 L of water in 1000 MWCO tubing then freeze dried. PEG-VS-CWK$_{18}$ was resolved from CWK$_{18}$ by injecting 0.5 $\mu$mol onto a semi-preparative C18 RP-HPLC column (2×25 cm) eluted at 10 ml/min with 0.1% TFA and a gradient of acetonitrile (5 to 65% over 30 min) while detecting by $A_{280\,nm}$. The peak eluting at 25 min yielded 0.8 $\mu$mol of PEG-VS-CWK$_{18}$ (80%) based on tryptophan absorbance ($\epsilon_{280\,nm}$=5600 M$^{-1}$cm$^{-1}$).

A disulfide bond exchange reaction was used to prepare PEG-SS-CWK$_{18}$. Prior to conjugation of PEG-OPSS, dimeric-CWM$_{18}$ was reduced and then purified by RP-HPLC eluted as described above. Reduced CWK$_{18}$ (1 $\mu$mol) was reacted with 4 $\mu$mols of PEG-OPSS in 1 ml of 0.1 M sodium phosphate pH 7 at RT for 30 min. The reaction was monitored by analytical RP-HPLC, which detected a single new produced peak eluting at 25 min. PEG-SS-CWK$_{18}$ was purified by injecting 0.5 $\mu$mol portions onto semi-preparative RP-HPLC eluted as described above resulting in an isolated yield of 95%.

PEG-VS-CWK$_{18}$ and PEG-SS-CWK$_{18}$ (1 $\mu$mol) were prepared for $^1$H-NMR by D$_2$O exchange followed by dissolving the sample in 0.5 ml of D$_2$O (99.96%) containing acetone as an internal standard. $^1$H-NMR spectra were generated on a Bruker 500 MHz spectrometer operated at 23° C. PEG-peptides were prepared for MALDI-TOF by dissolving 5 nmol in 20 $\mu$l of water. These (0.5 $\mu$l) were combined 0.5 $\mu$l of saturated $\alpha$-cyano-4-hydroxycinnamic acid in 50 vol/vol % acetonitrile and 0.3% trifluoroacetic acid and then analyzed on a Vestec LasterTec™ MS (PerSeptive Biosystems, Framingham, Mass.) operated in the linear mode at 20 kV.

3. Formulation of Peptide DNA Condensates

Peptide DNA condensates were formed by adding 75 $\mu$g of DNA (pCMVL in 750 $\mu$l of 5 mM Hepes pH 7.4) to varying amounts of peptide (7.5 to 90 nmol in 750 $\mu$l of Hepes) while vortexing, followed by equilibration at RT for 1 h. Peptide binding to DNA was monitored by a fluorescent dye displacement assay (Wadhwa et al. 1997). A 1 $\mu$g aliquot of the peptide DNA condensate was diluted to 1 ml in Hepes containing 0.1 $\mu$M thiazole orange. The fluorescence of the intercalated dye was measured on an LS50B fluorimeter (Perkin Elmer, UK) in a microcuvette by exciting at 500 nm while monitoring emission at 530 nm.

The particle size of peptide DNA condensates were analyzed at a DNA concentration of 50 $\mu$g/ml in Hepes by quasielastic light scattering (QELS). The particle surface change was determined by zeta potential analysis using a Brookhaven ZetaPlus™ (Brookhaven Instruments). The solubility of peptide DNA condensates were determined by measuring particle size as a function of DNA concentration (50 $\mu$g/ml to 2 mg/ml) at a constant peptide:DNA stoichiometry of 0.4 nmol of peptide per $\mu$g of DNA corresponding to a charge ratio (NH$_4^+$:PO$_4^-$) of 2.3:1.

DNA co-condensates were prepared by add-mixing AlkCWK$_{18}$ and PEG-VS-CWK$_{18}$ in ratios ranging from 0 to 100 mol %, and condensing DNA at a charge ratio of 2.3:1 as described above. To establish the mol ratio of peptides bound to DNA, condensates were dialyzed in a fixed volume (0.5 ml) dialyzer for 75 h against water using a 100,000 MWCO membrane. Peptide DNA condensates in the retentate (0.5 ml) were dissociated by adding 50 $\mu$l of 5 M sodium chloride in 0.1% TFA. AlkCWK$_{18}$ and PEG-VS-CWK$_{18}$ were quantified by injecting 1 nmol of peptide (100 $\mu$l) onto analytical RP-HPLC eluted with 0.1% TFA and a gradient of acetonitrile (5 to 65% over 30 min) while detecting tryptophan by fluorescence ($\lambda_{ex\,280\,nm}$, $\lambda_{em\,350\,nm}$). The peak integration areas were used to quantify AlkCWK$_{18}$ and PEG-VS-CWK$_{18}$ with reference to standard curves developed for each peptide.

4. In Vitro Gene Expression and Cell Binding

HepG2 cells were plated at 1.5×10$^5$ cells per 35 mm well and grown to 40–70% confluence in MEM supplemented with 10% fetal calf serum (FCS). Peptide DNA condensates (10 $\mu$g of DNA) were added dropwise to triplicate sets of cells in 2% FCS containing 80 $\mu$M chloroquine. After 5 h incubation at 37° C., the media was replaced with MEM supplemented with 10% FCS, and luciferase expression was determined at 24 h. Cells were washed twice with ice-cold phosphate buffered saline (calcium and magnesium free) and then treated with 0.5 ml of ice-cold lysis buffer (25 mM Tris hydrochloride pH 7.8, 1 mM EDTA, 8 mM magnesium chloride, 1% Triton X-100, 1 mM DTT) for 10 min. The cell lysate was scraped, transferred to 1.5 ml micro centrifuge tubes, and centrifuged for 7 min at 13,000 g at 4° C. to pellet debris.

Lysis buffer (300 $\mu$l), sodium-ATP (4 $\mu$l of a 180 mM solution, pH 7, 4° C.) and cell lysate (100 $\mu$l, 4° C.) were combined in a test tube, briefly mixed and immediately placed in the luminometer. Luciferase relative light units (RLU) were recorded on a Lumat™ LB 9501 (Berthold Systems, Germany) with 10 sec integration after automatic injection of 100 $\mu$l of 0.5 mM D-luciferin (prepared fresh in lysis buffer without DTT). The expression level of luciferase was normalized for protein using the Bradford assay (1976), and the relative light units were converted to fmol of luciferase/mg of protein using a standard curve developed by adding luciferase to cell supernatant. Each experimental result represents the mean and standard deviation derived from a triplicate set of transfections.

LipofectAce™ (Gibco BRL, 1:2.5 w/w dimethyl diocta-decylammonium bromide and dioleoylphosphatidylethanolamine) was optimized for use to mediate gene transfection in HepG2 cells according to the manufacturer's instructions. DNA/LipofectAce™ complexes were prepared by combining 10 $\mu$g of DNA in 100 $\mu$l of serum free media (SFM) with 60 $\mu$l of LipofectAce™ prepared in 150 $\mu$l of SFM. The LipofectAce™ DNA complex was then diluted with 1.7 ml of SFM and used to transfer HepG2 cells for 5 h followed by replacement of the transfecting media with MEM supplemented with 10% FBS. The cells were incubated for a total of 24 h, then harvested, and analyzed for luciferase as described above.

Iodinated plasmid DNA was prepared with specific activity of 300 nCi per $\mu$g of DNA as described previously (Teribesi et al., 1998). Prior to forming DNA condensates, the specific activity of the $^{125}$I DNA was adjusted to 4.5 nCi per $\mu$g of DNA by combining with unlabeled plasmid. DNA condensates were prepared using AlkCWK$_{18}$, PEG-SS-CWK$_{18}$ or PEG-VS-CWK$_{18}$ as described above. Peptide $^{125}$I-DNA condensates (10 $\mu$g) were used to transfer HepG2 cells for 5 h according to the procedure described above. The radioactive media was removed, cells were washed with phosphate buffered saline, harvested with lysis buffer, and the cell-associated radioactivity was quantified by gamma counting.

C. Results

1. PEG-Peptide Synthesis

Figures 1, 18A:
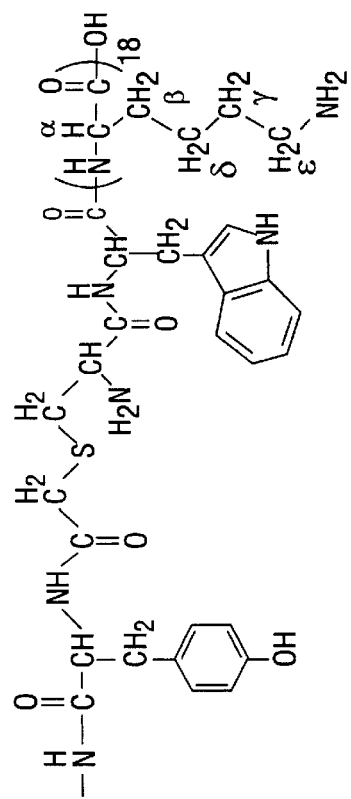
FIG. 18A and FIG. 18B. Structure of Synthetic Glycopeptides.

PEG was covalently attached to the Cys residue of a 20 amino acid synthetic peptide ($CWK_{18}$) to prepare two PEG-peptides possessing either a reversible (PEG-SS-$CWK_{18}$) or irreversible (PEG-VS-$CWK_{18}$) covalent linkage (FIG. 1). Each reaction was optimized by systematically changing the pH and the stoichiometry of peptide to PEG while monitoring the product formation by analytical RP-HPLC. Since the reaction of $CWK_{18}$ with PEG-VS at pH 7 was slow (12 h), TCEP was added to reduce dimeric-$CWK_{18}$ and also inhibit its re-formation during conjugation with PEG-VS. At pH 7, a mol ratio of PEG-VS:$CWK_{18}$ of 30:1 resulted in optimal conjugation to form PEG-VS-$CWK_{18}$. AT suboptimal stoichiometries or lower pH the reaction was incomplete whereas at a higher pH, dimeric-$CWK_{18}$ re-formed as the major product.

In contrast to the synthesis of PEG-VS-$CWK_{18}$, the optimal reaction conditions to prepare PEG-SS-$CWK_{18}$ only required a 4 mol excess of PEG-OPSS over $CWK_{18}$ at pH 7. In this case, attempts to block the formation of dimeric-$CWK_{18}$ with TCEP led to the reduction of PEG-OPSS, completely inhibiting the desired reaction. Instead, reduced $CWK_{18}$ was prepared and found to react rapidly (30 min) with PEG-OPSS with minimal formation of dimeric-$CWK_{18}$.

Figure 3A:
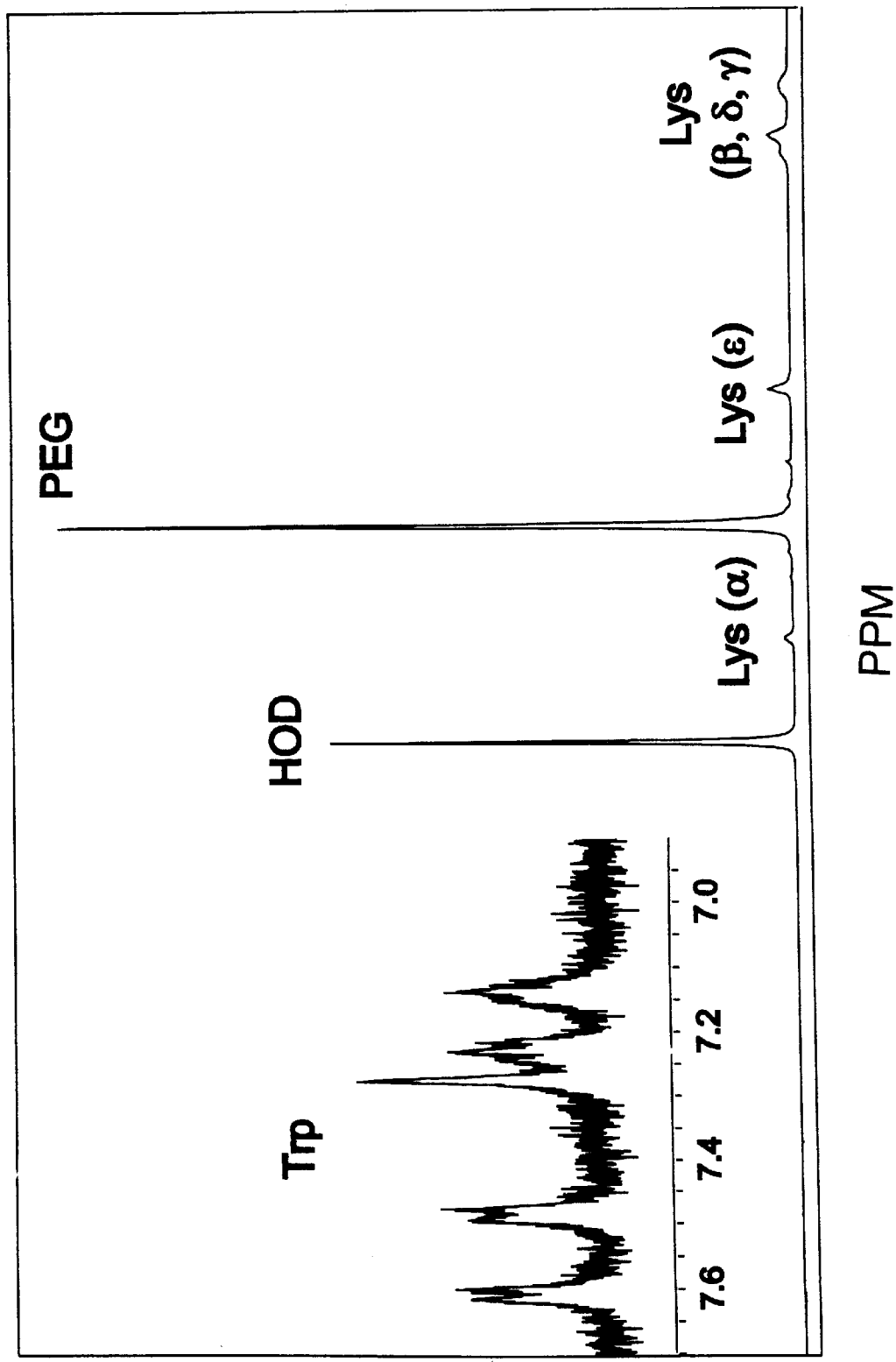
FIG. 3A and FIG. 3B. $^1$H-NMR Analysis of PEG-CWK$_{18}$ Conjugates. The 500 MHz $^1$H-NMR spectrum of PEG-VS-CWK$_{18}$ (FIG. 3A) and PEG-SS-CWK$_{18}$ (FIG. 3B) are illustrated with the key signals of the Lys, Trp and PEG identified according to FIG. 1. The integration of the $\epsilon$ proton of Lys relative to the PEG protons established a degree of polymerization of 122 for PEG-VS-CWK$_{18}$ and 123 for PEG-SS-CWK$_{18}$.
Figures 2, 18A:
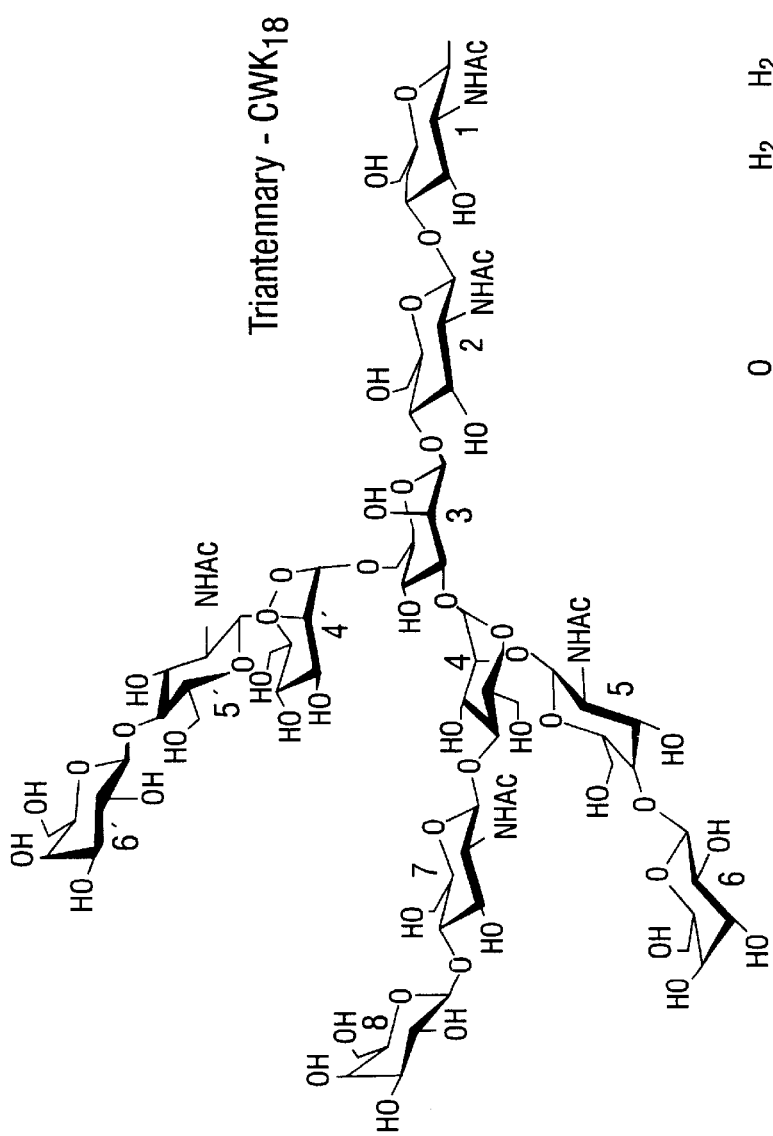

RP-HPLC analysis of the crude reaction product of PEG-VS-$CWK_{18}$ demonstrated a nearly complete disappearance of $CWK_{18}$ with the formation of a new peak eluting at 25 min (FIG. 2B). Despite the apparent complete resolution of the desired product, careful examination revealed that PEG-VS co-eluted with PEG-VS-$CWK_{18}$. This was evident from NMR analysis, which determined a 10-fold excess of PEG relative to $CWK_{18}$ in the HPLC purified product. Consequently, PEG-VS-$CWK_{18}$ was purified using cation exchange to remove excess PEG-VS and then by RP-HPLC to remove unreacted $CWK_{18}$ resulting in a product that rechromatographed as a single peak on RP-HPLC (FIG. 2D). Proton NMR analysis identified resonances assigned to the $\alpha$, $\beta$, $\gamma$, $\delta$ and $\epsilon$ protons of the Lys residues as well as the Trp aromatic resonances (FIG. 3A). Integration of protons at $\delta$ 3.67 ppm (PEG) relative to the signal at 2.97 ppm (Lys $\epsilon$) produced a peak area ratio of 13.5:1 corresponding to a 1:1 conjugate of $PEG_{122}$ and $CWK_{18}$.

Figure 3B:
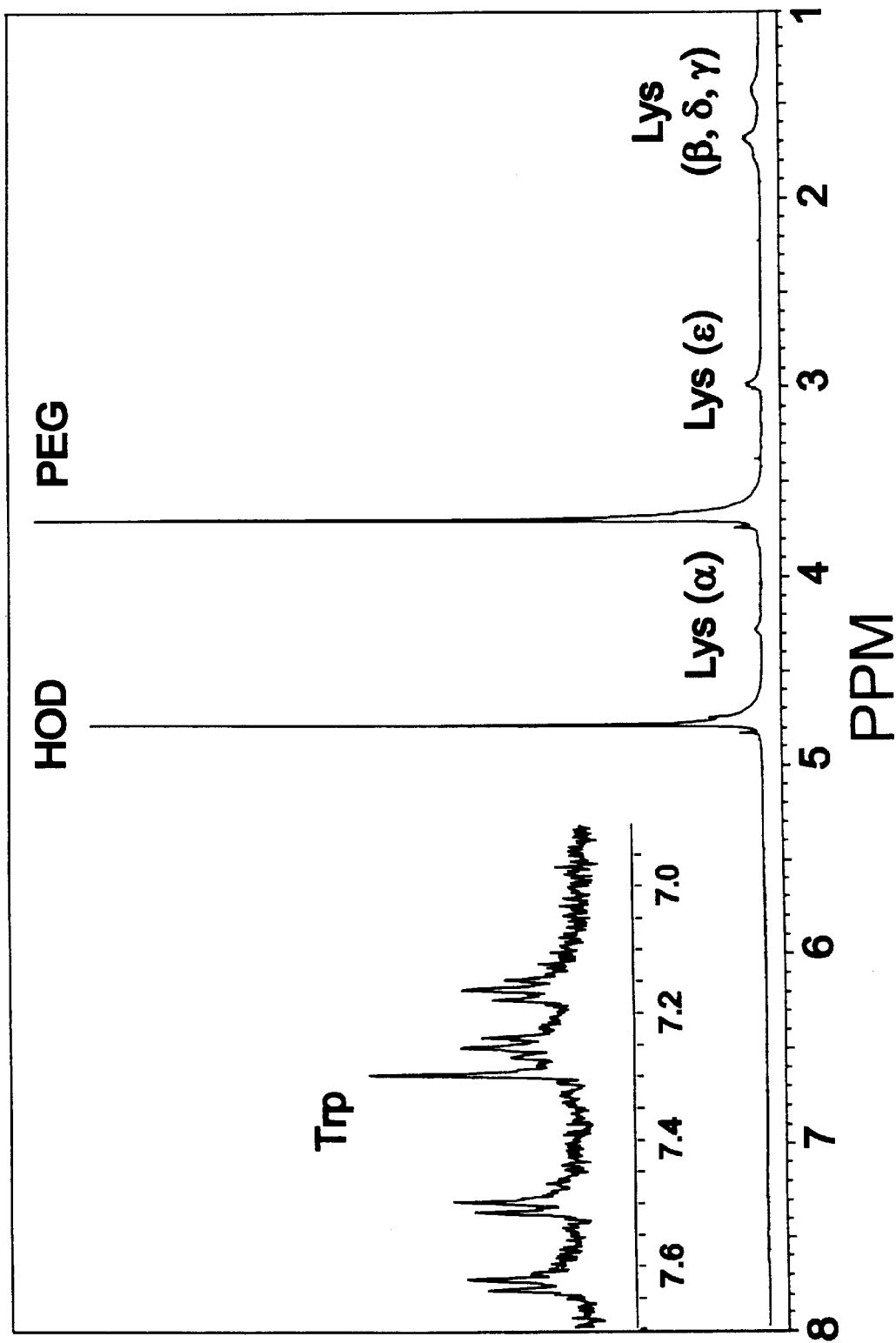

RP-HPLC analysis of the crude reaction product of PEG-OPSS and $CWK_{18}$ identified a product peak eluting at 25 min, a PEG-OPSS reagent peak at 28 min, a thiol pyridine (TP) by-product peak at 5 min and a trace of dimeric-$CWK_{18}$ eluting at 15 min (FIG. 2C). PEG-SS-$CWK_{18}$ was isolated in a single step by semi-preparative RP-HPLC, rechromatographed as a single peak on analytical HPLC (FIG. 2E), and produced an NMR spectrum with an integration ratio of PEG:Lys also establishing a 1:1 conjugate of $PEG_{123}$ and $CWK_{18}$ (FIG. 3B).

MALDI-TOF analysis of PEG-VS-$CWK_{18}$ and PEG-SS-$CWK_{18}$ produced a broad peak centered at 8433 and 8297 m/z, respectively. These results were consistent with the formation of conjugates of $CWK_{18}$ (2648 amu) and polydisperse PEG of approximately 5800 Da.

2. PEG-Peptide DNA Condensate Formulation

Figure 4:
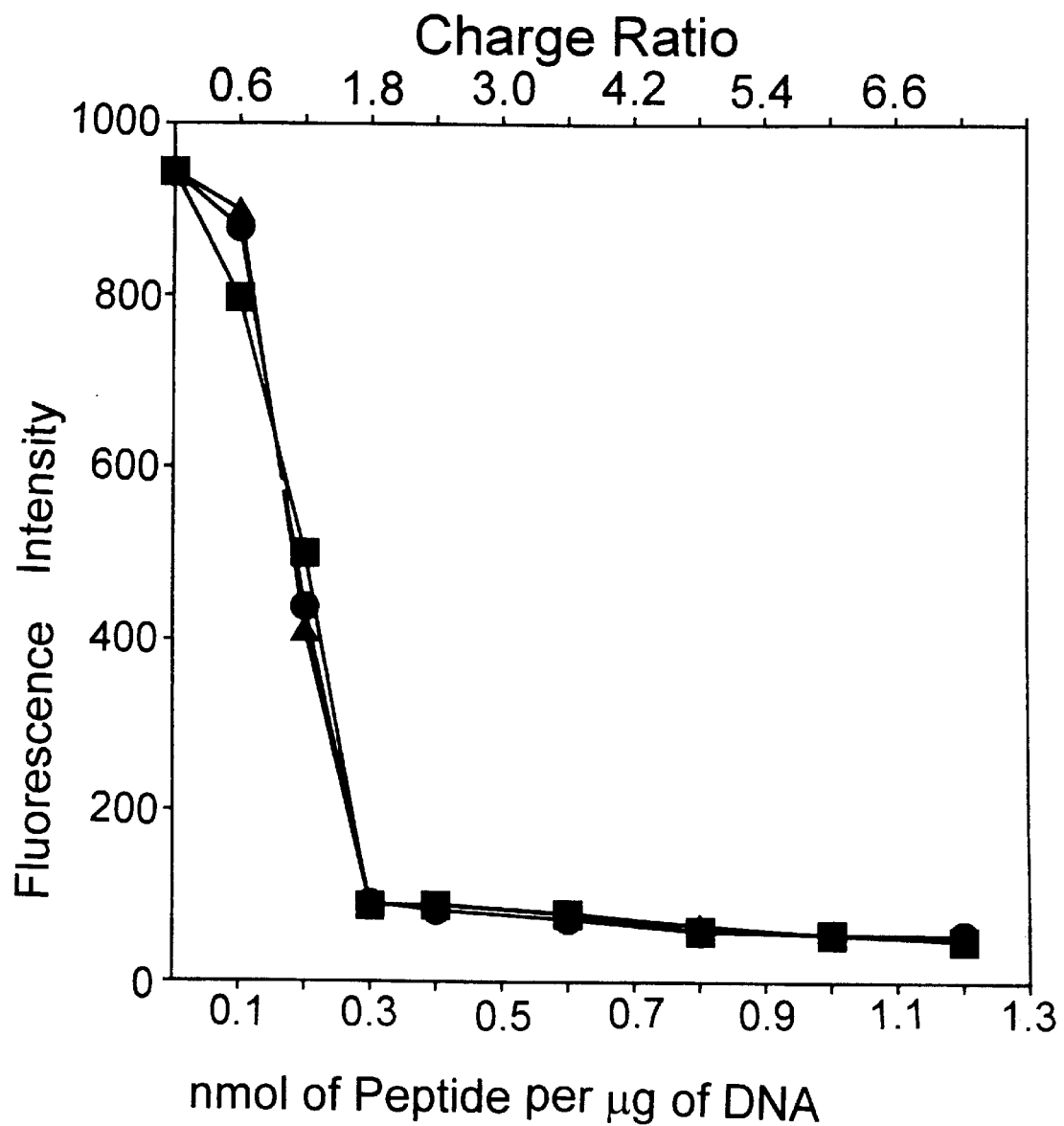
FIG. 4. Relative Binding Affinity of PEG-CWK$_{18}$ Conjugates to DNA. The fluorescence intensity resulting from the titration of AlkCWK$_{18}$ (●), PEG-SS-CWK$_{18}$ (■), and PEG-VS-CWK$_{18}$ ($\pi$) to compete for intercalator dye binding to DNA is shown. An asymptote at 0.3 nmol of each peptide per $\mu$g of DNA established that each peptide binds to DNA with equivalent affinity.

The DNA binding affinity of $AlkCWK_{18}$, PEG-VS-$CWK_{18}$ and PEG-SS-$CWK_{18}$ were compared using a fluorescent dye displacement assay. A coincident titration curve for each peptide with an asymptote at 0.3 nmol per µg of DNA corresponding to a charge ratio of 1.8:1 suggested that both PEG-peptides bind to DNA with equivalent affinity as $AlkCWK_{18}$ (FIG. 4).

The particle size and zeta potential of DNA condensates prepared with $AlkCWK_{18}$, PEG-VS-$CWK_{18}$ and PEG-SS-$CWK_{18}$ were examined as a function of peptide: DNA stoichiometry (FIG. 5A and FIG. 5B). The mean diameter for both PEG-peptide DNA condensates was 90 nm at a charge ratio of 1.8:1 or higher whereas the mean diameter for $AlkCWK_{18}$ DNA condensates was 60 nm (FIG. 5A). In contrast, a large decrease in zeta potential of +25 mV was identified for PEG-peptide DNA condensates at a charge ratio of 1.8:1 compared to $AlkCWK_{18}$ DNA condensates (FIG. 5B).

Figures 6A, 6B:
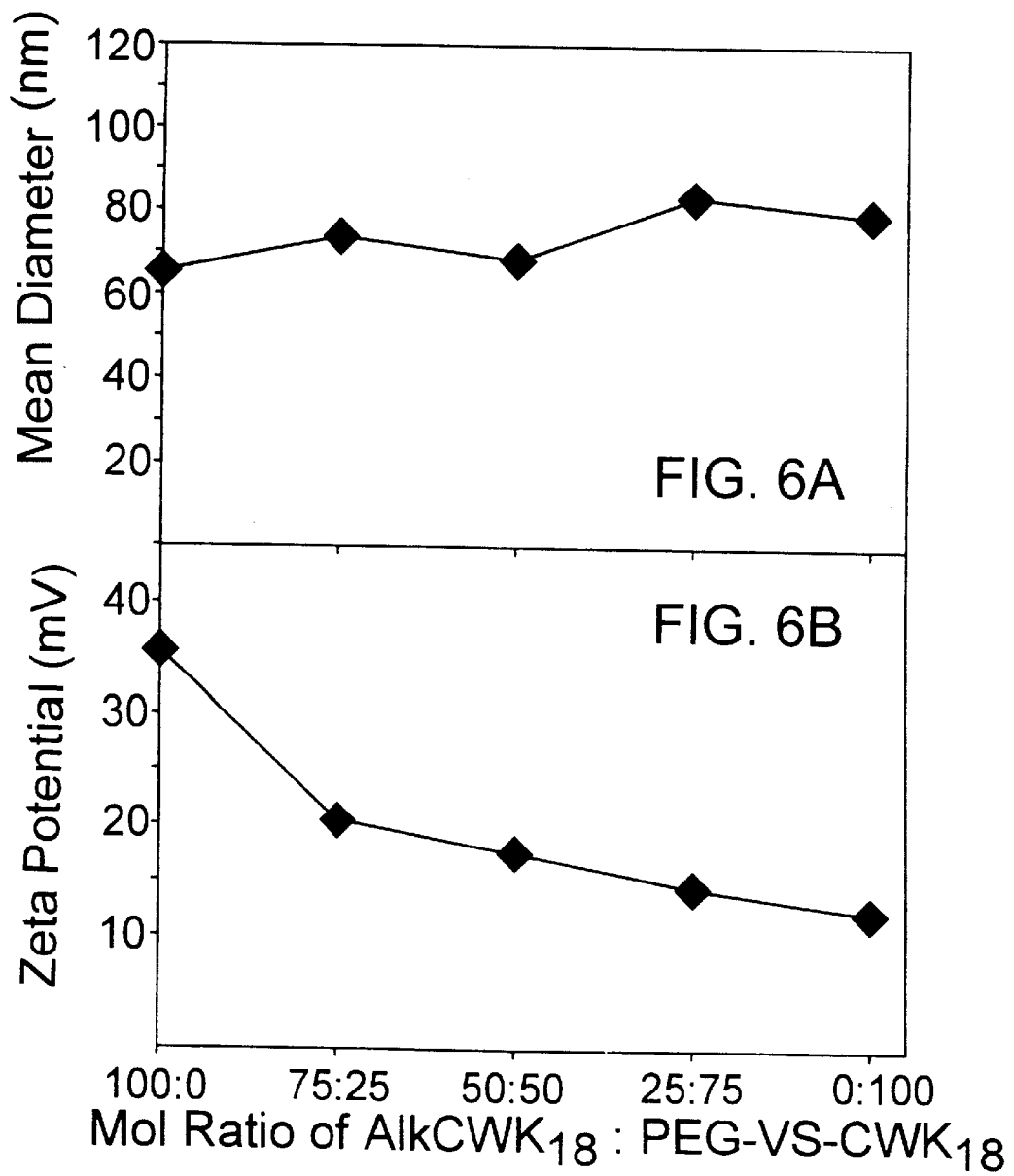
FIG. 6A and FIG. 6B. QELS Particle Size and Zeta Potential Analysis of Peptide DNA Co-Condensates.

Since PEG-VS-$CWK_{18}$ and $AlkCWK_{18}$ possess equivalent DNA binding affinity, add-mixtures of the two peptides were used to prepare DNA co-condensates. The average particle size increased from 65 to 80 nm using add-mixtures of $AlkCWK_{18}$ and PEG-VS-$CWK_{18}$ varying from 0 to 100 mol % while keeping the charge ratio constant at 2.3:1 (FIG. 6A). Likewise, the zeta potential decreased from +35 mV to +10 mV as the stoichiometry of PEG-VS-$CWK_{18}$ increased (FIG. 6B), suggesting the formation of DNA co-condensates with intermediate PEG loading.

Figure 7A:
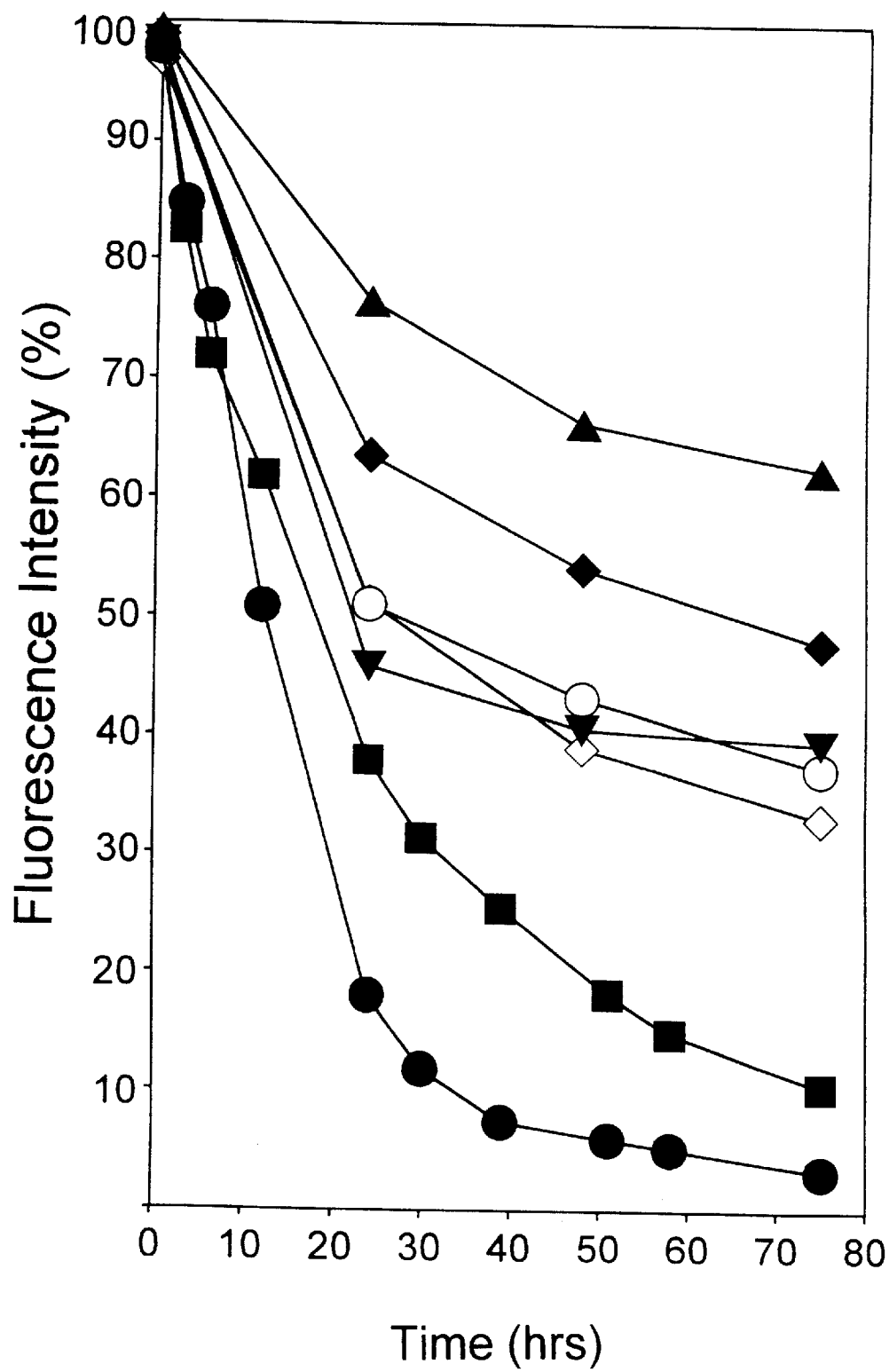

To further confirm the formation of DNA co-condensates, unbound peptides were removed by microdialysis and the ratio of peptides bound to DNA was determined by HPLC. Control studies established the nearly complete removal (>90%) of free $AlkCWK_{18}$ or PEG-VS-$CWK_{18}$ from the retentate after 75 h of dialysis (FIG. 7A). However, the dialysis of DNA co-condensates prepared at charge ratios of 2.3:1 resulted in the removal of unbound peptide and retention of <35% of the tryptophan fluorescence. Dissociation and RP-HPLC analysis of the retained peptide (FIG. 7B, FIG. 7C, FIG. 7D, FIG. 7E and FIG. 7F) allowed recovery of $AlkCWK_{18}$ and PEG-VS-$CWK_{18}$ at ratios that agreed to within 16% of the input ratio for each DNA co-condensate (Table 1) in which the loss of PEG-VS-$CWK_{18}$ was greater than that of $AlkCWK_{18}$.

TABLE 1

Quantitative Analysis of DNA Co-Condensates

| (mol % $AlkCWK_{18}$:mol % PEG-VS-$CWK_{18}$) | Recovery Ratio[a] (mol % $AlkCWK_{18}$:mol % PEG-VS-$CWK_{18}$) |
|---|---|
| 0:100 | 0:100 |
| 25:75 | 41:59 |
| 50:50 | 59:41 |
| 75:25 | 82:17 |
| 100:0 | 100:0 |

[a]Based on HPLC standard curves developed for $AlkCWK_{18}$ and PEG-VS-$CWK_{18}$.

Figure 8:
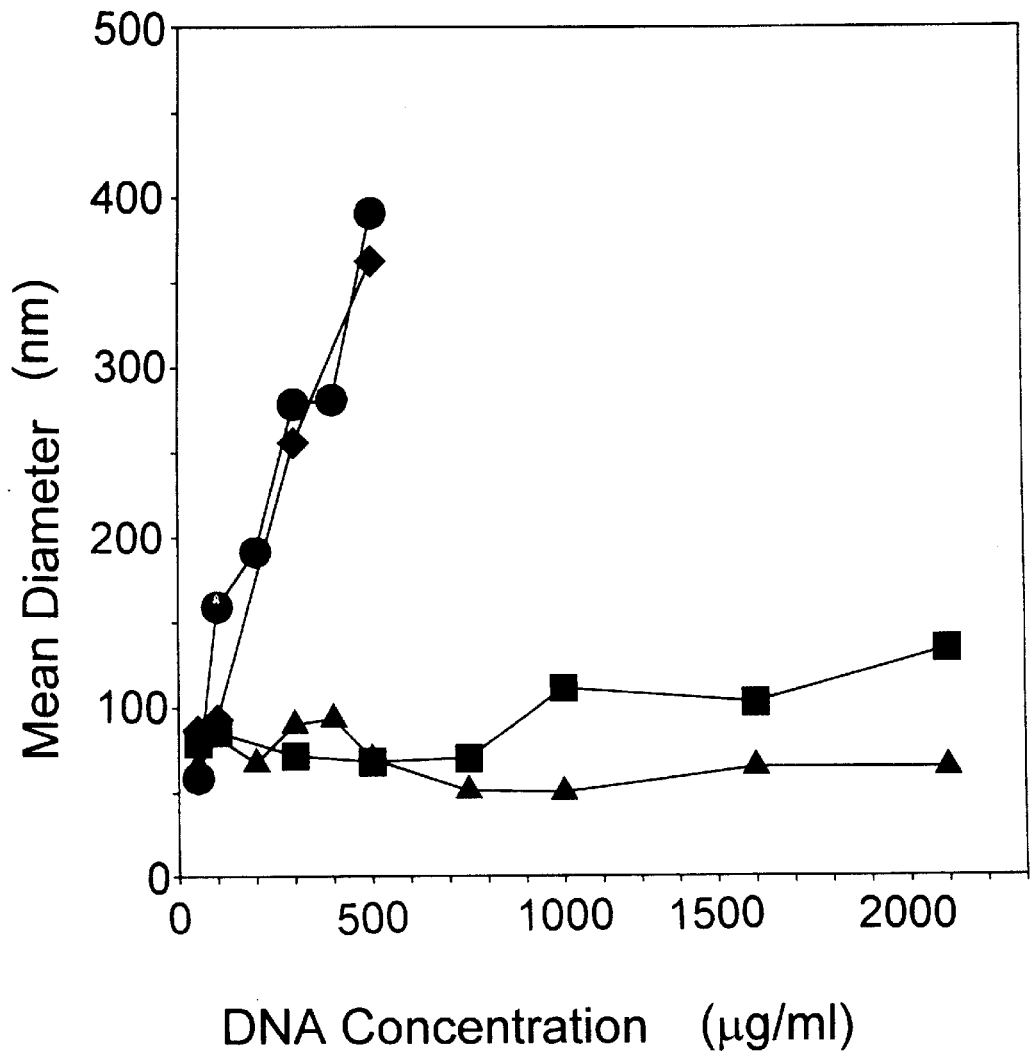
FIG. 8. Solubility of Peptide DNA Condensates. Particle size analysis was performed as a function of DNA concentration using 100 mol % AlkCWK$_{18}$ (●) and 100 mol % PEG-VS-CWK$_{18}$ (π) DNA condensates and using AlkCWK$_{18}$:PEG-VS-CWK$_{18}$ DNA co-condensates prepared with 50 (◇) and 90 (■) mol % PEG-VS-CWK$_{18}$. The particle size increased to >400 nm above 500 μg/ml for AlkCWK$_{18}$ DNA condensates but remained at <100 nm for PEG-VS-CWK$_{18}$ DNA condensates throughout concentrations up to 2 mg/ml.

DNA condensate solubility was evaluated by examining the particle size of concentrated solutions. $AlkCWK_{18}$ DNA condensates increased in particle size from 60 to 400 nm when increasing DNA concentration from 50 to 500 µg/ml, then formed visible flocculates at higher concentrations. Alternatively, PEG-VS-$CWK_{18}$ DNA condensates maintained a mean diameter of <100 nm throughout concentrations ranging from 0.05–2 mg/ml and showed no sign of increasing in size (FIG. 8). Likewise, substitution of PEG-SS-$CWK_{18}$ for PEG-VS-$CWK_{18}$ resulted in the formation of DNA condensates with 88 nm mean diameter at 2 mg/ml.

DNA co-condensates containing 50 mol % PEG-VS-$CWK_{18}$ and $AlkCWK_{18}$ possessed similar poor solubility properties to that of 100 mol % $AlKCWK_{18}$ DNA condensates. However, DNA co-condensates composed of 90 mol % PEG-VS-$CWK_{18}$ and 10 mol % $AlkCWK_{18}$ also maintained a particle size of <100 nm up to 750 µg/ml, and then formed larger particles (>100 nm) at DNA concentrations of 1 mg/ml or higher (FIG. 8).

Figure 9:
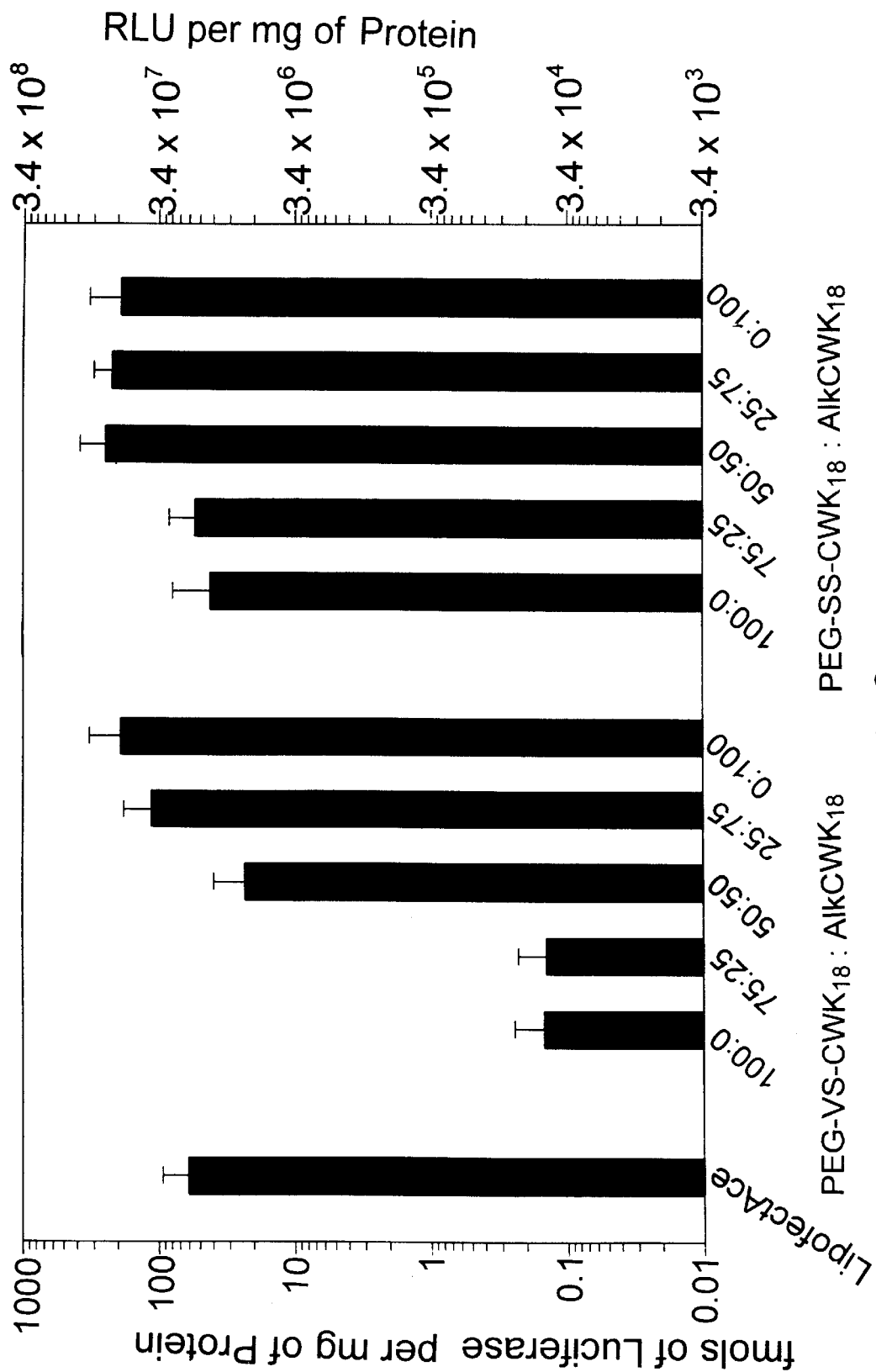
FIG. 9. In Vitro Gene Transfer Efficiency of PEG-CWK$_{18}$ DNA Condensates. The in vitro expression of luciferase in HepG2 cells is compared for PEG-VS-CWK$_{18}$ and PEG-SS-CWK$_{18}$ as well as co-condensates prepared with AlkCWK$_{18}$ at the ratios indicated. LipofectAce™ is included as a control gene transfer agent.

DNA condensates prepared with PEG-VS-CWK$_{18}$, PEG-SS-CWK$_{18}$, AlkCWK$_{18}$ and add-mixtures of AlkCWK$_{18}$ and PEG-peptides were compared by measuring luciferase expression in HepG2 cells 24 h post-transfection (FIG. 9). PEG-VS-CWK$_{18}$ DNA condensates reduced spontaneous gene transfer by three-orders of magnitude compared to AlkCWK$_{18}$ DNA condensates. The reduction was only ten-fold when transfecting with DNA co-condensates prepared with 50 mol % PEG-VS-CWK$_{18}$ and only two-fold using co-condensates composed of 25 mol % PEG-VS-CWK$_{18}$ (FIG. 9).

The gene transfer properties of PEG-SS-CWK$_{18}$ DNA condensates were significantly different than PEG-VS-CWK$_{18}$ DNA condensates. DNA condensates prepared with 100 or 75 mol % PEG-SS-CWK$_{18}$ reduced spontaneous gene transfer by five-fold relative to AlkCWK$_{18}$ DNA condensates while DNA co-condensates prepared with 50 or 25 mol % of PEG-SS-CWK$_{18}$ were equivalent to AlkCWK$_{18}$ DNA condensates (FIG. 9).

Figure 10:
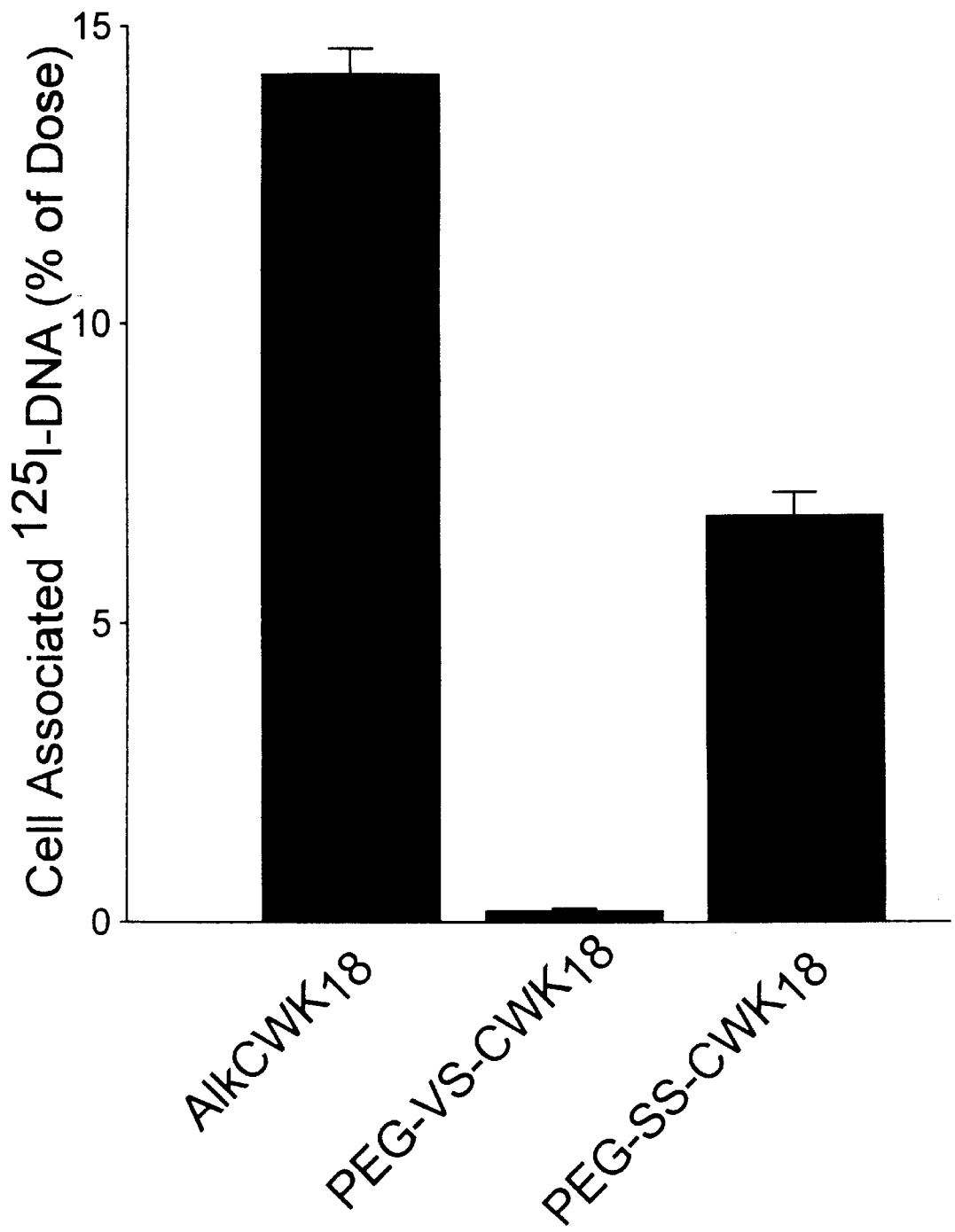
FIG. 10. HepG2 Cell Binding of Peptide DNA Condensates. HepG2 cells were transfected for 5 h with 45 nCi (10 μg) of $^{125}$I-DNA condensates prepared with either AlkCWK$_{18}$, PEG-VS-CWK$_{18}$ or PEG-SS-CWK$_{18}$. The cell associated DNA recovered is expressed as the percent of $^{125}$I-DNA dosed onto cells. The results represent the mean ±S.D for three determinations.

The cell binding of $^{125}$I-DNA was compared for AlkCWK$_{18}$, PEG-VS-CWK$_{18}$ and PEG-SS-CWK$_{18}$ DNA condensates during a 5 h transfection. Approximately 14% of the radioactivity was cell associated for AlkCWK$_{18}$ DNA condensates whereas only 6.8% and 0.2% was cell associated when using PEG-SS-CWK$_{18}$ and PEG-VS-CWK$_{18}$ as DNA condensing agents, respectively (FIG. 10). These results correlated well with the observed gene transfer efficiency for each peptide DNA condensate, suggesting differences in the uptake of these condensates was the main cause of their difference in gene expression.

D. Discussion

The targeting of DNA to specific cells in vivo for the purpose of mediating therapeutically relevant levels of gene expression will require systematic optimization of the drug delivery system (Pouton and Seymour, 1998). The design of such delivery systems must attempt to minimize the carrier's toxicity and antigenicity, increase the DNA's metabolic stability, control the particle size and charge, increase the DNA condensate solubility as well as provide a means to target DNA to the nucleus of the cell. Thus far, PEG-peptides have been reported to decrease toxicity (Wolfert et al., 1996; Toncheva et al., 1998; Choi et al., 1998), increase DNA stability (Choi et al., 1999; Katayose and Kataoka, 1998) and improve DNA solubility (Toncheva et al., 1998).

In the present example, the inventors report the synthesis of two PEG-peptides that simultaneously create very soluble DNA condensates and significantly inhibit spontaneous gene transfer of peptide DNA condensates in vitro. A major finding is that both of these properties are influenced to different degrees by the load level of PEG on DNA condensates.

The directed synthesis of the low molecular weight PEG-peptides reported here is a major distribution of this work compared to others. The conjugation of PEG (5000 Da) to a single cysteine of CWK$_{18}$ afforded highly purified PEG-peptides that controlled the PEG attachment size and allowed comparison of reducible and non-reducible linkages. Notably, the apparent binding affinity of both PEG-peptides for DNA were equivalent to AlkCWK$_{18}$ as determined by the intracalator exclusion assay (FIG. 4), indicating that conjugates of CWK$_{18}$ retain their ability to bind and condense DNA. Due to the homogeneity of the peptide portion of PEG-VS-CWK$_{18}$, DNA condensates formed at charge ratios of 1.8:1 or higher achieved a constant particle size and zeta potential, establishing both the absence of interfering peptides and that excess PEG-peptide does not bind to fully condensed DNA.

Zeta potential measurements revealed evidence that PEG-peptides altered the surface properties of DNA condensate. The zeta potential of PEG-VS-CWK$_{18}$ and PEG-SS-CWK$_{18}$ DNA condensates were indistinguishable and reached a minimum of +10 mV at a calculated charge ratio of 1.8:1 (FIG. 5B). The decrease in zeta potential resulted from the covalent attachment of PEG since the addition of equivalent amounts of free PEG to AlkCWK$_{18}$ DNA condensates did not influence its zeta potential. Likewise, analysis of DNA co-condensates established a correlation between the zeta potential and the mol % of PEG-VS-CWK$_{18}$ incorporated into the co-condensate (FIG. 6B). The recovery of the approximate input ratio of AlkCWK$_{18}$ and PEG-VS-CWK$_{18}$ following prolonged dialysis confirmed the formation of DNA co-condensates. This allows add-mixing of two condensing peptides (AlkCWK$_{18}$ and PEG-VS-CWK$_{18}$) to systematically alter both physical and biological properties of peptide DNA condensates.

The formation of a steric layer is dependent on the amount PEG loaded onto DNA condensate (Torchilin, 1998; Toncheva et al., 1998). This is most evident with DNA co-condensates possessing between 0–25 mol % PEG-peptide where the zeta potential decreased sharply to +20 mV and then only declined gradually to reach +10 mV at 25–100 mol % PEG-peptide. Even though the zeta potential only changed by +10 mV when titrating between 25–100 mol % of PE-peptide (FIG. 6B), these DNA condensates were most altered in solubility and gene transfer efficiency.

The solubility achieved for 100 mol % PEG-peptide DNA condensates (2 mg/ml) is far greater than the solubility reported (60 μg/ml) for other PEG-peptides DNA condensates (Toncheva et al., 1998). This physical property appears to be very dependent on the loading density of PEG since co-condensates prepared with 50 mol % PEG-VS-CWK$_{18}$ were not improved in solubility relative to AlkCWK$_{18}$ DNA condensates. Even co-condensates formed with as much as 90 mol % PEG-VS-CWK$_{18}$ demonstrated an increase in particle size at concentrations greater than 750 μg/ml, indicating that even slightly less PEG on the DNA condensate will result in lower solubility.

Earlier studies demonstrated that the in vitro gene transfer efficiency for peptide DNA condensates was dependent on the charge ratio (Wadhwa et al., 1997; Wadhwa et al., 1995). The expression reached a maximum when AlkCWK$_{18}$ DNA condensates were formed at charge ratio of 1.8:1 or higher, suggesting that the positive charge on DNA condensates contributes to their spontaneous transfection in cell culture. In support of this hypothesis, fully condensed PEG-VS-CWK$_{18}$ DNA condensates prepared at a charge ratio of 2.3:1 possess a lower zeta potential of +10 mV and reduced spontaneous gene transfer by 1000-fold compared to AlkCWK$_{18}$ DNA condensates. Likewise, DNA co-condensates possessing intermediate zeta potential partially reduced gene transfer, further demonstrating a correlation between DNA condensate charge and the level of spontaneous gene transfer. However, these data also established that the PEG load level needed to block spontaneous gene transfer in vitro is much lower than that required to create soluble PEG-peptide DNA condensates.

Even though PEG-VS-CWK$_{18}$ and PEG-SS-CWK$_{18}$ DNA condensates were equivalent in their physical properties, they proved to be unequivalent in their ability to reduce spontaneous gene transfer (FIG. 9). Since the two peptides only differ in their linkage between PETG and peptide, a possible explanation was the reduction of PEG-SS-CWK$_{18}$ either outside or inside the cell to form CWK$_{18}$ DNA condensates during the time of transfection. To test this hypothesis, radioiodinated DNA condensates were used to determine the percent cell associated after a 5 h transfection (FIG. 10).

PEG-VS-CWK$_{18}$ DNA condensates did not significantly bind to cells, with only 0.2% of the dose being cell associated. In contrast, 14% of AlkCWK$_{18}$ DNA condensates and 6.8% of PEG-SS-CWK$_{18}$ DNA condensates dose was cell associated following 5 h transfection, supporting the hypothesis that differences in cell uptake are responsible for the two order of magnitude difference in gene expression mediated by PEG-SS-CWK$_{18}$ and PEG-VS-CWK$_{18}$ DNA condensates.

To determine whether PEG-SS-CWK$_{18}$ underwent reduction during gene transfer, its stability was analyzed while incubating in cell culture media containing 2% FCS. This led to its partial reduction over time suggesting that the removal of PEG by disulfide bond scission results in the formation of CWK$_{18}$ DNA condensates in situ and is a likely explanation of the difference between PEG-SS-CWK$_{18}$ and PEG-VS-CWK$_{18}$ DNA condensates.

Therefore, the best utility of PEG-SS-CWK$_{18}$ will likely be in generating soluble DNA condensates that can be formulated within a gene activated matrix intended for implantation in which targeting is not necessary and spontaneous transfection of infiltrating cells is desired (Fang et al., 1996). Alternatively, the greater stability of PEG-VS-CWK$_{18}$ will likely result in its utility in modifying the surface of DNA condensates used during intravenous gene delivery. The ability to form DNA co-condensates that incorporate both PEG and targeting ligands attached to CWK$_{18}$ provides a unique approach to systematically optimize gene delivery formulations for maximum efficiency in vivo.

EXAMPLE 2

Maintaining Particle Size After Freeze-Drying

The present examples shows that the particle size of PEG-CWK$_{18}$ peptide-DNA condensates is preserved after freeze-drying and rehydration. This conclusion was reached by studying the particle size of peptide DNA condensates after freeze-drying and rehydration as a function of sugar excipient, concentration, pH, DNA concentration, and peptide condensing agent.

In the absence of an excipient, freeze-dried 50 μg/ml AlkCWK$_{18}$ (iodoacetic acid alkylated Cys-Typ-Lys$_{18}$; SEQ ID NO:1) DNA condensates formed large fibrous flocculates on rehydration. Of the sugars tested as lyoprotectants, sucrose proved most effective at preserving particle size during rehydration. The addition of 5 wt/vol % sucrose preserved a mean particle diameter of less than 50 nm during rehydration of AlkCWK$_{18}$ DNA condensates prepared at DNA concentrations up to 200 μg/mL; however, higher DNA concentrations led to the formation of insoluble fibrous flocculates. Substitution of polyethylene glycol (PEG)-CWK$_{18}$ as a DNA condensing peptide eliminated the need for sucrose, resulting in peptide DNA condensates that retained particle size when rehydrated in water or normal saline at concentrations up to 5 mg/mL.

These results show that sucrose functions primarily as a bulking agent during freeze-drying that only preserves the particle size of AlkCWK$_{18}$ DNA condensates up to a maximum concentration of 200 μg/mL. Alternatively, the steric layer created on the surface of PEG-CWK$_{18}$ DNA condensates provides far more efficient lyoprotection, preserving their particle size at a concentration of 5 mg/mL without a bulking agent.

A. Introduction

The development of controlled release gene delivery formulations is an attractive approach to sustain gene expression at or near an implantation site. Manufacturing these delivery systems using well-established solvent evaporation methods applicable to small hydrophobic drugs presents a serious problem when formulating DNA due to its poor solubility in organic solvents. Recently demonstrated solutions involve DNA-matrix fabrication, as exemplified by lyophilizing plasmid DNA with granular polylactide glycolic acid (PLGA) followed by gas foaming in carbon dioxide to form a PLGA sponge (U.S. Pat. Nos. 5,763,416; 5,942,496; Shea et al., 1999; each specifically incorporated herein by reference).

To further improve this controlled release formulation, peptide DNA condensates could be substituted for naked plasmid DNA. This is likely to enhance the gene delivery performance of PLGA sponges by reducing DNA metabolism (Adami et al., 1998) and increasing DNA uptake into cells (Wadhwa et al., 1997). However, prior to the present invention, incorporating peptide DNA condensates into PLGA sponges was problematic due to the tendency of condensed DNA to aggregate on freeze-drying (Ma et al., 1998), creating large particles that are poorly internalized into cells (Anchordoquy et al., 1997; Cherng et al., 1997; Wadhwa et al., 1997; Bettinger et al., 1999). Hence, the present example concerns the influence of lyoprotectants on the collidal particle size of peptide DNA condensates following freeze-drying and rehydration.

Several earlier studies have investigated the relationship between particle size and transfection efficiency after lyophilization of nonviral gene delivery systems (Anchordoquy et al., 1997; Cherng et al., 1997; Leong et al., 1998; De Jaeghere et al., 1999). In the absence of excipients, lyophilized and rehydrated lipid/DNA complexes lost approximately 70% of their ability to transfect cells in culture (Anchordoquy et al., 1997). The addition of sucrose or trehalose preserved the size of lipid/DNA complexes allowing recovery of the transfection efficiency, leading these authors to propose the sugars may replace water as hydrogen bond patterns during the freeze-drying of lipid/DNA complexes, as they have been shown to do so for liposomes and proteins (Crowe et al., 1985, Allison et al., 1999).

Similar results from Cherng et al. demonstrated that sucrose also protected polymer-based DNA complexes from aggregation during freeze-drying, which rehydrated to produce equivalent gene expression as freshly prepared samples (Cherng et al., 1997). More recently, Anchordoquy et al., showed that sucrose protected lipid/DNA complexes during rapid freeze-thawing resulting in retention of particle size and transfection efficiency (Anchordoquy et al., 1998).

Two earlier reports addressed the use of sugars as lyoprotectants to maintain the particle size of freeze-dried and rehydrated polyethylenimine (PEI) (Talsma et al., 1997) or peptide DNA condensates (Ma et al., 1998). Talsma et al. found that 10 wt/vol % sucrose was necessary to recover full transfection potency of freeze-dried PEI-transferrin DNA condensates. Ma et al. also reported that 1 wt/vol % sucrose and mannitol preserved the rehydrated particle size of dilute solutions of fibroblast growth factor (FGF-II) polylysine$_{80}$ DNA condensates and allowed rehydration to higher concentrations of DNA condensates (Ma et al., 1998).

In the present example, the influence of excipient, concentration, pH, DNA concentration, and peptide condensing agent is investigated in order to produce peptide DNA condensates that preserve their particle size following rehydration. Consistent with the results of earlier studies, sucrose was found to be the best lyoprotectant to maintain the particle size of dilute (50–200 µg/ml) peptide DNA condensates, but failed to lyoprotect DNA condensates above this concentration. These aspects of the present invention show that PEG-peptide conjugates remarkably improve the rehydration properties of freeze-dried peptide DNA condensates, thus preserving the particle size following rehydration of DNA condensates at concentrations as high as 5 mg/ml. This advancement allows the convenient formulation of PEG-peptide DNA condensates with PLGA following dry mixing.

B. Materials and Methods

1. Materials

Plasmid NT-βGal (7.5 kb) was produced in E. coli and purified using a Qiagen Ultrapure™-100 kit (Santa Clarita, Calif.). AlkCWK$_{18}$ and PEG-CWK$_{18}$ were prepared as reported previously (Wadhwa et al., 1997; Kowk et al., 1999; Examples herein). Glucose, mannitol, galactose, dextran (500 kDa), sucrose, sodium chloride and Hepes were purchased from Sigma, (St. Louis, Mo.). PEG-VS (5 kDa) was purchased from Fluka (Ronkonkoma, N.Y.).

2. Formulation and Freeze-drying of Peptide DNA Condensates

The concentration of AlkCWK$_{18}$ and PEG-CWK$_{18}$ were determined by UV absorbance (Trp, $\epsilon_{280\ nm}$=5,600 M$^{-1}$ cm$^{-1}$). Peptide DNA condensates were prepared in 5 mM Hepes pH 5 at a peptide/DNA stoichiometry of 0.3 nmol of peptide/µg of DNA. The condensates were formed by adding 450 µL of 100 µg/mL NT-βGal drop wise to 450 µL of 30 nmol/mL AlKCWK$_{18}$ or PEG-CWK$_{18}$ while vortexing. Each sample was prepared in triplicate, and after a 30 min equilibration, 20–100 µL of 50 wt/vol % solutions of either glucose, mannitol, galactose, dextran or sucrose were added followed by normalization to 1 mL to give a final sugar concentration of 1–5 wt/vol % and DNA concentration of 50 µg/mL.

The mean particle size of 50 µg/mL AlkCWK$_{18}$ DNA condensates were determined by quasielastic light scattering (QELS) on a Brookhaven ZetaPlus™. Samples (1 mL) were frozen rapidly in dry ice ethanol in a 1.5 mL microcentrifuge tube and then lyophilized on a Labconco™ freeze dryer for 24 h operated at a constant vacuum of 55×10$^{-6}$ mBar while maintained at room temperature (22° C.). The maximal vacuum was achieved within 2 min after applying the sample.

At the highest sucrose concentration of 5 wt/vol %, samples remained frozen throughout freeze-drying but dried to form a glassy solid after 24 h. Samples possessing 1 wt/vol % sucrose dried to a crystalline powder whereas PEG-peptide DNA condensates dried to from a light fluffy powder. Freeze-dried samples prepared in triplicate were reconstituted in 1 mL of deionized water, allowed to equilibrate for 30 min and then analyzed by QELS as described above. Large peptide DNA condensates were measured by light microscopy with magnification of 100X. The particle size of PEG-peptide DNA condensates were also measured by transmission electron microscopy (TEM) according to a published procedure (Wadhwa et al., 1997).

The relationship between pH and rehydrated peptide DNA condensate particle size was examined in 5 mM Hepes at a pH range of 3–7. The particle size of 50 µg/mL DNA condensates in 5 wt/vol % sucrose was determined by QELS before and after freeze-drying as described above.

The rehydrated particle size of AlkCWK$_{18}$ or PEG-CWK$_{18}$ DNA condensates were also examined at a concentration of 0.05–5 mg/mL in 5 mM Hepes pH 5 with (AlkCWK$_{18}$ DNA) or without (PEG-CWK$_{18}$ DNA) the addition of 5 wt/vol % sucrose. DNA condensates were freeze-dried and reconstituted to the original concentration. QELS particle size analysis before and after freeze-drying required dilution of an aliquot of the sample to concentration of 50 µg/mL. Freeze-dried 5 mg/mL PEG-CWK$_{18}$ DNA condensates were also reconstituted in 0.9 wt/vol % sodium chloride and analyzed for particle size.

C. RESULTS AND DISCUSSION

The objective of the present example was to investigate parameters to maintain peptide DNA condensate particle size when rehydrated following freeze-drying. This is especially important when designing controlled release drug delivery systems that lypophilize DNA with PLGA prior to gas foaming (Shea et al., 1999), since the formation of large flocculates during freeze-drying or rehydration of condensed DNA in the PLGA sponge would significantly reduce the gene transfer efficiency.

Initial observations indicated that rehydration of freeze-dried AlkCWK$_{18}$ DNA condensates resulted in large fibrous flocculates observed by light microscopy to be approximately 100 µm in diameter. This apparently occurs either during dehydration or rehydration but not during rapid freezing since the particle size of freeze-thawed AlKCWK$_{18}$ DNA condensates, with or without added sucrose, were only slightly larger than controls. Likewise, increasing the rehydration volume did not decrease the degree of flocculation suggesting that either the flocculates from very rapidly during rehydration or when concentrated during dehydration.

Other studies have noted that sugar excipients serve as lyoprotectants to preserve the particle size of lipid/DNA and polymer/DNA complexes (Cherng et al., 1997; Anchordoquy et al., 1998; De Jaeghere et al., 1999), which may result from both their ability to bulk DNA complexes and through direct hydrogen bonding to the surface of DNA complexes. To establish whether sugar excipients could also suppress the formation of flocculates formed on freeze-drying peptide DNA condensates, the inventors analyzed the ability of different sugar excipients added at 5 wt/vol % to preserve the particle size of 50 µg/mL AlkCWK$_{18}$ DNA condensates on rehydration.

Figure 11:
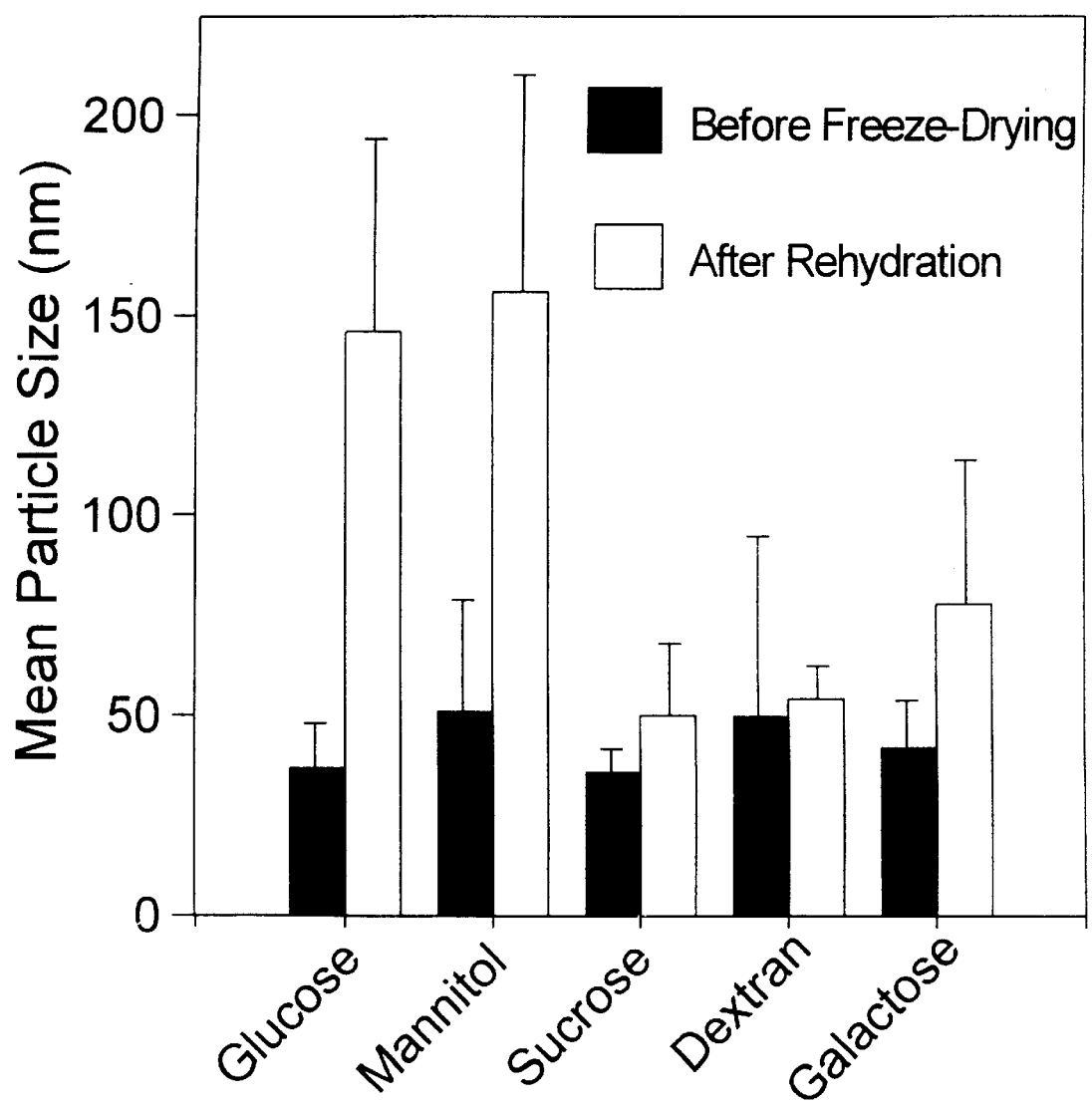
FIG. 11. The effect of different sugar excipients on preserving AlkCWK$_{18}$ DNA condensate particle size following freeze-drying and rehydration to 50 μg/ml. The QELS particle size for peptide DNA condensates prepared with sugar excipients at a concentration of 5 wt/vol % in 5 mM Hepes pH 5. Each sample was analyzed in triplicate and produced a mean particle diameter of less than 50 nm before freeze-drying (closed bar). After freeze-drying and rehydration (open bar) a significantly (P<0.05) larger particle size was determined when using glucose or mannitol as a lyoprotectant relative to sucrose. Also, light micrographs illustrated 100 μm flocculates formed following freeze-drying and rehydration of 50 μg/ml AlkCWK$_{18}$ DNA condensates without lyoprotectant.

The results presented in FIG. 11 demonstrate that sucrose, dextran and galactose were equally effective in preserving the rehydrated peptide DNA condensate particle size, whereas glucose and mannitol afforded slightly larger DNA condensates (FIG. 11). As discussed in more detail below, these subtle differences in the lyoprotection afforded to peptide DNA condensates by different sugars are most likely related to their bulking properties rather than to differences in the degree of hydrogen bonding to the surface of peptide DNA condensates.

It is important to note that throughout these studies multimodel QELS particle size analysis typically yielded two populations of particles composed of a dominant (95 vol %) population with diameters ranging from 30–45 nm and a minor population of 130–180 nm representing approximately 5 vol %. The data in FIG. 11, FIG. 12, FIG. 13, FIG. 14 and FIG. 15 represent the mean diameter based on averaging the size and intensity of these two populations.

Peptide DNA condensates composed of a single 7.2 kb plasmid (4.44×10$^6$ g/mol) bond by approximately 757 peptides (assuming a 1:1 NH$_4$PO$_4$ ratio and each peptide is 2,672 g/mol, total=2.02×10$^6$ g/mol), have a calculated molecular weight of 6.46×10$^6$ g/mol. Assuming collapse into spherical particles of the same density (5.9×10$^{-22}$ g/nm$^3$) as a protein (Sugio et al., 1999), they could occupy a minimal diameter of 32 nm. Under the same assumptions, if two peptide condensed plasmids are contained in a single particle they would occupy a minimal particle size of 40 nm, whereas 4 plasmids would represent a particle of 52 nm.

Based on this calculation, the majority of peptide DNA condensates are assumed to be multiplexes containing from 1–4 plasmids that make up the dominant 30–45 nm population of particles whereas a smaller percentage appear to be fused multiplexes with diameters of 130–180 nm. An increase in mean diameter on rehydration was typically accompanied by an increase in both the mean diameter and intensity (vol %) of the fused multiplex population whereas the formation of flocculates results from the aggregation of many fused multiplexes.

Figure 12:
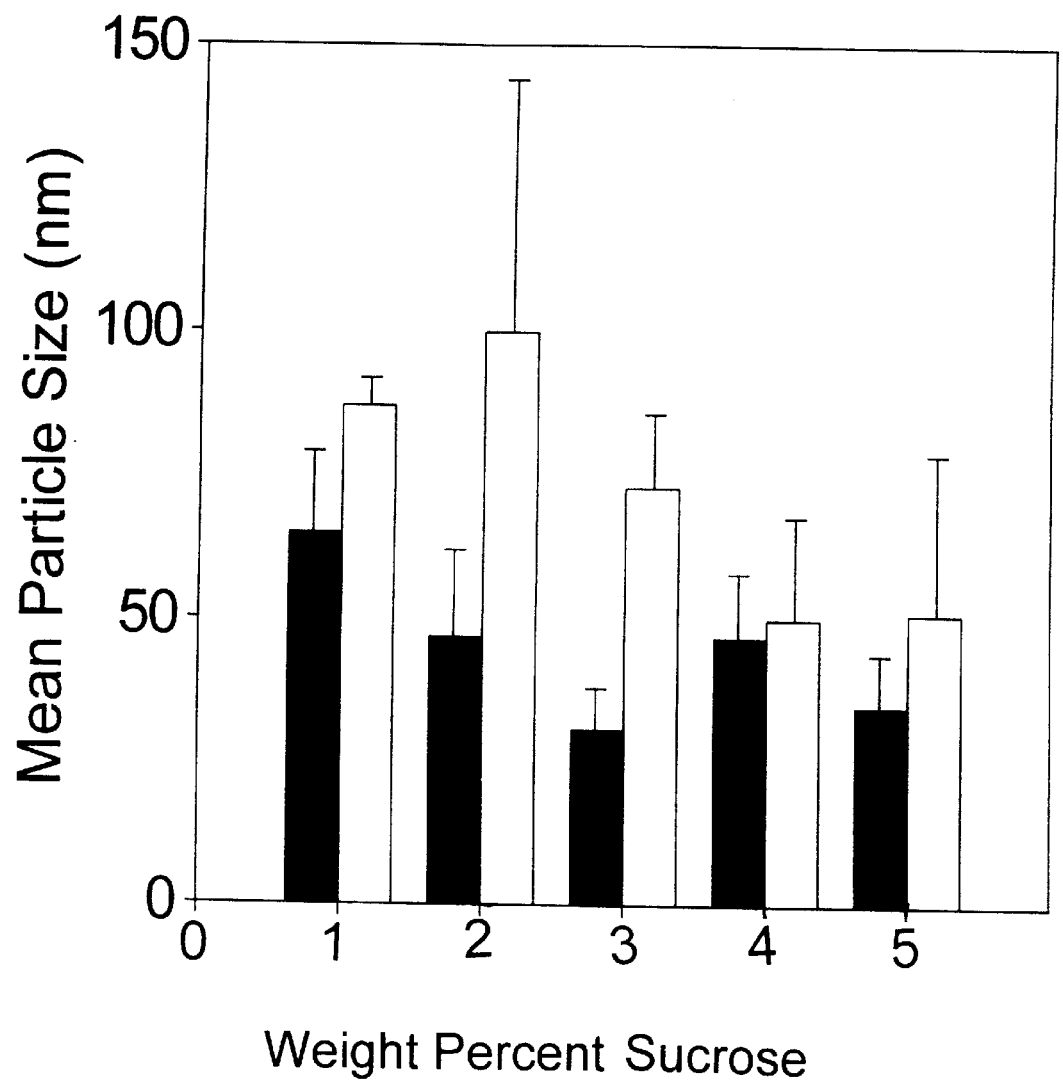
FIG. 12. The effect of sucrose concentration on preserving AlkCWK$_{18}$ DNA condensate particle size after freeze-drying and reconstitution to 50 μg/ml. The peptide DNA condensates were prepared with varying sucrose concentration from 1–5 wt/vol % in 5 mM Hepes pH 5. Each sample was analyzed in triplicate and the mean particle diameter±standard deviation before (closed bar) and after freeze-drying and rehydration (open bar) is reported. There was no statistical significance in the rehydrated particle size when using 1–5 wt/vol % sucrose as a lyoprotectant.
Figure 13:
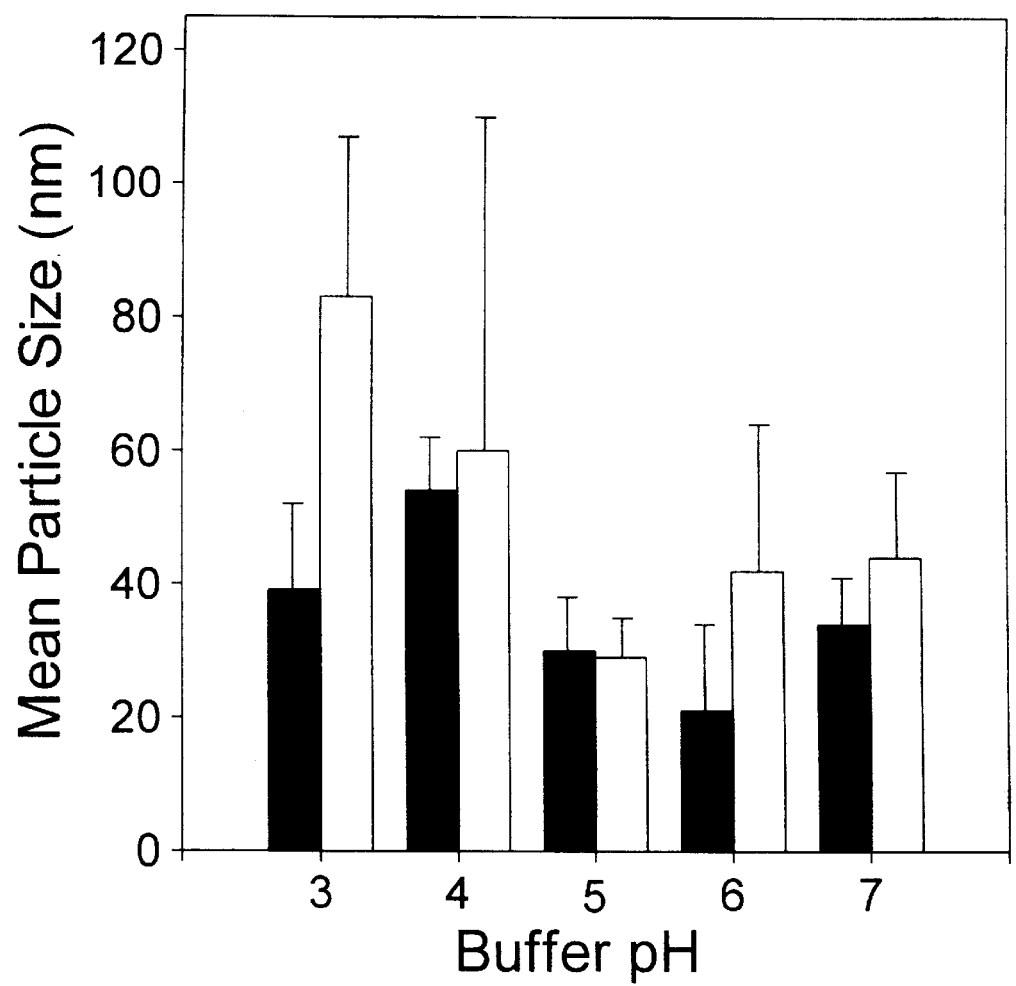
FIG. 13. The effect of pH on preserving AlkCWK$_{18}$ DNA condensate particle size after freeze-drying. Peptide DNA condensates were prepared in 5 mM Hepes buffer with pH ranging from 3–7 at a sucrose concentration of 5 wt/vol %. Each sample was analyzed in triplicate and the mean particle diameter±standard deviation before (closed bar) and after freeze-drying and rehydration (open bar) is reported. The rehydrated particle size at pH 3 was significantly (P<0.05) larger than that determined at pH 5 whereas the rehydrated particle size at pH 4, 6, or 7 was not significantly larger than 5.

The results presented in FIG. 12 demonstrate that the rehydrated particle size of AlkCWK$_{18}$ DNA condensates was not influenced by decreasing the sucrose concentration from 5 to 1 wt/vol %. However, sucrose concentrations less than 1 wt/vol % resulted in the formation of flocculates following rehydration, suggesting that 1 wt/vol % is the minimum sucrose concentration to effectively bulk 50 $\mu$g/ml peptide DNA condensates during freeze-drying.

In addition to the concentration of the sugar excipient, the pH of the buffer may influence the particle size of rehydrated peptide DNA condensates by affecting the affinity of peptide binding to DNA or the surface properties (Kabanov and Kabanov, 1998). However, the data in FIG. 13 demonstrate that the particle size of rehydrated AlkCWK$_{18}$ DNA condensates were not strongly influenced by pH. Likewise, the zeta potential only decreased from ±35 mV at pH 7 to +30 mV at pH 3 establishing that the surface charge only changed slightly by lowering the pH.

Figure 14:
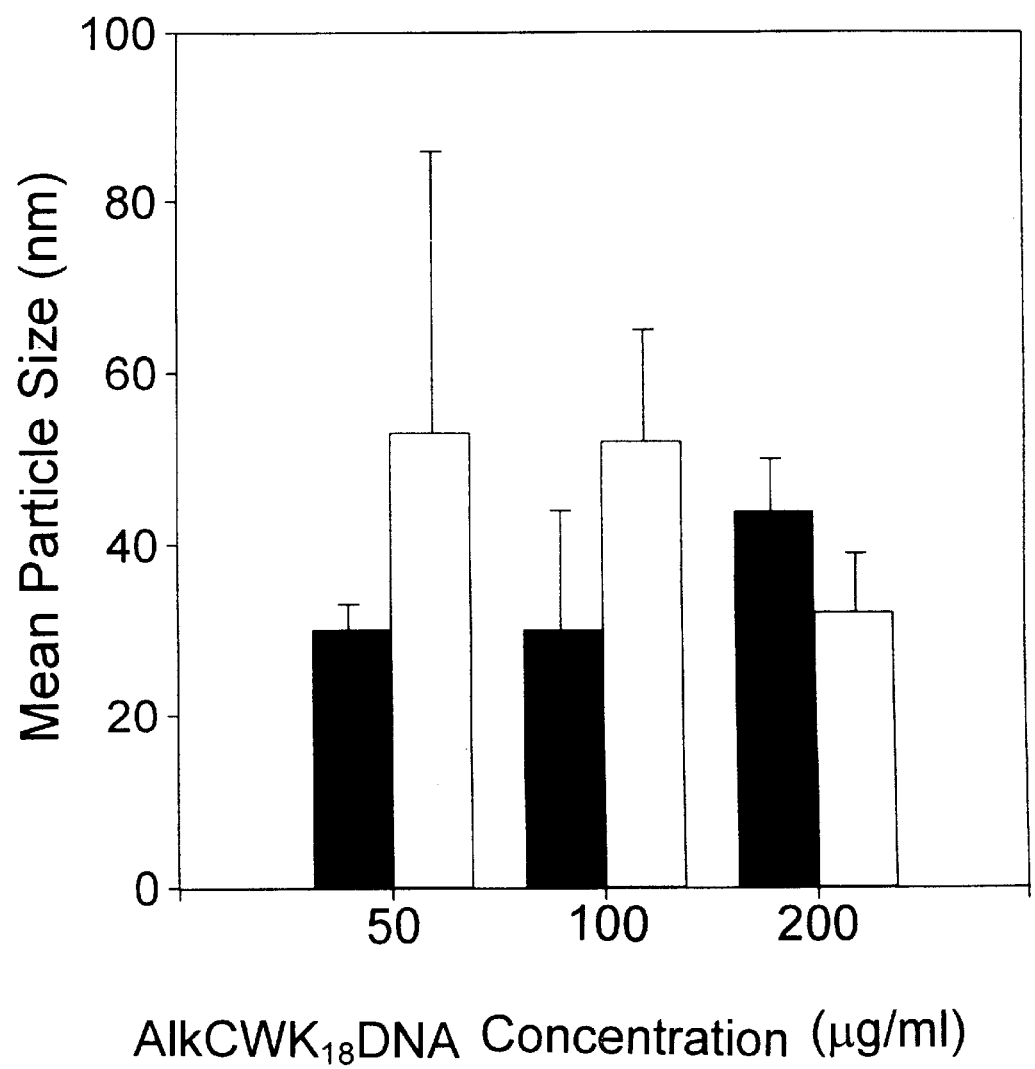
FIG. 14. The effect of DNA concentration on particle size after freeze-drying and rehydration. Comparison of the QELS particle size of AlkCWK$_{18}$ DNA condensates prepared at concentrations varying from 50 to 200 μg/mL in the same lyoprotectant. Each sample was analyzed in triplicate and the mean particle diameter±standard deviation before (closed bar) and after freeze-drying and rehydration (open bar) is reported. At low DNA concentrations (<200 μg/mL) there was no statistical significance in the rehydrated particle size, whereas the particle size grew very large at higher concentrations. Light micrographs illustrated 100 μm flocculates formed following freeze-drying and rehydration of 400 μg/ml AlkCWK$_{18}$ DNA condensates prepared in 5 mM Hepes pH 5 containing 5 wt/vol % sucrose.

Analysis of the rehydrated particle size as a function of AlkCWK$_{18}$ DNA condensate concentration revealed an upper limit of 200 $\mu$g/mL below which the particle size was maintained (FIG. 14) and above which gave rise to large fibrous flocculates that were measured by light microscopy to be approximately 100 $\mu$m in diameter (FIG. 14). Thereby, the proposed bulking effect of 5 wt/vol % sucrose that lyoprotects peptide DNA condensates at dilute concentrations (50 $\mu$g/ml) appears insufficient at even moderately higher DNA concentrations. These results are also consistent with a primary mechanism involving sucrose as a bulking agent and not as a hydrogen bond partner as noted for proteins and liposomes (Allison et al., 1999, Crowe et al., 1985) since this latter mechanism would not be expected to be sensitive to small differences in peptide DNA concentration.

Since bulking agents such as sucrose are apparently limited in their ability to lyoprotect DNA condensates, an alternate strategy is to directly modify the colloid surface of peptide DNA condensates to block inter-particle interactions that lead to the formation of flocculates during dehydration. PEG-CWK$_{18}$ is a unique DNA condensing peptide that decreases the zeta potential to +10 mV and forms DNA condensates of less than 100 nm up to DNA concentrations of 2 mg/mL (Example 1, Kwok et al., 1999; Example 3). To determine whether PEG-CWK$_{18}$ could also stabilize the particle size of freeze-dried DNA condensates, the relationship between DNA condensate concentration and particle size following freeze-drying and rehydration was examined.

Figure 15:
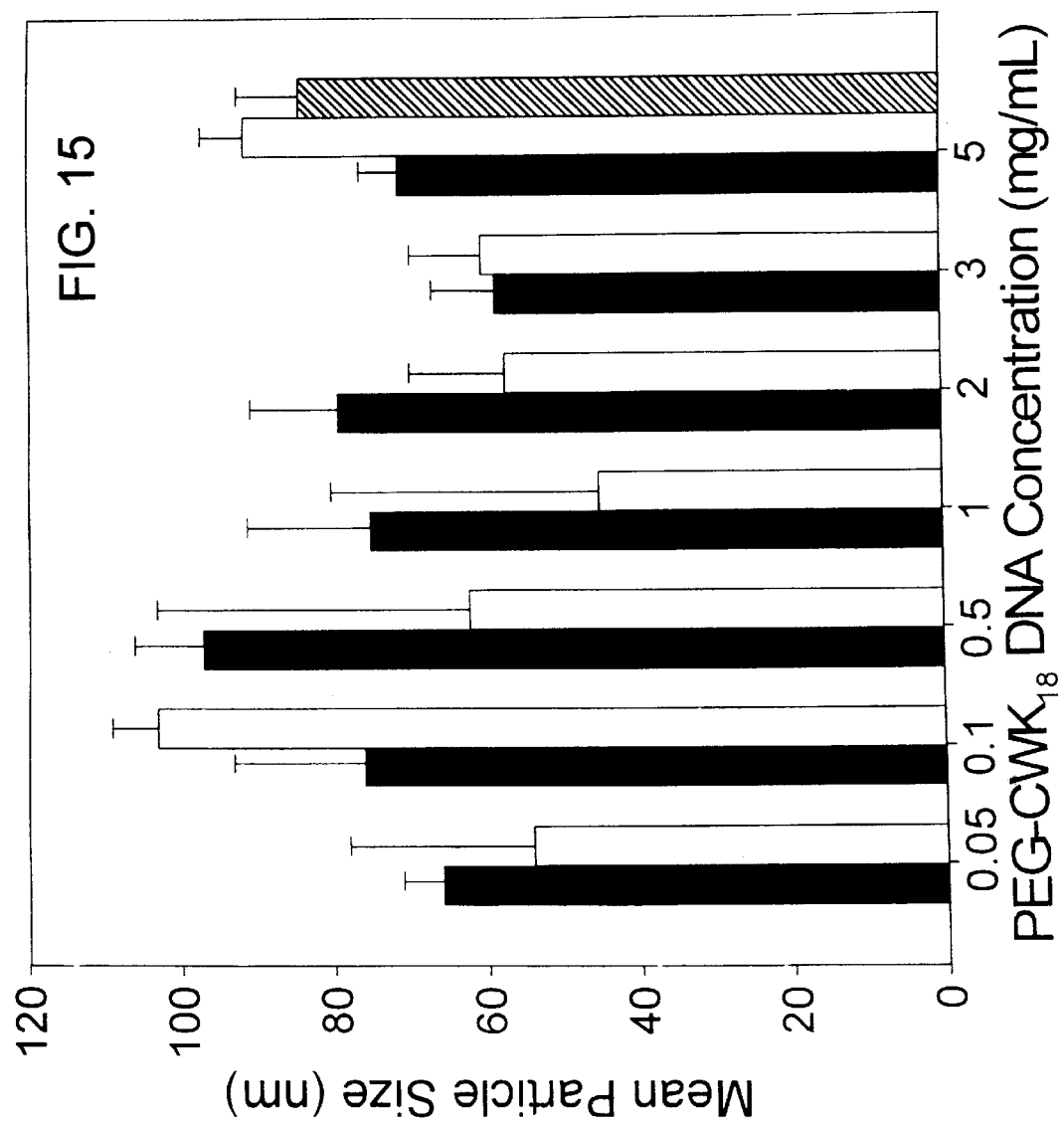
FIG. 15. Particle size of PEG-CWK$_{18}$ DNA condensates following freeze-drying. The DNA concentration of PEG-CWK$_{18}$ DNA condensates was varied from 0.05 to 5 mg/mL in 5 mM Hepes pH 5. Each sample was analyzed in triplicate and the mean particle diameter±standard deviation before (closed bar) and after freeze-drying and rehydration (open bar) is reported. PEG-CWK$_{18}$ DNA condensates prepared at 5 mg/mL were also freeze dried and reconstituted in normal saline (striped bar) prior to measuring particle size. There was no statistical significance in the particle size of rehydrated PEG-CWK$_{18}$ DNA condensates across the concentration range of 0.05 to 5 mg/mL. TEM of 5 mg/mL PEG-CWK$_{18}$ DNA condensates that were freeze-dried and rehydrated in water resulted in small (<100 nm) particles.

The results presented in FIG. 15 establish that PEG-CWK$_{18}$ preserved the particle size of freeze-dried and rehydrated 5 mg/mL DNA condensates without the addition of sucrose as a bulking agent. TEM analysis of rehydrated 5 ml/mL PEG-CWK$_{18}$ DNA condensates also confirmed the presence of only small particles that appeared to be less than 100 nm in diameter (FIG. 15). The inventors hypothesize that the hydrated flexible PEG chains provide steric stabilization by producing a dense layer over the particle surface that prevents peptide DNA condensate aggregation during dehydration. In support of this hypothesis, the covalent attachment of PEG to the surface of DNA condensates was found to be essential, since the addition of 10-fold excess (300 $\mu$g) PEG-VS (5 kDa) to preformed AlkCWK$_{18}$ DNA condensates failed to alter their zeta potential or afford lyoprotection.

The finding that the particle size of freeze-dried 5 mg/mL PEG-CWK$_{18}$ DNA condensates were even preserved when rehydrated in normal saline (FIG. 15) established the value of this approach in formulating isotonic dosage forms. These results also indicate that PEG-CWK$_{18}$ DNA condensates will likely rehydrate to form small particles following implantation of a PLGA sponge containing encapsulated condensated DNA.

The present example therefore shows that concentrations below 200 $\mu$g/mL of AlkCWK$_{18}$ DNA condensates can be freeze-dried and rehydrated while preserving particle size provided that a lyoprotectant such as 5 wt/vol % sucrose is included to serve primarily as a bulking agent. In contrast, the lyoprotection afforded using PEG-CWK$_{18}$ as a condensing peptide preserved the particle size of freeze-dried 5 mg/mL DNA condensates when rehydrated in water or normal saline without a bulking agent. These data support a proposed mechanism involving modification of the DNA condensate surface by creating a steric layer that blocks inter-particle interactions during dehydration and rehydration, resulting in a far more efficient lyoprotection relative to the application of bulking agents. The results of this study are valuable in developing advanced delivery systems for peptide DNA condensates in which dry mixing of freeze-dried DNA colloids is desired as a formulation step.

EXAMPLE 3

Homogeneous Glycopeptides as DNA Condensing Agents

The present example concerns the production of glycopeptide DA condensates for use as receptor mediated gene delivery agents. Two glycopeptides were synthesized by attaching purified N-glycans to a twenty amino acid peptide. Triantennary and Man9 Boc-tyrosinamide N-glycans were treated with trifluoroacetic acid to remove the Boc group and expose a tyrosinamide amine. The amine group was coupled with iodoacetic acid to produce N-iodoacetyl-oligosaccharides. These were reacted with the sulfhydryl group of a cysteine-containing peptide (CWK$_{18}$) resulting in the formation of glycopeptides in good yield that were characterized by $^1$H-NMR and ESIMS. Both glycopeptides were able to bind to plasmid DNA and form DNA condensates of approximately 110 nm mean diameter with zeta potential of +31 mV. The resulting homogeneous glycopeptide DNA condensates will be valuable as receptor mediated gene delivery agents.

A. INTRODUCTION

Nonviral gene delivery utilizes carrier molecules designed to bind ionically to plasmid DNA resulting in the formation of DNA colloids of approximately 100 nm diameter. Targeted nonviral gene delivery relies on the incorporation of ligands into the DNA carrier, which are presented on the surface of the DNA colloid and function to mediate receptor recognition and cellular uptake of the DNA-carrier complexes (Christiano and Roth, 1995).

One of the earliest ligands used for DNA delivery was the glycoprotein asialoooromucoid (ASOR) possessing Gal terminated N-glycans that bind to the asialoglycoprotein receptor (ASGP-R) on hepatocytes with high affinity (Connolly et al., 1983). ASOR was conjugated to high-molecular-weight (HMW) polylysine (DP 100–250) to prepare a DNA carrier capable of ionically binding to and condensing plasmid DNA (Wu and Wu, 1988a). Although this carrier protected DNA from metabolism and targeted DNA to hepatocytes via the ASGP-R (Wu and Wu, 1988b), it was difficult to purify from free polylysine (McKee et al., 1994) and proved to be antigenic (Stankovics et al., 1994).

To circumvent problems associated with HMW carriers, lower molecular weight neoglycopeptides have been prepared by coupling multiple lactose (40–50%), Gal (1%), or Man (1%) residues to HMW polylysine (DP 146–190) Perales et al., 1994; Midoux et al., 1993; Erbacher et al., 1995; Marinez-Fong et al., 1994; Ferkol et al., 1996). Although chemically simpler to prepare, these carriers are still heterogeneous, making further modification with polyethylene glycol (Wolfert et al., 1996) or subcellular targeting peptides difficult to control (Plank et al., 1994).

Further refinements in carrier design were reported by Wagner and co-workers who utilized a synthetic tetraantennary neoglycopeptide ligand covalently linked to polylysine (DP 190 or 290) to achieve receptor-mediated gene expression in hepatocytes (Plank et al., 1992). Although the ligand portion was chemically defined, and possessed high affinity for the ASGP-R, the resulting carriers were also HMW and heterogeneous due to random coupling of the neoglycopeptide to polydisperse polylysine.

A carrier composed of a high affinity neoglycopeptide prepared by attaching three terminal GalNAc residues to a tripeptide backbone (YEE) was also reported as a ligand for ASGP-R mediated gene delivery (Merwin et al., 1994). Although the ligand was well defined, its attachment to low-molecular-weight (LMW) polylysine (DP 10–30) using human serum albumin as an intermediate spacer produced a heterogeneous carrier of approximately 70 kDa.

To date, the most chemically defined carrier developed for ASGP-R mediated gene delivery is a 4–6 kDa triantennary glycopeptide (Wadhwa et al., 1995). The glycopeptide is composed of a single natural triantennary N-linked oligosaccharide attached to a short polylysine (DP 10–30) chain. Even though this LMW glycopeptide mediate specific gene transfer to HepG2 cells relative to LMW polylysine, the heterogeneity within polylysine (Example 5; McKenzie et al., 2000; Example 6) makes it less desirable for further development into a carrier for in vivo applications.

To develop structurally defined LMW glycopeptides useful for targeted gene delivery, the inventors first synthesized a panel of peptides and determined that a minimal polylysine chain of Cys-Trp-Lys$_{18}$ (CWK$_{18}$) was sufficient to condense DNA into small condensates and protect DNA from metabolism (Wadhwa et al., 1997; Adami et al., 1998). In the present example, the inventors demonstrate the derivatization of CWK$_{18}$ with purified N-glycans to form homogeneous glycopeptide carriers that bind and condense DNA into small colloids. The ability to substitute different oligosaccharides into these glycopeptide DNA condensates provides a means to design a variety of chemically well-defined gene targeting agents for in vivo use.

B. MATERIALS AND METHODS

1. Materials

TCEP [tris(2-carboxyethyl)phosphine hydrochloride] was purchased from Aldrich Chemical Co., (Milwaukee, Wis.). Iodoacetic acid N-hydroxysuccinimide ester was purchased from Sigma (St. Louis, Mo.). The 5.6 kb plasmid (pCMVL) encoding the luciferase gene under the control of the cytomegalovirus promoter was produced in E. coli and purified using a Qiagen Ultrapure™-100 kit (Santa Clarita, Calif.). Preparative and analytical C$_{18}$ reverse-phase HPLC columns were purchased from Vydac (Herperia, Calif.). HPLC was performed using a computer-interfaced HPLC and fraction collector from ISCO (Lincoln, Nev.).

2. Synthesis and characterization of glycopeptides

CWK$_{18}$ was synthesized on solid phase and purified as previously reported (Wadhwa et al., 1997). The terminal cysteine was either alkylated with iodoacetic acid to prepare AlkCWK$_{18}$ (Wadhwa et al., 1997) or used as an attachment site for oligosaccharides. A triantennary and a Man9 N-glycan were purified as Boc tyrosinamide derivatives from bovine fetuin and soy bean agglutinin, respectively (Tamura et al., 1994; Evers et al., 1998). The Boc group was removed by treating the dry tyrosinamide oligosaccharide (0.5 μmol) with 100 μL of neat TFA for 10 min at RT followed by freeze drying.

The resulting amine terminus was N-iodoacetylated by dissolving 0.5 μmol of the tyrosinamide oligosaccharide in 0.5 mL of 100 mM sodium bicarbonate pH 8 followed by reaction with 20 μmols of iodoacetic acid N-hydroxysuccinimide ester in 50 μL of DMF. After 3 h at RT, an additional 20 μmol of iodoacetic acid N-hydroxysuccinimide ester was added and reacted for an additional 12 h. The reaction was acidified with 50 μL of 10% (vol/vol) acetic acid and purified on a Sephadex™ G-25 column (2.5 cm×45 cm) eluted with 0.1% (vol/vol) acetic acid while detecting absorbance at 280 nm. The peak eluting at 75–125 mL was pooled and freeze dried, resulting in 80–90% yield of N-iodoacetyl-oligosaccharide that eluted as a single peak on RP-HPLC as described below.

CWK$_{18}$ (1 μmol) was reduced by reaction with 25 μmol of TCEP in 0.5 mL of 0.1 M sodium phosphate pH 7 for 4 h at RT. Reduced CWK$_{18}$ was purified by injecting 0.5 μmol onto a semipreparative C$_{18}$ RP-HPLC column (2×25 cm) eluted at 10 mL/min with 0.1% TFA and a gradient of 5 to 25% acetonitrile over 25 min while detecting by ABs$_{280nm}$. The peak eluting at 14 min was collected, freeze dried, and stored frozen in 0.1% TFA.

N-iodoacetyl-oligosaccharide (200 nmol) was conjugated to CWK$_{18}$ (250 nmol) by reaction at RT for 12 h in 200 μL of 0.2 M Tris pH 8.0. The resulting glycopeptide was purified by injecting up to 200 nmol onto semipreparative RP-HPLC (2×25 cm) column eluted at 10 mL/min with 0.1% TFA and a gradient of 5–25% acetonitrile over 25 min. The glycopeptide peak eluting at 23 min was pooled, freeze dried, reconstituted in water and quantified by absorbance ($\epsilon_{280}$=6930 M$^{-1}$cm$^{-1}$) resulting in a isolated yield of 40%. Purified glycopeptides (triantennary-CWK$_{18}$ and Man9-CWK$_{18}$) rechromatographed as single peaks and were characterized as described below.

Glycopeptides (500 nmol) were prepared for 500-MHz $^1$H-NMR spectroscopy by repeated freeze drying in D$_2$O. Samples were prepared in 0.5 mL of 99.98% D$_2$O containing 0.01% acetone as an internal standard and analyzed on a Bruker 500 MHz NMR spectrometer operating at 23° C. glycopeptides were characterized by ESIMS by injecting 2 nmol onto RP-HPLC eluted at 1 mL/min with 0.1 vol/vol % acetic acid and 0.02% TFA and a gradient of 5–25% acetonitrile over 30 min. The eluting glycopeptide was directly infused into the electrospray source of a Finnigan™ LCQ mass spectrometer and ions were collected in the positive mode.

3. Preparation and characterization of glycopeptide DNA condensates

Glycopeptide DNA condensates were formed at a plasmid DNA concentration of 50 μg/mL in HBM (5 mM Hepes 0.27

M mannitol pH 7.4). DNA condensates were formed by combining 750 µL of plasmid DNA (100 µg/mL) with 750 µL of triantennary-$CWK_{18}$ (50 nmol/mL), Man9-$CWK_{18}$, or Alk$CWK_{18}$ while vortexing. The particle size of glycopeptide and peptide DNA condensates were analyzed at a DNA concentration of 50 µg/mL in HBM by quasielastic light scattering (QELS) (Cohen et al., 1990). The particle surface charge was determined at 50 µg/mL in HBM by zeta potential analysis using a Brookhaven ZetaPlus™ (Brookhaven Instruments).

C. RESULTS

Figure 16:
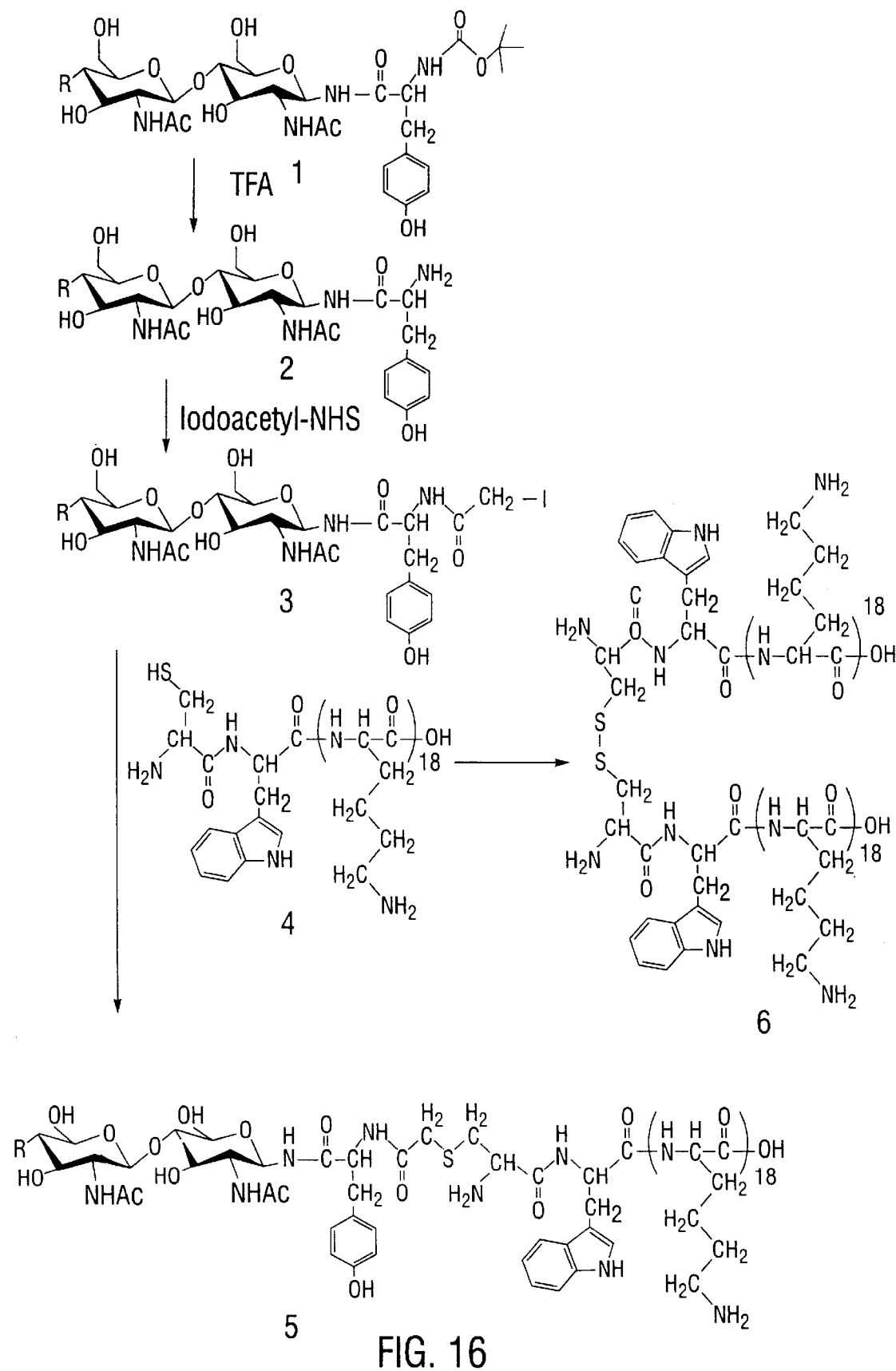
FIG. 16. Glycopeptide Synthetic Scheme. R represents the remainder of the triantennary or Man9 N-glycan illustrated in FIG. 18A and FIG. 18B.

The synthetic scheme used to prepare glycopeptides is illustrated in FIG. 16. Boc-tyrosinamide oligosaccharide 1 was protected with TFA to produce tyrosinamide oligosaccharide 2 with an exposed primary amine. The amine was selectively derivatized with iodoacetic acid resulting in the formation of N-iodoacetyl-oligosaccharide 3. The iodo group was readily displaced by the sulfhydryl on $CWK_{18}$ 4 resulting in the formation of either triantennary-$CWK_{18}$ or Man9-$CWK_{18}$ glycopeptides 5.

Each reaction was monitored by RP-HPLC (FIG. 17A, FIG. 17B, FIG. 17C, FIG. 17D, FIG. 17E and FIG. 17F). Removal of Boc from 1 under acidic conditions (TFA) produced an earlier eluting product 2 (FIG. 17B). Attachment of iodoacetic acid to form 3 resulted in a shift back to a longer retention time (FIG. 17C). Reaction of 3 and 4 (FIG. 17D) resulted in the formation of 5 and 6 (FIG. 17E) with the complete disappearance of 3. Product 5 eluting at 23 min was identified as the desired glycopeptide, even though it eluted coincident with starting material 4. By-product 6 eluting at 28 min resulted from the oxidation of residual 4 at pH8.

When studying the reaction of 3 with 4, a reduction in pH to 7.5 decreased the yield of 5 due to the increased formation of by-product 6. Likewise, at a stoichiometry of 1:1, the reaction of 3 and 4 was judged incomplete due to residual 3. Under optimal conditions, the reaction was complete in 2 h at pH 8 at a stoichiometry 1:1.25 of 3:4. Glycopeptides were purified by RP-HPLC resulting in a 40% yield that was <95% pure on re-chromatography on analytical RP-HPLC (FIG. 17F).

Figure 18B:
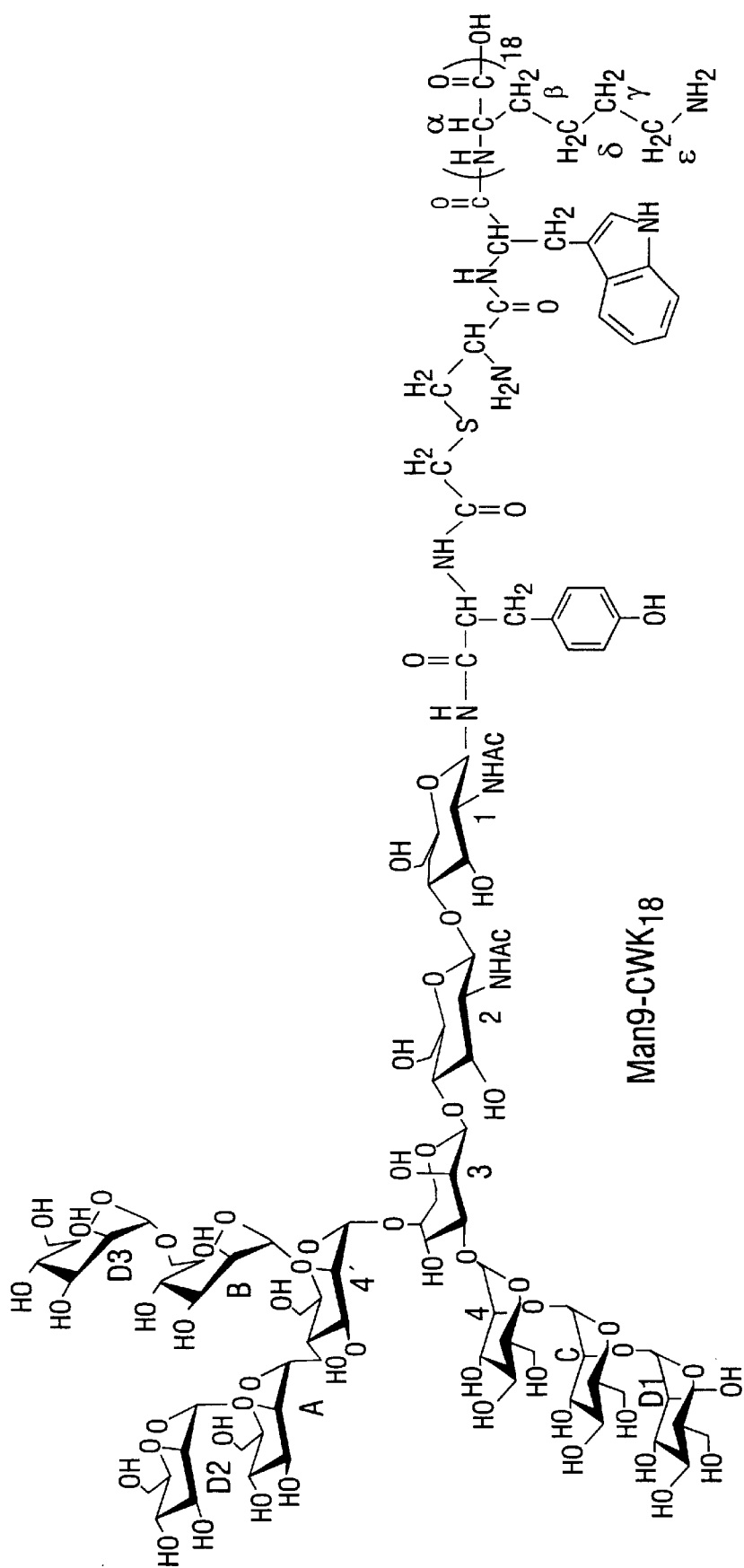
Figure 19A:
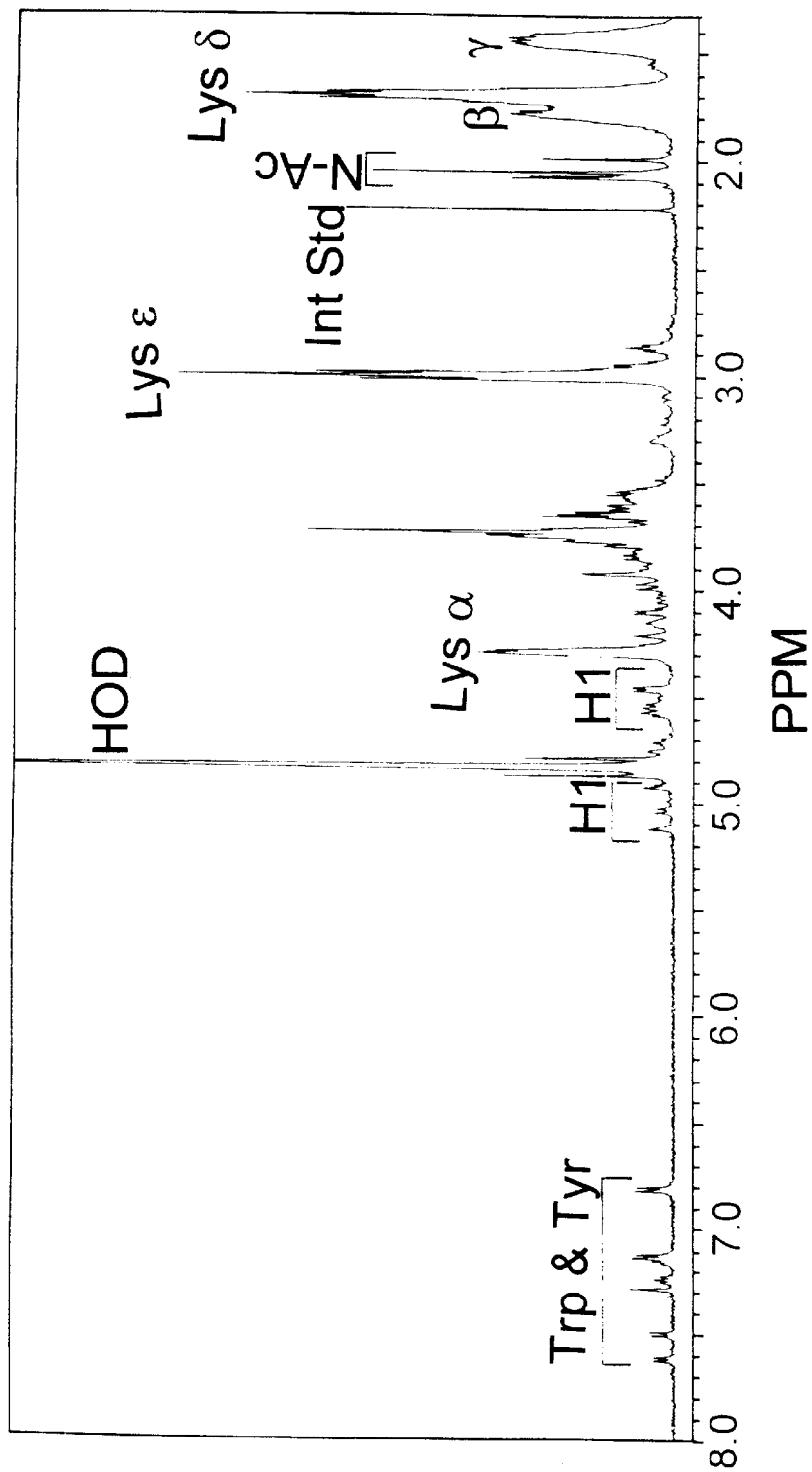
FIG. 19A and FIG. 19B. $^1$H NMR Analysis of Triantennary-CWK$_{18}$ and Man9-CWK$_{18}$.
Figure 19B:
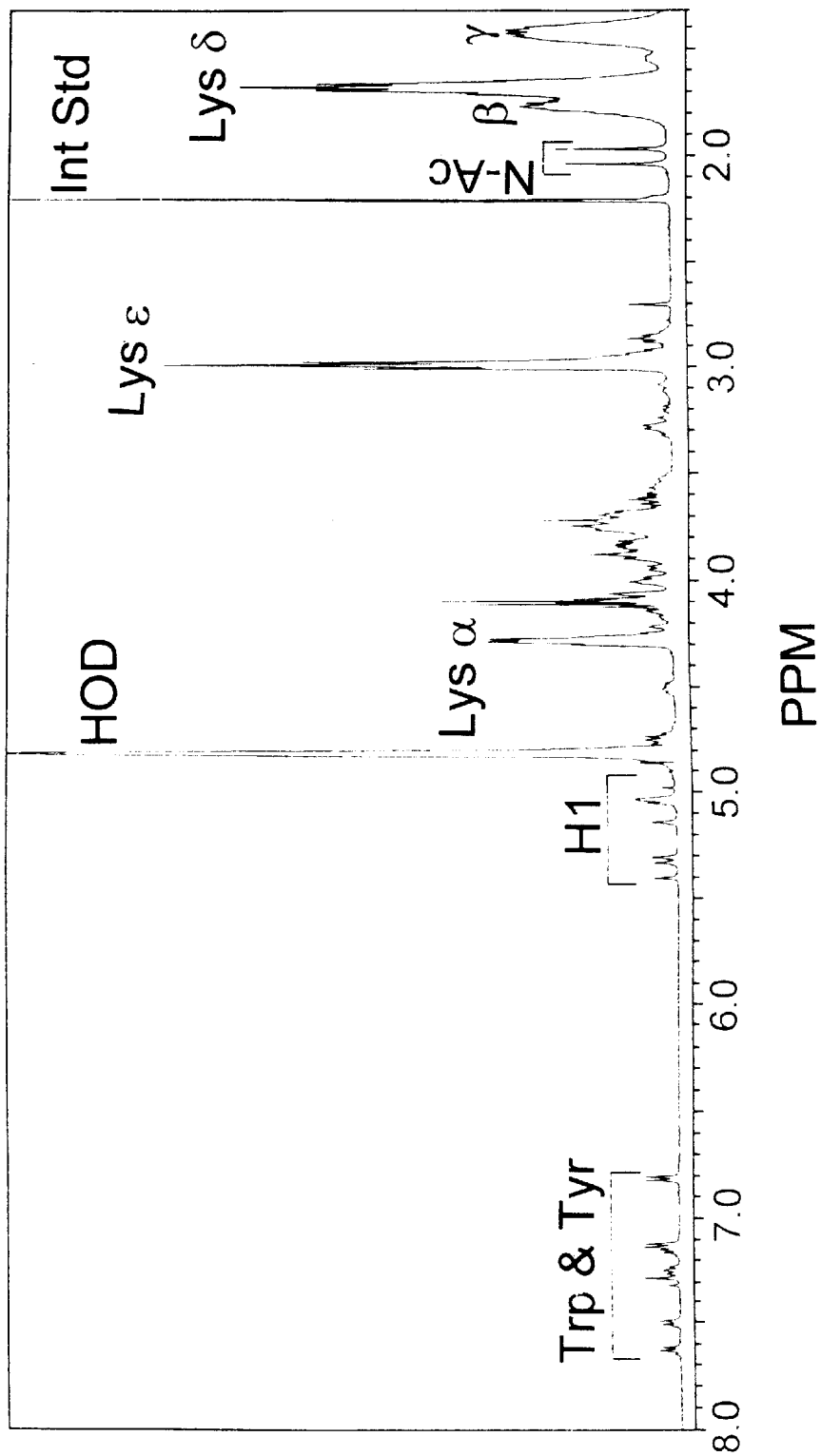

$^1$H-NMR spectroscopy was used to verify the presence of signals arising from both the peptide and the oligosaccharide of triantennary-$CWK_{18}$ and Man9-$CWK_{18}$ (FIG. 18A and FIG. 18B). Resonances arising from the eighteen Lys side chains ($CH_2$ 1.48 (γ), $CH_2$ 1.69 (δ), $CH_2$ 1.77 (β), and $CH_2$ 2.99 ppm (ε)), and CH α protons (4.29 ppm) were present in the spectra of both glycopeptides (FIG. 19A and FIG. 19B). Likewise, the tryptophan and tyrosine resonances at 6.8–7.7 ppm were indistinguishable in both glycopeptides. In contrast, the anomeric protons of each glycopeptide were characteristic of triantennary or Man9 oligosaccharide. Triantennary-$CWK_{18}$ possessed Gal (6,6', and 8), GlcNAc (5, 5' and 7) and Man (4 and 4') anomeric resonances that closely matched the chemical shifts identified for Boc tyrosinamide triantennary oligosaccharide, with only subtle shifts in the anomeric resonance for GlcNAc 1 and 2 (Admai et al., 1998) (FIG. 19A).

In addition, the chemical shift of all five N-acetyl groups were readily assigned by comparison to the same resonance in a Boc tyrosinamide triantennary. The NMR spectrum of Man9-$CWK_{18}$ also possessed similar chemical shifts for the anomeric protons of Man D1-3, A-C, and 4, 4' relative to that reported for Boc tyrosinamide Man9 oligosaccharide with only minor perturbation of the anomeric resonances of GlcNAc 1 and 2 (Tamura et al., 1994) (FIG. 19B). Likewise, the two N-acetyl groups were well-resolved from the lysine signals in the glycopeptide and possessed nearly identical chemical shifts as the Boc tyrosinamide oligosaccharide.

LC-MS analysis of triantennary-$CWK_{18}$ produced ions at 1608.7, 1206.7 and 965.5, which identified a molecule of 4822.8 amu (FIG. 20A). This correlated well with the calculated average mass of 4823.2 for triantennary-$CWK_{18}$. Man9-$CWK_{18}$ produced ions of 940.9, 1175.9 and 1567.4 (FIG. 20B) corresponding to a molecule of 4699.2 amu, which agrees with the calculated average mass of 4700.3.

To establish that each glycopeptide could bind to plasmid DNA and form small DNA condensates, the particle size and zeta potential of glycopeptide DNA condensates were compared to alkylated-$CWK_{18}$ (Alk$CWK_{18}$) DNA condensates using QELS. Previous titration studies involving displacement of an intercalator dye from DNA established that Alk$CWK_{18}$ binding to plasmid DNA was complete at a stoichiometry of 0.3 nmol per µg or greater (Wadhwa et al., 1997). The same titration were performed with each glycopeptide, which were found to have identical binding affinity to DNA as Alk$CWK_{18}$.

The mean particle size of DNA condensates prepared at an identical stoichiometry (0.5 nmol of peptide or glycopeptide per µg of DNA) was slightly greater when using triantennary-$CWK_{18}$ (107 nm) and Man9-$CWK_{18}$ (109 nm) as condensing agents as compared to Alk$CWK_{18}$ (81 nm). Each glycopeptide and peptide condensed DNA to form two populations of particles. The major population (75–85%) possessed a mean diameter less than 100 nm (FIG. 21A, FIG. 21B and FIG. 21C) whereas a minor population (15–25%) having a slightly larger size (150–200 nm diameter) was present for Alk$CWK_{18}$ DNA condensates and both glycopeptide DNA condensates. In addition, the surface charge of glycopeptide DNA condensates (+31 ±5 mV) were indistinguishable from Alk$CWK_{18}$ DNA condensates.

D. DISCUSSION

The design of glycoconjugate targeted drug delivery systems for in vivo use requires an understanding of the specificity of mammalian lectins to properly cluster and orient non-reducing residues for optimal multivalent recognition by the target lectin (Rice et al., 1990). Although many Gal and Man terminated glycoconjugates have been prepared for targeting DNA to liver hepatocytes (Wu and Wu, 1988a, 1988b; Stankovics et al., 1994; Perales et al., 1994; Midoux et al., 1993; Erbacher et al., 1995; Marinez-Fong et al., 1994; Merwin et al., 1994; Wadhwa et al., 1995) and macrophages (Ferkol et al., 1996), few studies have attempted to design LMW carriers that bind and condense DNA while possessing high affinity ligands for their target receptor.

The strategy of the present example differs significantly from others in that natural N-glycans are used as ligands that are conjugated site specifically to a LMW DNA condensing peptide. The triantennary oligosaccharide used has been studied extensively for its ability to bind to the ASGP-R both in vitro and in vivo (Rice et al., 1990; Chiu et al., 1994). Likewise, $CWK_{18}$ was selected as the minimal polylysine peptide that could bind and condense DNA into small condensates that mediate non-specific in vitro gene delivery (Wadhwa et al., 1997). The present study demonstrates the synthesis of homogeneous glycopeptides by forming a conjugate between well-characterized N-glycans and $CWK_{18}$ to create carriers of less than 5000 Da.

N-glycans were prepared as an N-iodoacetyl-tyrosinamide oligosaccharides to allow conjugation to a cysteine containing peptide. This required the removal of Boc with acid, which may be accomplished without hydrolysis of glycosidic linkages (even NeuAc and Fuc), provided neat TFA is used. Once exposed, the single amine group acts as a regioselective conjugation site to attach iodoacetic acid. The N-iodoacetyl-tyrosinamide oligosaccharides were found to be stable products that reacted at near 1:1 stoichiometry with $CWK_{18}$. A slight excess of peptide was found to be optimal to completely consume the oligosaccharide. Surprisingly, the attachment of an N-glycan to $CWK_{18}$ did not influence its retention time on RP-HPLC. This was true of both triantennary-$CWK_{18}$ and Man9-$CWK_{18}$, which were chromatographically equivalent to $CWK_{18}$ despite numerous attempts to resolve the glycopeptides and peptide. However, their coelution did not preclude their purification from excess $CWK_{18}$, which readily formed dimeric-$CWK_{18}$ at pH 8.0 resulting in its complete resolution on RP-HPLC.

Purified glycopeptides were determined to be <95% pure by HPLC analysis and produced $^1H$ NMR spectra in which the integration of carbohydrate anomeric signals to the lysine side chain resonance provided evidence of a 1:1 conjugate free of unmodified $CWK_{18}$. Likewise, each glycopeptide produced multiply charged ions on ESIMS that closely corresponded to the predicted mass for each glycopeptide.

The ability of glycopeptides to ionically bind and condense DNA is an important parameter for their use in gene delivery. The inventors have previously demonstrated that polylysine peptides shorter than $AlkCWK_{18}$ have low DNA binding affinity and produce large (<500 nm) DNA condensates (Wadhwa et al., 1997), Likewise, derivatization of $CWK_{18}$ with polyethylene glycol (5000 Da) failed to alter the binding affinity of $CWK_{18}$ for DNA but did slightly increase the particles size and significantly decreased the zeta potential determined for PEG-peptide DNA condensates (Example 1, Kwok et al., 1999; Example 3).

The present study compared the particle size and zeta potential when using $AlkCWK_{18}$, triantennary-$CWK_{18}$ or Man9-$CWK_{18}$ as the DNA condensing agent. QELS analysis revealed two populations particles for glycopeptides and peptides also resulting in slightly larger mean diameters such as determined for PEG-peptide DNA condensates (Example 1, Kwok et al., 1999; Example 3). However, unlike PEG-peptides, the zeta potential was found to be equivalent for both glycopeptide and peptide DNA condensates demonstrates that incorporation of an oligosaccharide into the carrier did not alter DNA condensate surface charge. These results suggest that a variety of neutral N-glycans may be substituted onto $CWK_{18}$ without interfering with DNA condensate formation.

The present study thus establishes an efficient route to the synthesis of glycopeptides resulting in glycoconjugates that form small plasmid DNA condensates with utility as targeted gene delivery systems. Given the diversity of carbohydrate lectin interactions in nature (Wadhwa and Rice, 1995), it will be possible to alter the oligosaccharide structure within these glycopeptides to select unique target sites in vivo.

EXAMPLE 4

Glutaraldehyde Crosslinked Peptide DAN Condensates

A. INTRODUCTION

The present example concerns the stability of peptide DNA condensates after introducing glutaraldehyde to crosslink surface amine groups. A twenty amino acid peptide ($CWK_{18}$) was used to condense DNA into small (70 nm) condensates. The reaction between glutaraldehyde and peptide DNA condensates was monitored using a fluorescence based assay to establish reaction completion in 4–5 h when using glutaraldehyde to peptide ratios of 1 to 4 mol equivalents. Higher levels of glutaraldehyde crosslinking led to significant increases in particle size.

The improved stability imparted by glutaraldehyde crosslinking was demonstrated by the increased resistance of DNA condensates to shear stress induced fragmentation. The crosslinked condensates were also significantly more resistant to in vitro metabolism by serum endonucleases. The transient gene expression profiles for crosslinked condensates established a delay in gene expression with increasing crosslinking level which was unique from that produced by high molecular weight polylysine DNA condensates. The results show that crosslinking DNA condensates provide a means to alter the time course of transient gene expression by inhibiting DNA metabolism. These attributes allow the design of non-viral gene delivery carriers that mediate prolonged transient gene expression in vivo.

B. MATERIALS AND METHODS

1. Materials $CWJ_{18}$ (alkylated Cys-Trp-$Lys_{18}$) and dimeric $CWK_{18}$ were synthesized and characterized as described previously (Wadhwa et al., 1997). Glutaraldehyde, SDS, ethidium bromide, proteinase K, DNase I (EC 3.1.21.1) from bovine pancreas, and polylysine$_{(99)}$, polylysine$_{(476)}$ and polylysine$_{(1007)}$ were obtained from Sigma. Plasmid pSEAP (secreted alkaline phosphates with SV40 promoter and late polyadenylation sequence) and SEAP chemiluminescent detection kit were obtained from Clontech™. pSEAP was expressed in E. coli and purified using a Qiagen miniprep column (Valencia, Calif.). TPCK-treated trypsin was obtained from Worthington Biochemicals (Freehold, N.J.). Bradford protein assay was obtained from BioRad (Hercules, Calif.). MEM, fetal calf serum and electrophoresis grade agarose were obtained from Gibco BRL (Gaithersburg, Md.). SYBR-Gold™ was obtained from Molecular Probes (Eugene, Oreg.).

2. Preparation and Characterization of Crosslinked DNA Condensates $CWK_{18}$ DNA condensates were formed by adding 10 µg of pSEAP (4.7 kBp) in 100 µl to 3 nmol of $CWK_{18}$ in 100 µL of 5 mM Hepes, pH 7.4, while vortexing to prepare DNA condensates possessing a calculated amine:phosphate ratio of 2:1. HMW polylysines$_{(99-1007)}$ were prepared at 10 mg/ml in Hepes and used to form DNA condensates at a 2:1 amine:phosphate ratio for each.

After 30 min, $CWK_{18}$ DNA condensates were reacted with either 3, 6, 9, or 12 nmol of glutaraldehyde (1 nmol/µL) for 12 h at 4° C. resulting in 1, 2, 3, or 4 mol equivalents (mol of glutaraldehyde per mol of $CWK_{18}$) of crosslinking. The reaction of glutaraldehyde with DNA condensates was studied using a fluorophore exclusion assay. Following the addition of glutaraldehyde, 10 µL aliquots were removed at time intervals ranging from 0 to 4 h and immediately combined with 490 µL of 0.35 M sodium chloride. Prior to measuring fluorescence, 10 µl of SYBR-Gold™ (diluted 1:200 in DMSO) was added and the fluorescence intensity (Ex: 495 nm, Em: 537 nm) was measured on a Perkin-Elmer™ LS-50B fluorimeter.

The particle size was measured by quasielastic light scattering (QELS) using 350 µL of 50 µg/mL crosslinked DNA condensate in Hepes. Zeta potential measurements were conducted at the same DNA concentration in Hepes using an average of 10 runs to determine the mean and standard deviation on a Brookhaven ZetaPlus™.

3. Shear Stress Stability of DNA Condensates

Peptide DNA condensates (200 µL) were combined with 0–100 µL of 5 M sodium chloride and normalized to 300 µL with Hepes to obtain a final concentration of 0, 0.1, 0.3, 0.5, 0.7, 0.9, 1.2 or 1.5 M sodium chloride. A 100 W Microson XL-2000 ultrasonic probe homogenizer (Kontes, Vineland, N.J.) set at a vibrational amplitude of 5 was used throughout the study. The probe tip was placed ¾ depth into a 1.5 mL microfuge tube containing 300 µL of sample then sonicated for 30 s. DNA samples (15 µL) were brought to 1 M sodium chloride by adding 4.6 µL of 5 M sodium chloride then digested with trypsin (3 µL containing 7 U) for 12 h at 37° C. The samples were combined with 3 µl of loading buffer and 18 µl was applied to a 1% agarose gel electrophoresed in TAE buffer at 70 V for 80 min followed by 12 h destaining in deionized water. Transilluminated gels were photographed on Polaroid™ 667 film.

4. Serum Stability of DNA Condensates

DNA condensates (100 µL) were combined with 100 µL of DNase I augmented mouse serum (0.12 U of DNase I per 100 µl serum) and 3 µL of 5 M sodium chloride to bring the final salt concentration to 150 mM. Samples were incubated at 37° C. for 3 h while rapidly freezing 20 µL aliquots at time points ranging from 0 to 180 min. Serum samples were processed by adding 3 µL (0.31 U) of proteinase K and then incubated at 37° C. for 30 min to remove endonuclease activity. Sodium chloride was then added (4.6 µL of 5 M) along with trypsin (3 µL containing 7 U) and allowed to digest for 12 h at 37° C. to remove the crosslinked peptide. Samples were applied to a 1% agarose gel containing 0.05% SDS and electrophoresed as described above.

5. Transient Gene Expression

HepG2 cells ($3\times10^5$) were plated on 6×35 mm wells and grown for 48 h to 40% confluence in MEM supplemented with 10% fetal calf serum (FCS). Crosslinked DNA condensates (10 µg of DNA in 200 µL) were transfected in triplicate by drop wise addition to cells in 2% FCS either with or without 80 µM chloroquine followed by 5 h incubation, after which the media was replaced with 2 mL of MEM containing 10% fetal calf serum and allowed to incubate for an additional 19 h. Wells were sampled for 10 days at 24 h intervals by removing and freezing (−20° C.) the media and replacing it with 2 mL of fresh 10% FCS MEM.

The amount of SEAP in each well was determined using a chemiluminescent kit. Media (50 µL) was combined with 50 µl of dilution buffer followed by incubation at 65° C. for 30 min to denature endogenous alkaline phosphatase. Assay buffer (100 µL) was added and incubated for 10 min at 25° C. followed by the addition of CSPD [(disodium 3-(4-methoxyspiro{1,2-dioxetane-3,2'-(5'-chloro) tricyclo [$3.3.1.1^{3,7}$]decan}-4-yl) phenyl phosphate)] substrate in chemiluminescent enhancer. After 30 min, the luminescence was measured with a 10 s integration on a Berthold Lumat™ LB 9501 luminometer. Light units were converted to µg/ml of SEAP using a standard curve constructed by adding known quantities of SEAP to cell homogenate. Background alkaline phosphatase production was determined from a 10 day null control that was subtracted from each data set.

C. RESULTS

1. Crosslinked Condensates

Figure 22:
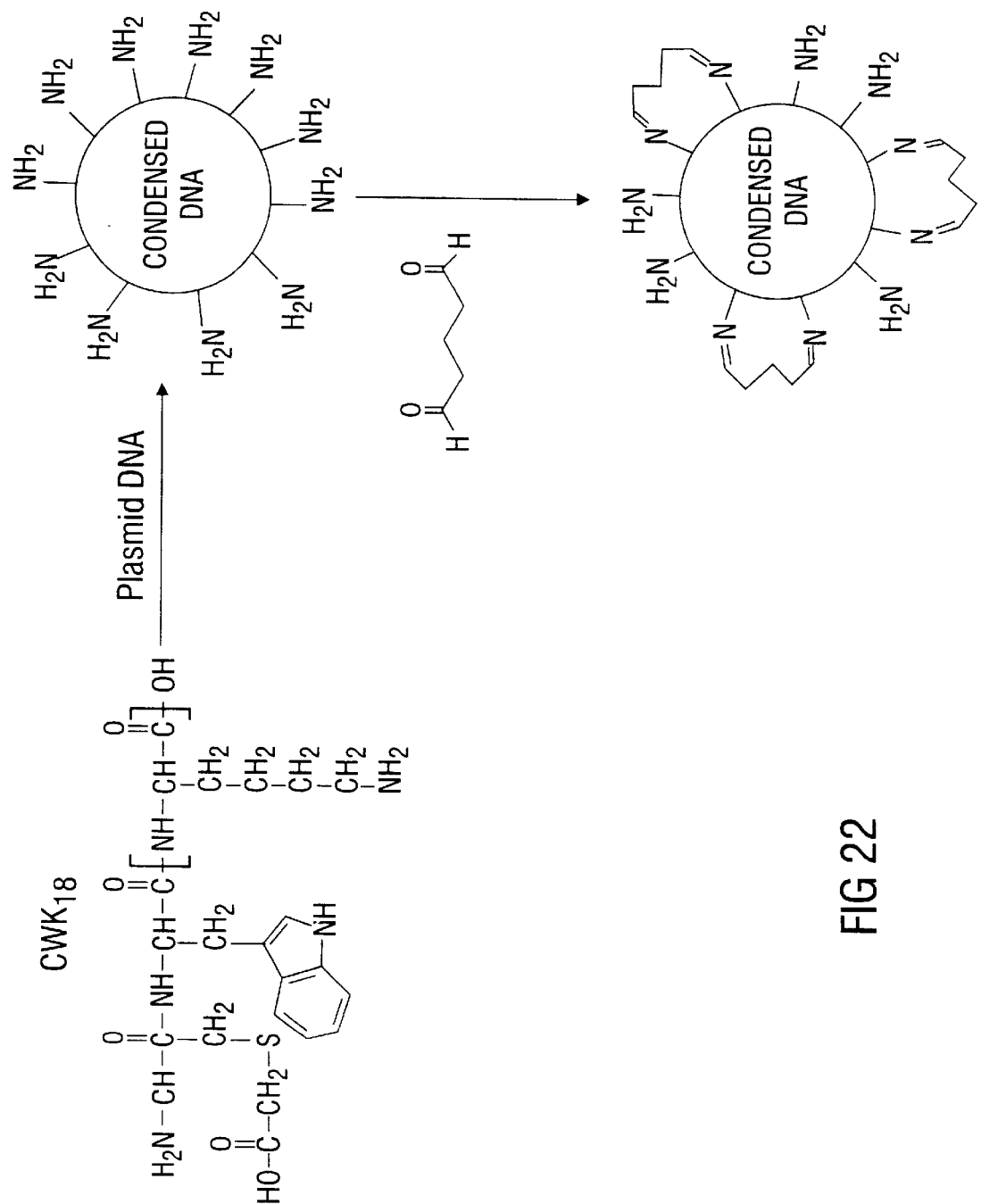
FIG. 22. Glutaraldehyde Crosslinking DNA Condensates. CWK$_{18}$ reacts with plasmid DNA to spontaneously form condensed DNA possessing residual surface amines. Glutaraldehyde reacts with condensed DNA resulting in the formation of two Schiffs base between neighboring amine groups resulting in crosslinked DNA condensates. The degree of crosslinking is expressed as the mols of glutaraldehyde added relative to mols of CWK$_{18}$.

The metabolic stability and the duration of transient gene expression were investigated in relationship to the degree of crosslinking applied to peptide DNA condensates. Peptide DNA condensates are colloids that possess primary amines on their surface that can be crosslinked with homobifunctional agents such as glutaraldehyde (FIG. 22). The resulting inter-peptide crosslinks should stabilize condensed DNA from peptide dissociation and from metabolism since it has been previously established that condensed DNA resists endonuclease attack (Chiou et al., 1994; Adami et al., 1998).

To establish that glutaraldehyde reacts with condensed DNA to form inter-peptide crosslinks, the time course of the reaction was evaluated using a fluorescent intercalator dye. SYBR-Gold™ was selected since its intercalation into DNA is not significantly inhibited in sodium chloride up to 1 M. In the absence of sodium chloride, the reaction of SYBR-Gold™ with $CWK_{18}$ DNA condensates produces minimal fluorescence whereas the partial dissociation of condensates that occurred in 0.35 M sodium chloride produced a maximal fluorescence following intercalation (FIG. 23).

Figure 23:
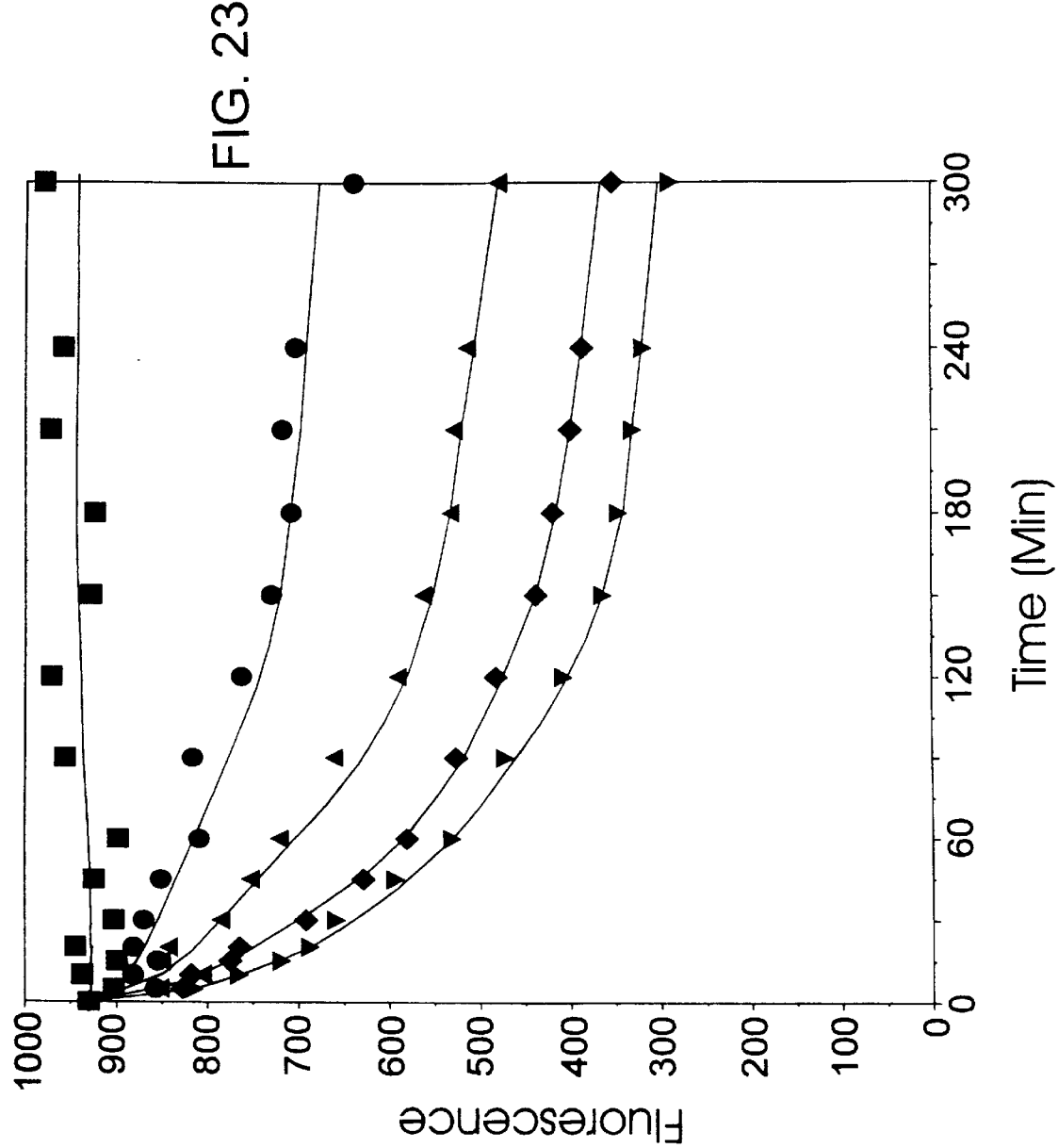
FIG. 23. Kinetics of Glutaraldehyde Crosslinking CWK$_{18}$ DNA Condensates. The reaction between glutaraldehyde and condensed DNA was measured by a fluorescence assay described in Example 4. An inverse relationship between the amount of glutaraldehyde added and fluorescence intensity indicated an increased reaction rate corresponding to increased glutaraldehyde crosslinking. The data represents un-crosslinked (■), 1 mol equiv (●), 2 mol equiv (π), 3 mol equiv (♦), and 4 mol equiv (θ) crosslinked DNA condensates.

After the addition of glutaraldehyde, the formation of inter-peptide crosslinks stabilized $CWK_{18}$ DNA condensates from dissociating in 0.35 M sodium chloride, leading to a decrease in the fluorescence intensity as the reaction proceeded over 5 h (FIG. 23). Analysis of the reaction profile while varying the stoichiometry of glutaraldehyde from 1 to 4 mol equivalents established a progressive decrease influorescence intensity while still reaching reaction completion in 5 h, suggesting that increasing the glutaraldehyde concentration leads to the formation of additional crosslinks and further stabilization of DNA condensates (FIG. 23).

Figure 24A:
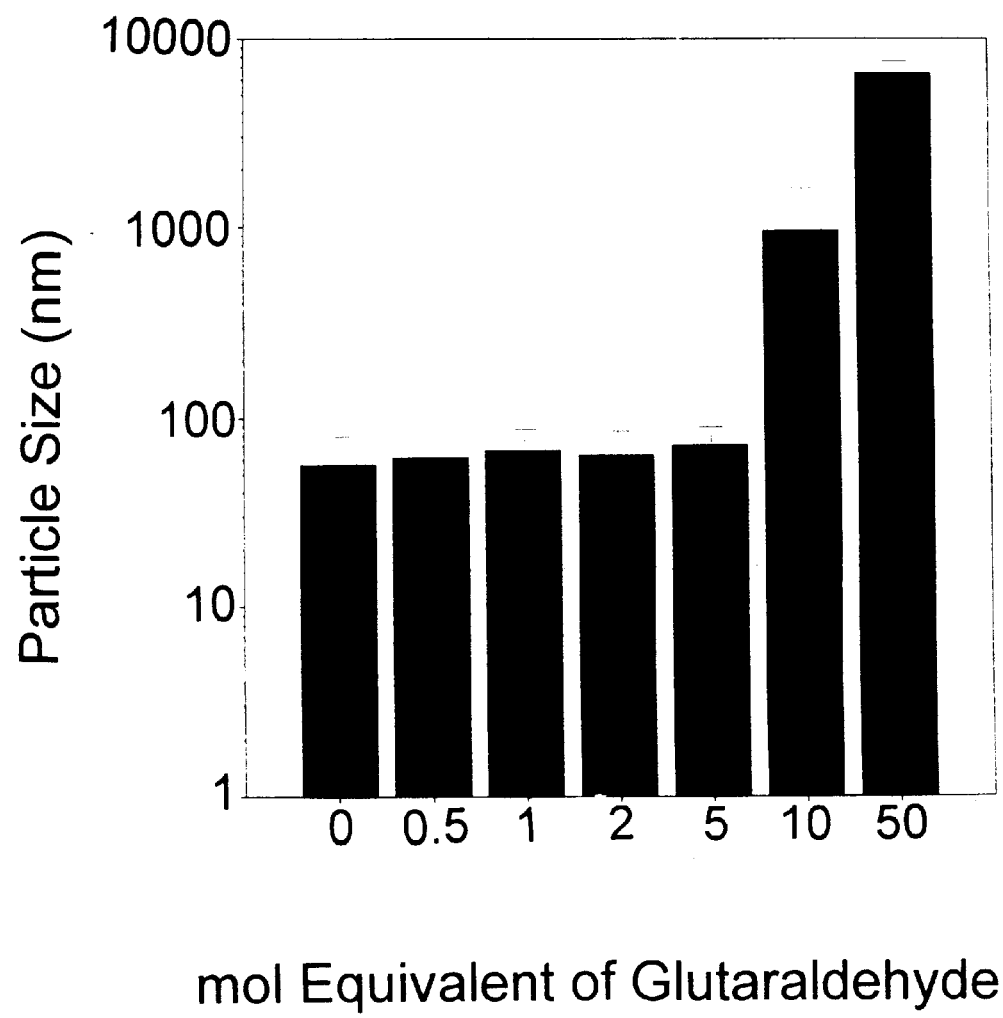
FIG. 24A and FIG. 24B. Particle Size and Zeta Potential Analysis of Crosslinked DNA Condensates.
Figure 24B:
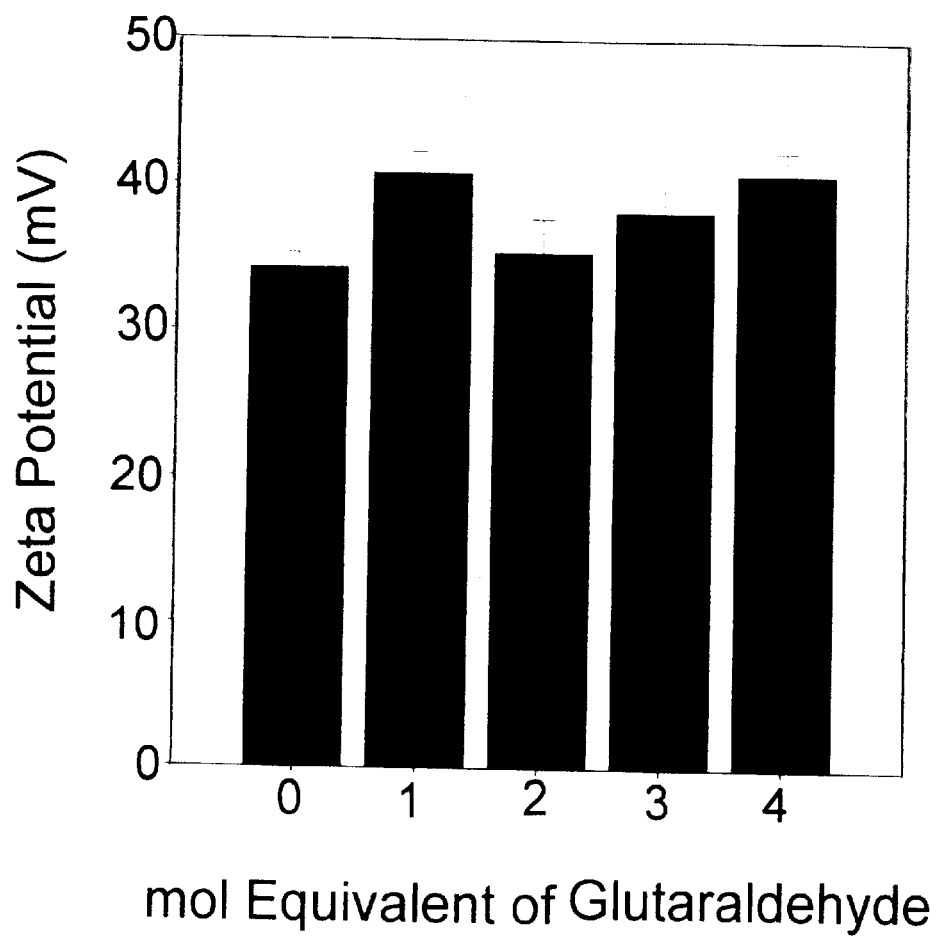

Since glutaraldehyde could potentially also produce inter-particle crosslinks leading to larger DNA condensates, the relationship between the degree of crosslinking and the particle size was investigated by QELS analysis. DNA condensates prepared with 1 to 5 mol equivalents of glutaraldehyde maintained a particle size of 60–70 nm, whereas stoichiometries of 10 mol equivalents or higher caused a significant increase in size suggesting the formation of inter-particle crosslinks (FIG. 24A). At 4 mol equivalents of glutaraldehyde or lower, the zeta potential of DNA condensates remained between +34–41 mV, establishing minimal change in the overall charge of DNA condensates (FIG. 24B).

2. Shear Stress Stability

Figures 25A, 25B, 25C:
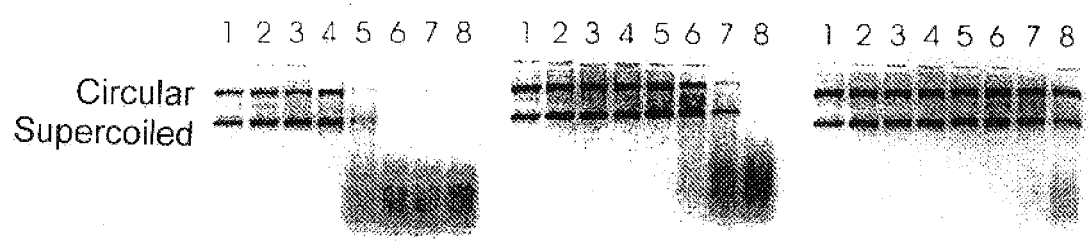
FIG. 25A, FIG. 25B, FIG. 25C, FIG. 25D, FIG. 25E and FIG. 25F. Shear Stress Stability of Crosslinked DNA Condensates. The stability of crosslinked DNA condensates was measured by 30 s sonication in the presence of increasing sodium chloride concentration as described in Example 4. The electrophotoretic analysis of $CWK_{18}$ DNA condensates prepared with 0 (FIG. 25A), 1 (FIG. 25B), 2 (FIG. 25C), 3 (FIG. 25D) and 4 (FIG. 25E) mol equivalent of glutaraldehyde were compared to polylysine$_{1007}$ DNA condensates (FIG. 25F). Lanes 1 through 8 contain 0, 0.1, 0.3, 0.5, 0.7, 0.9, 1.2, and 1.5 M sodium chloride. The dissociation of $CWK_{18}$ from DNA occurs at 0.7 M sodium chloride (FIG. 25A, lane 5) as determined by the formation of fragments during sonication. Alternatively, 1 mol equivalent of glutaraldehyde extended the DNA stability to 0.9 M sodium chloride (FIG. 25B, lane 6), 2 mol equivalent of glutaraldehyde increased the stability to 1.2 M sodium chloride (FIG. 25C, lane 7), and 3 and 4 mol equivalents of glutaraldehyde resulted in DNA condensates that were stable in 1.5 M sodium chloride (FIG. 25D and FIG. 25E). In contrast, polylysine$_{107}$ DNA condensates dissociate in 1.5 M sodium chloride (FIG. 25F, lane 8).
Figures 25D, 25E, 25F:
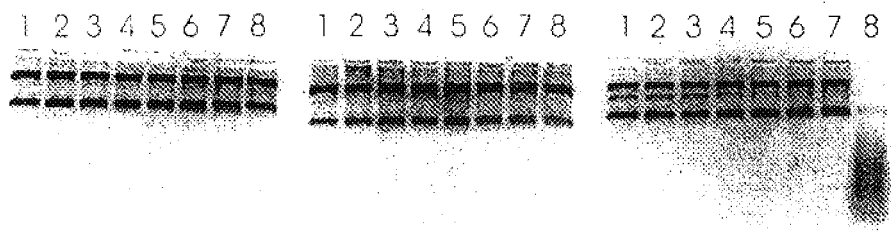

The shear stress stability of glutaraldehyde crosslinked DNA condensates was evaluated by gel electrophoresis. $CWK_{18}$ DNA condensates resist fragmentation when subjected to 30 s sonication until the sodium chloride concentration reached 0.7 M or higher, causing dissociation of peptide resulting in DNA fragmentation during sonication (FIG. 25A). By comparison, DNA condensates crosslinked with 1 mol equivalent of glutaraldehyde resist fragmentation in 0.9 M sodium chloride (FIG. 25B). Reaction with 2 mol equivalents of glutaraldehyde led to further stabilization resulting in condensates that resist fragmentation in 1.2 M sodium chloride (FIG. 25C). Increasing the crosslinking to 3 and 4 mol equivalents of glutaraldehyde resulted in DNA condensates that were stable up to 1.5 M sodium chloride (FIG. 25D and FIG. 25E). Alternatively, polylysine$_{1007}$ DNA condensates were found less stable, undergoing fragmentation during sonication in 1.5 M sodium chloride (FIG. 25F).

These results suggest that the inter-peptide crosslinks formed with 3 and 4 mol equivalents of glutaraldehyde extend the stability of $CWK_{18}$ DNA condensates beyond that achievable with a HMW polylysine. Control studies established that plasmid DNA did not change its gel electrophoretic banding pattern when reacted with glutaraldehyde, suggesting that the exocylic amines on plasmid DNA bases are inaccessible to Shiffs-base formation.

3. Serum Stability

To be effective in gene delivery, crosslinked DNA condensates should also resist digestion with serum endonucleases. The metabolic stability of DNA was examined by gel electrophoretic analysis of DNA condensates incubated in mouse serum. Since uncrosslinked $CWK_{18}$ DNA condensates proved to be resistant to endogenous serum endonuclease during a 24 h incubation exogenous DNase I was added to accelerate the metabolism in a 3 h period.

Incubation of $CWK_{18}$ DNA condensates in 50% serum containing 0.12 units of DNase I resulted in metabolism into oligonucleotides after 60 min (FIG. 26A, lane 5). A trypsin contaminant produced a single strand nick in the DNA, such that even at time zero only circular and linear forms of DNA were recovered. Crosslinking $CWK_{18}$ DNA condensates with 1–4 mol equivalents of glutaraldehyde produced a progressive increase in metabolic stability with even 1 mol equivalent of glutaraldehyde extending the stability of DNA condensates from 60 to 90 min (FIG. 26B). The addition of 2 to 4 mol equivalents extended the stability even further as evidenced by an increase in band intensity at 90 to 180 min (FIG. 26C, FIG. 26D and FIG. 26E). By comparison, polylysine$_{1007}$ DNA condensates demonstrate slightly improved serum stability to that of glutaraldehyde crosslinking at 4 mol equivalents (FIG. 26F).

4. Gene Expression

The cytotoxity of both free glutaraldehyde and crosslinked DNA condensates were examined in cell culture. The total protein of cell homogenates harvested 24 h after transfecting cells in the presence of free glutaraldehyde or crosslinked DNA condensates were indistinguishable from control, indicated no toxicity when using 1–4 mol equivalents of glutaraldehyde corresponding to 1.5–6 μM.

The ability of crosslinked DNA condensates to release DNA and mediate gene transfer was examined by measuring the alkaline phosphates secreted from HepG2 cells over a 10 days period. When using chloroquine to augment endosomal escape and increase gene expression, uncrosslinked peptide DNA condensates produced a transient gene expression profile that peaked at day 3 and then decreased to near background by day 10 (FIG. 27A), with total transgene expression reaching 1.5 μg (FIG. 27B).

The moderate increase in stability afforded by 1 mol equivalent of glutaraldehyde resulted in an expression profile and cumulative SEAP production identical to that afforded by uncrosslinked condensates. Alternatively, crosslinking with 2 mol equivalent of glutaraldehyde resulted in a peak expression level that was nearly two-fold greater than uncrosslinked DNA condensates (FIG. 27A). These results are in contrasted with those using 3 mol equivalent of glutaraldehyde which led to overall lower expression but a peak which occurred at day 4. Likewise, the expression profile determined for 4 mol equivalent crosslinked DNA condensate was significantly reduced in magnitude but peaked at day 5.

Comparison of the cumulative SEAP production for each condensate established a range of 0.3 to 2.2 μg over the ten day period (FIG. 27B). Condensates possessing 2 and 3 mol equivalents of glutaraldehyde reached a plateau in total SEAP production at day 6. The day 7–10 SEAP production continued at a rate that was two-fold greater than that of uncrosslinked or 1 mol equivalent crosslinked DNA condensates. However, the SEAP production mediated by $CWK_{18}$ DNA condensates crosslinked with 4 mol equivalent of glutaraldehyde was constant throughout day 1–10 resulting in a linear regression line with a slope of 42 ng/day and $r^2=0.986$ (FIG. 27B).

Figure 28A:
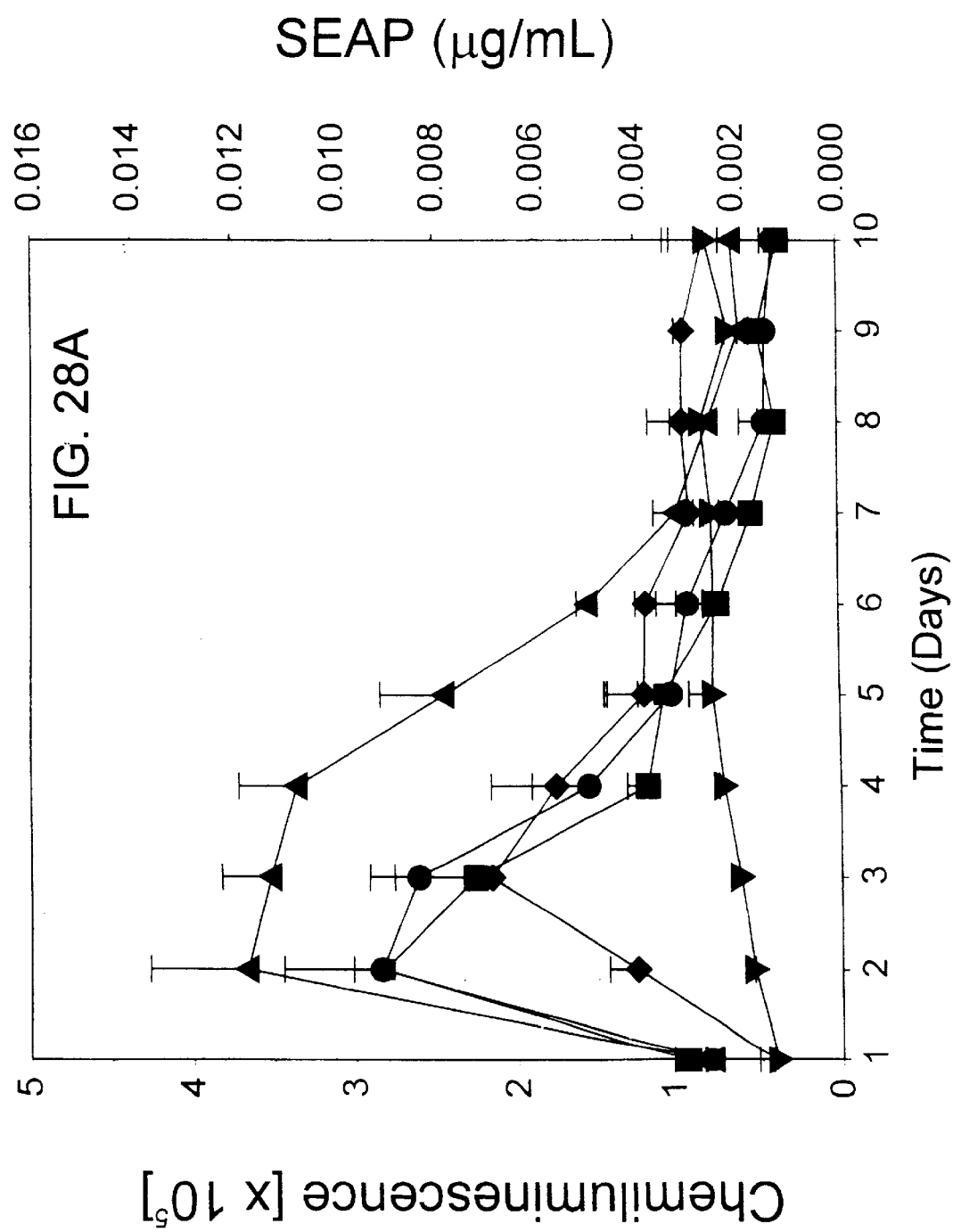

When chloroquine was omitted from the assay, the transient gene expression mediated by each peptide DNA condensate was reduced by over one order of magnitude (FIG. 28A). However, the delay in gene expression identified for condensates prepared with 3 and 4 mol equivalents of glutaraldehyde was similar both with and without chloroquine (FIG. 28A). Likewise, cumulative gene production for 2 and 3 mol equivalent crosslinked DNA condensates produced day 7–10 slopes that were two-fold greater than uncrosslinked or 1 mol equivalent crosslinked DNA condensates (FIG. 28B). In addition, the slope for day 1–10 cumulative SEAP production was two-fold greater (5.7 ng/day with an $r^2=0.999$) for $CWK_{18}$ DNA condensates prepared with 4 mol equivalents of glutaraldehyde compared to uncrosslinked DNA condensates, providing further evidence for the controlled expression of SEAP (FIG. 28B).

Figure 29B:
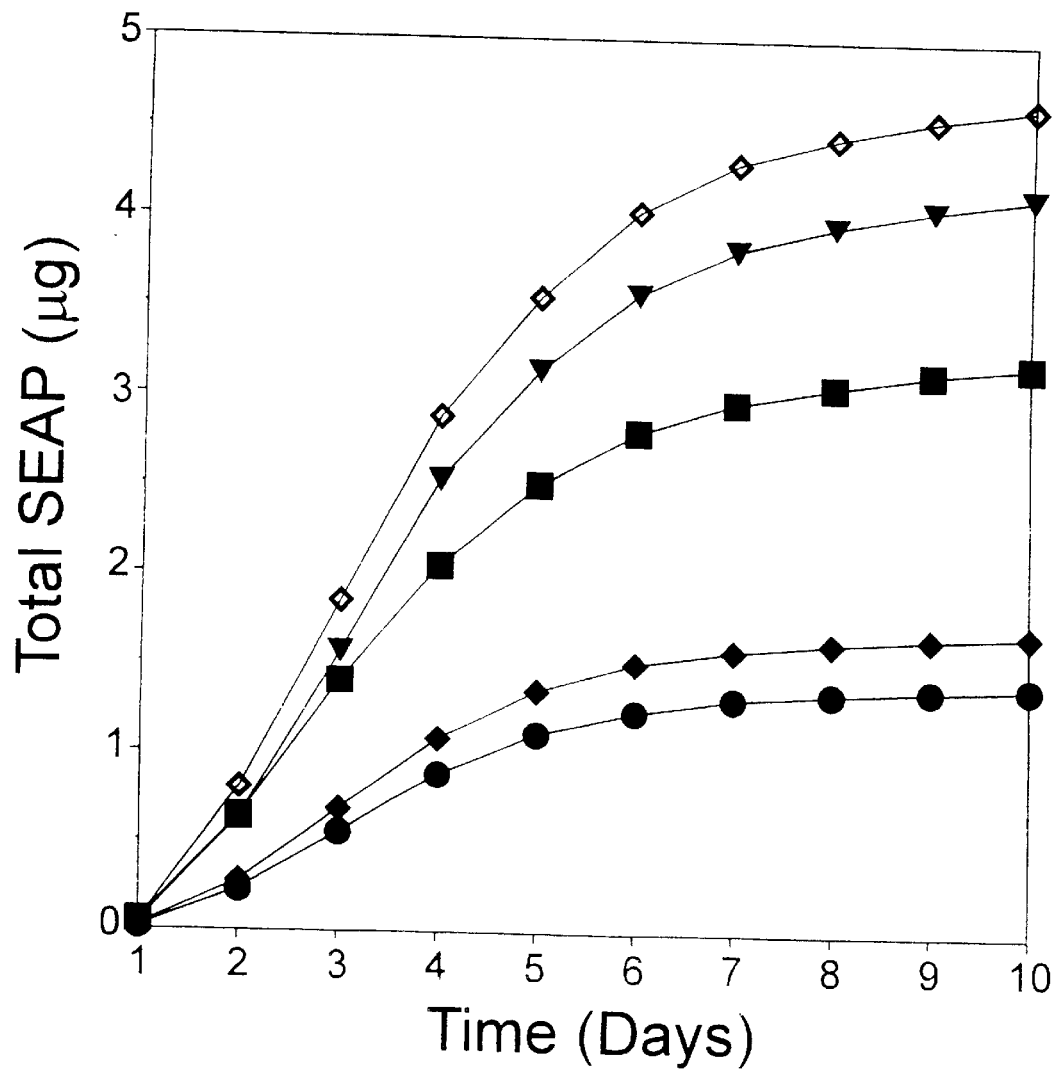

A possible consequence of glutaraldehyde crosslinking could be the formation of long polylysine chains. To confirm that the expression profiles are not the result of linear polymerization of $CWK_{18}$ the transient gene expression profile was studied using DNA condensates prepared with a panel of HMW polylysines (FIG. 29A). The expression of SEAP exhibited a peak intensity correlating directly with the increase in chain length of polylysine, with each peptide DNA condensate mediating a maximum in the gene expression at day 3–4 (FIG. 29A). Dimeric $CWK_{18}$ DNA condensates produced approximately 10% more gene product relative to $CWK_{18}$ DAN condensates. Polylysine$_{99}$ resulted in nearly 1.5-fold greater gene expression, whereas the greatest levels of transient gene expression were achieved with polylysine$_{476 \text{ and } 1007}$ DNA condensates which produced 2.1 and 3.2-fold greater gene expression than $CWK_{18}$ DNA condensates (FIG. 29B). Likewise, the cumulative SEAP expression (days 7–10) following plateau after day 6 also demonstrated a 3-fold increase in slope when comparing $CWK_{18}$ DNA and polylysine$_{(1007)}$ DNA condensates.

D. DISCUSSION

A DNA formulation for successful application in vivo should avoid metabolism, which that results in the generation of fragmented DNA that no longer mediates gene expression. HMW polylysines are variable, are uncontrolable in terms of conjugation and are cytotoxic. In contrast, the present example provides LWM DNA carriers that are homogeneous, condense DNA into small condensates, may be selectively derivatized, and that are minimal in size to reduce toxicity.

Using glutaraldehyde, the surface amine groups on $CWK_{18}$ DNA condensates undergo crosslinking over a 4–5 h period when very low concentrations of glutaraldehyde (1–4 mol equivalents relative to $CWK_{18}$) are added. This amount of glutaraldehyde is below the amounts needed to observe toxicity in cells grown in culture. Crosslinked DNA condensates were increasingly stable to sonicative fragmentation at crosslinking levels ranging from 1–4 mol equivalents of glutaraldehyde and were even found to be more stable than HMW polylysine$_{(99-1007)}$ DNA condensates.

The present example establishes the principle of crosslinking DNA condensates using glutaraldehyde and advances the field of non-viral gene delivery through the application of crosslinkers to transiently stabilize peptide DNA condensates leading to intercellular controlled release of DNA and prolonged gene expression profiles in vivo.

EXAMPLE 5

Low Mr Self-Crosslinking Peptides

A. INTRODUCTION

A variety of nonviral gene delivery carriers have been developed and tested as in vitro transfection agents used to transiently express foreign DNA. Attempted in vivo use has revealed many complications related to their toxicity (Wolfert and Seymor, 1996), antigenicity (Stankovics et al., 1994), complement activation (Plank et al., 1996), solubility (Toncheva et al., 1998), blood compatibility (Yang and Huang, 1997), and stability (Kwoh et al., 1999). These complications relate to the size and charge of DNA carrier complexes and ultimately to the molecular characteristics of the carrier itself. High molecular weight (HMW) DNA carriers can be cytotoxic (Wolfert and Seymor, 1996), are able to activate the complement system (Plank et al., 1996) and can elicit an immune response (Stankovics et al., 1994). The size and heterogeneity of these polymers also significantly complicates regio-specific derivatization with ligands or polyethylene glycol (Wolfert et al., 1996).

To circumvent these problems, several low molecular weight (LMW) carrier peptides have been developed that mediate in vitro gene transfer as efficiently as their HMW counterparts (Gottschalk et al., 1996; Wadhwa et al., 1997; Plank et al., 1999). These offer the advantage of controlled synthesis and defined purity that then allows strategic optimization to increase expression levels and eliminate side effects. However, when analyzed for in vivo efficacy, LWM peptide DNA condensates lacked sufficient stability to survive circulation, were not able to significantly protect DNA from metabolism, and could not effect targeting (Kwoh et al., 1999; Collard et al., 2000a; Collard et al., 2000b).

A solution of the present inventors is to increase LMW peptide DNA condensate stability by forming intra-particle cross-links to inhibit the dissociation of condensing peptides. Glutaraldehyde was evaluated as one type of cross-linking agent that forms Schiff-bases between neighboring peptides and increases the metabolic stability of LMW peptide DNA condensates (Admai and Rice, 1999; Example 4). Gutaraldehyde cross-linked DNA condensates were significantly more metabolically stable both in vitro and in vivo (Example 4; Collard et al., 2000a; Example 7; Collard et al., 2000b; Adami and Rice, 1999), and were able to facilitate specific receptor targeting in vivo (Example 4; Colland et al., 2000a; Example 7; Collard et al., 2000b).

However, the present inventors continued to design improved stabilized LMW peptide DNA condensates that are reversibly cross-linked and simultaneously enhance gene expression. To achieve this, multiple cysteine residues were incorporated into LMW condensing peptides to provide components that form inter-peptide disulfide bonds while bound to DNA. Once internalized, it was reasoned that the reducing environment of the cell (Mellman et al., 1986) would allow disulfide cross-linked DNA condensates to undergo reduction and release DNA more readily than glutaraldehyde cross-linked DNA condensates.

The present example describes the synthesis of a panel of novel LMW cross-linking peptides that not only undergo disulfide cross-linking to form small stabilized DNA condensates, but also enhance in vitro gene expression. These findings show that cross-linking peptides are promising candidates for further development into LMW DNA carriers that function in vivo.

B. MATERIALS AND METHODS

1. Materials

N-terminal Fmoc protected amino acids, 9-hydroxybenzotriazole (HOBt), diisopropylcarbodiimide (DIC), and diisopropylethylamine were obtained from Advanced Chem Tech (Lexington, Ky.). Substituted Wang™ resin for peptide synthesis was obtained from ChemImpex (Wood Dale, Ill.). Polylysine$_{1007}$™ was purchased from Sigma Chemical Co. (St. Louis, Mo.). N,N-dimethylformamide, trifluoroacetic acid (TFA), acetic acid, acetontrile, and piperidine were purchased from Fisher Scientific (Pittsburgh, Pa.). Tris(2-carboxyethyl)-phosphine hydrochloride (TCEP) was obtained from Pierce (Rockford, Ill.) LB media, LB agar, D-luciferin, and luciferase from *Photinus pyralis* (EC 1.13, 12.7) were obtained from Boehringer Mannheim (Indianapolis, Ind.). HepG2 and COS 7 cells were from the American Type Collection (Rockville, Md.) Inactivated "qualified" fetal bovine serum (FBS) was from Gibco BRL (Grand Island, N.Y.). Bradford reagent was purchased from BioRad (Hercules, Calif.), and thiazole orange was obtained from Beckton Dickinson Immunocytometry Systems (San Jose, Calif.). SYBR-Gold™ was purchased from Molecular Probes, Inc. (Eugene, Oreg.).

The 5.6 kb plasmid pCMVL encoding the reporter gene luciferase under the control of the cytomegalovirus promoter was obtained from Dr. M. A. Hickman at the University of California, Davis (Hickmann et al., 1994). A 7.5 kb plasmid expressing nuclear targeted β-galactosidase (NTβGal) under the control of the CMV promoter was obtained from the University of Michigan core vector laboratory (Ann Arbor, Mich.). Endotoxin free plasmids were purified from *E. coli* on a Qiagen ultrapure™ column used according to the manufacturers instructions that typically yielded plasmid DNA that was 50:50 supercoiled and open circular as determined by agarose gel electrophoresis.

Peptide synthesis was performed on a computer interfaced Model 90 Advanced ChemTech solid phase peptide synthesizer (Lexington, Ky.). Peptide purification was performed using a semi-preparative (10 μm) $C_{18}$ RP-HPLC column from Vydac (Hesperia, Calif.). Preparative HPLC was performed using a computer-interfaced HPLC and fraction collector from ISCO (Lincoln, Neb.). Electrospray mass spectrometry (ES-MS) was performed using a Finnigan LCQ mass spectrometer (San Jose, Calif.) interfaced with an analytical HPLC from Hitachi (San Jose, Calif.).

2. Peptide Synthesis and Characterization

Cys-Trp-Lys$_{18}$ (CWK$_{18}$), alkylated (Alk)CWK$_{18}$ and dimeric (Di)CWK$_{18}$ were synthesized as described previously (Wadhwa et al., 1997). All other peptides were synthesized using standard Fmoc procedures with 9-hydroxybenzotriazole (HOBt) and diisopropylcarbodiimide (DIC) double couplings followed by N-capping with acetic anhydride after each coupling to avoid deletion sequences. Peptides were cleaved from the resin and side-chain protecting groups were removed by reaction with TFA/EDT/water (95:2.5:2.5 vol/vol/vol) for 1 h.

Peptides were purified to homogeneity on RP-HPLC by injecting 2 μmol onto a Vydac $C_{18}$ semi-preparative column (2×25 cm) eluted at 10 ml/min with 0.1% TFA and a gradient of acetonitrile (5 to 25% over 30 min) while monitoring tryptophan absorbance at 280 nm. The major peak eluting at 23 min was collected and pooled from multiple runs, concentrated by rotary evaporation, lyophilized, and stored dry at −20° C. Purified peptides were reconstituted in 0.1% TFA (degassed with nitrogen) and quantified by tryptophan absorbance ($\epsilon_{280}$=5600 $M^{-1}$ $cm^{-1}$) to determine the isolated yield which was typically 20%.

Purified peptides were characterized by LC-MS by injecting 5 nmol onto a Vydac $C_{18}$ analytical column (0.47×25 cm) eluted at 1 ml/min with 0.1 vol/vol % acetic acid containing 0.02 vol/vol % TFA and an acetonitrile gradient of 1 to 30% over 30 min. The RP-HPLC eluent was directly infused into the electrospray ionization source of a Finnigan LCQ mass spectrometer and mass spectral data was obtained in the positive mode (Arnott et al., 1993; Smith et al., 1990).

3. Peptide DNA Condensation

Peptide DNA condensates were prepared by combining 25 μg of DNA in 500 μl of Hepes buffered mannitol (HBM) (0.27 M mannitol, 5 mM Hepes, pH 7.5) with 5 to 75 nmol of peptide in 500 μl of HBM while vortexing to create DNA condensates possessing a calculated charge ratio ($NH_4^+$: $PO_4^{-2}$) ranging from 0.1 to 2.4. Peptide DNA condensates were incubated for 2 h at RT to allow cross-linking.

The relative binding affinity of each peptide for DNA was monitored by a fluorophore exclusion assay (Wadhwa et al., 1997). Peptide DNA condensates (50 µl) were added to 950 µl of HBM containing 0.1 µM thiazole orange. The fluorescence of the intercalated dye was measured using an LS50B fluorometer (Perkin Elmer, UK) by exciting at 500 nm while monitoring emission at 530 nm with the slit width set at 15 and 20 nm, respectively. Fluorescence blanks were subtracted from all values before data analysis.

The particle size of each peptide DNA condensate was determined by quasielastic light scattering (QELS) at a scatter angle of both 15° and 90° on a Brookhaven Zeta-Plus™ particle sizer. Condensates were prepared at a DNA concentration of 50 µg/ml in 400 µl HBM at a stoichiometry of 0.4 nmol of peptide per µg of DNA corresponding to a charge ratio of approximately 2:1 for each. The mean diameter and population distribution were computed from the diffusion coefficient using a unimodal cummulant analysis supplied by the manufacturer.

The particle size and zeta peptide IV DNA condensates were determined by titrating 7.5 to 37.5 nmol of peptide with 75 µg of DNA in 1.5 ml of HBM to produce 50 µg/ml DNA condensates with charge ratio of 0.5–2.5. The zeta potential was averaged from 10 determines.

4. Kinetics of Peptide Cross-linking

The kinetics of disulfide bond formation in solution was monitored by EM-MS. Fully reduced peptide V (80 nmol) (Table 2) was dissolved in 800 µl of 50:50 vol/vol % methanol:ammonium acetate (1 mM pH 7.5) and directly infused via a syringe pump into the electrospray ionization source of a Finnigan LCQ™ mass spectrometer at 3 µl/min. Single ion monitoring (SIM) scans were taken at 20 sec intervals over 2 h while monitoring the disappearance of the $M+2H^+$ parent ion (1258 amu) and formation of the $M+2H^+$ ion of the oxidized species (1256 amu).

The kinetics of cross-linking within peptide DNA condensates was studied indirectly by monitoring the displacement of SYBR-Gold™ intercalator dye from DNA condensates as a function of time. Peptide DNA condensates were prepared (200 µl of 50 µg/ml) at a peptide stoichiometry of 0.4 nmol per µg of DNA. Immediately after mixing peptide and DNA, a 10 µl aliquot was combined with 990 µl of SYBR-Gold™ (1X) and the fluorescence intensity (Ex 495 nm, Em 537 nm) was continuously monitored for 30 min.

The rate of cross-linking was also examined as a function of peptide concentration. The stoichiometry of peptide IV was increased from 0.4 to 1.2 nmol per µg of DNA and the rate of declining fluorescence intensity was determined as described above.

5. Chemical Reactivity of Cross-linking Peptides with DNA

A synthetic oligonucleotide (TCATGCATCC) (Gibco Life Sciences, Grand Island, N.Y.) was reconstituted in 10 mM ammoniumacetate (pH 7.4) and combined with either $AlkCWK_{18}$ or peptide V resulting in an oligonucleotide concentration of 17 µM and a stoichiometry of 0.4 nmole peptide per µg oligonucleotide. Peptides were allowed to react with the oligonucleotide for 2 h at 37° C., lyophilized and then reconstituted in 500 µl of 70:20:5:5 vol/vol % acetonitrile:water:triethylamine:acetone to a final DNA concentration of 10 µM. The reaction products were directly infused at 25 µl/min into the electrospray source of a Finnigan LCQ™ mass spectrometer. The mass of the oligonucleotide and peptide-oligonucleotide conjugates was monitored by acquiring spectra in the negative mode.

6. Shear Stress Stability of Cross-linked DNA Condensates

Peptide DNA condensates (200 µl of 50 µg/ml) were formed and incubated at RT for 30 min and then combined with 0 to 200 µl of 5 M sodium chloride and normalized to 400 µl with HBM to achieve a final sodium chloride concentration of 0, 0.2, 0.4, 0.8, 1.0, 1.5, 2.0, and 2.5 M. Each sample was sonicated for 30 sec with a 100 W Microson™ XL-2000 ultrasonic probe homogenizer (Kontes, Vineland N.J.) with a vibrational amplitude of 6 to fragment uncondensed DNA (Adami et al., 1998). DNA condensates were digested with 30 µg of trypsin for 12 h at 37° C. then electrophoresed on an agarose gel and visualized by ethidium bromide staining.

7. In Vitro Gene Expression

HepG2 cells ($1.5 \times 10^5$) were plated on 6×35 mm wells and grown to 40–70% confluency in MEM supplemented with 10% FBS, penicillin and streptomycin (10,000 U/ml), sodium pyruvate (100 mM), and L-glutamine (200 mM). Transfections were performed in MEM (2 ml per 35 mm well) with 2% FBS and 80 µM chloroquine. Peptide DNA condensates (10 µg of DNA in 0.2 ml HBM) were added dropwise to triplicate wells. After a 5 h incubation at 37° C., the media was replaced with MEM supplemented with 10% FBS. After 24 h, cells were washed twice with ice-cold phosphate buffered saline (calcium and magnesium free) and then treated with 0.5 ml of ice-cold lysis buffer (25 mM Tris chloride pH 7.8, 1 mM EDTA, 8 mM magnesium chloride, 1% Triton X-100, 1 mM DTT) for 10 min. The cell lysate was scraped, transferred to 1.5 ml microcentrifuge tubes, and centrifuged for 7 min at 13,000 g at 4° C. to pellet debris.

Lysis buffer (300 µl), sodium-ATP (4 µl of a 180 mM solution, pH 7, 4° C.) and cell lysate (100 µl, 4° C.) were combined in a test tube, briefly mixed and immediately placed in the luminometer. Luciferase relative light units (RLU) were recorded on a Lumat™ LB 9501 (Berthold systems, Germany) with 10 sec integration after automatic injection of 100 µl of 0.5 mM D-luciferin (prepared fresh in lysis buffer without DTT). The RLU were converted in fmol using a standard curve generated by adding a known amount of luciferase (0.01 to 100 fmols with specific activity of 2.5 nU/fmol) to 35 mm wells containing 40–70% confluent HepG2 cells. The cells were processed as described above resulting in a standard curve with an average slope of $7.8 \times 10^6$ RLU per fmol of enzyme. Protein concentrations were measured by Bradford assay using bovine serum albumin as a standard (Bradford, 1976). The amount of luciferase recovered in each sample was normalized to milligrams of protein and reported as the mean and standard deviation obtained from triplicate transfections.

LipofectAce™ (Gibco BRL, 1:2.5 w/w dimethyl diotadecylammonium bromide and dioleoyl phosphatidylethanolamine) was used to mediate gene transfection according to the manufacturer's instructions. The ratio of DNA to LepofectAce™ was optimized for HepG2 cells. An optimal DNA/LipofectAce™ ratio was achieved by dissolving 10 µg of DNA in 100 µl serum free media (SFM) followed by adding 60 µl of LipofectAce™ prepared in 140 µl of SFM. The LipfectAce™ DNA complex was then diluted with 1.7 ml of SFM and used to transfect HepG2 cells for 5 h followed by replacing the transfecting media with media supplemented with 10% FBS. The cells were incubated for a total of 24 h, harvested and analyzed for luciferase as described above.

COS 7 cells (72,000) were plated in 35 mm wells and grown to 50% confluency in DMEM (Gibco BRL) supplemented with penicillin and streptomycin (10,000 U/ml), L-glutamine (200 mM), and 10% FBS for 24 h. The cells were transfected as described for HepG2 cells.

The number of cells transfected in vitro was examined using a plasmid encoding nuclear targeted β-galactosidase followed by X-gal (5-bromo-4-chloro-3-indolyl-β-galactopyranoside) staining. HepG2 and COS 7 cells were transfected for 5 h as described above with either AlkCWK$_{18}$ DNA, peptide II DNA condensates, or plasmid DNA and then grown in fresh media for an additional 43 h. After removing media, cells were fixed for 5 min in phosphate-buffered saline (PBS, pH 7.3) containing 1.25 vol/vol % glutaraldehyde and then stained by incubation with 0.05 wt/v % X-gal, 1 mM magnesium chloride, 10 mM potassium ferricyanide, and 10 mM potassium ferrocyanide in PBS. After 4 h at 37° C., the X-gal solution was removed and the nuclear stained blue cells were counted with a light microscope under ten power magnification by averaging the number of transfectants from nine fields. Values were analyzed for significance by one-way analysis of variance.

8. Cell Uptake Studies

Iodinated plasmid DNA (pCMVL) was prepared with specific activity of 300 nCi per μg of DNA as described previously (Terebesi et al., 1998). Prior to forming DNA condensates, the specific activity of the $^{125}$I DNA was adjusted to 4.5 nCi μg of DNA by combining with unlabeled plasmid. DNA condensates were prepared using AlkCWK$_{18}$ or peptide II as described above. Peptide $^{125}$I-DNA condensates (10 μg) were used to transfect HepG2 and COS 7 cells for 5 h according to the procedure described above. The radioactive media was removed, cells were washed once with 2 ml of 1 M sodium chloride and three times with 2 ml of cold PBS and then harvested with 1 ml of lysis buffer. The cell-associated radioactivity from triplicate transfections was quantified by gamma counting.

C. RESULTS AND DISCUSSION

1. Crosslinked Condensates

Figure 30:
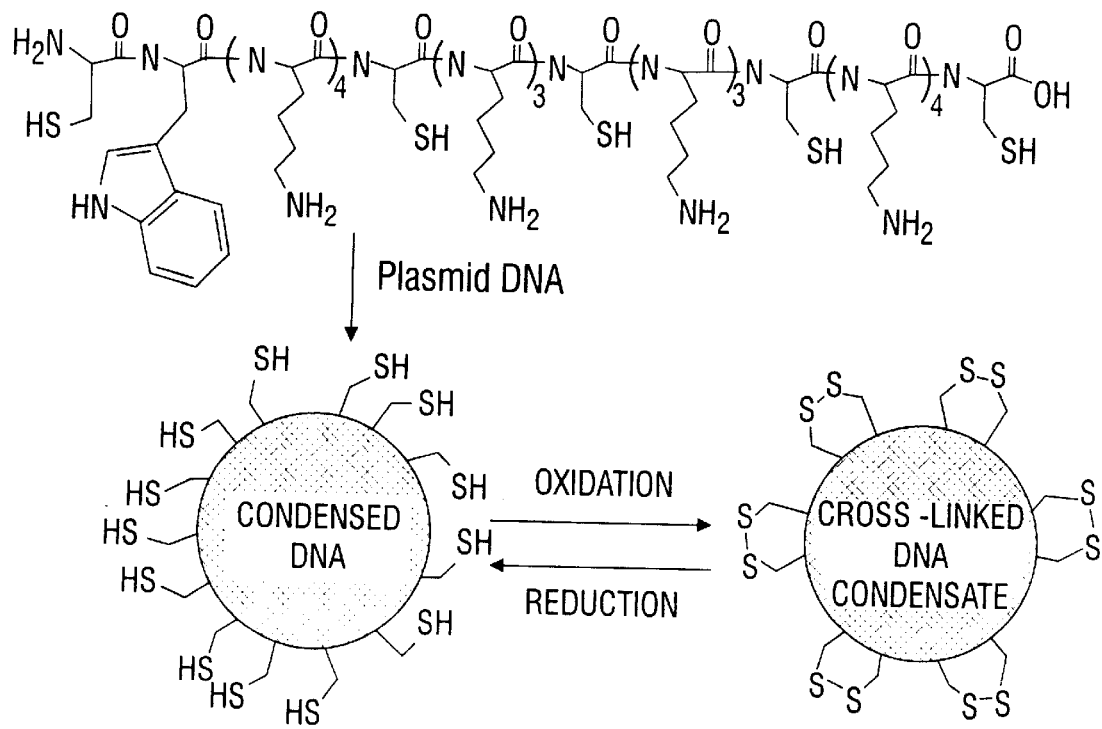
FIG. 30. Formation of Cross-linked Peptide DNA Condensates. Peptide DNA condensates are formed instantly through ionic binding of the peptide to the DNA backbone followed by inter-peptide oxidazation to form disulfide bonds that reversibly stabilize the DNA condensates.

Substituting cysteine residues into CWK$_{18}$ produced a panel of cross-linking peptides (II, III, IV, and V) possessing 2–5 cysteine residues, respectively (Table 2). Following binding and condensation of plasmid DNA, cross-linking peptides could potentially form inter-peptide disulfide bonds that would stabilize the DNA carrier complex (FIG. 30). Hence, the number of cysteine residues would influence the number of disulfide bonds formed and the overall stability and transfection efficiency of the peptide DNA carrier complex.

Figure 31:
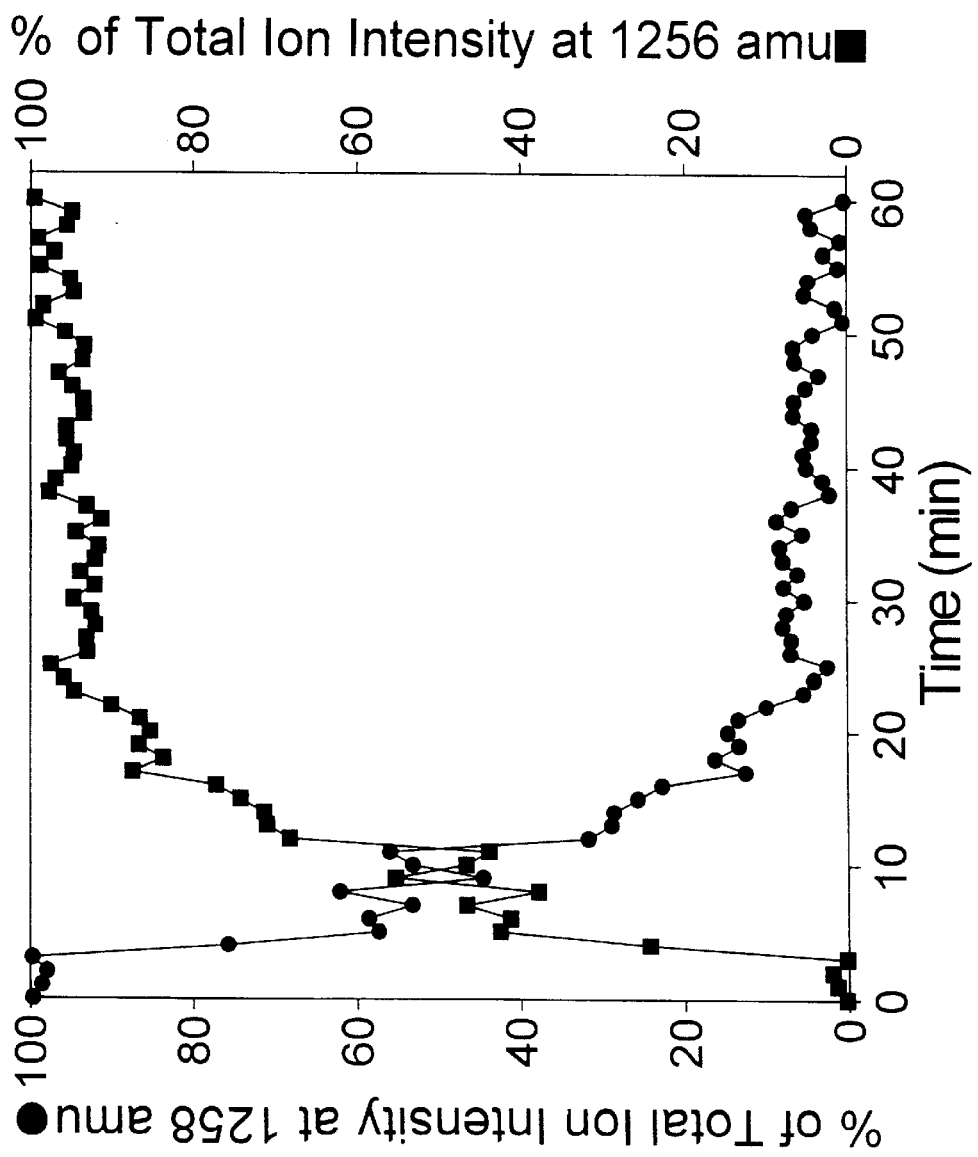
FIG. 31. Kinetics of Peptide Oxidation in Solution. ES-MS was used to monitor the intra-peptide disulfide bond formation of peptide V in solution. The loss of parent peptide ($M+2H^+$ at 1258 amu) was continuously monitoring along with the formation of the intra-peptide disulfide bonded product at 1256 amu. The kinetic profile indicated complete loss of the parent ion and formation of the oxidized peptide within 25 min.

Despite the presence of multiple cysteine residues, each cross-linking peptide released from resin produced essentially a single peak on RP-HPLC indicating the cysteines remained in a reduced form during acidic cleavage and work-up. Purified cross-linking peptides each produced molecular ions on ES-MS that matched the expected mass of the fully reduced peptide (Table 2). The peptides were maintained in their reduced form at low pH by removing oxygen; however, at neutral pH, the cysteine residues became very reactive in forming disulfide bonds. When cross-linking peptide V was adjusted to pH 7.5 and directly infused into ES-MS, the parent ion completely disappeared within 25 min with a $t_{1/2}$ of approximately 10 min resulting in the formation of an intra-molecular disulfide bonded peptide as the primary oxidation product (FIG. 31).

When bound to DNA, cross-linking peptides are less flexible such that inter-molecular peptide cross-linking may be the preferred route of oxidation. To determine whether this occurs, the time course of inter-peptide disulfide bond formation for peptides bound to DNA was studied using a continuous fluorescence assay. A SYBR-Gold™ DNA intercalator dye was sued because it maintains its fluorescence even with peptide bound to DNA (FIG. 32A).

Figures 32A, 32B:
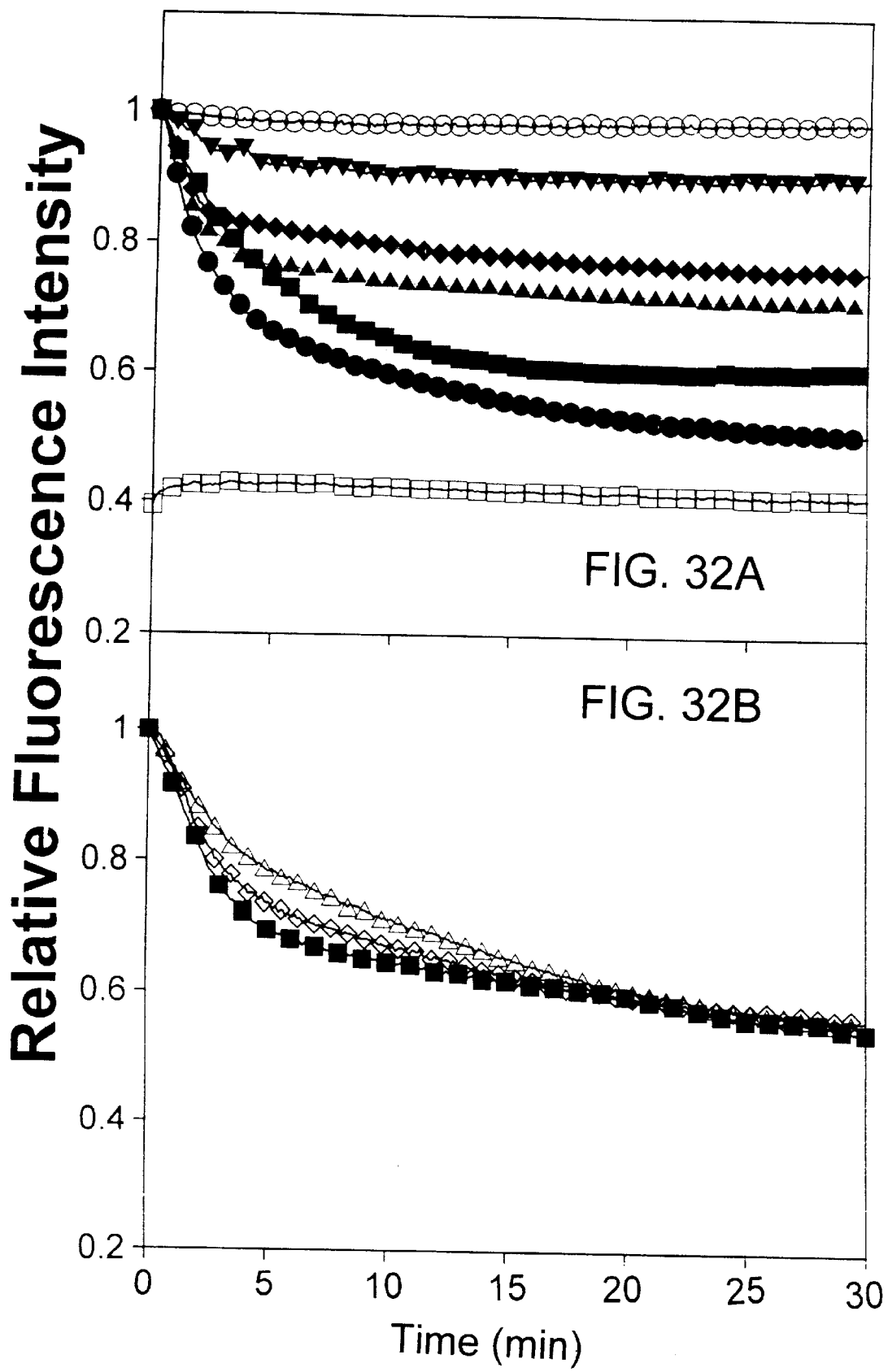
FIG. 32A and FIG. 32B. Kinetics of Cross-linking DNA Condensates.

When prepared at a charge ratio of 2:1, both AlkCWK$_{18}$ and polylysine$_{1007}$ instantly form DNA condensates and produce a constant SYBR-Gold™ fluorescence intensity over time with magnitude inversely related to the peptide binding affinity for DNA (FIG. 32A). In contrast, the fluorescence intensity decreased over time when peptides II–V were used to form DNA condensates at a charge ratio of 2:1 (FIG. 32A), due to displacement of the intercalator dye as cross-linking proceeds and peptide binding affinity increases.

The kinetic decrease in SYBR-Gold™ fluorescence was interpreted as the approximate time course of disulfide formation for peptides bound to DNA. Inter-peptide cross-linking of V occurred in less than 30 min, similar to that predicted by ES-MS. Increasing the number of cysteine residues in the series II–V increased both the time required to achieve complete cross-linking ($t_{1/2}$=1–10 min) and the stability of the cross-linked DNA condensates (FIG. 32A). Likewise, the rate of kinetic decrease in SYBR-Gold™ fluorescence and the final fluorescence intensity were not significantly influenced by the cross-linking peptide concentration (FIG. 32B), indicating that the disulfide bonds did not appreciably quench the SYBR-Gold™ fluorescence.

To establish the peptide to DNA stoichiometry needed to achieve maximal condensation, the ability of peptides II–V to displace thiazole orange from DNA were compared. Titration of 5–75 nmols of peptides II–V with 50 μg of DNA,

TABLE 2

Mass Spectral Analysis of DNA Condensing Peptides

| Name | Sequence | SEQ ID NO: | Mass (obs/calc$^a$) |
| --- | --- | --- | --- |
| AlkCWK$_{18}$ | Alk-S-Cys-Trp-Lys$_{18}$ | Alk-No. 1 | 2672.5/2672.5 |
| DiCWK$_{18}$ | Lys$_{18}$-Trp-Cys-S-S-Cys-Trp-Lys$_{18}$ | No. 2 | 5227.8/5227.9 |
| CWK$_{18}$ | Cys-Trp-Lys$_{18}$ | No. 1 | 2614.1/2614.6 |
| II | Cys-Trp-Lys$_{17}$-Cys | No. 3 | 2588.9/2589.6 |
| III | Cys-Trp-Lys$_8$-Cys-Lys$_8$-Cys | No. 4 | 2564.3/2564.6 |
| IV | Cys-Trp-Lys$_5$-Cys-Lys$_5$-Cys-Lys$_5$-Cys | No. 5 | 2539.2/2539.6 |
| V | Cys-Trp-Lys$_4$-Cys-Lys$_3$-Cys-Lys$_3$-Cys-Lys$_4$-Cys | No. 6 | 2514.0/2514.6 |
| Polylysine$_{1007}$ | Lys$_{1007}$ | | nd$^b$/150,000 |

Figure 33:
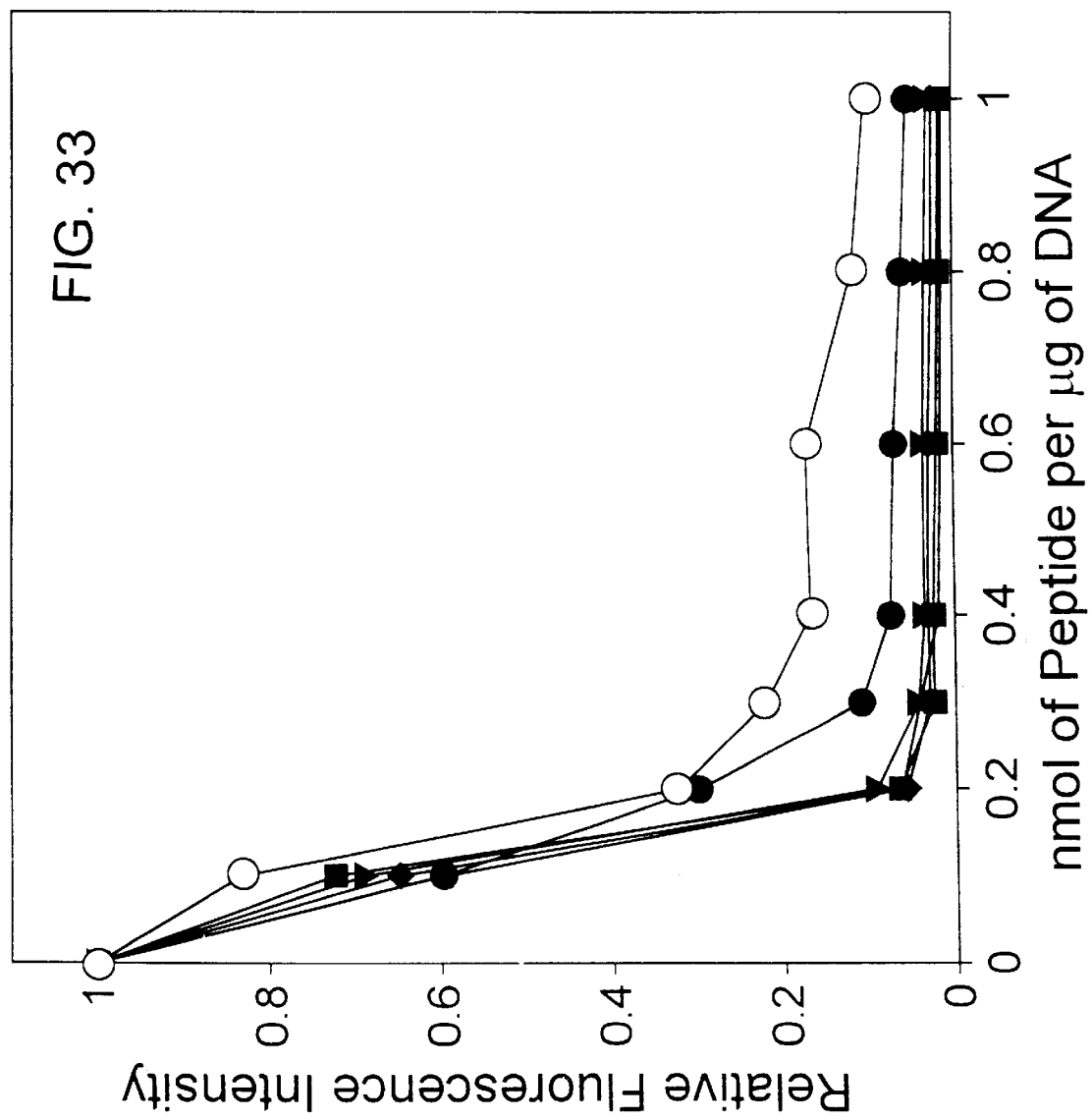
FIG. 33. Binding of Cross-linking Peptides to DNA. Thiazole Orange was used in a fluorescent dye exclusion assay to determine the relative binding affinity of each peptide to plasmid DNA. Condensates were formed with AlkCWK$_{18}$ (), CWK$_{18}$ (▼), II (♦), III (▲), IV (■), and V (●) at an increasing peptide to DNA stoichiometry. Each peptide formed fully condensed DNA at a peptide to DNA ratio of 0.3–0.4 nmol of peptide per μg of DNA corresponding to a ($NH_4^+$:$PO_4^-$) charge ratio of approximately 2:1.

$^a$Masses are calculated as the average mass of the free base.
$^b$The mass of polylysine$_{1007}$ was not determined due to polydispersity.

followed by a 2 h incubation to allow cross-linking, resulted in a decrease in the thiazole orange fluorescence (FIG. 33). At 0.4 nmol of peptide per μg of DNA or greater, corresponding to a calculated charge ratio of 2:1, each peptide was able to fully condense DNA as determined by a plateau in the residual fluorescence intensity (FIG. 33).

2. Particle Size

The particle size of each cross-linked peptide DNA condensate was evaluated by QELS at both 15° and 90° scatter angles to minimize the influence of internal motion that is detected at 90° (Lewis et al., 1985). At a charge ratio of 2:1, $CWK_{18}$ and peptides II–V each formed essentially a single population of DNA condensates determined by QELS at both 15° and 90° to approximate a mean diameter of 40 to 60 nm (Table 3). A slightly larger population of particles with mean diameter of 70 to 100 nm resulted when $AlkCWK_{18}$, $DiCWK_{18}$, and $polylysine_{1007}$ were used to condense DNA (Table 3).

TABLE 3

QELS Particle Size Analysis[a] of Peptide DNA Condensates

| Peptide DNA Condensate[b] | SEQ ID NO: | Oxidized[c] 15°[f] | Oxidized[c] 90°[f] | Reduced[d] | Saline[e] |
|---|---|---|---|---|---|
| | | Particle Size Mean Diameter (nm) | | | |
| $AlkCWK_{18}$ | Alk-No. 1 | 97 | 95 | 74 | 1215 |
| $Polylysine_{1007}$ | | 54 | 67 | 84 | 109 |
| $DiCWK_{18}$ | No. 2 | 74 | 68 | 153 | 171 |
| $CWK_{18}$ | No. 1 | 39 | 51 | 105 | 225 |
| II | No. 3 | 31 | 42 | 121 | 257 |
| III | No. 4 | 26 | 39 | 136 | 157 |
| IV | No. 5 | 57 | 44 | 158 | 324 |
| V | No. 6 | 41 | 57 | 171 | 93 |

[a]Deconvolution of quasielastic light scattering data assumes spherical particles of identical density.
[b]Peptide DNA condensates were prepared at a concentration of 50 µg/ml and at a stoichiometry of 0.4 nmol of peptide per µg of DNA corresponding to charge ratio of 2:1.
[c]Particle size measure in HBM after 2 h incubation.
[d]Particle size following addition of TCEP (1 mM).
[e]Particle size in HBM with added saline (0.15 M) after 15 min.
[f]QELS light scattering angle.

The role of disulfide bond stabilization was investigated by treating DNA condensates with TCEP, which caused a negligible change in mean particle size when either $AlkCWK_{18}$ or $polylysine_{1007}$ were used as condensing agents. In contrast, TCEP reduction of peptide DNA condensates prepared with $DiCWK_{18}$, $CWK_{18}$ and II–V more than doubled the mean particle size (Table 3).

Since sodium chloride has been shown to increase the particle size of peptide DNA condensates in a time dependent fashion (Plank et al., 1999), the inventors examined the particle size stability of $AlkCWK_{18}$, $CWK_{18}$, $polylysine_{1007}$ and peptide II–V DNA condensates prepared in 0.15 M sodium chloride (Table 3). After 15 min the particle size grew significantly due the formation of a large (>5 µm) population which represented 10–20% of the DNA with 80% maintained as small (<100 nm) particles. After 24 h incubation in sodium chloride, each of the peptide DNA condensates formed large flocculates.

3. Shear Stress Stability

The stability of cross-linking peptide DNA condensates were studied by determining their sonicative shear stress stability as a function of increasing sodium chloride concentration.

$AlkCWK_{18}$ DNA condensates protected DNA from fragmentation in sodium chloride up to 0.4 M, above which, higher salt concentrations led to the dissociation of the peptide and fragmentation of the DNA (FIG. 34A). The generation of $DiCWK_{18}$ when using $CWK_{18}$ as a condensing agent led to a negligible change in the shear stress stability since peptides with either 18 or 36 lysine residues dissociate from DNA at sodium chloride concentration between 0.4 and 0.8 M (FIG. 34B) (Adami et al., 1998).

However, the substitution of a second cysteine into $CWK_{18}$, resulted in peptide II DNA condensates that were stable to sonicative shear stress in sodium chloride concentrations up to 1.0 M (FIG. 34C). Increasing the number of cysteine residues to 3, 4, and 5 produced very stable DNA condensates that were protected from sonicative fragmentation up to 2.5 M sodium chloride (FIG. 34D and FIG. 34E) and could not be dissociated even with saturated (4 M) sodium chloride. However, reduction of peptide V DNA condensates with TCEP reverted the DNA condensate stability back to 0.4 M sodium chloride (FIG. 34G). Likewise, when V was allowed to fully oxidize prior to making peptide DNA condensates, it also failed to protect DNA from sonicative shear stress above 0.4 M sodium chloride (FIG. 34H). $Polylysine_{1007}$ only protected DNA from shear stress up to 1 M sodium chloride (FIG. 34I) which was equal to the stability afforded by peptide II.

Peptide IV DNA condensates were prepared at charge ratios of 0.5–2.5 and analyzed for particle size, zeta potential, and sonicative shear stress stability to determine whether the degree of inter-peptide cross-linking was a function of peptide DNA stoichiometry (FIG. 35A and FIG. 35B). Peptide IV formed small (62 nm) electronegative (−18 mV) DNA condensates at a charge ratio of 0.9 that resisted fragmentation up to 2.5 M sodium chloride (FIG. 35A and FIG. 35B), indicating that even at low stoichiometry a sufficient number of peptides were bound to DNA to effect cross-linking. However, it is interesting to note that the DNA was almost completely converted to open circular, indicating partial susceptibility of the DNA to shear stress induced strand breakage as a result of peptide vacancies.

To determine whether cross-linking peptides could react covalently with DNA, mass spectrometry was used to study the reaction of a deca oligonucleotide with peptides. Both control peptide ($AlkCWK_{18}$) and peptide V yielded identical spectra to the oligonucleotide alone, producing only a $(1480)^{M-2}$ m/z ion corresponding to the predicted mass of the oligonucleotide. There was no evidence of higher mass products representing a covalent reaction between the cross-linking peptide and the oligonucleotide.

4. Gene Expression

Figure 36A:
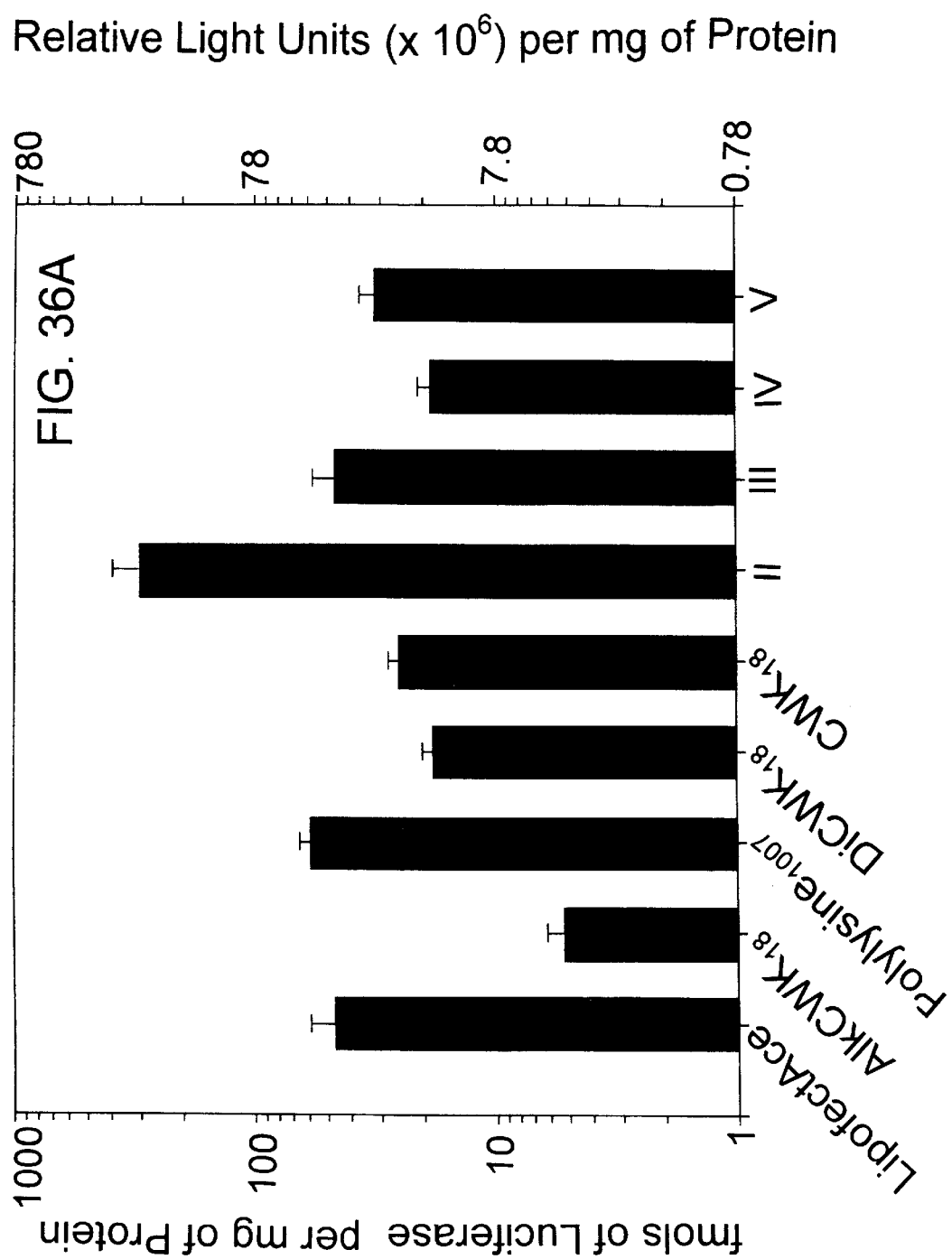
FIG. 36A and FIG. 36B. Luciferase Expression in HepG2 and COS 7 Cells. The luciferase reporter gene expression for each peptide DNA condensate in HepG2 (FIG. 36A) and COS 7 cells (FIG. 36B) is illustrated. The results established a 60-fold increase in the gene expression mediated by peptide II relative to that mediated by AlkCWK$_{18}$ and a 5-fold increase over that mediated by polylysine$_{1007}$ or LipofectAce™ in HepG2 cells. Peptide II mediated a 10-fold increase in gene expression relative to AlkCWK$_{18}$ and equivalent expression as polylysine$_{1007}$ in COS 7 cells.
Figure 36B:
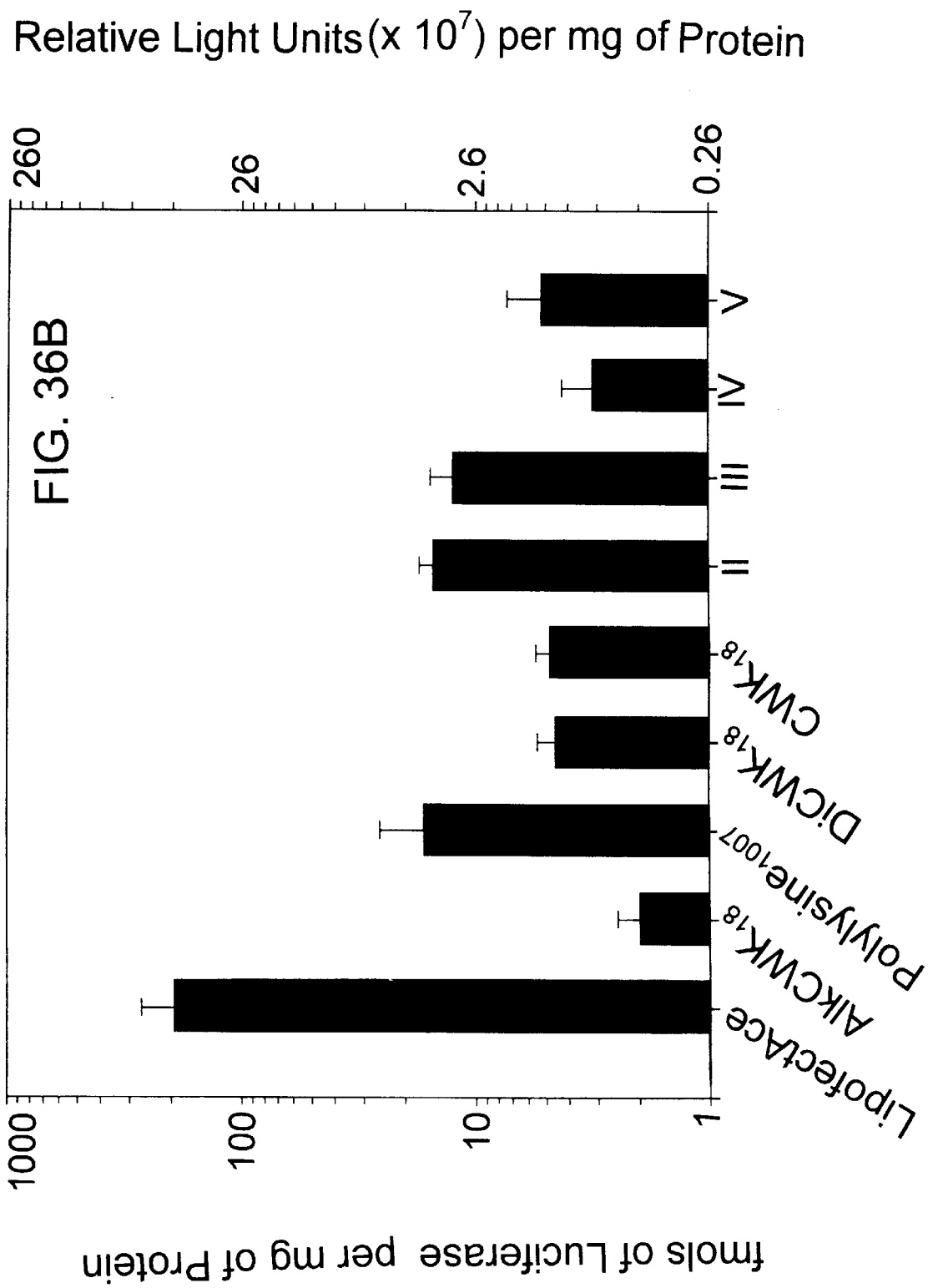

The luciferase reporter gene expression in HepG2 and COS 7 cells provided evidence that cross-linked peptide DNA condensates were reversibly once endocytosed (FIG. 36A and FIG. 36B). The presence of a single cysteine in $CWK_{18}$ resulted in a 4-fold increase in gene expression over $AlkCWK_{18}$, similar to the level mediated by $DiCWK_{18}$.

In contrast, cross-linking peptide II mediated 60-fold higher gene expression in HepG2 cells relative to $AlkCWK_{18}$ DNA condensates (FIG. 36A). Cross-linking peptides III–V also yields higher levels (4 to 10-fold) of reporter gene expression than $AlkCWK_{18}$ DNA condensates but not as high as peptide II.

The enhancement in gene expression mediated by cross-linking peptide II–V DNA condensates was cell-type dependent. Transfection of COS 7 cells only resulted in a 2.5 to 10-fold increase in gene expression over $AlkCWK_{18}$ (FIG. 36B) compared to the 4 to 60-fold increase observed in HepG2 cells.

The magnitude of gene expression mediated by $AlkCWK_{18}$, $CWK_{18}$ and peptides II–V was also chloroquine dependent. However, chloroquine enhanced the gene expression of peptide II DNA condensates approximately 5-fold more than $AlkCWK_{18}$ DNA condensates.

Figure 37:
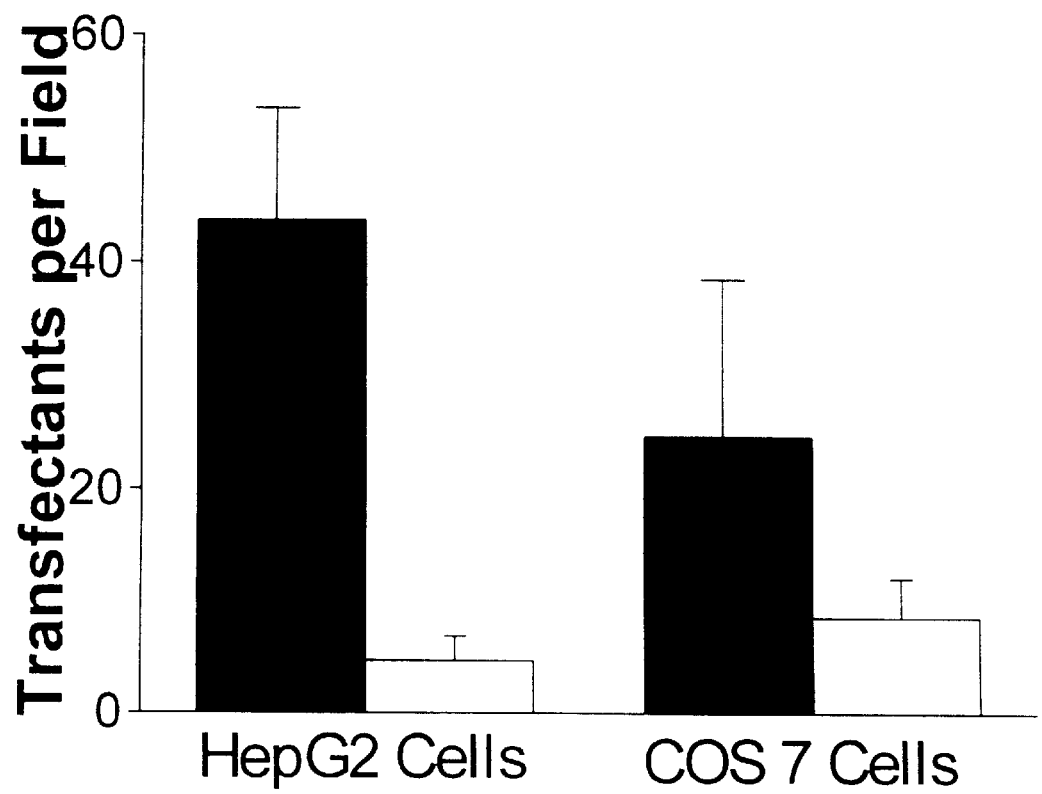
FIG. 37. β-Galactosidase Expression in HepG2 and COS 7 Cells. X-gal stained HepG2 cells were quantitated following 48 h transfection with AlkCWK$_{18}$ or peptide II. Quantitative analysis of the number of nuclear stained cells following transfection of either HepG2 or COS 7 cells with cross-linking peptide II DNA condensates (closed bars), AlkCWK$_{18}$ DNA condensates (open bars), or naked plasmid DNA (none detected) are shown. The results demonstrate a 9-fold (HepG2) and 4-fold (COS 7) increase in the number of nuclear stained cells when transfecting with II relative to AlkCWK$_{18}$. The significance was P<0.005 for each results.

Since the elevated levels of transgene expression mediated by peptide II could be related to either an increased uptake of DNA by cells or to an improved transduction within cells, further studies were performed to distinguish between these possibilities. Transfection of HepG2 cells with plasmid encoding NTβGal demonstrated approximately 9-fold more cells were transduced using peptide II vs. AlkCWK$_{18}$ as a gene transfer agent (FIG. 37). Likewise, 4-fold more COS 7 cells were positively stained for nuclear targeted β-galactosidase using peptide II vs. AlkCWK$_{18}$ to effect gene transfer (FIG. 37).

Figure 38:
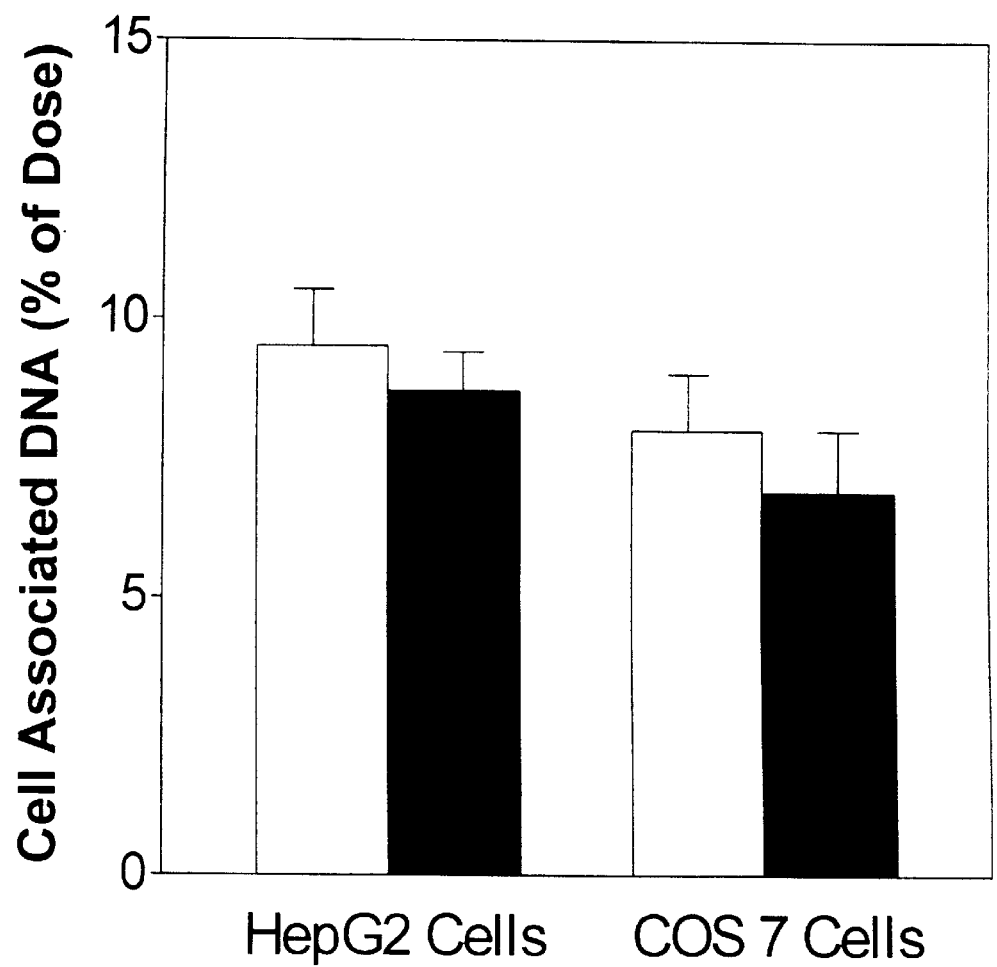
FIG. 38. HepG2 and COS 7 Cell Binding of Peptide DNA Condensates. HepG2 and COS 7 cells were transfected for 5 h with 45 nCi (10 µg) of $^{125}$I-DNA condensates prepared with either AlkCWK$_{18}$ (open bar) or cross-linking peptide II (closed bar). The cell associated DNA recovered is expressed as the percent of $^{125}$I-DNA dosed onto cells.

A 5 h transfection of HepG2 cells with $^{125}$I-labeled plasmid DNA revealed that AlkCWK$_{18}$ was nearly equivalent (9.5% of dose) to peptide II (8.7% dose) at mediating DNA uptake (FIG. 38). A similar result in COS 7 cells demonstrated a nearly identical amount (7–8% of dose) of $^{125}$I-DNA taken up when using either transfecting agent. Together, these data support a hypothesis involving enhanced transduction mediated by peptide II.

The present example shows the development of cross-linking peptides that allow the formation of stable LMW DNA condensates that mediate efficient gene transfer. Further derivatization of cross-linking peptides with polyethylene glycol (Example 1, Kwok et al., 1999; Example 3) and targeting ligands (Example 3; Collard et al., 2000a; Example 7; Collard et al., 2000b) will allow the generation of DNA condensates possessing optimal ratios of these LMW carriers for use in gene therapy.

EXAMPLE 6

His-CONTAINING low mR Self-Crosslinking Peptides

The present example further develops the self-crosslinking peptides of Example 5 (McKenzie et al., 2000). In the present study, a minimal peptide of four Lys and two terminal Cys residues was found to substitute for Cys-Trp-(Lys)$_{17}$-Cys, resulting in DNA condensates with similar particle size and gene expression in HepG2 cells. Substitution of His for Lys residues resulted in an optimal peptide of Cys-His-(Lys)$_6$-His-Cys that, in addition to the attributes above (Example 5), also provided buffering capacity to enhance in vitro gene expression in the absence of chloroquine. The reported structure activity relationships systematically explore peptides with combinations of Lys, Cys, and His residues resulting in low molecular weight peptides with improved gene transfer properties.

A. INTRODUCTION

The size and homogeneity of carrier molecules play an important role in the success of a nonviral gene delivery system. These two parameters impact the toxicity, antigenicity and the ability to systematically optimize gene delivery carriers for in vivo applications. A variety of Lys containing polypeptides (Wanger et al., 1990; Wyman et al., 1997; Morris et al., 1997; Toncheva et al., 1998; McKee et al., 1994), dendrimers (Tang et al., 1996; Page and Roy, 1997) and polymers such as polyethylenimine (PEI) (Boussif et al., 1995: Godbey et al., 1999) have been tested for in vitro and in vivo gene delivery. The molecular weight of polylysine or polyethyleneimine typically used for gene delivery ranges from 25,000 to over 300,000 amu (Toncheva et al., 1988; Boussif et al., 1995). The high molecular weight (HMW) and heterogeneity of these polymers (Godbey et al., 1999; McKenzie et al., 1999) significantly complicates the ability to develop chemically well-defined conjugates and develop structure activity relationships to optimize gene expression.

Low molecular weight (LMW) carriers could circumvent these problems, provided that they molecular in vitro and in vivo gene transfer as efficiently as their HMW counterparts. Peptides as short as twenty amino acids are able to form small DNA condensates that mediate efficient in vitro gene transfer (Wadhwa et al., 1997; Niidome et al., 1999; Niidome et al., 1997); however, these fail as carriers when tested in vivo due to their lower affinity for DNA, prompting attempts to stabilize LMW carriers bound to DNA to increase their in vivo gene expression (Example 3, Collard et al., 2000a; Example 7; Collard et al., 2000b).

Trobetskoy et al., inserted stable cross-links onto preformed peptide DNA condensates with heterobifunctional agents, but was unable to demonstrate that these were active in transfecting cells in culture (Trubetskoy et al., 1999; Trubetskoy et al., 1998). Blessing et al. and Ouyang et al. attempted to increase gene expression using cationic detergents (Blessing et al., 1998; Ouyang et al., 2000).

The present invention provides LMW peptides possessing multiple Cys residues as gene delivery agents that form multiple interpeptide disulfide bonds when bound to DNA (Example 5; McKenzie et al., 2000). After internalization by the cell, reduction of the cross-linked peptide DNA condensate yielded enhanced levels of gene expression. The present example provides peptides containing His residues that incorporate endosomal buffering capacity into cross-linking peptides.

B. MATERIALS AND METHODS

1. Materials

N-terminal Fmoc protected amino acids, 9-hydroxybenzotriazole (HOBt), diisopropylcarbodiimide (DIC), and diisopropylethylamine were obtained from Advanced ChemTech (Lexington, Ky.). Substituted Wang resin for peptide synthesis was obtained from ChemImpex (Wood Dale, Ill.). N,N-dimethyformamide, trifluoracetic acid (TFA), acetic acid, acetonitrile, piperidine, and acetic anhydride were purchased from Fisher Scientific (Pittsburgh, Pa.). LB media, LB agar, D-luciferin, and luciferase from *Photinus pyralis* (EC 1.13.12.7) were obtained from Boehringer Mannheim (Indianapolis, Ind.).

HepG2, COS 7 and CHO cells were from the American Type Culture Collection (Rockville, Md.). Inactivated "qualified" fetal bovine serum (FBS) was from Gibco BRL (Grand Island, N.Y.). Bradford reagent was purchased from BioRad (Hercules, Calif.), and thiazole orange was obtained from Beckton Dickinson Immunocytometry Systems (San Jose, Calif.). SYBR-Gold™ was purchased from Molecular Probes, Inc. (Eugene, Oreg.). The 5.6 kb plasmid pCMVL encoding the reporter gene luciferase under the control of the cytomegalovirus promoter was obtained form Dr. M. A. Hickman at the University of California, Davis (Hickmann et al., 1994). Endotoxin free plasmids were purified from *E. coli* on a Qiagen ultrapure ™ column used according to the manufacturer's instructions, yielding plasmid DNA that was 50:50 supercoiled and open circular as determined by agarose gel electrophoresis.

Peptide synthesis was performed on a computer interfaced Model 90 Advanced ChemTech™ solid phase peptide synthesizer (Lexington, Key.). Peptide purification was performed using a semi-preparative (10 μm) C$_{18}$ RP-HPLC column from Vydac (Hesperia, Calif.) on a computer-interfaced HPLC and fraction collector from ISCO (Lincoln, Nebr.). Electrospray mass spectrometry (ES-MS) was performed using a Finnigan LCQ™ mass spectrometer (San Jose, Calif.) interfaced with an analytical HPLC from Hitachi (San Jose, Calif.) using an analytical C18 (5 μm) reverse-phase column from Vydac.

2. Peptide Synthesis and Characterization

Peptides 1–3 (Table 4) were synthesized as previously described (Wadhwa et al., 1997; Example 5; McKenzie et al., 2000). All other peptides were synthesized using standard Fmoc procedures with HOBt and DIC double couplings followed by N-capping with acetic anhydride to avoid deletion sequences. The trityl group was used to protect the side-chains of both Cys and His while the Lys side-chain was protected with tert-butoxycarbonyl. Peptides were cleaved from the resin and side-chain protecting groups were simultaneously removed by reaction with TFA/EDT/water (95:2.5:2.5 vol/vol/vol) for 1 h at RT.

Peptides were purified to homogeneity using RP-HPLC by injecting up to 6 µmol onto a Vydac $C_{18}$ semi-preparative column (2×25 cm) eluted isocratically at 10 ml/min with 0.05 vol/vol % TFA and 2% acetonitrile while monitoring the UV absorbence at 220 nm. The major peak eluting near 20 min was pooled from multiple runs, concentrated by rotary evaporation, lyophilized, and stored dry at $-20°$ C. Purified peptides were reconstituted in 0.1% TFA (degassed with nitrogen) and characterized by LC-MS by injecting 5 nmol onto a Vydac C18 reverse phase HPLC column (0.47×25 cm) eluted at 1 ml/min with 0.1 vol/vol % acetic acid containing 0.02 vol/vol % TFA and an acetonitrile gradient of 0 to 5% over 15 min. The RP-HPLC eluent was directly infused into the electrospray ionization source of a Finnigan LCQ™ mass spectrometer and mass spectral data was obtained in the positive mode. The amino acid sequence was verified by data dependent ms/ms analysis (Smith et al., 1990; Arnott et al., 1993).

The concentration of each purified peptide was determined by fluorescamine analysis using peptide 2 as a standard (Weigele et al., 1972). The concentration of each peptide was further verified by $^1$H-NMR using acetone as an internal calibrant. The final purified yield of each peptide was approximately 30%.

The mean pKa for His residues in peptides 12–16 was determined by $^1$H-NMR (Gasparovic et al., 1998; Markley, 1975; Rabenstein and Sayer, 1976). Each peptide (1 µmol) was prepared in 500 µl of 90:10 vol/vol % of $H_2O:D_2O$ with 0.02 vol/vol % acetone as an internal standard. $^1$H-NMR spectra were obtained on a Bruker™ 500 MHz spectrometer operated at 23° C. The pH was measured over the range of 2.5–9.5 using a microelectrode following the addition of 10 µl aliquots of 10 mM sodium hydroxide. The chemical shift of the H2' proton (8.5–7.6 ppm) was determined at each pH. The mean pKa was calculated by plotting pH vs. the chemical shift as described previously (Gasparovic et al., 1998).

The buffering capacity of peptides 7 and 12–16 (Table 4) were compared by dissolving 100 nmol of the acetate salt form of each peptide into 1 ml of 150 mM sodium chloride. The initial pH of 5.5 was titrated down by adding 5 µl aliquots of 5 mM hydrochloric acid while measuring pH using a microelectrode.

3. Peptide DNA Condensation

Peptide DNA condensates were prepared by combining 50 µg of DNA in 500 µl of Hepes buffered mannitol (HBM) (5 w/v% mannitol, 5 mM Hepes, pH 7.5) with 0.1 to 6.5 nmol of peptide in 500 µl of HBM while vortexing to form peptide DNA condensates with a calculated primary amine to phosphate charge ratio between 0.25 and 8.0 ($NH_4^+:PO_4$). The condensates were allowed to cross-link for 30 min prior to performing physical measurements. The binding of each peptide to DNA was assayed by combining peptide DNA condensates (50 µl) with 950 µl of HBM containing 0.1 µM thiazole orange. The fluorescence of the intercalated dye was measured using an LS50B fluorometer (Perkin Elmer, UK) by exciting at 500 nm while monitoring emission at 530 nm with the slit width set at 15 and 20 nm, respectively. Fluorescence blanks were substracted from all values before data analysis.

The kinetics of disulfide bond formation of peptides bound to DNA was analyzed indirectly by monitoring the displacement of SYBR-Gold™ from DNA condensates. Peptide DNA condensates were formed by combining 20 µg of DNA in 500 µl of HBM containing 1× SYBR-Gold™ with 500 µl (26–52 nmol) of peptide in HBM containing 1 × SYBR-Gold to achieve a charge ratio of 4:1 ($NH_4^+:PO_4$). The fluorescence intensity (Ex 495 nm, Em 600 nm) was continuously monitored for 30 min to determine kinetics of cross-linking.

The particle size and zeta potential of peptide DNA condensates were determined by quasielastic light scattering (QELS) using a Brookhave ZetaPlus™. Particle size analysis was performed in triplicate at a DNA concentration of 50 µg/ml in HBM at a charge ratio of 4:1 and a scattering angle of 90°. Data analysis utilized a multimodal volume distribution option included with the instrument. Zeta potential was also determined using 50 µg/ml peptide DNA condensates prepared at a 4:1 charge ratio in HBM. The reported zeta potential was averaged from ten determinations.

4. Shear Stress Stability

The relative stability of peptide DNA condensates were examined using a salt sonication assay (Adami and Rice, 1999). Peptide DNA condensates (200 µl of 50 µg/ml) were formed as described above, incubated at RT for 30 min and then combined with 0–200 µl of 5 m solution chloride and normalized to 400 µl with HBM to achieve a final sodium chloride concentration of 0, 0.2, 0.4, 0.8, 1.0, 1.5, 2.0 and 2.5 M. Each sample was sonicated for 30 sec with a 100 W Microson™ XL-2000 ultrasonic probe homogenizer (Kontes, Vineland N.J.) with a vibrational amplitude of 5 fragment uncondensed DNA. DNA condensates were digested with 30 µg to trypsin for 12 h at 37° C., electrophoresed on a 1% agarose gel electrophoresed in TEA buffer for 2 h, then visualized by ethidium bromide staining and destaining prior to photography on a transilluminator.

5. In vitro Gene Expression

HepG2 cells ($1.5×10^5$) were plated on 6×35 mm wells and grown to 50% confluencey in MEM supplemented with 10% FBS, penicillin and streptomycin (100 U/ml), sodium pyruvate (100 mM), and L-glutamine (2 mM). Transfections were performed in MEM (2 ml per 35 mm well) with 2% FBS with and without 80 µM chloroquine. Peptide DNA condensates (10 µg of DNA of 0.2 ml HBM) were added dropwise to triplicate wells. After a 5 h incubation at 37° C., the medium was replaced with MEM supplemented with 10% FBS. After 24 h, cells were washed with ice-cold phosphate buffered saline (calcium and magnesium free) and then treated with 0.5 ml of ice-cold lysis buffer (25 mM) Tris chloride pH 7.8, 1 mM EDTA, 8 mM magnesium chloride, 1% Triton X-100, 1 mM DTT) for 10 min. The cell lysates were scraped, transferred to 1.5 ml microcentrifuge tube, and centrifuged for 7 min at 13,000 g at 4° C. to pellet debris.

Lysis buffer (300 µl), sodium-ATP (4 µl of a 180 mM solution, pH 7, 4° C.) and cell lysate (100 µl, 4° C.) were combined in a test tube, briefly mixed and immediately placed in the luminometer. Luciferase relative light units (RLU) were recorded on a Lumat™ LB 9501 (Berthoid Systems, Germany) with 10 sec integration after automatic injection of 100 µl of 0.5 mM D-luciferin (prepared fresh in lysis buffer without DTT). The RLU were converted into fmol using a standard curve generated by adding a known amount of luciferase (0.01 to 100 fmols with specific activity of 2.5 nU/fmol) to 35 mm wells containing 50% confluent cells and lysis buffer. Protein concentrations were measured by Bradford assay using bovine serum albumin as a standard (Bradford, 1976). The amount of luciferase recovered in each sample was normalized to milligrams of protein and reported as the mean and standard deviation obtained from triplicate transfections.

LipofectAce™ (Gibco BRL, 1:2.5 w/w dimethyl dioctadecylammonium bromide and dioleoyl phosphatidylethanolamine) was used to mediate gene transaction according to the manufacturer's instructions. The ratio of DNA to LipofectAce™ was optimized for HepG2 cells. An optimal DNA/LipofectAce™ ratio was achieved by dissolving 10 μg of DNA in 100 μl serum free media (SFM) followed by adding 60 of LipofectAce™ prepared in 140 μl of SFM. The LipofectAce™ DNA complex was then diluted with 1.7 ml of SFM and used to transfect HepG2 cells for 5 h followed by replacing the transfecting media with media supplemented with 10% FBS. The cells were incubated for a total of 24 h, harvested and analyzed for luciferase as described above.

COS 7 cells (72,000) were plated in 35 mm wells and grown for 24 h to 50% confluency in DMEM (Gibco BRL) supplemented with penicillin and streptomycin (100 U/ml), L-glutamine (4 mM), and 10% FBS. The cells were transfected as described for HepG2 cells. CHO cells (72,000) were grown for 48 h as described above in Ham's F12 media supplemented with penicillin (100 U/ml), streptomycin (100 μg/ml) and 10% FBS then transfected as described above.

C. RESULTS

1. Peptide DNA Condensation

The number of Lys residues in a DNA condensing peptide can influence the particle size, stability and gene transfer efficiency of peptide DNA condensates (Wadhwa et al., 1997). Peptides with fewer than 13 Lys residues form increasing larger DNA condensates that dissociate from DNA below a physiological salt concentration (0.15 M) (Wadhwa et al., 1997; Adami et al., 1998).

Figure 39:
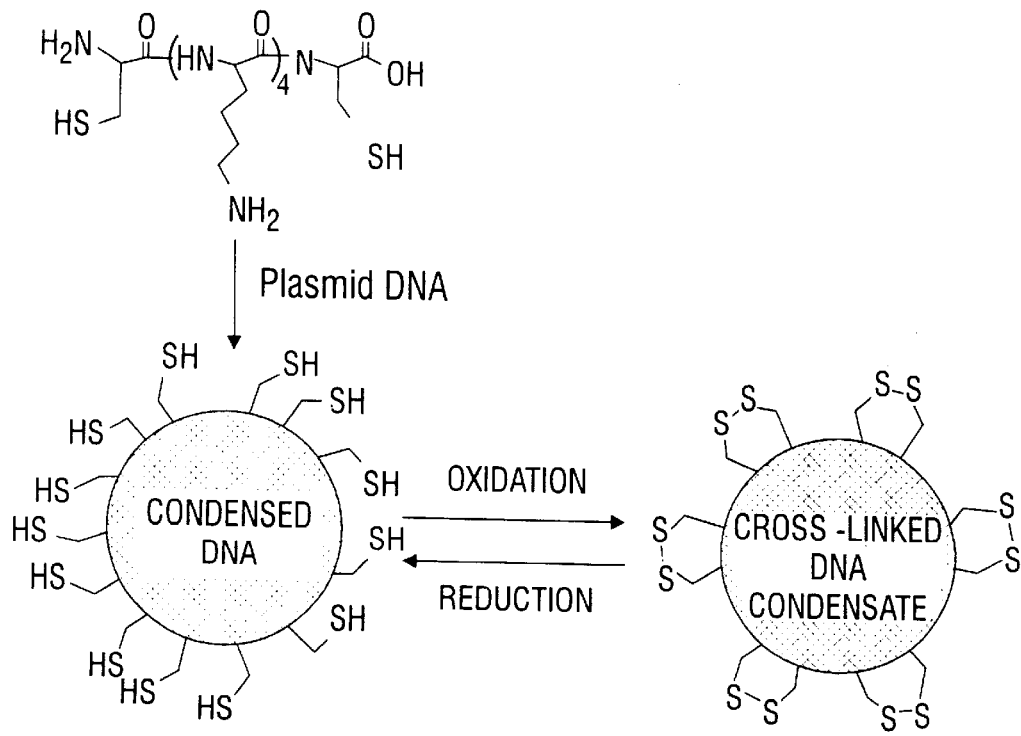
FIG. 39. Formation of Peptide DNA Condensates. Short polylysine peptides containing multiple Cys residues bind to plasmid DNA and spontaneously polymerize through disulfide bond formation resulting in stable peptide DNA condensates.

Peptide 1 possesses eighteen Lys residues and forms small DNA condensates that are stable in 0.4 M sodium chloride and mediate efficient in vitro gene transfer. However, substitution of an additional Cys residue into this sequence results in cross-linking peptide 3 that significantly increases both the stability of DNA condensates and the in vitro gene transfer efficiency (Example 5; McKenzie et al., 2000). Cross-linking peptides function by forming interpeptide disulfide bonds between adjacent peptides bound to DNA resulting in covalent linkages that revert once exposed to the reducing environment of the cell (FIG. 39).

The inventors reasoned that cross-linking peptides may be further decreased in size while retaining their ability to form small, stable DNA condensates with enhanced gene transfer efficiency. To investigate this, tetra, hexa, octa, and deca peptides 4–7 were prepared by systematically increasing the number of Lys residues while keeping the C- and N-terminal Cys residues constant (Table 4). Similarly, penta, septa, nona, and undeca peptides 8–11 were prepared by increasing the number of Lys residues while keeping three constant Cys residues (Table 4).

TABLE 4

Identity and Mass Spectral Analysis of DNA Condensing Peptides

| Number | Sequence | SEQ ID NO: | Mass (obs/calc[a]) |
|---|---|---|---|
| 1 | Alk-S-Cys-Trp-(Lys)$_{18}$ | Alk-No. 1 | 2672.5/2672.5 |
| 2 | Alk-S-Cys-Trp-(Lys)$_8$ | Alk-No. 7 | 1390.7/1390.8 |
| 3 | Cys-Trp-(Lys)$_{17}$-Cys | No. 3 | 2588.9/2589.6 |
| 4 | Cys-(Lys)$_2$-Cys | No. 8 | 480.2/480.7 |
| 5 | Cys-(Lys)$_4$-Cys | No. 9 | 736.4/736.4 |
| 6 | Cys-(Lys)$_6$-Cys | No. 10 | 993.5/993.6 |
| 7 | Cys-(Lys)$_8$-Cys | No. 11 | 1249.2/1249.7 |
| 8 | Cys-Lys-Cys-Lys-Cys | No. 12 | 583.3/583.9 |
| 9 | Cys-(Lys)$_2$-Cys-(Lys)$_2$-Cys | No. 13 | 839.4/839.4 |
| 10 | Cys-(Lys)$_3$-Cys-(Lys)$_3$-Cys | No. 14 | 1096.3/1096.6 |
| 11 | Cys-(Lys)$_4$-Cys-(Lys)$_4$-Cys | No. 15 | 1352.4/1352.9 |
| 12 | Cys-(Lys)$_4$-His-(Lys)$_3$-Cys | No. 16 | 1257.7/1257.7 |
| 13 | Cys-His-(Lys)$_6$-His-Cys | No. 17 | 1266.6/1267.6 |
| 14 | Cys-His-(Lys)$_3$-His-(Lys)$_2$-His-Cys | No. 18 | 1275.6/1275.6 |
| 15 | Cys-(His-Lys)$_4$-Cys | No. 19 | 1284.6/1284.1 |
| 16 | Cys-His-Lys-His-Lys-(His)$_2$-Lys-His-Cys | No. 20 | 1293.5/1294.5 |

[a]Masses are calculated as the average mass of the free base.

Each peptide was synthesized and purified to homogeneity by RP-HPLC resulting in a purified yield of approximately 30%. LC-MS analysis identified a single peak with molecular weight corresponding to the predicted sequence (Table 4). LC-MS/MS analysis also established y and b fragment ions corresponding to the sequence of the fully reduced peptide. Peptides were maintained in the fully reduced form at pH 2 in deoxygenated 0.1% TFA. However, at neutral pH, and in the absence of a DNA template, cross-linking peptides rapidly oxidized to form disulfide bonds yielding a mixture of cyclic products.

Figure 40A:
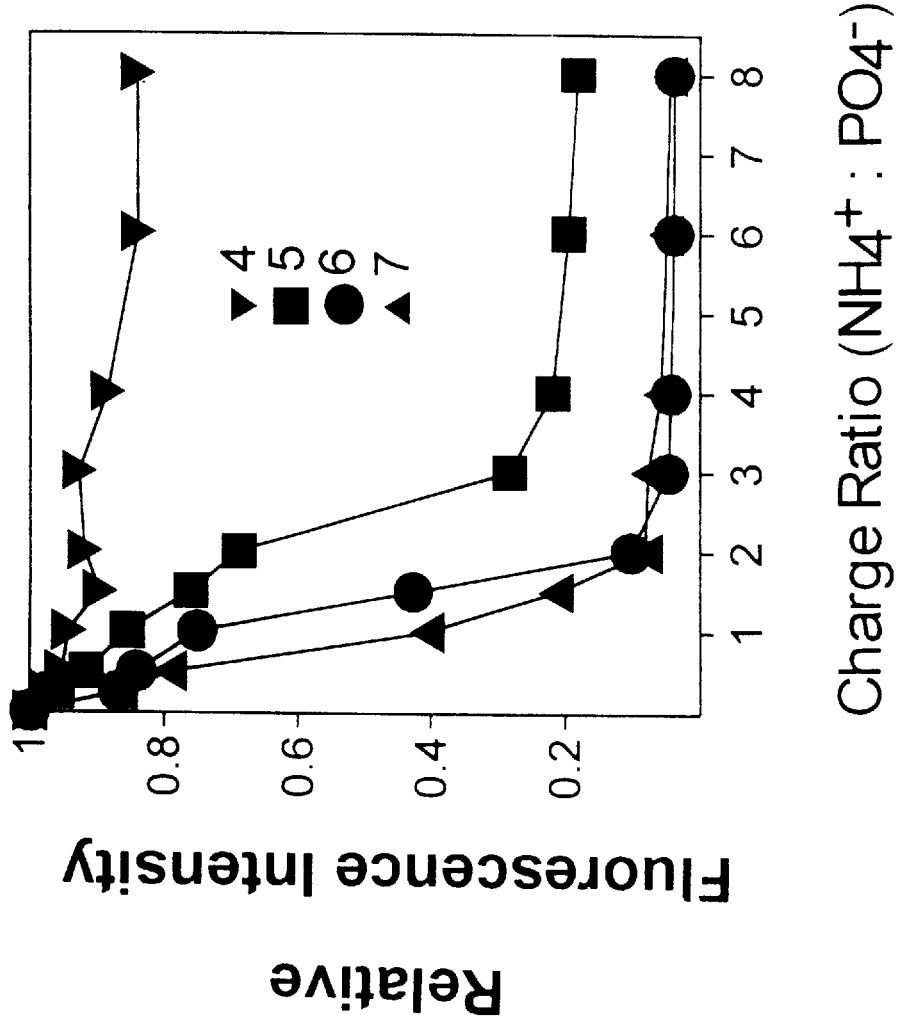
FIG. 40A, FIG. 40B and FIG. 40C. Binding of Peptides to DNA. Thiazole orange was used as a displaceable intercalator dye in a peptide titration assay to determine the charge ratio needed to form DNA condensates.

To establish the peptide to DNA stoichiometry needed to form DNA condensates, the displacement of thiazole orange from DNA was measured by a decrease in fluorescence intensity as a function of increasing peptide concentration. Titration of DNA with peptides 4–7 across charge ratios of 0.25–8 ($NH_4^+$: $PO_4$) resulted in a decrease in the thiazole orange fluorescence that reached a minimum for fully formed peptide DNA condensates (FIG. 40A). Peptides 6 and 7 were equivalent at displacing thiazole orange resulting in a maximal inflection at a charted ratio of 2. Peptide 5 was less efficient, requiring a charge ratio of 3 condense DNA whereas peptide 4 was even less effective at displacing thiazole orange and apparently failed to form DNA condensates even at a charge ratio of 8.

Figure 40B:
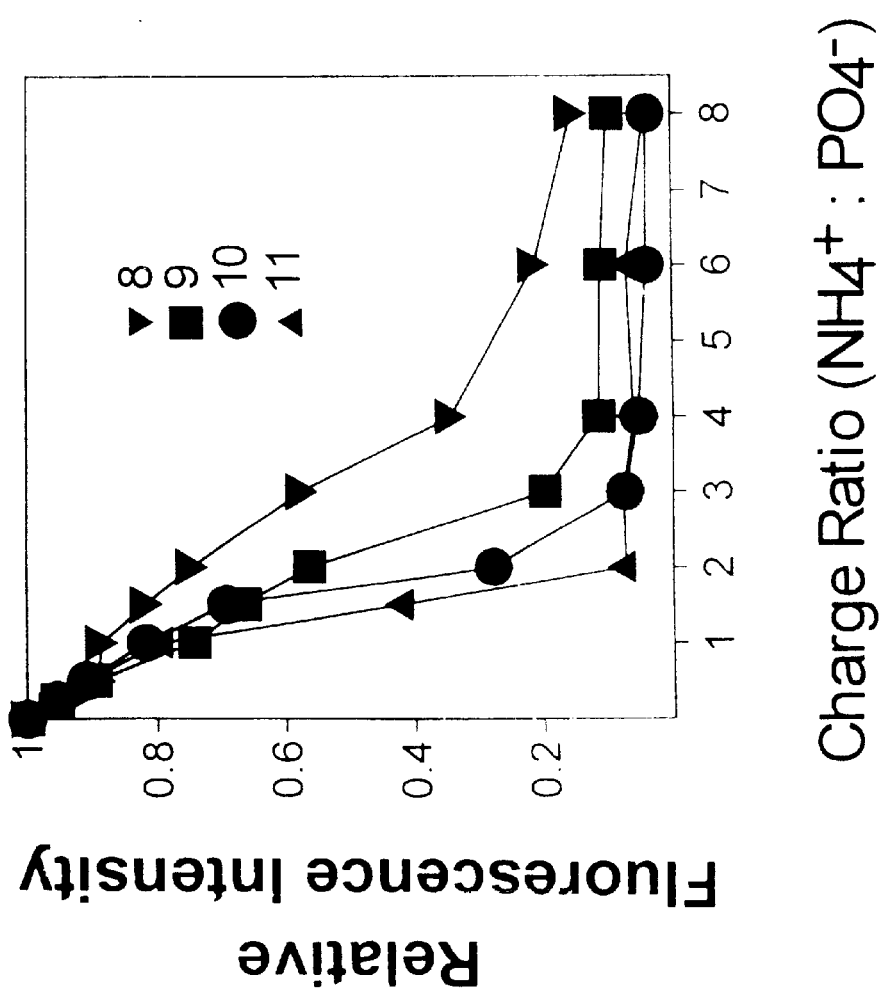

Similar results were obtained for peptides 8–11, establishing that peptide 8 was only able to weakly condense DNA at a charge ratio of 6–8 whereas peptides 9–11 efficiently displaced thiazole orange resulting in a fluorescence minimum at a charge ratios of 2–4 (FIG. 40B). Based on these results, subsequent studies utilized a peptide to DNA charge ratio of 4:1 to compare DNA condensates prepared with peptides 5–7 and 9–11.

2. Kinetics of Cross-Linking

Figure 41:
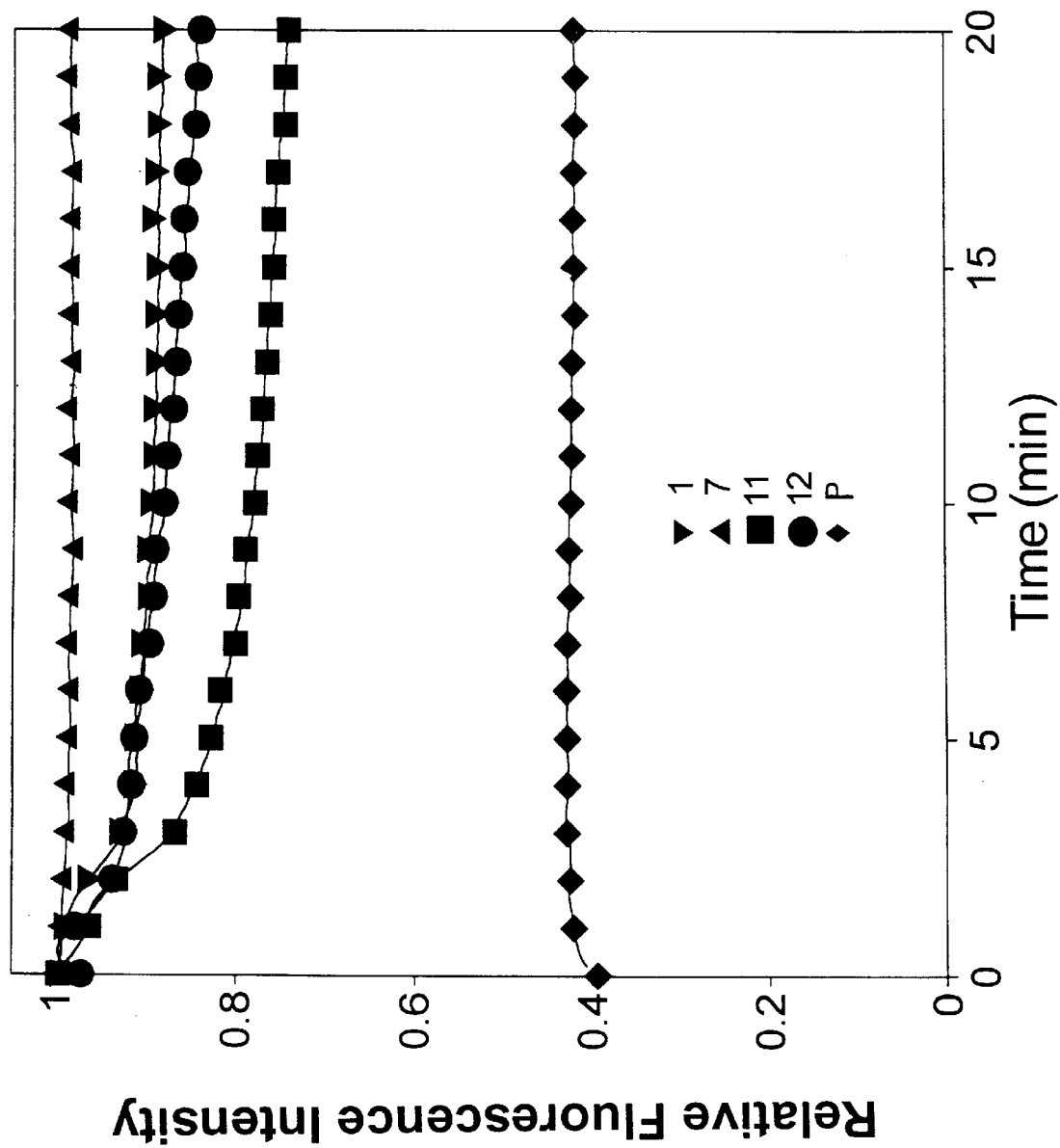
FIG. 41. Kinetics of Peptide Cross-linking on DNA. SYBR-Godl fluorescence intensity was continuously monitored to determine the kinetics of peptide cross-linking on DNA. Representative plots illustrating the kinetics of cross-linking using peptide 7, 11 and 12 are compared to the constant fluorescence resulting from noncross-linking peptide 1 or polylysine$_{1007}$ (P) binding to DNA.

The kinetics of peptide cross-linking on DNA was evaluated using SYBR-Gold as an intercalator dye (Example 5; McKenzie et al., 2000). The rapid formation of condensates using peptides incapable of cross-linking, such as 1 or polylysine$_{1007}$, results in a constant SYBR-Gold intensity over time with intensity inversely related to the affinity of the peptide for DNA (FIG. 41). Alternatively, a time-dependent decrease in SYBR-Gold fluorescence intensity results from displacement of fluorophore due to peptide cross-linking on DNA (FIG. 41).

The results illustrated for peptides 7 and 11 are representative of 4–7 and 8–11, respectively, each of which caused a decrease in the SYBR-Gold fluorescence intensity over time reaching an asymptote in 15 min or less indicating reaction completion (FIG. 41).

3. Shear Stress Stability

Direct evidence of peptide cross-linking on DNA was determined by measuring the stability of peptide DNA condensates using a salt sonication assay (Adami and Rice, 1999). Peptide 1 protected DNA from fragmentation up to a sodium chloride concentration of 0.4 M, above which, higher salt concentrations led to dissociation of the peptide and sonicative induced fragmentation of the DNA (FIG. 42A). Polylysine$_{1007}$ DNA condensates were found to dissociate above 1 M sodium chloride establishing their greater stability (FIG. 42B).

Although peptide 3 possesses a similar number of Lys residues as 1, peptide 3 DNA condensates were also stable in sodium chloride concentrations up to 1 M before dissociation led to sonicative degradation of the DNA (FIG. 42C). The enhanced stability of peptide 3 DNA condensates is due to disulfide bond formation since pre-oxidation of 3, or reduction of peptide 3 DNA condensates with TCEP, reverted the stability to that of peptide 1 DNA condensates as demonstrated previously (Example 5; McKenzie et al., 2000).

By comparison, peptide 7 DNA condensates dissociate between 0.8–1 M sodium chloride indicating that they are nearly as stable as peptide 3 and polylysine$_{1007}$ DNA condensates (FIG. 42D). Peptide 5, and 6 produced DNA condensates that were somewhat less stable (0.4–0.6 M) than those produced by peptide 7, but were still much more stable than peptide 2 DNA condensates which dissociate in 0.1 M sodium chloride (Adami et al., 1988). The stability of peptide 11 DNA condensates established that the addition of a third Cys residue resulted in complete resistance to dissociation up to 2.5 M sodium chloride (FIG. 42E). Likewise, peptide 9 DNA condensates resisted dissociation up to 1.5 M sodium chloride and peptide 10 DNA condensates were stable up to 2.5 M sodium chloride.

4. Particle Size

The particle size and zeta potential of each peptide DNA condensate were compared at a charge ratio of 4 and a cross-linking time of 30 min. As indicated above, peptide 4 failed to appreciably bind to DNA and could not form DNA condensates detected by QELS. The mean diameter of DNA condensates formed with peptides 5–7 was less than 55 nm and compared favorably to DNA condensates prepared using peptide 1 (Table 5). However, the mean diameter of DNA condensates prepared with peptides 9–11 were significantly larger (738–1668 nm), most likely resulting from interparticle cross-linking of the internal Cys due to the high molar concentration (163–325 nmol/ml) required to form peptide 9–11 DNA condensates (Table 5). In each case, peptides 1–3, 6, 7, 10 and 11 DNA condensates prepared at a charge ratio of 4 had a positive zeta potential ranging from +18–37 mV (Table 5).

TABLE 5

QELS Particle Size Analysis[a] of Peptide DNA Condensates

| Number | SEQ ID NO: | Particle Size (nm)[b] | Zeta Potential[c] (mV) |
|---|---|---|---|
| 1 | Alk-No. 1 | 64 ± 11 | 26 ± 1 |
| 2 | Alk-No. 7 | 159 ± 76 | 18 ± 2 |
| 3 | No. 3 | 53 ± 16 | 28 ± 9 |
| 4 | No. 8 | —[d] | —[d] |
| 5 | No. 9 | 38 ± 10 | —[e] |
| 6 | No. 10 | 52 ± 4 | 37 ± 1 |
| 7 | No. 11 | 53 ± 16 | 26 ± 2 |
| 8 | No. 12 | —[d] | —[d] |
| 9 | No. 13 | 1668 ± 154 | —[e] |
| 10 | No. 14 | 1375 ± 324 | 34 ± 2 |
| 11 | No. 15 | 738 ± 154 | 31 ± 3 |
| 12 | No. 16 | 87 ± 20 | 30 ± 2 |
| 13 | No. 17 | 97 ± 40 | 31 ± 1 |
| 14 | No. 18 | 183 ± 64 | 20 ± 2 |
| 15 | No. 19 | 205 ± 104 | 23 ± 1 |
| 16 | No. 20 | 320 ± 169 | 23 ± 1 |

[a]Deconvolution of quasielastic light scattering data assumes spherical particles of identical density.
[b]Mean diameter determined from the multimodal volume distribution. Average and standard deviation of three determinations.
[c]Zeta Potential determined from the average and standard deviation of ten determinations.
[d]No particles formed.
[e]Peptide concentration at 4:1 charge ratio was too high for stable signal.

5. Gene Expression

Figure 43A:
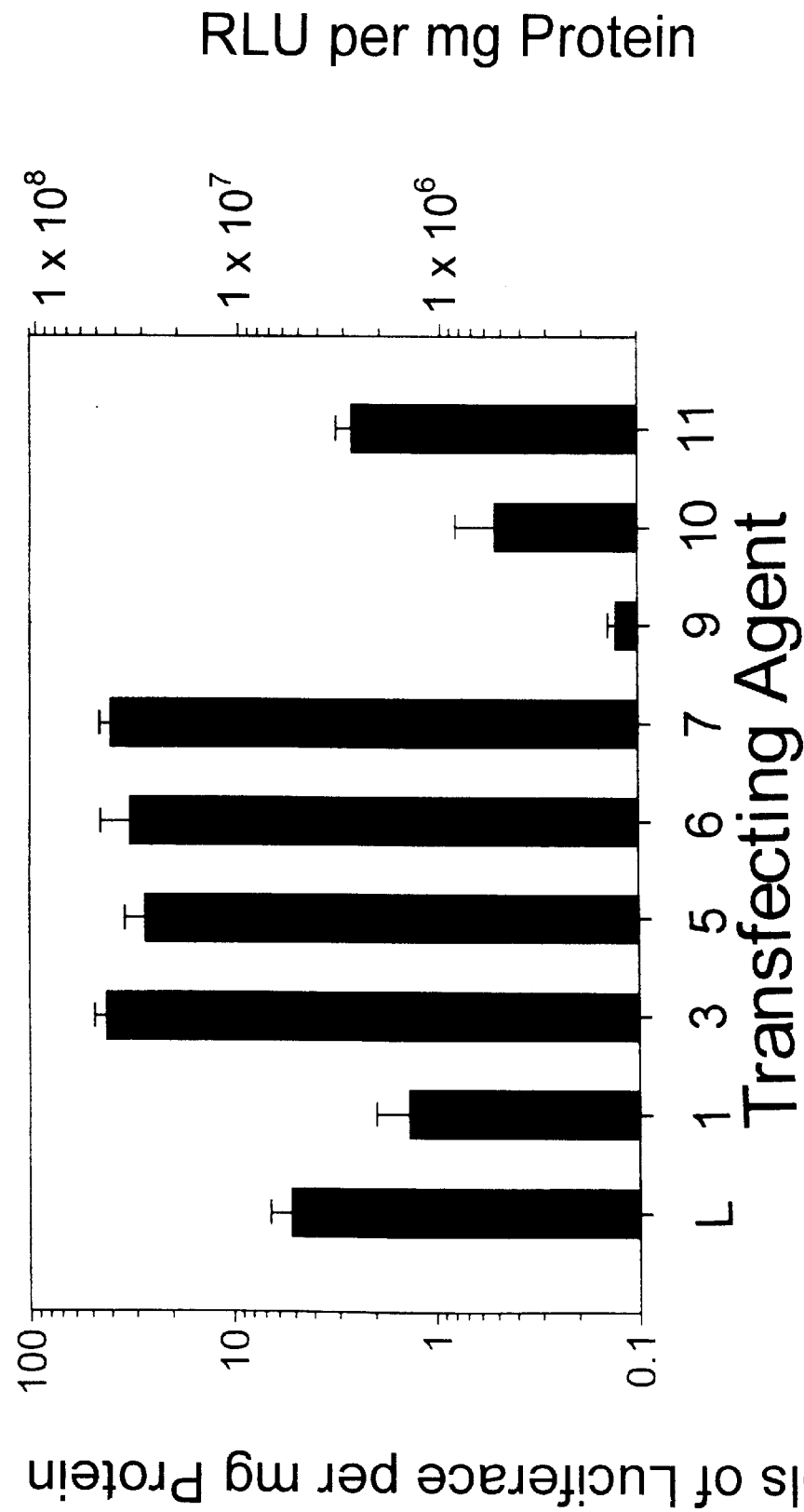
FIG. 43A, FIG. 43B and FIG. 43C. Luciferace Expression in HepG2, COS 7 and CHO Cells. The luciferace reporter gene expression for each peptide DNA condensate was measured in HepG2 (FIG. 43A), COS 7 (FIG. 43B) and CHO (FIG. 43C) cells using 80 µM chloroquine during the transfection. Each result represents the mean and standard deviation of three determinations. See Table 5 for peptide structures. L represents LipofectAce™.
Figure 43B:
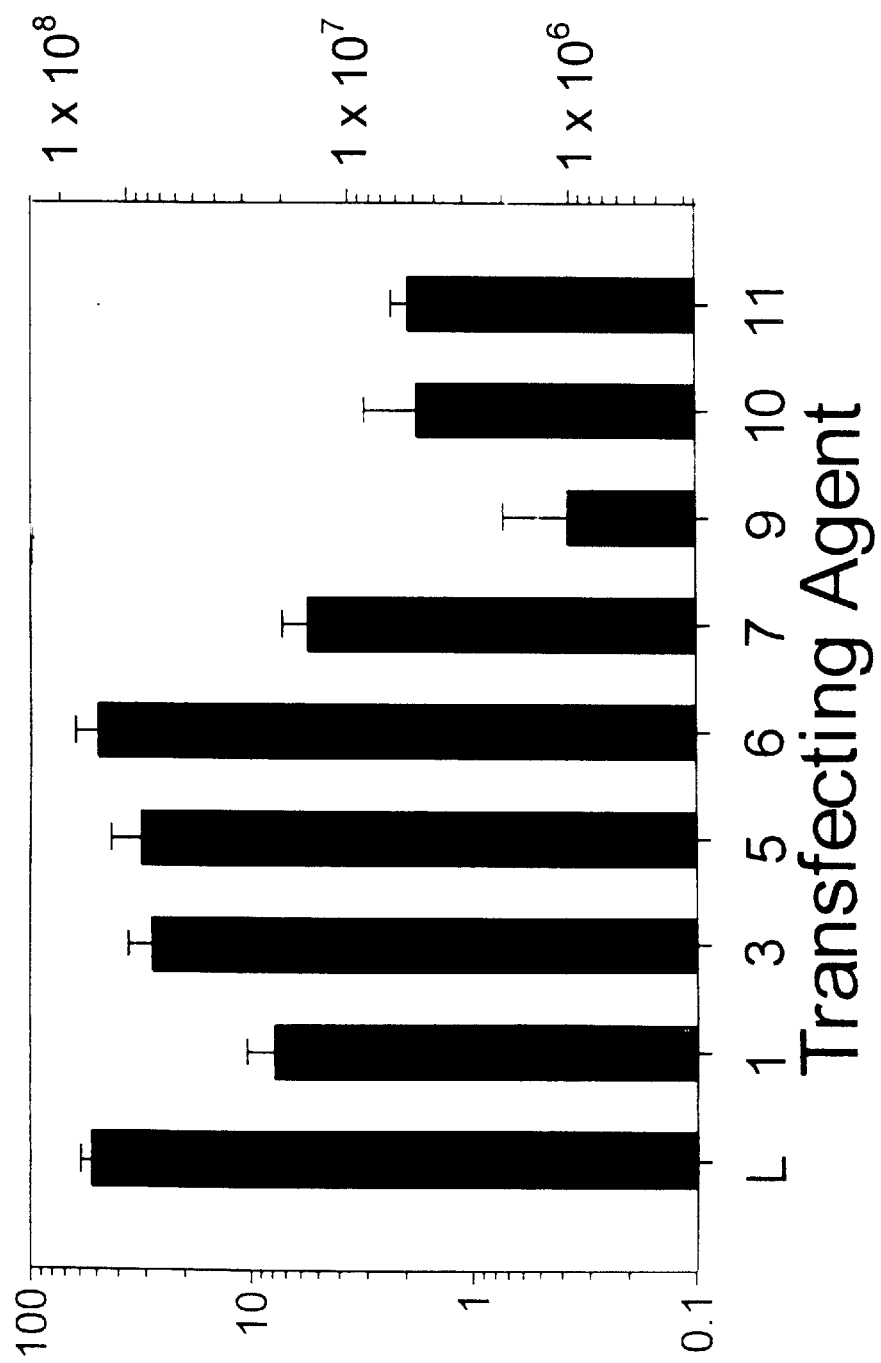
Figure 43C:
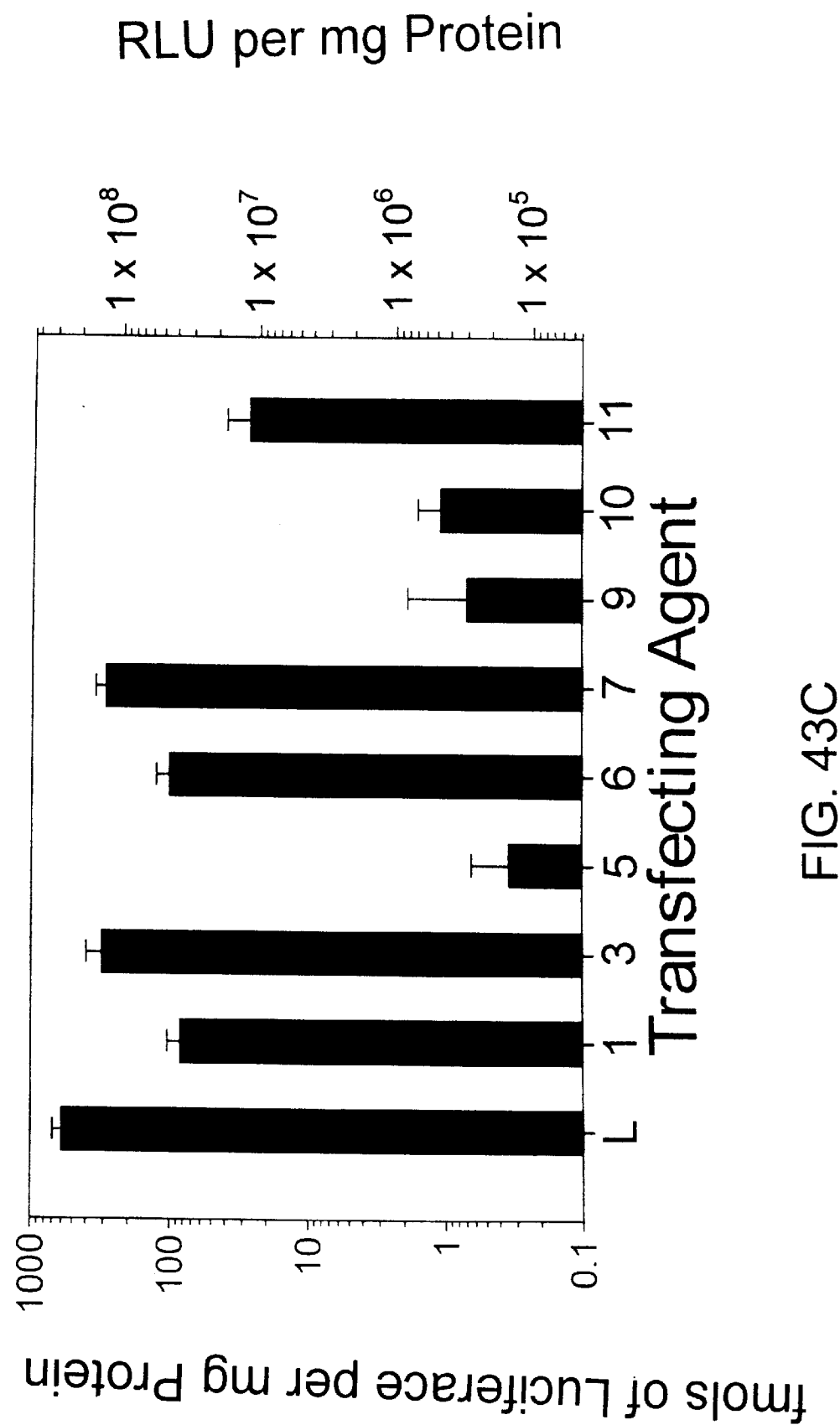

The in vitro gene transfer efficiency of peptide 1, 3, 5–7 and 9–11 DNA condensates prepared at a charge ratio of 4 was directly compared in three different cell lines (FIG. 43A, FIG. 43B and FIG. 43C). In each cell line tested, peptide 3 enhanced gene expression by 10 to 40-fold over peptide 1 DNA condensates (FIG. 43A, FIG. 43B and FIG. 43C). Comparison of peptide 3 to that of peptide 5, 6 and 7 DNA condensates indicated that the gene expression in HepG2 cells was maintained when decreasing peptide length by eliminating Lys residues (FIG. 43A). The gene expression in COS 7 cells was inexplicably 5-fold lower for peptide 7 relative to peptide 3, 5 and 6 DNA condensates despite otherwise identical physical properties (FIG. 43B).

The finding that peptide 5 mediated three-orders of magnitude lower gene expression in CHO cells relative to peptide 3, 6 and 7 (FIG. 43C) might be due to the decreased reducing capacity of CHO cells (Merkel et al., 1995; Shorts et al., 1996; Mendel et al., 1991). Since peptide 5 DNA condensates theoretically possess twice as many disulfide bonds as peptide 7 DNA condensates, CHO cells that produce lower levels of cytosolic glutathione (Merkel et al., 1995; Shorts et al., 1996; Mendel et al., 1991) may be less efficient at reducing endocytosed peptide 5 DNA condensates resulting in lower gene expression.

DNA condensates formed with peptide 9, 10 and 11 yielded overall lower levels of gene expression in each cell line relative to peptide 7 DNA condensates (FIG. 43A, FIG. 43B and FIG. 43C). This is most likely related to the large particle size (Table 5) which appeared to be inversely related to gene expression in all three cell lines (FIG. 43A, FIG. 43B and FIG. 43C).

6. Endosomal Buffering

The gene expression mediated by peptide DNA condensates is enhanced approximately 10-fold due to the presence of 80 µM chloroquine in the transfecting media which serves as a lyosotropic agent (Pouton and Seymour, 1998). Derivatization of polylysine with His produced DNA condensates that buffer the endosomal compartment and thereby substitute for chloroquine in enhancing peptide mediated gene delivery (Midoux and Monsigny, 1999). To show enhanced gene transfer of LMW cross-linking peptides, one to five His residues were substituted for Lys residues in 7 to prepare peptides 12–16 (Table 4).

Figure 40C:
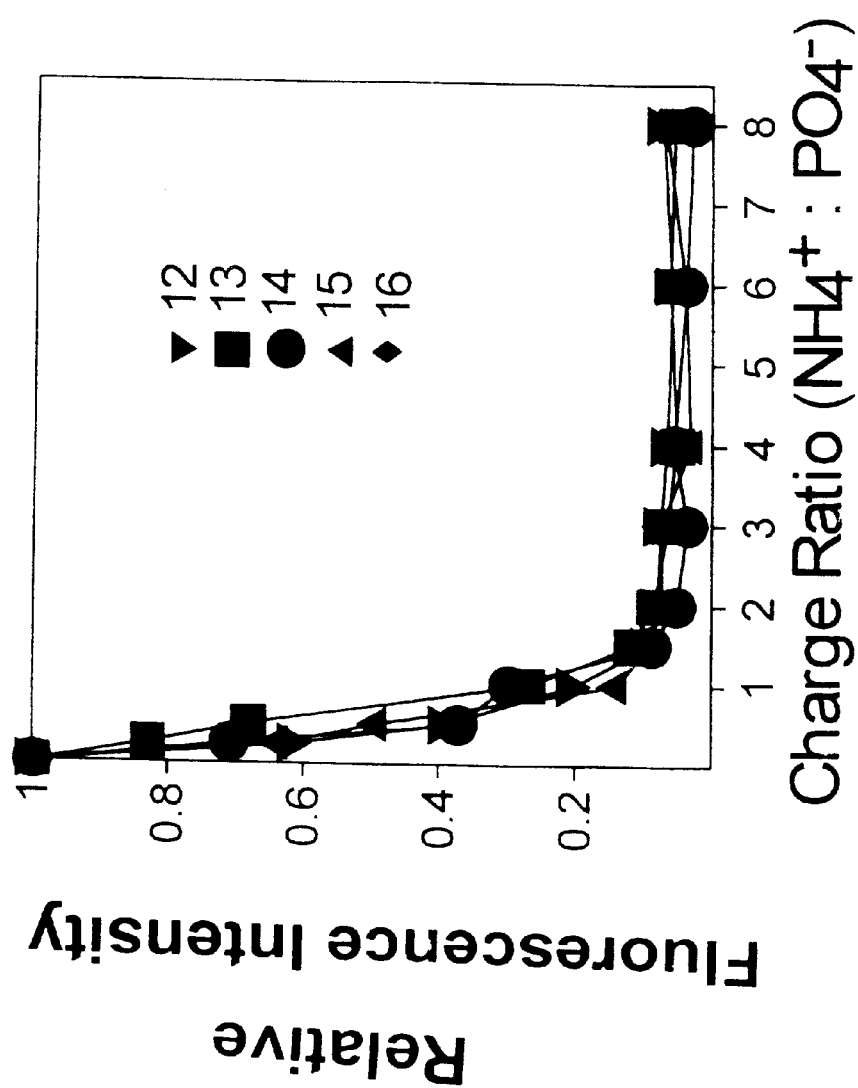

Titration of peptides 12–16 with plasmid DNA demonstrated each was equally effective of displacing thiazole orange from DNA, resulting in fully condensed DNA at a charge ratio of 2 (FIG. 40C). Likewise, analysis of the cross-linking kinetics of peptides 12–16 while bound to DNA established reaction completion in less than 10 min as illustrated by the results for peptide 12 (FIG. 41). Application of the salt sonication assay demonstrated that, like peptide 7, peptide 12–16 formed stable DNA condensates that dissociated above 0.8 M sodium chloride as illustrated using peptide 12 DNA condensates (FIG. 42F).

In contrast to the similarities between peptide 7 and 12–16 described above, particle size analysis revealed that DNA condensates formed with peptides 12–16 possessed mean diameters ranging from 87–320 nm that increased in proportion to the number of His residues, compared to DNA condensates formed with peptide 7 that had a mean diameter of 53 nm. Despite the larger particle size, peptides 12–16 DNA condensates prepared at a charge ratio of 4 each had a positive zeta potential ranging from +20–31 mV (Table 5).

The pKa of cationic polymers such as PEI or dendrimers that buffer endosomes is generally between 5.5 and 7.5 (Pouton and Seymour, 1988). To determine whether the His residue(s) in peptides 12–16 buffer in a similar range, an NMR based titration established the immidazole side chain in each peptide had a pKa between 5.5 to 6.0.

Peptides 12–16 were compared to peptide 7 in a pH titration study to determine whether the number of His residues in 12–16 would correlate with increasing buffering capacity (FIG. 44). Although there was no correlation between and the apparent buffering capacity and the number of His residues in peptides 12–16, each His containing peptide did buffer more efficiently than peptide 7.

The gene transfer efficiency of peptide 12–16 DNA condensates were compared to condensates prepared with peptide 1 and 7 in three cell lines (FIG. 45A, FIG. 45B and FIG. 45C). In the absence (−) of chloroquine, peptide 1 DNA condensates mediated 10–15 fold lower gene expression relative to in the presence (+) of 80 $\mu$M chloroquine in each cell line (FIG. 45A, FIG. 45B and FIG. 45C). Peptide 12-DNA condensates possessing 10% His content mediated 3-fold higher gene expression compared to peptide 7-DNA condensates in HepG2 cells (FIG. 45A). Increasing the His content to 20% or 30% in peptides 13- and 14- resulted in a 4-fold enhancement in gene transfection relative to peptide 7-DNA condensates in HepG2 cells (FIG. 45A). The combined contribution of cross-linking and His resulted in gene expression levels for peptide 13- and 14- DNA condensates that were equivalent to peptide 1+ DNA condensates in HepG2 cells (FIG. 45A).

Peptide 15- and 16-DNA condensates were progressively less effective in mediating gene transfer in HepG2 cells despite possessing His content of 40% and 50%, respectively (FIG. 45A), presumably the result of an increase in particle size (Table 5). In contrast to the results in HepG2 cells, peptide 12- through 14- failed to enhance gene expression in COS 7 cells relative to peptide 7-DNA condensates (FIG. 45B). Likewise, the gene expression of peptide 14- and 15-DNA condensates were also significantly less in COS 7 cells relative to condensates prepared with peptide 12- and 13-. The same comparison in CHO cells established that peptide 13-, 14- and 16- DNA condensates mediated a 10 to 15-fold enhancement in gene expression relative to peptide 7-DNA condensates (FIG. 45C). The enhanced gene expression of peptide 16- DNA condensates in CHO cells has been reproduced several times and appears to be contradictory to the trends observed in HepG2 and COS 7 cells.

D. DISCUSSION

The high molecular weight and polydispersity (Toncheva et al., 1998; Page and Roy, 1997; Godbey et al., 1999; McKenzie et al., 1999) inherent to many nonviral gene transfer agents complicates region-specific derivatization, characterization and formulation with DNA. The design of LMW gene transfer agents is an attractive alternative since these can be systematically optimized and may present fewer side effects when used clinically.

In previous studies the inventors determined peptide 1, possessing eighteen Lys residues, was minimal peptide to form small (<80 nm) DNA condensates that are stable in 0.4 M saline and transfect cells in culture as efficiently as higher molecular weight polylysine peptides (Wadhwa et al., 1997). Decreasing the number of Lys residues to further shorter chain length such as in peptide 2, not only led to an increase in the particle size and a three-order of magnitude decrease in the in vitro gene expression level, but also to a loss of stability in normal saline (0.15 M) due to a decrease in DNA binding affinity (Wadhwa et al., 1997; Adami et al., 1998).

The stability of LMW peptide DNA condensates directly relates to in vivo efficacy. Without the aid of a cross-linking strategy, i.v. dosed peptides 1 DNA condensates lack stability in the circulation and are rapidly metabolized without mediating gene expression (Example 3; Collard et al. 2000a; Example 7; Collard et al., 2000b). Glutaraldehyde cross-linking provides a means to stabilize LMW DNA condensates for in vivo use but still requires the use of a twenty amino acid peptide to form small condensates.

The present example provides improved LMW peptides due to the substitution of one to five His residues. The His derivatized polylysine peptides provide endosomal buffering to enhance gene expression. The iterative engineering of LMW cross-linking peptides has thus arrived at an identification of the minimal Cys and Lys peptide that polymerizes while bound to DNA leading to enhanced gene expression. Such peptides will be particularly useful in increasing the level of gene expression in vivo as part of gene therapy.

EXAMPLE 7

Low MR Glycopeptide PEG-Peptide DNA Co-Condensates

A. INTRODUCTION

The present example concerns the biodistribution, metabolism, cellular targeting and gene expression of a nonviral peptide DNA gene delivery system. $^{125}$I-labeled plasmid DNA was condensed with low molecular weight peptide conjugates and dosed i.v. in mice to determine the influence of peptide DNA formulation parameters on specific gene targeting to hepatocytes.

Optimal targeting to hepatocytes was obtained with the combined use of a triantennary glycopeptide (Tri-CWK$_{18}$) and a polyethylene glycol-peptide (PEG-CWK$_{18}$) to mediate specific recognition by the asialoglycoprotein receptor and to reduced non-specific uptake by Kupffer cells. Tri-CWK$_{18}$/PEG-CWK$_{18}$ DNA co-condensates were stabilized and protected from metabolism by glutaraldehyde cross-linking. An optimized formulation targeted 60% of the dose to the liver with 80% of the liver targeted DNA localized to hepatocytes. Glutaraldehyde cross-linking of DNA condensates reduced the liver elimination rate from a $t_{1/2}$ of 0.8 h and 3.6 h. An optimized gene delivery formulation produced detectable levels of human $\alpha$1-antitrypsin in mouse serum which peaked at day 7 compared to no expression using control formulations. The results demonstrate the application of formulation optimization to improve the targeting selectivity and gene expression of a peptide DNA delivery system.

B. MATERIALS AND METHODS

1. Materials

Sodium $^{125}$iodide was purchased from Dupont NEN, Boston, Mass. Chloramine T, sodium metabisulfite, heparin, Sephadex™ G-25, D-mannitol, bovine serum albumin, Hepes, collagenase from clostridium histolyticum type IV (lot number: 47H6865), carbonyl iron, 70% glutaraldehyde, 2,2'-azion-bis(3-ethylbenzthiaxoline-6-sulfonic acid (ABTS), Tween 20, anti-human α-1-antitrypsin IgG from goat and rabbit, and human α-1 antitrypsin were purchased from Sigma, St. Louis, Mo. Zeta probe cationic membranes were purchased from BioRad Hercules, Calif. Agarose was purchased from Gibco-BRL, Gaithersburg, Md. Methoxy-PEG-vinylsulfone 5000 Da was purchased from Fluka, Ronkonkoma, N.Y. Ketamine hydrochloride was purchased from Fort Dodge Laboratories, Fort Dodge, Iowa. Zylazine hydrochloride was purchased from Miles Inc., Shawnee Mission, Kans. Silastic catheters (0.305 mm inner diameter× 0.365 mm outer diameter) were purchased from Baxter, Obetz, Ohio.

ICR mice (30–35 g) were purchased from Harlan, Indianapolis, Ind., and housed in cages located in a limited access area maintaining a 12 h light-dark cycle and controlled temperature (26–28° C.). β-galactosidase from bovine tests (EC 3.2.1.23) and anti-rabbit IgG-peroxidase from goat were purchased from Boehringer Mannheim, Indianapolis, Ind. Ultrapure™ 100 and tip100, DNA purification columns were purchased from Qiagen, Santa Clarita, Calif. Analytical and semi-preparative HPLC columns were purchased from Vydac, Hesperia, Calif.

2. Radiolabeling Plasmid DNA

Endotoxin free plasmid DNA encoding human alpha-1-antitrypsin (hAAT) driven by a cytomegalovirus promoter (pCMVhAAT) (Hickman et al., 1994) was purified from $E. coli$ using a Qiagen ultrapure™ column according to the manufacturers instructions. Plasmid DNA was radiolabeled with $^{125}I$ as described previously resulting in supercoiled and circular DNA with specific activity of 200 nCi/μg (Terebesi et al., 1998).

3. Glycopeptide and PEG-peptide Synthesis $CWK_{18}$ was prepared and alkylated with iodoacetic acid to form $AlkCWK_{18}$ as described previously (Wadhwa et al., 1997). A triantennary N-glycan was purified from bovine fetuin as the Boc-tryosine derivative (Tamura et al., 1994). The oligosaccharide was converted to an iodoacetylated tyrosinamide oligosaccharide and then reacted with $CWK_{18}$ to form $Tri-CWK_{18}$. (Example 3; Collard et al., 2000a; Example 7; Collard et al., 2000b). Agalactosyl $Tri-CWK_{18}$ was prepared by treating 400 nmol of $Tri-CWK_{18}$ with 4 mU of β-galactosidase in 5 mM citrate phosphate pH 4.3 at 37° C. for 24 h.

The glycopeptide was purified by injecting 50 nmol on an analytical RP-HPLC column (0.47×25 cm) eluted at 1 mL/min with 0.1% TFA and a gradient of acetonitrile from 5–25% over 30 min. The product eluting at 20 min was collected and freeze dried. The complete removal of galactose from the purified glycopeptide was confirmed using ES-MS, $^1H$-NMR and monosaccharide composition analysis (Example 3; Collard et al., 2000a; Example 7; Collard et al., 2000b).

Polyethylene glycol vinyl sulfone (PEG-VS) was reacted with $CWK_{18}$ to prepare $PEG-CWK_{18}$, which was purified and characterized as reported previously (Example 1; Kwok et al., 1999; Example 3).

4. Formulation of Cross-linked Glycopeptide and PEG-peptide DNA Co-Condensates $Tri-CWK_{18}$, $PEG-CWK_{18}$ or $AlkCWK_{18}$ (250 μL of 40 nmol/mL in HBM, composed of 5 mM Hepes, 0.27 M mannitol pH 7.4) were combined with 250 μL of 100 μg/mL pCMVhAAT while vortexing. DNA condensates formed instantly but were allowed to equilibrate for 30 min prior to analyzing particle size and zeta potential on a Zeta-Plus (Brookhaven Instruments, Holtsville, N.Y.). DNA co-condensates were prepared by mixing $Tri-CWK_{18}$ with $PEG-CWK_{18}$ at either 50:50, 10:90 or 2:98 mol % ($Tri-CWK_{18}$:$PEG-CWK_{18}$) to form 40 nmol/mL admixtures used to condense DNA as described above.

Glutaraldehyde cross-linked DNA condensates were formed by adding 60 or 150 nmol of Glutaraldehyde (6 or 15 mol equivalents of glutaraldehyde per mol of $CWK_{18}$) to 500 μL of 50 μg/mL performed DNA condensates, followed by reaction for 24 h at 4° C. (Adami et al. 1999). The stability of cross-linked DNA condensates were evaluated by adjusting 200 μL aliquots (10 μg DNA) to 0.3, 0.5, 1.0, 1.5 M sodium chloride (normalized to 300 μL) followed by sonication for 30 s with a 100 W Microson XL-2000 ultrasonic probe homogenizer (Kontes, Vineland, N.J.) with a vibrational amplitude of 5 to fragment uncondensed DNA (Adami et al., 1999). DNA condensates (0.5 μg) were digested for 12 h at 37° C. with 40 μof trypsin and then electrophoresed on an agarose gel and visualized by ethidium bromide straining.

Cross-linked $Tri-CWK_{18}$/$PEG-CWK_{18}$ DNA co-condensates (50 μg in 1 mL) were dialyzed for 75 h in a fixed volume dialyzer against a 100,000 MWCO membrane to remove unbound peptides. DNA co-condensates (25 μg) in the retentate were then hydrolized in 4 N hydrochloric acid at 100° C. for 5 h to release glucosamine from $Tri-CWK_{18}$. The samples were dried, reconstituted in 200 μL of water, and 40 μL was analyzed by high pH anion exchange chromatography relative to a glucosamine standard (Hardy et al., 1988). Comparison of the glucosamine recovered before and after dialysis allowed quantification of the percent of $Tri-CWK_{18}$ incorporated into cross-linked DNA co-condensates.

5. Pharmacokinetic Analysis of DNA Condensates.

Mice were anesthetized by i.p. injection of ketamine hydrochloride (100 mg/kg) and xylazine hydrochloride (10 mg/kg) and then underwent a dual cannulation of the right and left jugular veins. An i.v. dose of $^{125}I$-DNA (5 μg in 50 μL of HBM, 1.2 μCi) or $^{125}I$-DNA condensate (5 μg) was administered via the left catheter, and blood samples were drawn from the right catheter at 1, 3, 6, 10, 15, 20, 30, 40, and 60 min, then replaced with 10 μL of normal saline. The amount of radioactivity in each blood time point was quantified by direct γ-counting followed by extraction of the DNA and analysis by gel electrophoresis as described below.

Blood time points (10 μL) were digested with proteinase K (500 L of 0.5 mg/mL proteinase K in 100 mM sodium chloride, 1% SDS and 50 mM Tris-HCl ph 8.0) for 12 h at 37° C. DNA was extracted with 500 μL of phenol:chloroform:isoamyl alcohol (24:25:1) and then precipitated with 1 mL of ethanol and centrifuged at 13,000×g for 15 min. The DNA pellet was air dried, dissolved in 10 μL Tris-EDTA buffer, γ-counted and then the entire sample was loaded and electrophoresed for 1 h at 70 V on an 1% agarose gel. The gel was dried on a zeta probe membrane and autoradiographed on a Phosphor Imager (Molecular Devices, Sunnyvale, Calif.) following a 15 h exposure.

6. Biodistribution Analysis of $^{125}I$-DNA and $^{125}I$-DNA Condensates

Mice were anesthetized and a single catheter was placed in the left jugular vein. $^{125}I$-DNA (2.5 μg in 50 μL of HBM, 0.6 μCi) or $^{125}I$-DNA condensates were dosed i.v. followed by vein ligation. After 5, 15, 30, 60, or 120 min, mice were sacrificed by cervical dislocation and the major organs (liver, lung, spleen, stomach, kidney, heart, large intestine, and small intestine) were harvested, rinsed with saline, and weighed. The radioactivity in each organ was determined by direct γ-counting and expressed as the targeting efficiency, defined as the percent of the dose in the target organ.

7. Isolation of Hepatocytes and Kupffer cells

Mice were dosed i.v. tail vein with 20 mg of carbonyl iron in 0.2 mL of saline. After 45 min, mice were anesthetized and a single catheter was inserted into the right jugular vein and used to dose $^{125}$I-DNA or $^{125}$I-DNA condensates (2.5 µg DNA in 50 µL, 0.6 µCi in HBM). Following 30 min of biodistribution, the portal vein was cannulated and used to administer 0.2 mL heparin (100 U/mL) followed immediately by the perfusion buffers.

The liver was first perfused at 5 mL/min for 2 min with oxygenated (95% oxygen, 5% carbon dioxide) preperfusion buffer (calcium and magnesium free Hepes solution, pH 7.45, 37° C.), and then at 3 mL/min for an additional 3 min. The liver was digested by perfusion with oxygenated Seglen's Buffer (pH 7.45, 37° C.) containing 0.058% (w/v) collagenase type IV at 3 mL/min for 16–20 min. At the start of the perfusion the vena cava and aorta were cut, and at the completion, the liver was excised and placed in a Petri dish (4° C.) and cut into small pieces.

Cells were dislodged and dispersed in ice-cold Hank's solution containing 10 mM Hepes, pH 7.45, 0.1% BSA and then incubated at 37° C. for 20 min with shaking (30 rev/min). The dispersed cells were passaged through a 73 µm mesh filter then transferred to a 35-mL glass tube. The iron-filled Kupffer cells were attracted to the wall of the tube with a magnet while other cells were decanted off. The procedure was repeated three times and the Kupffer cells were combined and resuspended in 0.8 mL Hank's Hepes Buffer. The remaining cell suspension was centrifuged at 50×g for 1 min and the supernatant was discarded. The pelleted hepatocytes were washed twice with ice-cold Hank's Hepes buffer followed by centrifuging at 50×g for 1 min. The hepatocytes were re-suspended in 2 mL Hank's Hepes buffer and the cell number and viability were determined by the trypan blue exclusion method. The amount of radioactivity associated with each cell fraction was determined by γ-counting.

8. In Vivo Gene Expression

Mice were dosed in the tail vein by infusing 1 mL of HBM containing either 50 µg of plasmid DNA (30 mice), 50 µg of cross-linked agalactosyl-Tri-CWK$_{18}$/PEG-CWK$_{18}$ (10:90) DNA co-condensates (30 mice) or 50 µg of cross-linked Tri-CWK$_{18}$/PEG-CWK$_{18}$ (10:90) DNA co-condensates (60 mice). Blood (1 mL) was collected via the jugular artery from 3–6 mice per day for 10 days after dosing. The blood was allowed to clot at room temperature, centrifuged at 13,000×g for 15 min, and the serum that was collected was stored frozen at −20° C. until assayed by ELISA.

A modified double antibody sandwich ELISA was used to determine the magnitude of hAAT gene expression (Michalski et al., 1985). After each incubation the wells were washed three times with phosphate-buffered saline pH 7.4 containing 0.05% Tween 20 (PBS-Tween). The goat anti-hAAT primary antibody was diluted 1:1000 in 0.1 M sodium bicarbonate pH 9.6 and 100 µL was added to each well and incubated overnight at 4° C. Non-specific binding was blocked with 100 µL of 5 w/v% non-fat dry milk in PBS incubated for 1 h at 37° C. Mouse serum samples (100 µL) or hAAT primary standards added to mouse serum were added to each well and allowed to bind for 2 h at 37° C. The rabbit anti-hAAT secondary antibody (diluted 1:1000 in PBS-Tween) was added (100 µL) to each well followed by incubation at 37° C. for 2 h. Anti-rabbit peroxidase conjugated antibody (diluted 1:1000 in PBS-Tween) was added (100 µL) and allowed to bind for 2 h at RT. Finally, substrate solution (100 µL of 1 mg/mL ABTS in 0.2 M sodium phosphate pH 7.6 with 0.003% hydrogen peroxide) was added and incubated at RT for 30 min prior to reading the absorbance at 415 nm on a BioRad™ 550 microplate reader. The amount of hAAT expressed was determined from a standard curve prepared from the addition of hAAT to mouse serum.

C. RESULTS AND DISCUSSION

1. Peptides and Glycopeptides

Tri-CWK$_{18}$, PEG-CWK$_{18}$, and AlkCWK$_{18}$ were prepared and used as LMW DNA carrier molecules (FIG. 46A, FIG. 46B, FIG. 46C and FIG. 46D). The terminal galactose residues of Tri-CWK$_{18}$ were removed with β-galactosidase to create agalactosyl-Tri-CWK$_{18}$ as a negative control for ASGP-R recognition. $^1$H-NMR, ES-MS and monosaccharide compositional analysis each confirmed the removal of all three terminals galactose residues (Example 3; Collard et al., 2000a; Example 7; Collard et al., 2000b).

Biodistribution analysis of radioiodinated Tri-CWK$_{18}$ and agalactosyl-Tri-CWK$_{18}$ established the liver as the major target site, resulting in a 30 min liver targeting efficiency (percent of dose in the target organ) of 1.3±0.1% for agalactosyl-Tri-CWK$_{18}$ vs. 52.9±3.5% determined for Tri-CWK$_{18}$. These results are in close agreement with similar biodistribution studies on triantennary tyrosinamide oligosaccharides (Chiu et al., 1994; Rice et al., 1995), establishing the requirement for galactose to mediate ASGP-R recognition of Tri-CWK$_{18}$.

2. Peptide-DNA Condensates

Figure 47A:
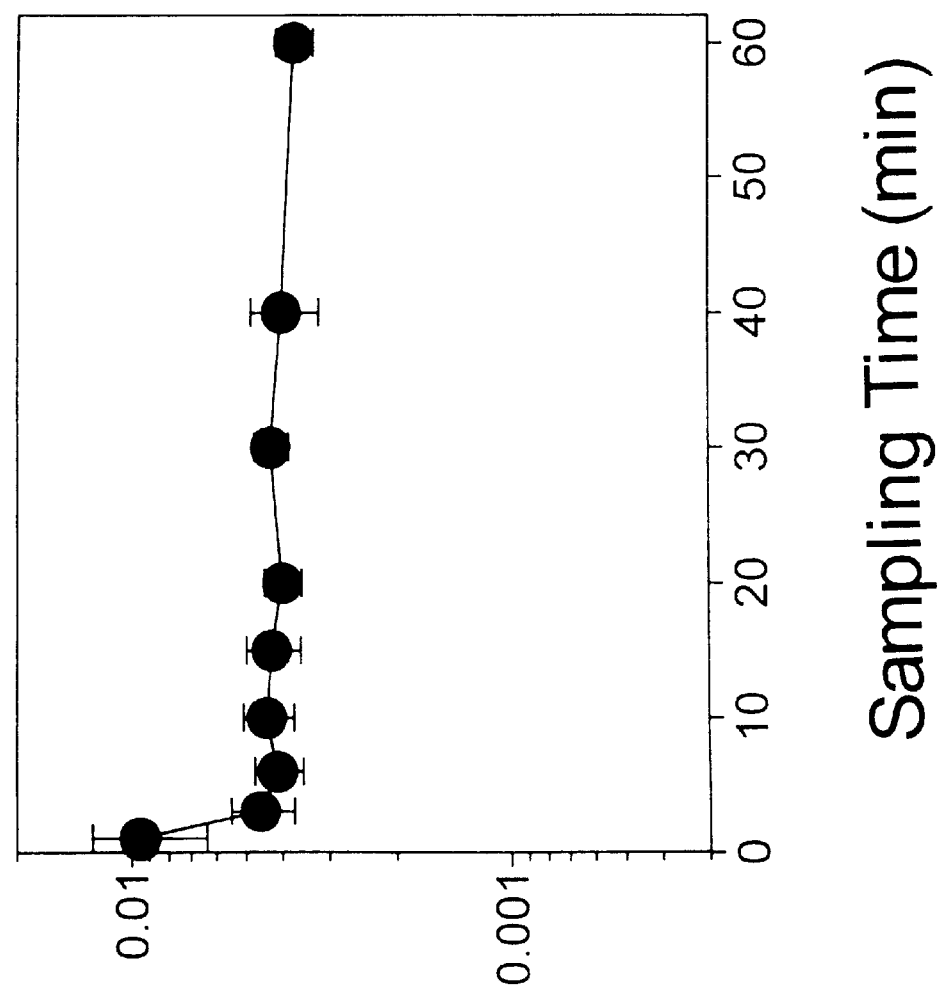
Figure 47D:
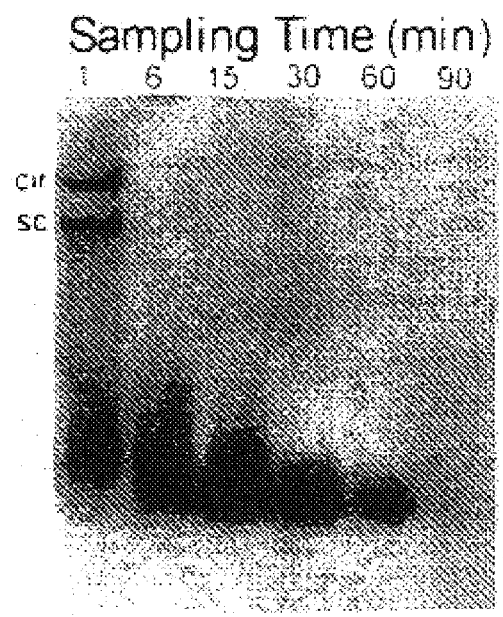
Figure 47E:
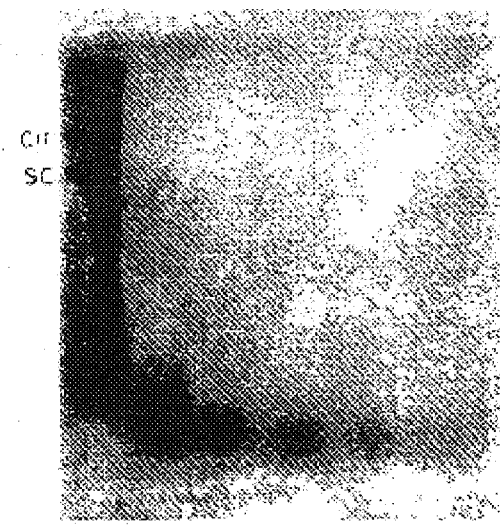
Figure 47F:
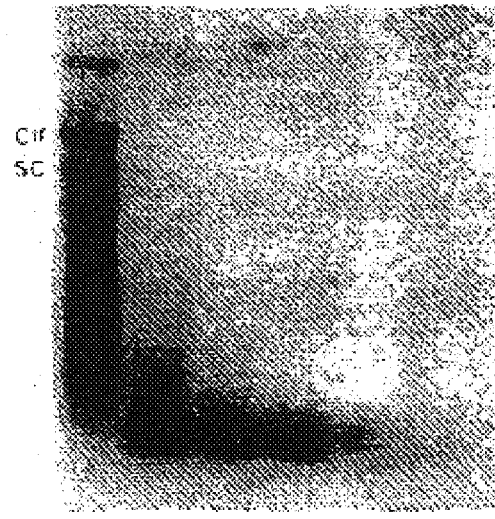

Plasmid DNA was radiolabeled with $^{125}$I to generate a DNA probe to determine the fate of i.v. dosed gene delivery formulations. Pharmacokinetic analysis of uncondensed plasmid DNA established its rapid removal from the circulation following i.v. dosing with less than 30% of the dose remaining in the blood after 1 min (FIG. 47A). Electrophoretic analysis of the DNA remaining in blood established it was completely fragmented within 6 min (FIG. 47A) indicating that the majority of the pharmacokinetic profile represented elimination of metabolites.

The analysis of AlkCWK$_{18}$ and Tri-CWK$_{18}$ DNA condensates established a similar profile of rapid elimination (FIG. 47B and FIG. 47C) and formation of metabolites within 6 min (FIG. 47B and FIG. 47C) suggesting that neither AlkCWK$_{18}$ nor Tri-CWK$_{18}$ significantly protected DNA from endonucleases either in the serum or tissues.

Figure 48A:
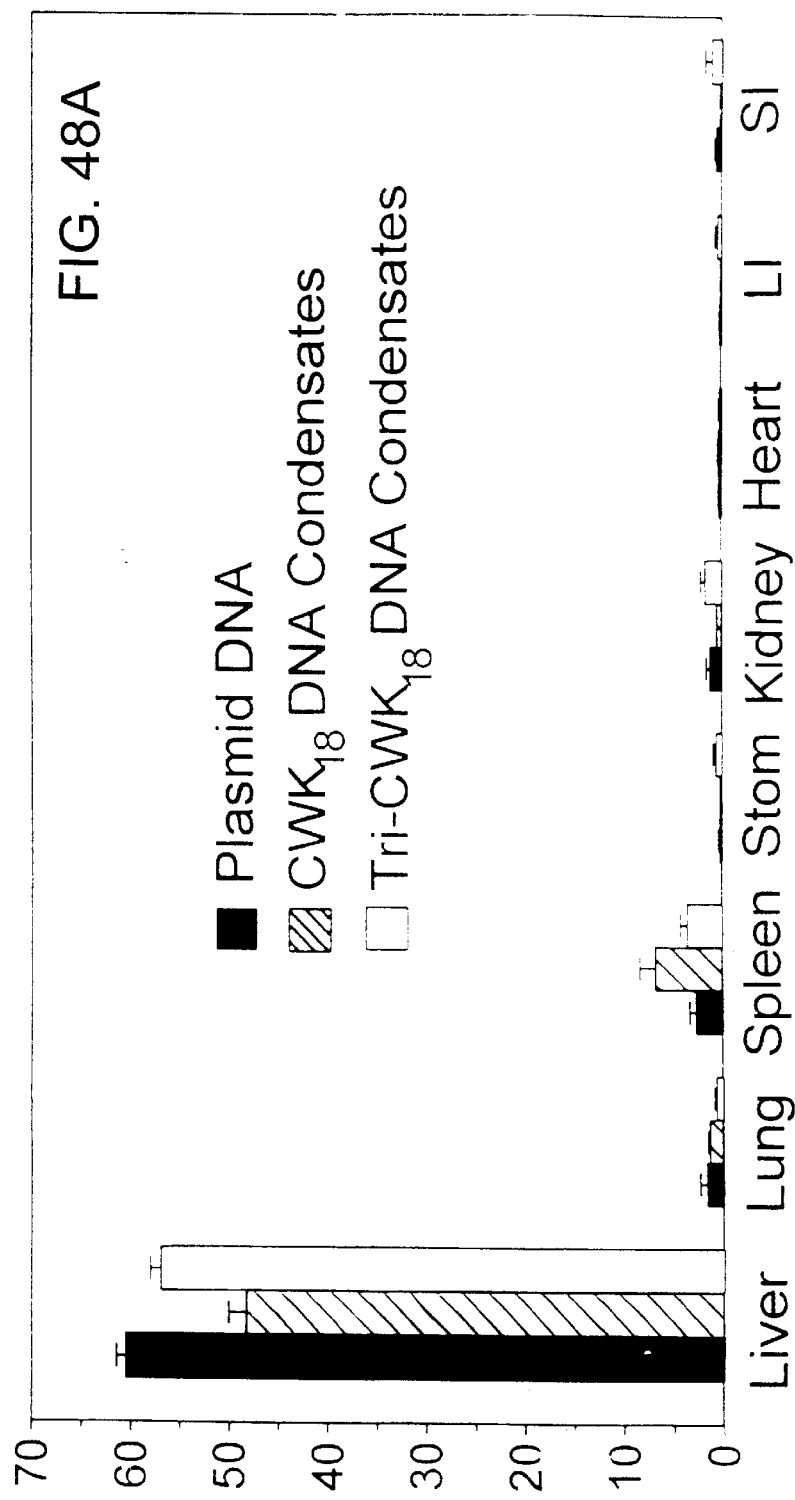
Figure 48C:
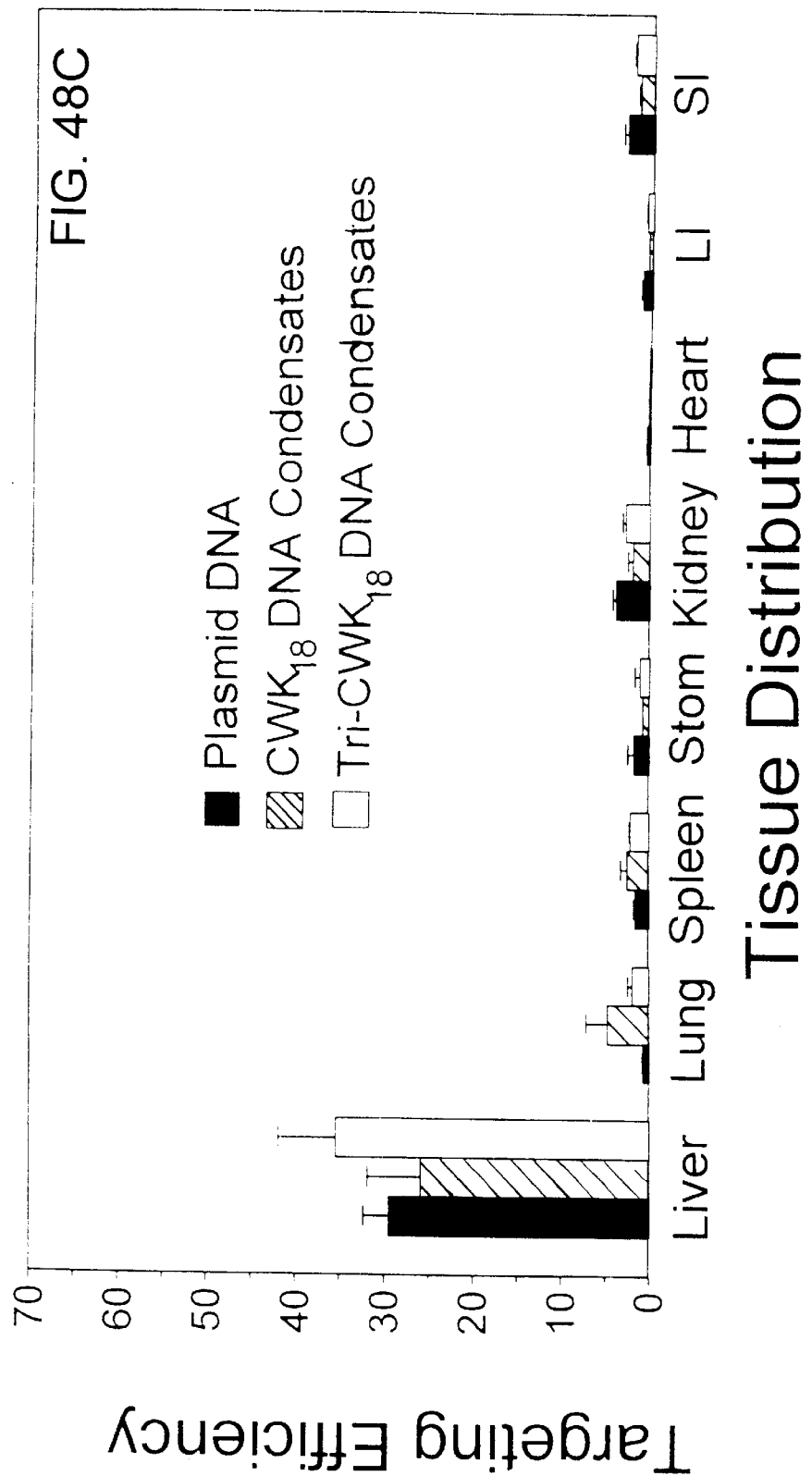

Biodistribution analysis of i.v. dosed plasmid DNA, AlkCWK$_{18}$, and Tri-CWK$_{18}$ DNA condensates established the liver as the major target site at 5 min for all three formulations, resulting in a targeting efficiency of 60% for plasmid DNA, 48% for AlkCWK$_{18}$ DNA condensates, and 57% for Tri-CWK$_{18}$ DNA condensates (FIG. 48A) with all other organs possessing <7% of the $^{125}$I-DNA dose. A similar biodistribution profile was observed at 15 and 30 min for each formulation with proportional decreases in the liver targeting over time without significant increases in the distribution to other tissues (FIG. 48B and FIG. 48C).

The biodistribution time was extended to 2 h to examine the half-life of $^{125}$I-DNA in the liver. Plasmid DNA was rapidly eliminated from the liver with a $t_{1/2}$ of 0.61 h, resulting in only 7% of the radioactive dose remaining in the liver after 2 h (FIG. 49A). AlkCWK$_{18}$ DNA condensates and Tri-CWK$_{18}$ DNA condensates were also rapidly eliminated from the liver with a similar $t_{1/2}$ of 0.8 and 0.63 h, respectively (FIG. 49B and FIG. 49C). These results suggested that either AlkCWK$_{18}$ and Tri-CWK$_{18}$ DNA condensates dissociate during circulation or they fail to significantly protect DNA from metabolism in the liver.

If stable during circulation, AlkCWK$_{18}$ and Tri-CWK$_{18}$ DNA condensates would likely produce altered cell-type specific targeting in the liver relative to plasmid DNA. Therefore, the cellular distribution of $^{125}$I-DNA in the liver was investigated by separating hepatocytes and Kupffer cells following collagenase perfusion. Plasmid DNA distributed with 65% to Kupffer cells and 35% to hepatocytes while AlkCWK$_{18}$ DNA condensates produced a nearly identical distribution with 68% associated with Kupffer cells and 32% with hepatocytes (Table 6).

These data supported a hypothesis involving the rapid serum dissociation of AlkCWK$_{18}$ DNA condensates with subsequent biodistribution of plasmid DNA. Analysis of Tri-CWK$_{18}$ DNA condensates established a slight improvement in the cell-type specific targeting with 55% distributed to Kupffer cells and 45% to hepatocytes, providing some evidence that Tri-CWK$_{18}$ DNA condensates are at least (Table 6). Presumably, polylysine$_{1007}$ DNA condensates are rapidly opsonized during circulation due to their electropositive surface charge (Table 7), causing their biodistribution to the lung.

The fact that there was minimal lung targeting associated with AlkCWK$_{18}$ DNA condensates supports the hypothesis that these dissociate during circulation. Notably, 54% of the polylysine$_{1007}$ $^{125}$I-DNA condensate recovered in the liver was associated with Kupffer cells whereas 46% was with hepatocytes (Table 6). This result established that both electronegative plasmid DNA and electropositive HMW polylysine DNA condensates produce a similar non-specific cell-type distribution when taken-up by the liver. Collectively, these results supported the hypothesis that the primary difference between polylysine$_{1007}$ and AlkCWK$_{18}$ DNA condensates was their stability during circulation.

TABLE 6

Liver Distribution of $^{125}$I-DNA Formulations

| Dosage Form[a] | Hepatocytes[b] | Kupffer cells[c] | Hep/Kup Ratio[d] | % Hepatocytes[e] | % Kupffer cells[e] | Liver $t_{1/2}^{f}$ (h) |
|---|---|---|---|---|---|---|
| A | 159 ± 57 | 251 ± 37 | 0.56 | 35 | 65 | 0.6 |
| B | 264 ± 53 | 522 ± 190 | 0.50 | 32 | 68 | 0.8 |
| c | 188 ± 48 | 211 ± 63 | 0.81 | 45 | 55 | 0.6 |
| D | 540 ± 108 | 394 ± 19 | 1.25 | 55 | 45 | 2.6 |
| E | 1161 ± 205 | 259 ± 33 | 4.50 | 80 | 20 | 2.1 |
| F | 526 ± 202 | 374 ± 76 | 1.40 | 55 | 45 | 2.5 |
| G | 922 ± 320 | 198 ± 41 | 4.63 | 80 | 20 | 3.6 |
| H | 573 ± 232 | 434 ± 139 | 1.29 | 54 | 46 | 2.4 |
| I | 477 ± 128 | 424 ± 224 | 1.20 | 53 | 47 | 2.4 |
| J | 416 ± 26 | 446 ± 34 | 0.93 | 46 | 54 | 2.8 |
| K | 762 ± 79 | 174 ± 27 | 4.47 | 80 | 20 | 4.7 |
| L | 1228 ± 40 | 403 ± 57 | 3.10 | 73 | 27 | n.d. |

[a]Dosage form dosed i.v.
A = Plasmid $^{125}$I-DNA.
B = AlkCWK$_{18}$ $^{125}$I-DNA (Alk-SEQ ID NO:1).
C = Tri-CWK$_{18}$ $^{125}$I-DNA.
D = Cross-linked (6 mol eq) Tri-CWK$_{18}$ $^{125}$I-DNA.
E = Cross-linked (15 mol eq) Tri-CWK$_{18}$/PEG-CWK$_{18}$ (50:50) $^{125}$I-DNA.
F = Cross-linked (15 mol eq) Agalactosyl-Tri-CWK$_{18}$/PEGCWK$_{18}$ (50:50) $^{125}$I-DNA.
G = Cross-linked (15 mol eq) Tri-CWK$_{18}$/PEG-CWK$_{18}$ (10:90) $^{125}$I-DNA.
H = Cross-linked (15 mol eq) Agalactosyl-Tri-CWK$_{18}$/PEG-CWK$_{18}$ (10:90) $^{125}$I-DNA.
I = Cross-linked (15 mol eq) PEG-CWK$_{18}$ $^{125}$I-DNA.
J = Polylysine$_{1007}$ $^{125}$I-DNA.
K = Cross-linked (15 mol eq) Tri-CWK$_{18}$/PEG-CWK$_{18}$ (2:98) $^{125}$I-DNA.
L = Cross-linked (15 mol eq) Tri-CWK$_{18}$/PEG-CWK$_{18}$ (10:90) $^{125}$I-DNA, 1 mL tail vein.
[b]Mean cpm per $10^6$ hepatocytes with standard deviation (n = 3).
[c]Mean cpm per $10^5$ Kupffer cells with standard deviation (n = 3).
[d]Calculated as the cpm ratio of hepatocytes ($10^6$)/Kupffer cells ($10^5$).
[e]Calculated as the percent of cpm in either hepatocytes ($10^6$) or Kupffer cells ($10^5$) over total.
[f]Calculated by $\ln C_0 = \ln C - kt$, $t_{1/2} = 0.693/k$, assuming first order kinetics from $C_{max}$.

partially stable during circulation and facilitate some recognition by the ASGP-R (Table 6).

The short half-life of DNA condensates in the liver also suggested that little or no metabolic protection was afforded using LMW DNA carriers (FIG. 49A, FIG. 49B, FIG. 49C). To determine whether this way only true of LMW carriers, the biodistribution of a HMW polylysine$_{1007}$ DNA condensate was analyzed since it is less likely to dissociate during circulation and is reportedly more resistant or in vitro DNA metabolism than AlkCWK$_{18}$ DNA condensates (Example 4; Adami et al., 1999).

Even though polylysine$_{1007}$ and AlkCWK$_{18}$ DNA condensates were similar in particle size and zeta potential (Table 7), polylysine$_{1007}$ DNA condensates biodistributed with only 25% associated with the liver and 25% in lung after 5 min. The longer liver elimination $t_{1/2}$ of 2.8 h implied that polylysine$_{1007}$ DNA condensates were intact in the liver

TABLE 7

Particle Size and Zeta Potential of DNA Formulations[a]

| Dosage Form[b] | Particle Size[c] (nm) | Zeta Potential[d] (+mV) |
|---|---|---|
| A | — | — |
| B | 81 | 33 ± 5 |
| C | 107 | 30 ± 6 |
| D | 56 | 20 ± 1 |
| E | 39 | 5 ± 3 |
| F | 72 | 6 ± 3 |
| G | 38 | 3 ± 2 |
| H | 49 | 6 ± 1 |
| I | 86 | 2 ± 1 |
| J | 36 | 38 ± 5 |

TABLE 7-continued

Particle Size and Zeta Potential of DNA Formulations[a]

| Dosage Form[b] | Particle Size[c] (nm) | Zeta Potential[d] (+mV) |
|---|---|---|
| K | 44 | 5 ± 5 |
| L | 50 | 34 ± 4 |

[a]Each prepared at 0.4 nmol of peptide per µg of DNA.
[b]Dosage form dosed i.v.
A = Plasmid DNA.
B = AlkCWK$_{18}$ DNA (Alk-SEQ ID NO: 1).
C = Tri-CWK$_{18}$ DNA.
D = Cross-linked (6 mol eq) Tri-CWK$_{18}$ DNA.
E = Cross-linked (15 mol eq) Tri-CWK$_{18}$/PEG-CWK$_{18}$ (50:50) DNA.
F = Cross-linked (15 mol eq) Agalactosyl-Tri.-CWK$_{18}$/PEG-CWK$_{18}$ (50:50) DNA.
G = Cross-linked (15 mol eq) Tri-CWK$_{18}$/PEG-CWK$_{18}$ (10:90) DNA.
H = Cross-linked (15 mol eq) Agalactosyl-Tri-CWK$_{18}$/PEG-CWK$_{18}$ (10:90) DNA.
I = Cross-linked (15 mol eq) PEG-CWK$_{18}$ DNA.
J = Polylysine$_{1007}$ DNA.
K = Cross-linked (15 mol eq) Tri-CWK$_{18}$/PEG-CWK$_{18}$ (2:98) DNA
L = Cross-linked (6 mol eq) AlkCWK$_{18}$ DNA.
[c]Particle size reported as the mean diameter of a major (90%) smaller diameter (30–40 nm) population and a minor (10%) larger diameter population (110–130 nm).
[d]Mean and standard deviation of 10 measurements.

3. Glutaradehyde-Crosslinked Peptide DNA Condensates

To overcome the short elimination half-life of LMW peptide DNA condensates, glutaraldehyde was used to cross-link and stabilize DNA condensates as reported previously (Adami et al., 1999). Note that cross-linking Tri-CWK$_{18}$ or PEG-CWK$_{18}$ DNA condensates required higher glutaraldehyde concentrations (6–15 equivalents) to achieve equivalent stability to AlkCWK$_{18}$ DNA condensates (4 mol equivalents) as determined by the salt sonication gel electrophoresis assay (Adami et al., 1999). The cross-linked DNA condensates were utilized without removing residual glutaraldehyde and afford stabilized DNA condensates that maintained particle size for up to 1 wk when stored at 4° C.

Cross-linked AlkCWK$_{18}$ DNA condensates were similar in size (50 nm) and charge (±34 mV) to HMW polylysine DNA condensates (Table 7). However when dosed i.v., 70% of the dose accumulated in the lung at 2 h with less then 1% recovered from the liver. These results further support the hypothesis that uncross-linked AlkCWK$_{18}$ DNA condensates dissociate during circulation, and that once stabilized by cross-linking, the electropositive surface charge results in rapid opsonization and significant lung targeting.

Cross-linked Tri-CWK$_{18}$ DNA condensates also possessed a mean diameter of 56 nm and a slightly reduced zeta potential of +20 mV (Table 7). However when dosed i.v., 59% of cross-linked Tri-CWK$_{18}$ DNA condensates targeted the liver at 5 min followed by elimination with a $t_{1/2}$ of 2.6 h, such that 38% of the dose remained in the liver at 2 h (FIG. 49D). In contrast to cross-linked AlkCWK$_{18}$ DNA condensates, cross-linked Tri-CWK$_{18}$ DNA condensates avoided targeting to the lung, suggesting that the triantennary oligosaccharide is sufficient to block opsonization of DNA condensates in the blood.

Despite the decrease in the liver elimination rate afforded by cross-linking, the cell-type specific targeting was only modestly improved over uncross-linked Tri-CWK$_{18}$ DNA condensates resulting in 45% targeting to Kupffer cells and 55% to hepatocytes (Table 6). These results suggested that the remaining positive charge on cross-linked Tri-CWK$_{18}$ DNA condensates may be responsible for the non-specific targeting to Kupffer cells.

4. PEG-Peptide DNA Co-Condensates

A further reduction in the surface charge of DNA condensates may improve the hepatocyte targeting of Tri-CWK$_{18}$ DNA condensates by masking their detection by Kupffer cells. Other gene delivery systems accomplish this by precisely titrating HMW carriers with DNA to form condensates having neutral or negative charge (Nishikawa et al., 1998; Hashida et al., 1998; Kwoh et al., 1999). This strategy is not suitable for the LMW carriers since these require cross-linking to remain intact during circulation, and glutaraldehyde cross-linking requires the presence of excess amine groups on DNA for the formation of Schiff-bases (Example 4; Adami et al., 1999).

Figure 50:
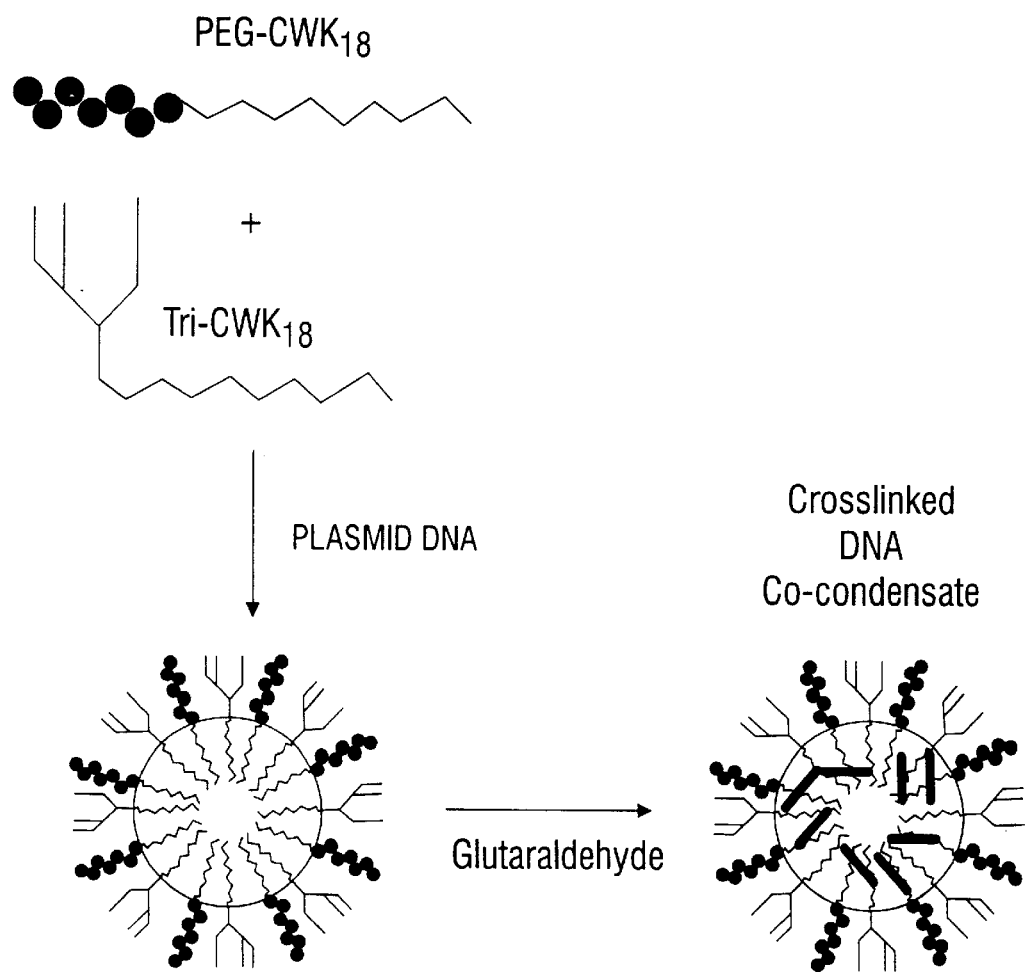
FIG. 50. Formulation of Cross-linked Tri-CWK$_{18}$/PEG-CWK$_{18}$ Co-condensates. Tri-CWK$_{18}$ and PEG-CWK$_{18}$ were admixed at either a 50:50, 10:90, or 2:98 mol %, then used to form DNA co-condensates. After 30 min, DNA co-condensate were cross-linked with 15 mol equivalents of glutaraldehyde.

An alternative approach is to mask the surface charge of DNA condensates by incorporating PEG-CWK$_{18}$ as previously demonstrated by the formation of PEG-CWK$_{18}$/AlkCWK$_{18}$ DNA co-condensates (Example 1, Kwok et al., 1999; Example 3). In this present study, PEG-CWK$_{18}$ and Tri-CWK$_{18}$ were admixed and used to prepare DNA co-condensates as shown in FIG. 50. Tri-CWK$_{18}$/PEG-CWK$_{18}$ (50 mol %) DNA co-condensates cross-linked with 15 mol equivalents of glutaraldehyde were 39 nm in diameter and possessed a zeta potential of +5 mV (Table 7). The ratio of Tri-CWK$_{18}$ and PEG-CWK$_{18}$ bound to DNA in co-condensates was nearly the same as the admix ratio used to condense DNA as revealed by glucosamine analysis which recovered 96% of the Tri-CWK$_{18}$ after prolonged dialysis.

Biodistribution analysis of cross-linked Tri-CWK$_{18}$/PEG-CWK$_{18}$ DNA co-condensates resulted in a lag in the liver accumulation of radioactivity that peaked at 61% of the dose at 30 min followed by elimination with a $t_{1/2}$ of 2.1 h resulting in 37% remaining in the liver at 2 h (FIG. 49E). As predicted, the cell-type specific targeting was dramatically improved with only 20% recovered in the Kupffer cells and 80% in hepatocytes, demonstrating the ability of PEG to mask the surface charge of DNA condensates reducing their non-specific recognition by liver Kupffer cells.

As a negative control, cross-linked agalactosyl-Tri-CWK$_{18}$/PEG-CWK$_{18}$ DNA co-condensates were studied. The liver targeting efficiency was similar to otherwise identical DNA condensates containing Tri-CWK$_{18}$ also resulting in an elimination $t_{1/2}$ of 2.5 h (FIG. 49F). However, only 55% of the liver targeted DNA was recovered in hepatocytes whereas 45% was found in Kupffer cells, establishing that terminal galactose residues on Tri-CWK$_{18}$ are responsible for approximately 25% of the cell-type specific targeting of these DNA condensates.

Figures 49G, 49H, 49I:
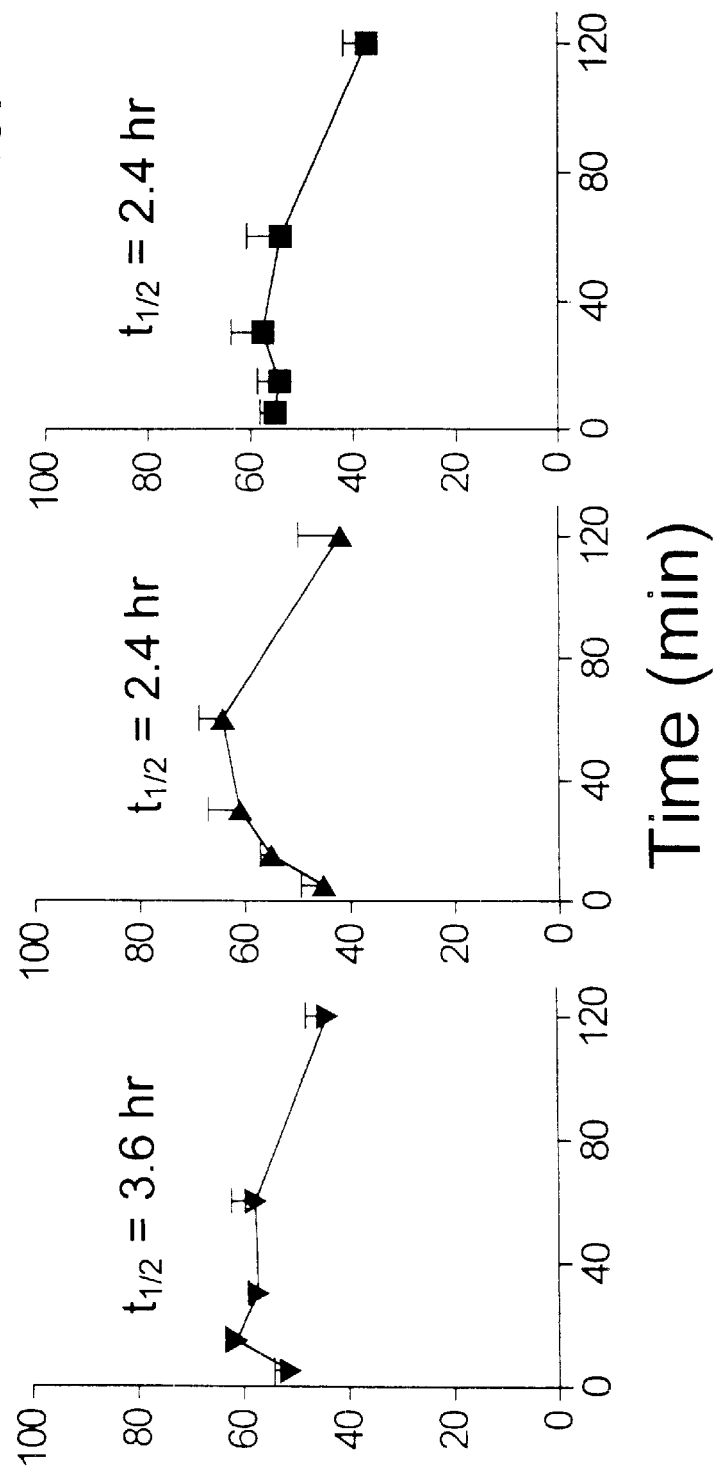

To determine whether the admix ratio could be adjusted to further reduce the amount of Tri-CWK$_{18}$ without compromising target site selectivity, biodistribution studies were conducted using a 10:90 admix ratio of cross-linked Tri-CWK$_{18}$/PEG-CWK$_{18}$ DNA co-condensates. The liver targeting efficiency reached approximately 61% in 15 min and remained at 57% at 30 min and was then eliminated with a $t_{1/2}$ of 3.6 h, resulting in 44% of the dose in the liver after 2 h (FIG. 49G). A control, which agalactosyl-Tri-CWK$_{18}$ was substituted for Tri-CWK$_{18}$ had a similar liver biodistribution profile with an elimination $t_{1/2}$ of 2.4 h (FIG. 49H). As was the case for condensates prepared with 50:50 Tri-CWK$_{18}$/PEG-CWK$_{18}$, 80% of the $^{125}$I-DNA was recovered in hepatocytes when using Tri-CWK$_{18}$ whereas only 54% was in hepatocytes using agalactosyl-Tri-CWK$_{18}$.

Further studies established that as little as 2 mol % of Tri-CWK$_{18}$ admixed with 98% PEG-CWK$_{18}$ formed cross-linked DNA co-condensates that mediated a targeting efficiency of 53% in the liver at 30 min of which 80% was recovered in hepatocytes (Table 6).

A final set of control studies examined the biodistribution of cross-linked 100 mol % PEG-CWK$_{18}$ DNA condensates.

The liver was still the major target site with approximately 58% of the dose taken up in 5 min and an elimination $t_{1/2}$ of 2.4 h (FIG. 49I). Interestingly, 53% of the liver target DNA was recovered in the hepatocyte fraction whereas the remaining 47% was associated with Kupffer cells (Table 6). These results indicated that even without incorporating a targeting ligand, cross-linked PEG-CWK$_{18}$ DNA condensates are still taken up through a non-specific process by both Kupffer cells and hepatocytes.

5. Gene Expression Results

Cross-linked DNA co-condensates were also evaluated for their ability to mediated hAAT expression in vivo. A 1 mL dose containing 50 μg of DNA condensates was administered via slow infusion into the tail vein of mice. The large dosing volume was used to ensure a small particle size since concentrations above 100 μg/mL result in larger particles (Example 1, Kwok et al., 1999; Example 3). However, when PEG-CWK$_{18}$ is included at 98 mol % of the admix ratio, small particles (<100 nm) can be maintained at high concentration (2 mg/ml) (Example 1, Kwok et al., 1999; Example 3), which will allow the dosing volume to be reduced and systematically explored in future studies. Even when dosing 50 μg of DNA, biodistribution studies using an $^{125}$I-DNA tracer established a 2 h liver targeting efficiency of 36% with 73% recovered in hepatocytes, suggesting the 50 μg dose did not saturate the ASGP-R (Table 6).

Figure 51:
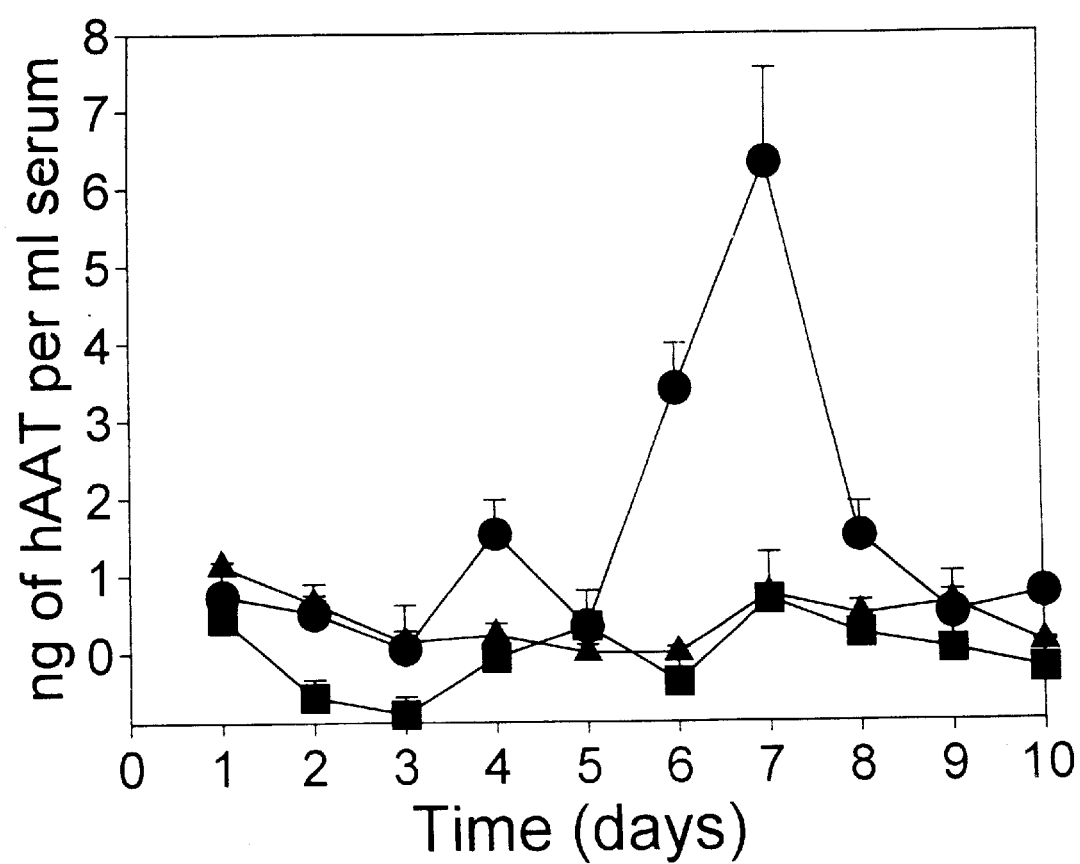
FIG. 51. In Vivo Transient Gene Expression. Mice were dosed tail vein with 50 μg of plasmid DNA and the hAAT produced over a 10-day period was determined by ELISA. The transient gene expression profile is presented for cross-linked (15 mol eq.) Tri-CWK$_{18}$/PEG-CWK$_{18}$ (10:90) DNA condensates (●), cross-linked (15 mol eq.) agalactosyl-tri-CWK$_{18}$/PEG-CWK$_{18}$ (10:90) DNA condensates (■), as well as plasmid DNA (π). Each data point represents the mean and standard error for 3–6 mice. Comparison of hAAT expression levels on day 7 to day 1 or 10 established statistical significance (ρ<0.025).

Analysis of the transient gene expression profile of hAAT after i.v. dosing 50 μg of cross-linked Tri-Cwk$_{18}$/PEG-CWK$_{18}$ (10:90) DNA co-condensates demonstrated a peak in the expression at day 7 at 6 ng/mL that returned to a baseline levels by day 9 (FIG. 51). Similar analysis of agalactosyl-Tri-CWK$_{18}$/PEG-CWK$_{18}$ (10:90)DNA co-condensates established the complete lack of gene expression, which was an identical result to a control using plasmid DNA (FIG. 51).

EXAMPLE 8

Man9-Glycopeptide PEG-Peptide DNA Co-Condensates

A complete set of studies, similar to those described above in Example 7, have also been conducted using a high-mannose glycopeptide (Man9-CWK$_{18}$) to target DNA to the mannose receptor on nonparenchymal cells (NPCs) within the liver. The results established that 50 mol % Man9-CWK$_{18}$/PEG-VS-CWK$_{18}$ achieve 80% NPC targeting. The rational for the need of a higher ratio of targeting ligand is that the mannose receptor recognizes mannose residues that are spaced at a greater distance compared to the topography of binding sites on the ASGP-R (Taylor and Drikamer, 1993).

As the mannose receptor is localized to NPCs, the particle size of cross-linked DNA condensates is not as critical as when targeting parenchymal cells (PCs). In a series of studies, the cross-linking applied to 50 mol % Man9-CWK$_{18}$/PEG-CWK$_{18}$ DNA co-condensates was increased from 6 to 50 eq. Although this also caused an increase in the mean particle size from 100 to 400 nm, this increase did not influence the biodistribution or alter the PC:NPC ratio (FIG. 52A, FIG. 52B and FIG. 52C).

Figure 52A:
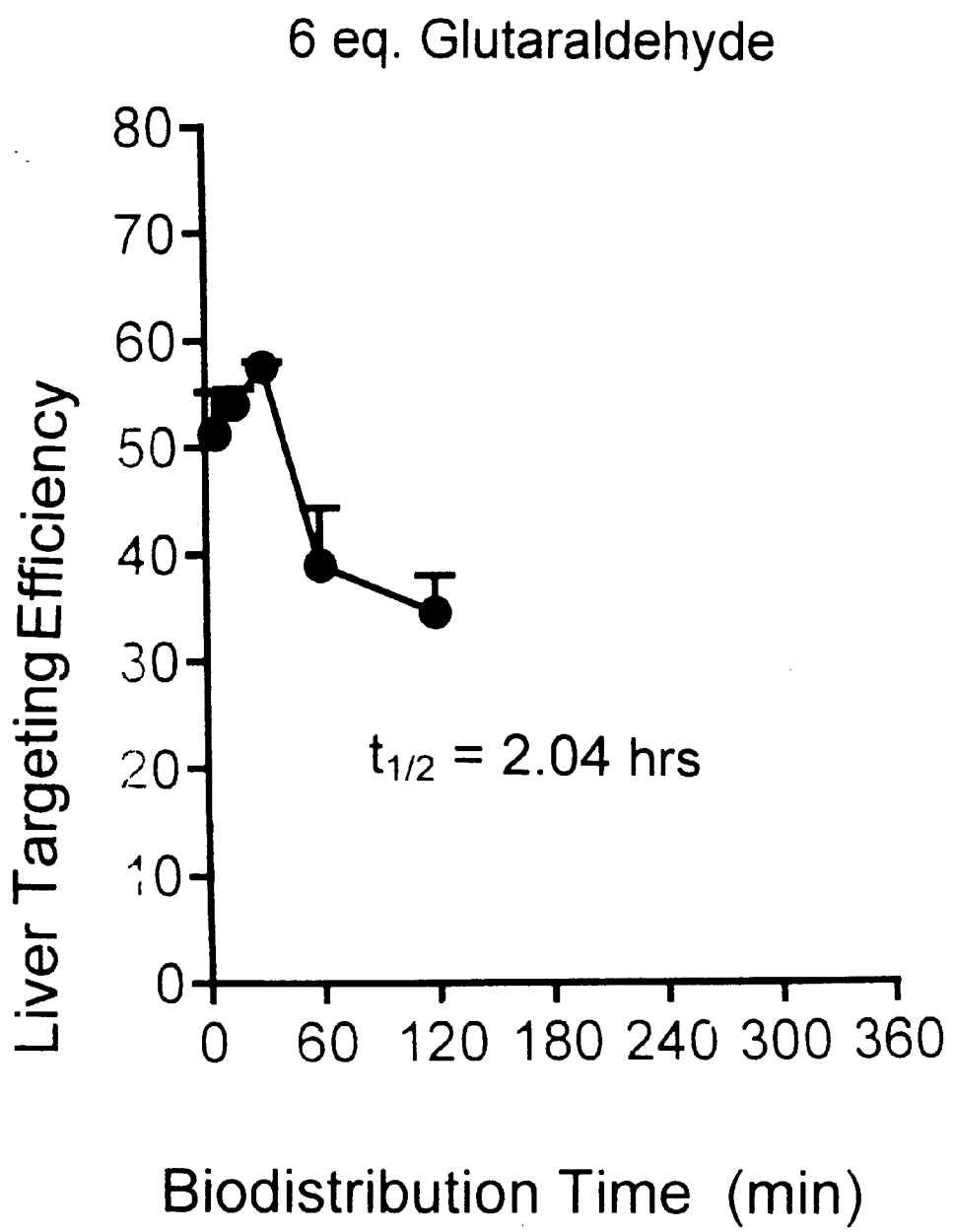
FIG. 52A, FIG. 52B and FIG. 52C. The influence of glutaraldehyde cross-linking ratio on liver elimination rate. Increasing the glutaraldehyde cross-linking level for 6 eq (FIG. 52A) to 15 eq (FIG. 52B) to 50 eq (FIG. 52C) systematically increases the half-life that cross-linked PEG-CWK$_{18}$Man9CWK$_{18}$ DNA co-condensates are retained in the liver.
Figure 52B:
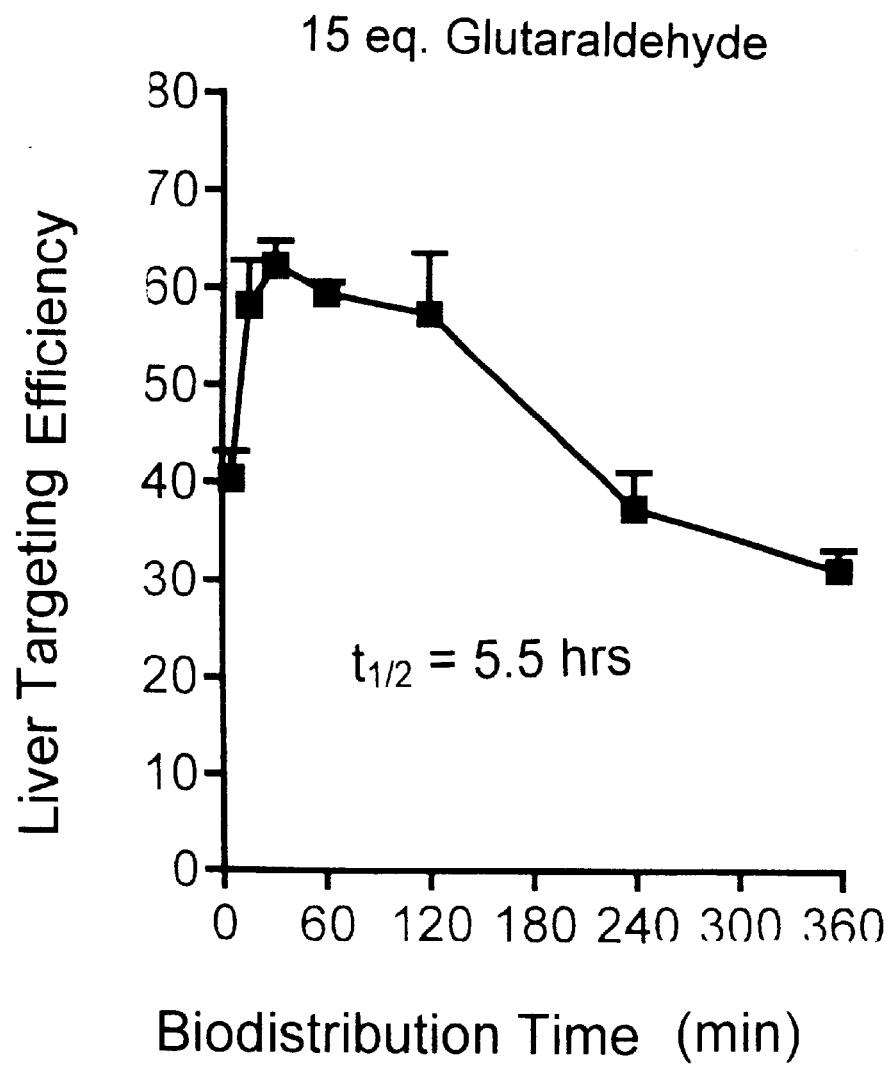
Figure 52C:
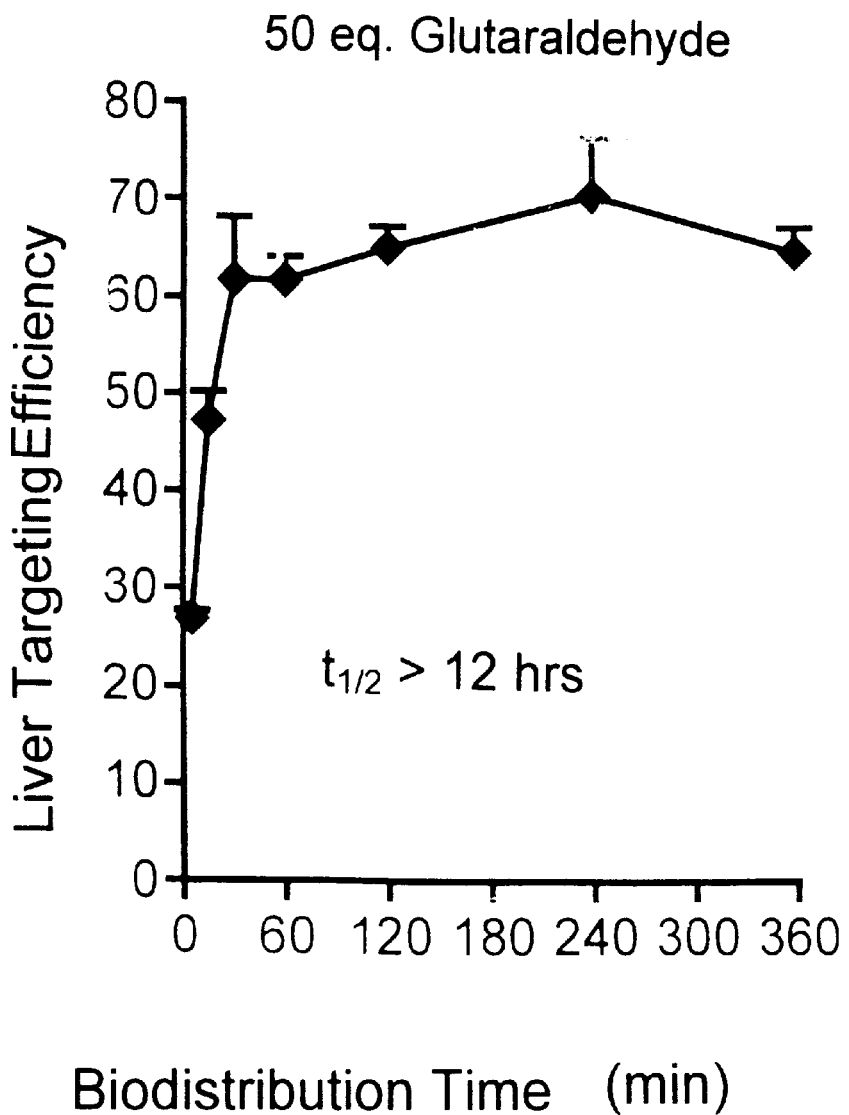

The major result was an increase in the liver $t_{1/2}$ from 2 h to >12 h estimated (FIG. 52A, FIG. 52B and FIG. 52C). This demonstrated that glutaraldehyde cross-linked DNA condensates can delay the metabolism of DNA delivered to NPCs. A second important result was the approximately 40 min lag in the maximal accumulation of radioactivity into the liver. The lag time appears to increase in duration when increasing cross-linking level, suggesting that heavily cross-linked glycopeptide/PEG-peptide DNA co-condensates may circulate longer.

Figure 53A:
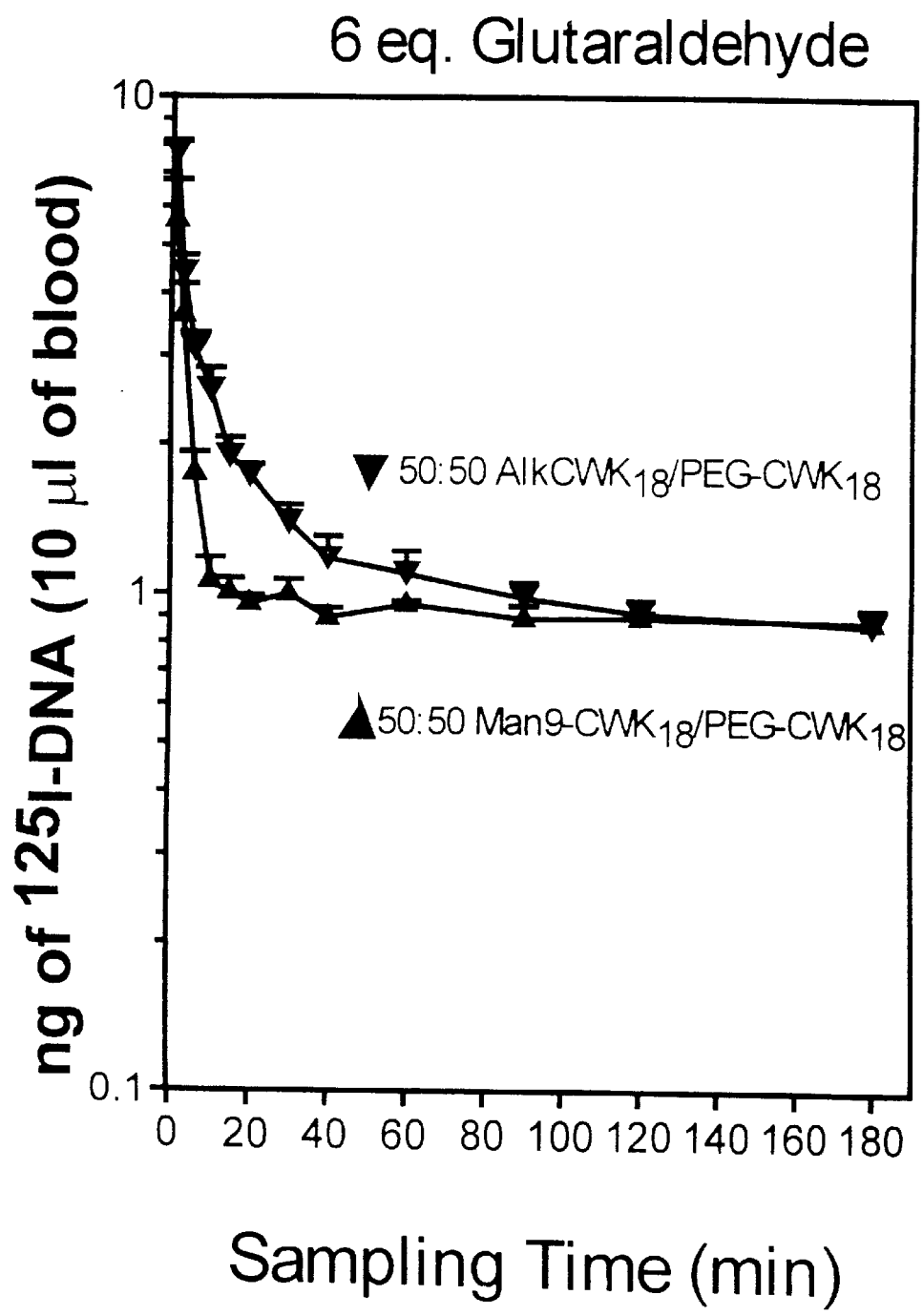
FIG. 53A and FIG. 53B. Pharmacokinetic analysis of cross-linked DNA condensates.

Further confirmation of this hypothesis was provided by comparing the pharmacokinetic profile of $^{125}$I-DNA co-condensates prepared with 50 mol % Man9-CWK$_{18}$/PEG-CWK$_{18}$ or 50 mol % AlkCWK$_{18}$/PEG-CWK$_{18}$ and cross-linked with either 6 or 50 eq. of glutaraldehyde (FIG. 53A and FIG. 52B).

Figure 53B:
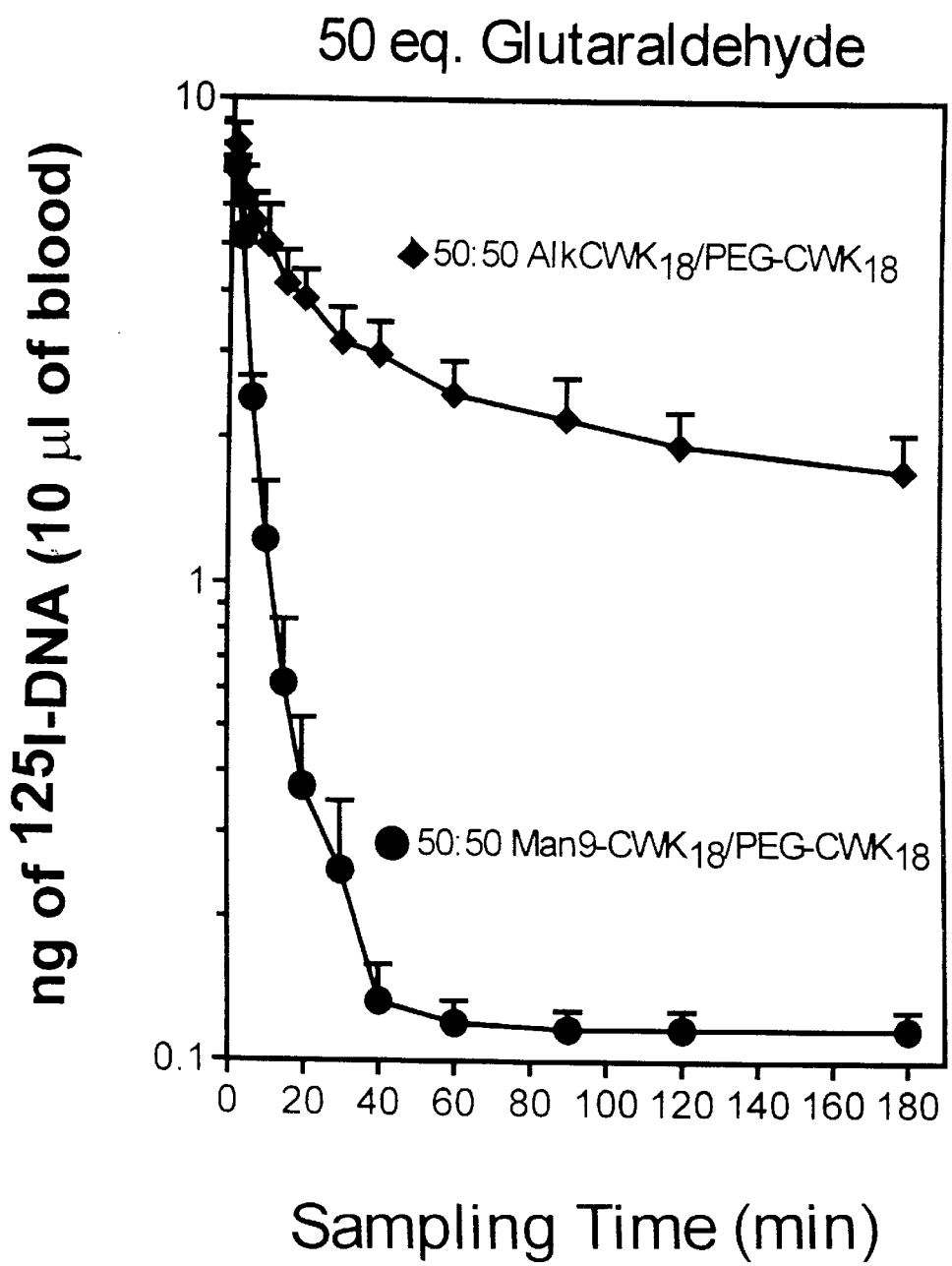

The cpms in blood over time indicated a slightly faster α $t_{1/2}$ for Man9-CWK$_{18}$/PEG-CWK$_{18}$ DNA condensate vs. AlkCWK$_{18}$/PEG-CWK$_{18}$ when both are cross-linked with 6 eq. of glutaraldehyde (FIG. 53A). The rapid uptake and lower stability provided by 6 eq. cross-linked Man9-CWK$_{18}$/PEG-CWK$_{18}$ DNA also leads to rapid metabolism and secretion of fragmented DNA back into the blood within 20 min. In contrast, the greater stability afforded by 50 eq. cross-linking led to a more complete extraction of Man9-CWK$_{18}$/PEG-CWK$_{18}$ DNA condensates from blood (FIG. 53B) with greatly reduced metabolism in the liver. By comparison, 50 eq. cross-linked AlkCWK$_{18}$/PEG-CWK$_{18}$ DNA co-condensates circulated longer, resulting in a mean residence time of 4.4 h (FIG. 53A).

These data suggest that cross-linking LMW peptide DNA condensates should not only stabilize DNA targeted into a specific cell type, but also provide a means for developing long circulating DNA condensates. This is an important property to achieve targeted gene delivery to sites outside the liver.

Figure 54B:
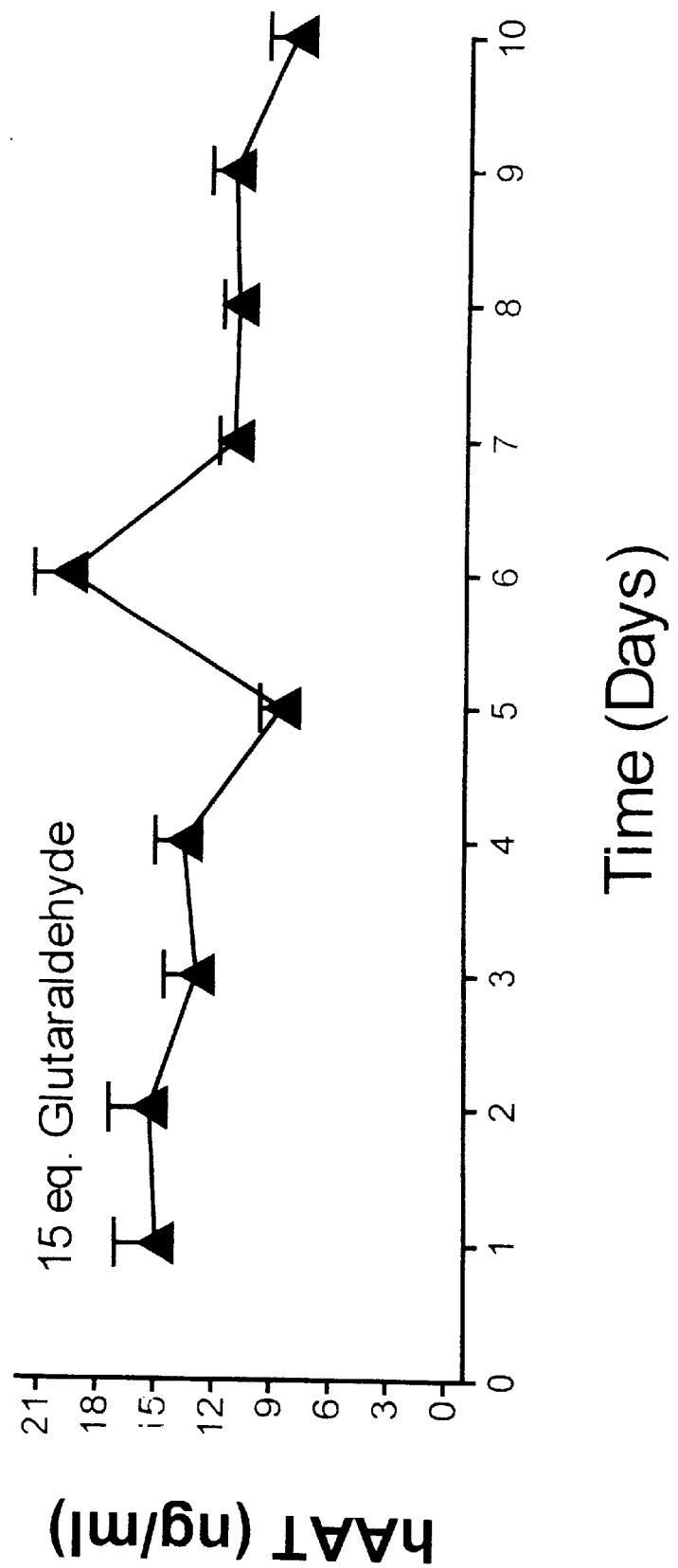
Figure 55A:
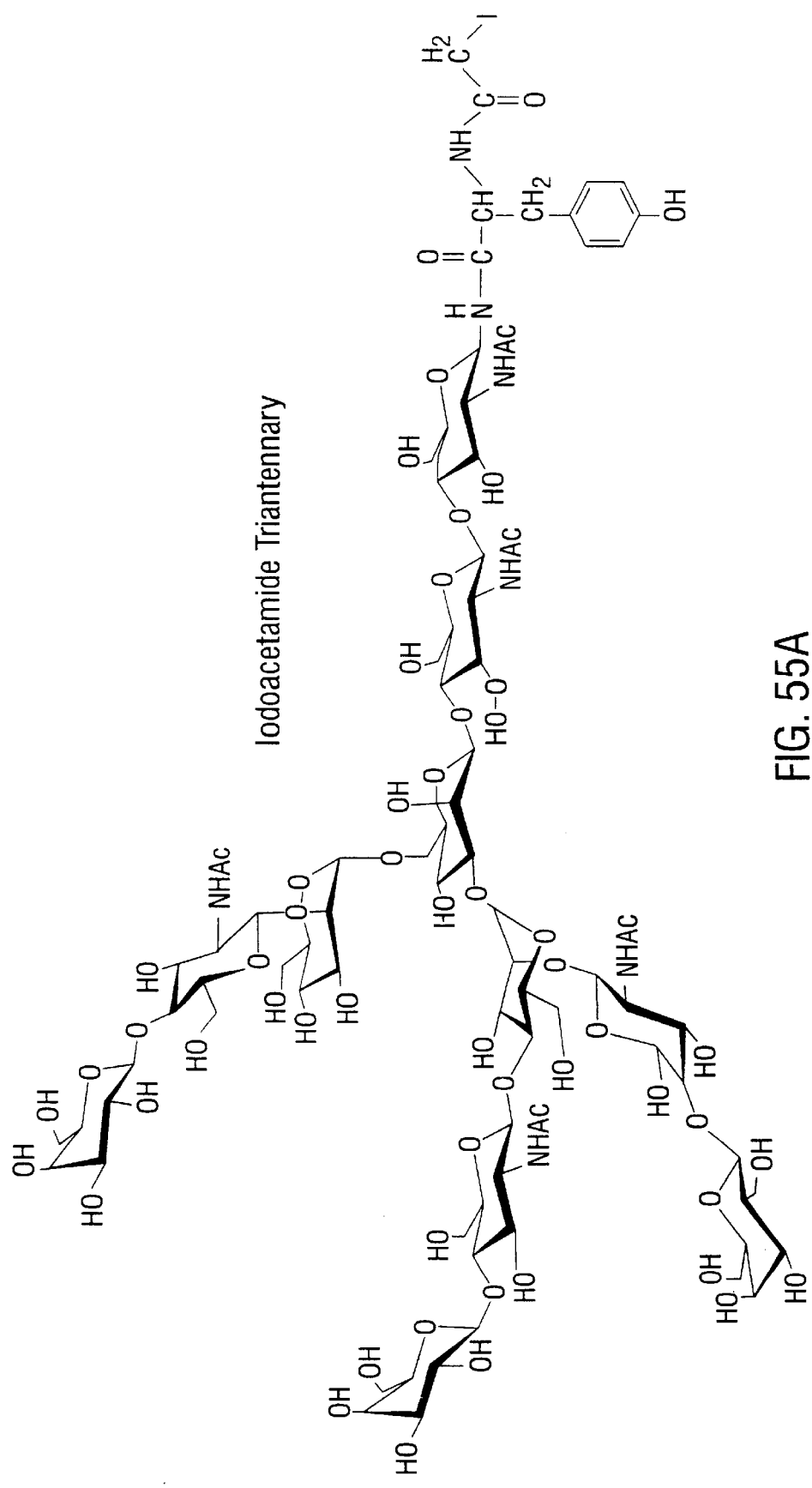
FIG. 55A, FIG. 55B and FIG. 55C. Synthetic strategy to prepare sulfhydryl cross-linking glycopeptides and PEG-peptide.
Figure 55B:
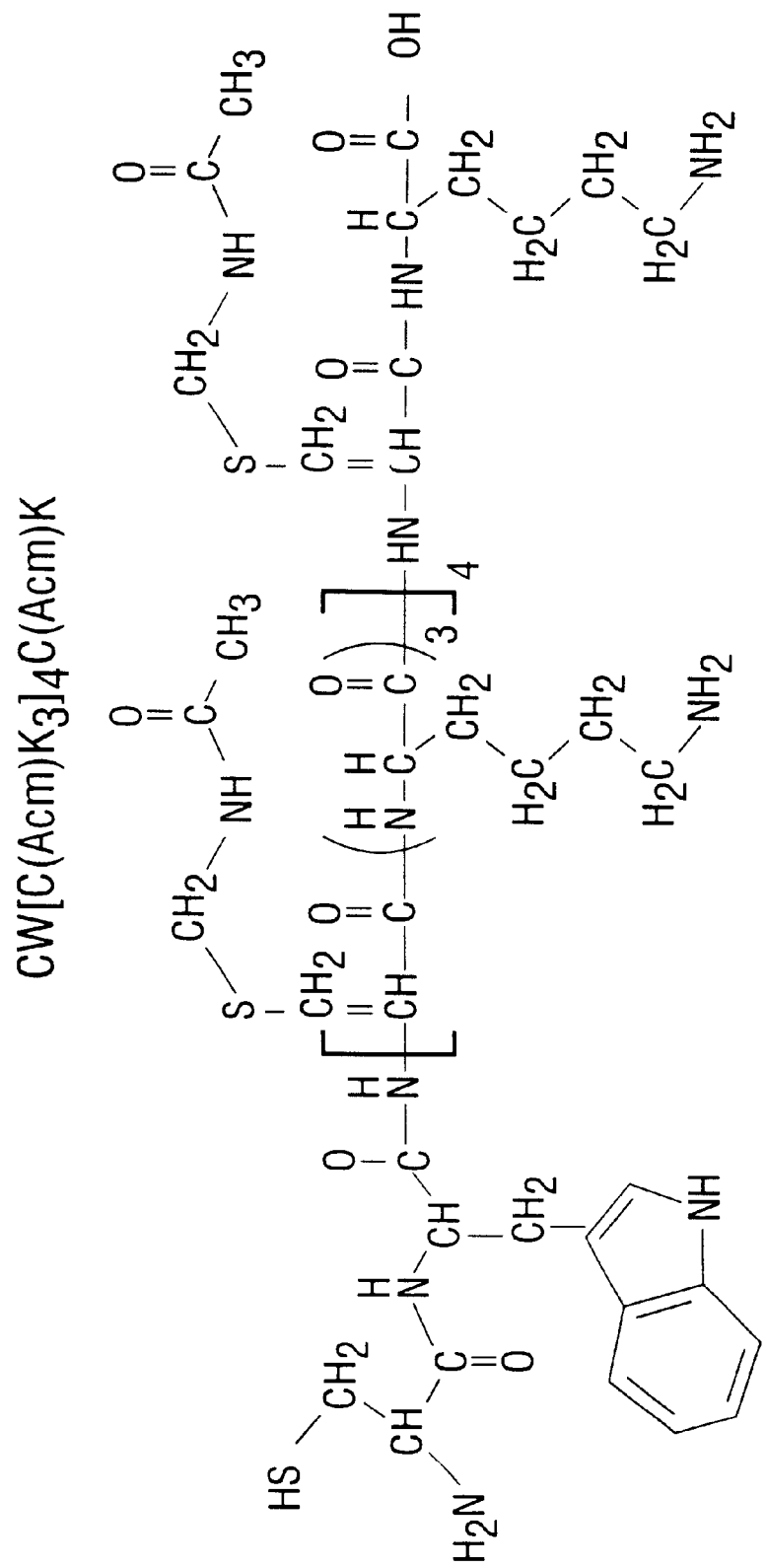
Figures 1, 55C:
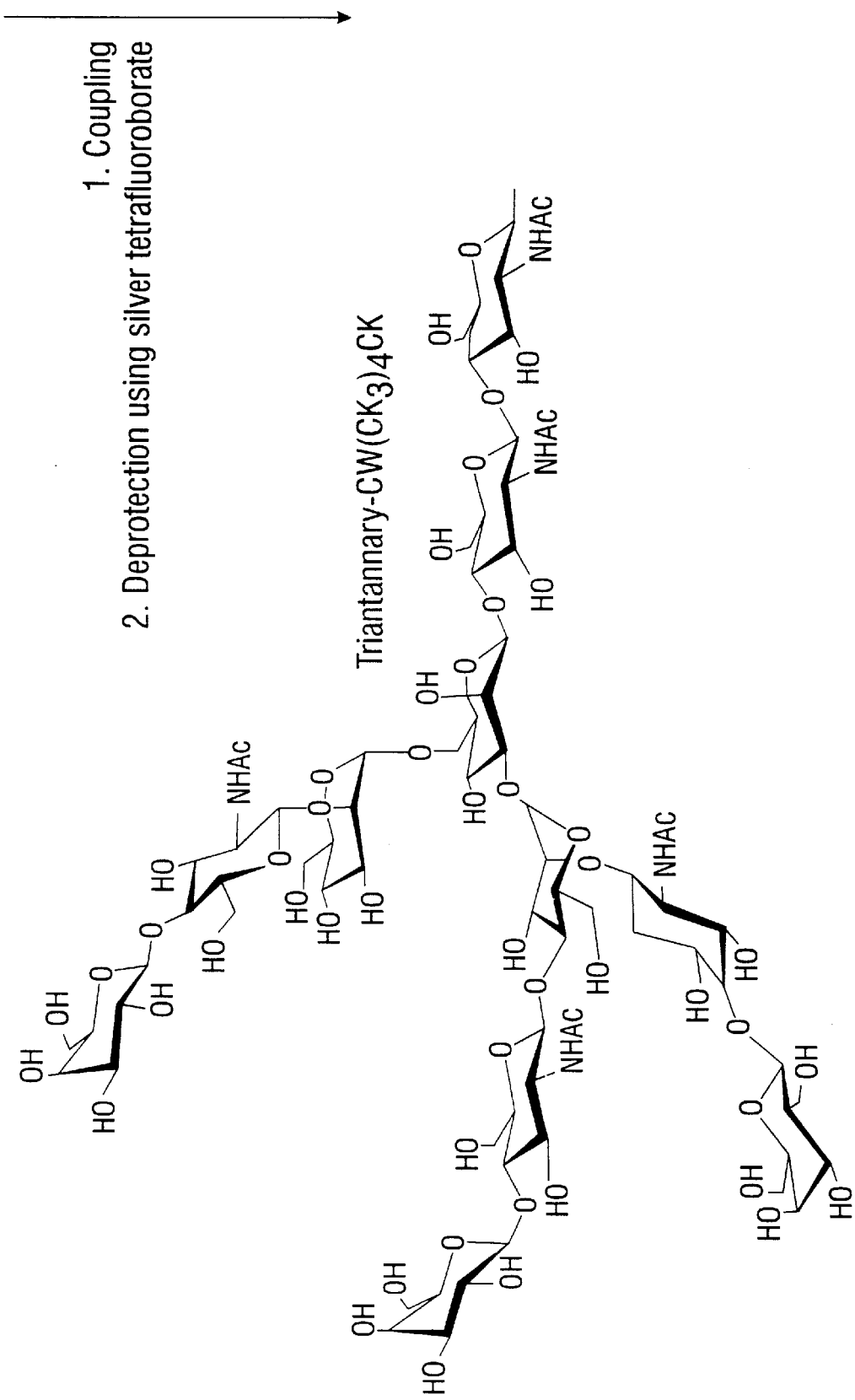
Figures 2, 55C:
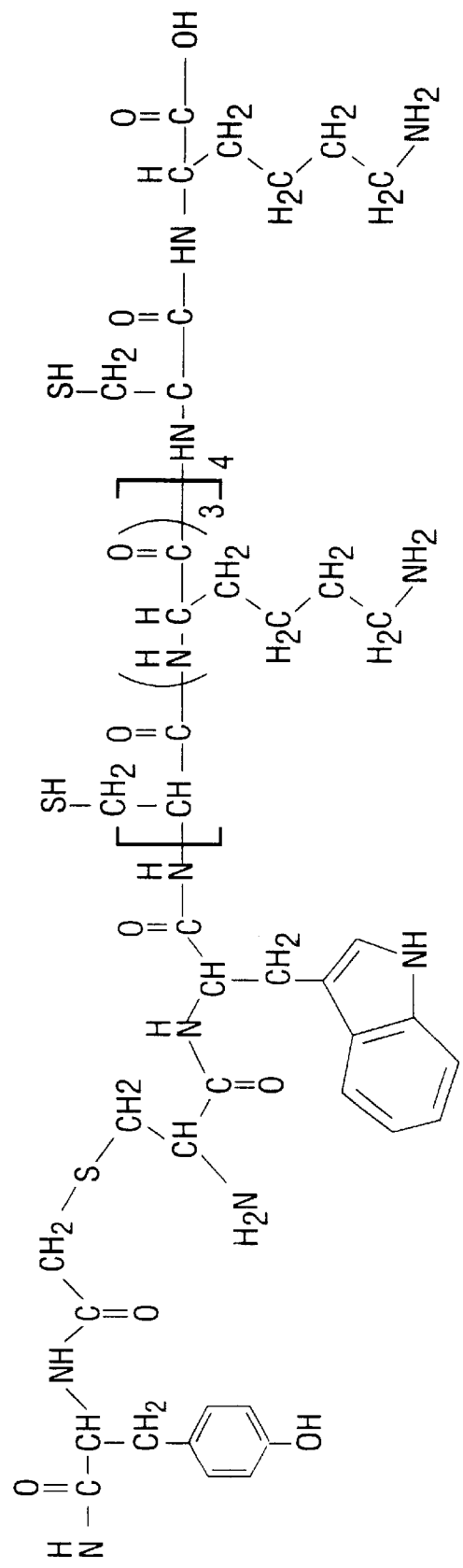

The transient in vivo gene expression mediated by glutaraldehyde cross-linked 50 mol % Man9-CWK$_{18}$/PEG-VS-CWK$_{18}$ was studied by dosing mice while monitoring hAAT production. In each case, a peak in gene expression occurred at day 6 (FIG. 54A, FIG. 54B and FIG. 54C), compared to the day 7 peak expression observed when targeting DNA to PCs. A significant (p<0.01) increase in gene expression was determined during days 1–9 when comparing formulations prepared with either 6 or 15 eq. of glutaraldehyde. An overall decrease in gene expression was noted when increasing glutaraldehyde cross-linking to 50 eq. This may indicate that a 50 eq. glutaraldehyde cross-linking DNA co-condensate is incapable of reversal within the time frame of the gene expression study.

Since the transient gene expression studies were only conducted for 10 days, it was not possible to determine the influence cross-linking will have on the duration of gene expression in vivo. Even though the expression data is still relatively short term (10 days), comparing the biodistribution and gene expression results of 6 and 15 eq. glutaraldehyde cross-linking suggests that decreasing the metabolism rate of plasmid DNA, by increasing cross-linking level, leads to an overall greater level of gene expression.

The preliminary studies using glutaraldehyde cross-linked DNA condensates support the hypothesis that in vivo metabolic stability is closely related to the level of gene expression. These studies are therefore important in the development of new gene delivery systems that allow systematic control over in vivo metabolic stability. The sulfyhydryl cross-linked DNA condensate elements of the overall invention allow for even further control of DNA condensate solubility, DNA stability in blood and tissues and of the release rate of DNA in the cell.

EXAMPLE 9

Glycopeptide and PEG-peptide Cross-linking Peptides

The self-crosslinking peptides of the invention (Example 5 and Example 6) can be best used to control the metabolic rate and mediate in vivo gene expression when converted into glycopeptides and PEG-peptides. The conjugation schemes described in the foregoing examples (utilizing CWK$_{18}$ to prepare PEG-CWK$_{18}$, Tri-CWK$_{18}$ and Man9-CWK$_{18}$) are adapted to prepare cross-linking glycopeptide and PEG-peptides.

To achieve site-specific coupling to a peptide containing multiple Cys residues, C-terminal and internal acetylcarboxymethyl (ACM) protected Cys residues are incorporate, with only the N-terminal Cys protected by a trityl (Trt) group. Following acidic work-up to remove Boc and Trt protecting groups, site-specific coupling of the iodoacetamide triantennary, Man9 N-glycan, or the PEG vinyl sulfone derivative will be directed to the N-terminal Cys (FIG. 55***CHECK vs. A, B, C). After conjugation, selective removal of the ACM groups from the internal and C-terminal Cys residues is accomplished using silver tetrafluoroborate (Yoshida et al., 1990). The deprotected PEG-peptide and glycopeptides are purified by RP-HPLC and characterized by $^1$H-NMR and MS.

Sulfhydryl cross-linking glycopeptides and PEG-peptides with two and five cross-linking Cys residues are contemplated to provide in vivo stability. The advantage of this strategy is that the single Trt protected Cys residue (C) can be positioned on the N-terminus, C-terminus or in the middle of the peptide to adjust the site of conjugation in the event that PEG or glycan positional effects influence cross-linking. This is particularly important as it allows Cys residues to be maintained at each terminus, for effective cross-linking. Thus, preferred sites for attachment of stealthing and targeting agents are internal.

The chemical scheme described has already been used to produce both PEG-CW(CK$_3$)$_4$CK and Tri-CW(CK$_3$)$_4$CK. Several preliminary DNA formulations were prepared using PEG-CW(CK$_3$)$_4$CK and Tri-CW(CK$_3$)$_4$CK. Since sulfhydryl cross-linking occurs even at low peptide:DNA charge ratios, an admixture of PEG-CW(CK$_3$)$_4$CK (10 mol %), Tri-CW(CK$_3$)$_4$CK (10 mol %) and CWK$_5$CK$_5$CK$_5$C (80 mol %) was prepared and used at a charge ratio of 0.9 to form electronegative (−20 mV) DNA co-condensates that cross-linked and were stable in 2.5 M sodium chloride as determined by the salt sonication assay.

Based on the foregoing solubility of PEG-CWK$_{18}$ DNA condensates, much less PEG may be necessary to form soluble electronegative DNA condensates. Consequently, the formulation described above formed small (70 nm), stable DNA co-condensates when prepared at concentrations as high as 500 μg/ml. These results are significant because they establish that stable, soluble, electronegative DNA co-condensates are formed using an admixture of sulfhydryl cross-linking peptides. This DNA formulation is an advancement over glutaraldehyde cross-linked DNA condensates because it lends itself to systematic control over stability, while simultaneously maintaining high solubility (Example 10).

EXAMPLE 10

Reductively Stable Sulfhydryl Cross-linking Peptides

Further improvements of the sulfhydryl cross-linking peptides of Example 5 and Example 6 concern engineering the reductive stability of these components. The reductive stability of cystine, glutathione disulfide and penicillamine disulfide has been studied in vitro (Drummer et al., 1987). Penicillamine disulfide was found to be approximately 26-fold more stable than cystine when challenged with glutathione reductase. The reason for its stability is related to substitution of the β-methylene with methyl groups to sterically block reduction (Drummer et al., 1987).

Figure 56:
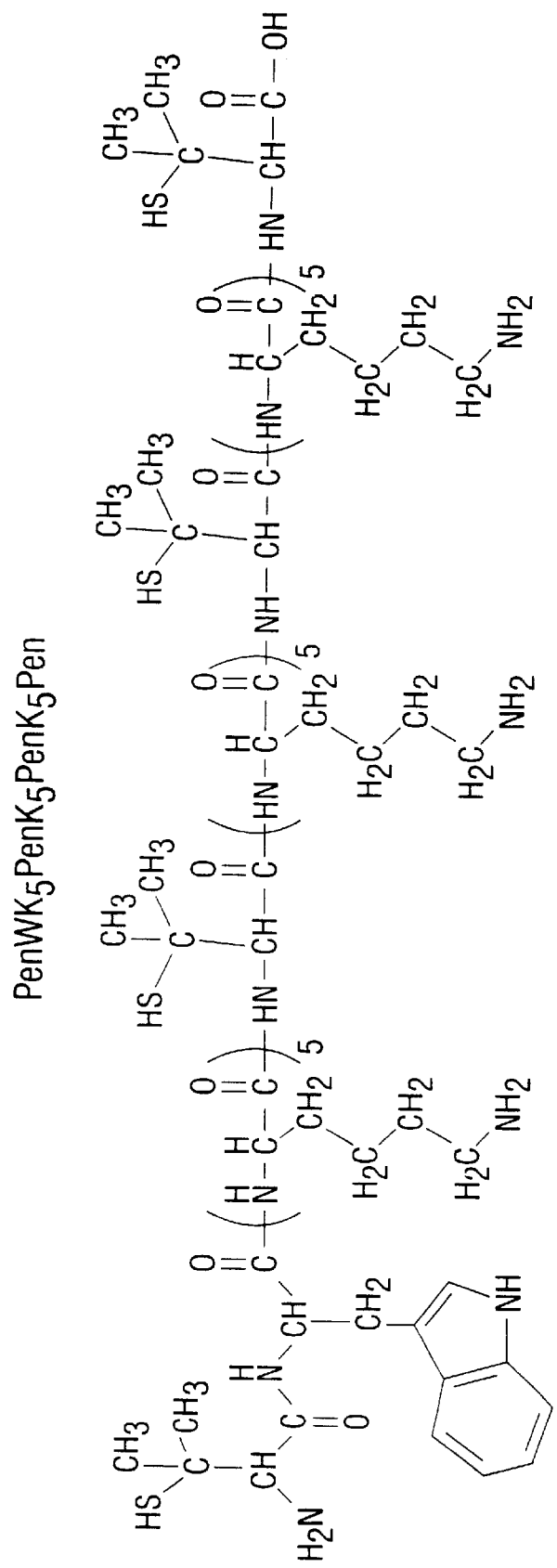
FIG. 56. Structure of penicillamine (Pen) cross-linking peptides. The structure of a twenty amino acid peptide containing 4 pen residues for cross-linking is illustrated.
Figure 57A:
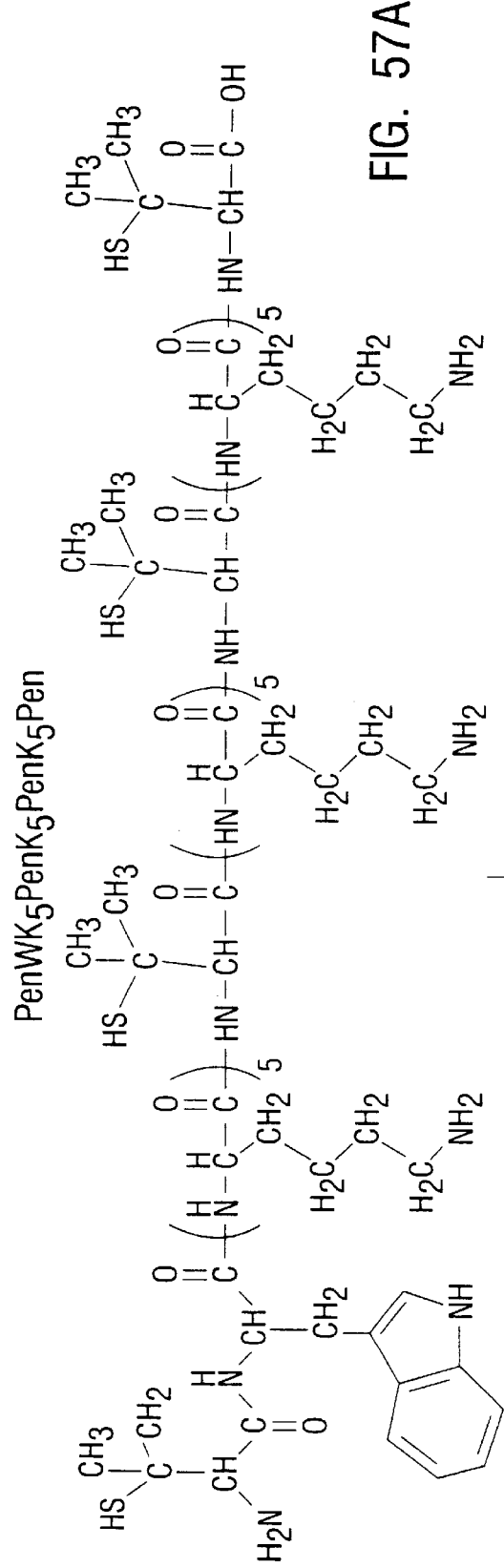
FIG. 57A and FIG. 57B. Reduction of Pen cross-linking peptides.
Figure 57B:
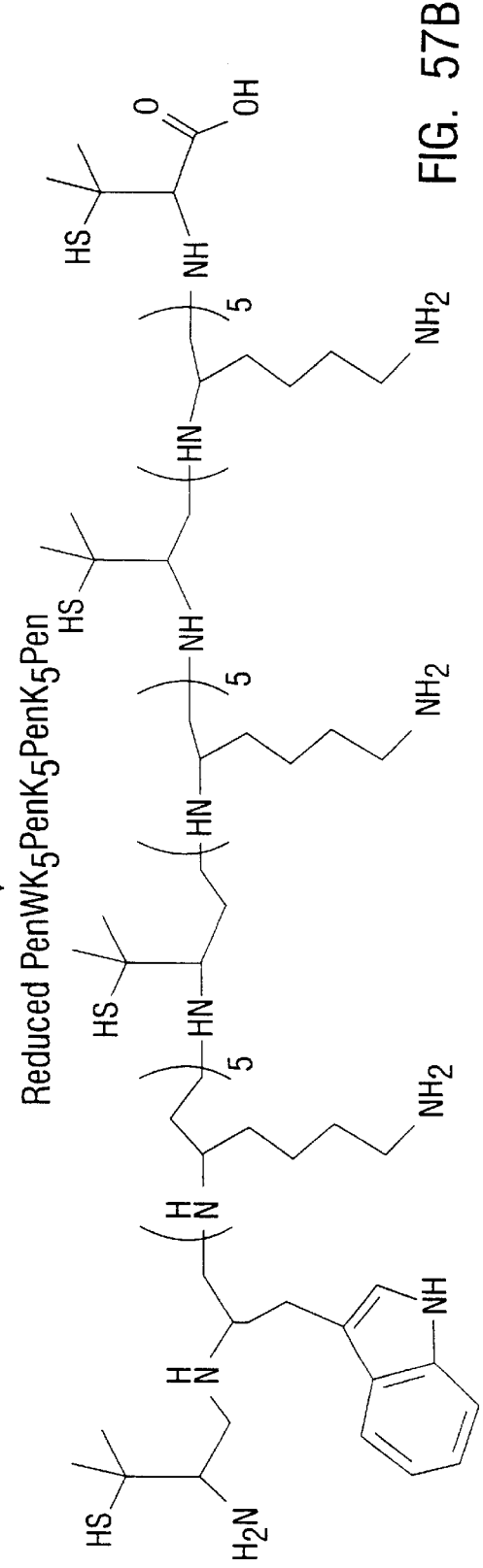

Thus, to further extend the stability of DNA condensates prepared using peptides possessing multiple Cys residues, Cys is substituted for penicillamine (Pen) to prepare "PenPeptides", e.g., PenWK$_5$PenK$_5$PenK$_5$Pen (FIG. 56; SEQ ID NO:21). A series of Pen peptide DNA condensates with peptides varying in the number of Pen residues from two to four (by replacing Cys and Lys residues in CWK$_{18}$) will provide advantages in the control of DNA binding, cross-linking kinetics, particle size, zeta potential, salt and reductive stability, and in vivo liver $t_{1/2}$. The formation of DNA co-condensates using admixtures of PEG-CW(CK$_3$)$_4$CK, Tri-CW(CK$_3$)$_4$CK and PenWK$_5$PenK$_5$PenK$_5$Pen or other Pen peptides is simplified by eliminating the need to prepare new glycopeptide and PEG-peptide derivatives.

Increasing the metabolic stability of peptide DNA condensates in liver should also lead to an increase in hAAT mRNA recovered from hepatocytes determined by Northern blot analysis (Krumlauf, 1996). Formulations containing fewer Cys or Pen residues will have both a shorter liver $t_{1/2}$ and a shorter expression of hAAT mRNA, whereas those with increasing number of Cys or Pen residues should have a longer liver $t_{1/2}$ and express hAAT mRNA over a longer time.

EXAMPLE 11

Reductively Stable Endosomal Buffering Cross-linking Peptides

Metabolic stabilization is an important goal to increase the level and duration of gene expression. However, it is also important to provide a mechanism for DNA condensates to escape the endocytic pathway to lysosomes, since this will also significantly influence DNA condensate stability. The present inventors have developed the use of endosomal buffering agents to achieve such objectives, preferring these agents over the typically used fusogenic peptides (Boussif et al., 1995; Midoux and Monsigny, 1999; Legendre and Szoka Jr., 1993; Plank et al., 1994).

The successful studies of Example 6 show that replacing Lys with His achieves endosomal buffering in HepG2 and CHO cells (McKenzie et al., 2000; Example 6). A variety of cross-linking peptides possessing a varying number of His residues will thus provide a gradation of endosomal buffering. Since two His residues in a deca peptide created a maximal endosomal buffering effect in vitro (Example 6), and interpreting this in light of the in vitro and in vivo glutaraldehyde data, peptides possessing two, four or six His residues will have advantages for in vivo gene delivery.

Comparison of the gene transfer efficiency of a His endosomal buffering cross-linking peptides to PEI in an in vitro transfection established a two-order of magnitude difference, indicating that agents containing secondary and tertiary amines are even more effective buffers than His. Therefore, further advantages result from introducing secondary amines into cross-linking peptides by chemical reduction of the amide backbone (Lane, 1976).

Reduction of a 20 mer peptide results in the formation of 19 secondary amines. The peptide is reduced using BH$_3$/THF at 70° C. for 24 h, as already confirmed using an AlkCWK$_{18}$ peptide. The reaction can be driven to completion with excess reducing agent. The reaction is optimized to form a product with mass corresponding to the fully reduced peptide as determined by LC-MS. The reduced peptides have advantages in binding to DNA, controlling particle size and zeta potential of DNA condensates and in gene expression. Reductions on Cys and Pen cross-linking peptides (Example 10) also give benefits in DNA condensate properties, stability and gene expression.

PEI is composed of both secondary and tertiary amines that have different pKa's resulting in optimal buffering of the endosomal compartment (Abdallah et al., 1996). In addition to introducing secondary amines, peptides that contain both secondary and tertiary amines are prepared using methods adapted from Houghten and coworkers (Dorner et al., 1996). Peptides such as PenWK$_5$PenK$_5$PenK$_5$Pen are prepared as the Boc and Trt protected peptide on p-methylbenzhydraylamine (MBHA) resin. Prior to cleavage of the peptide, the backbone and Lys side chains are per methylated using sodium hydride and methyl iodide. The peptide is cleaved from the resin and side chain protecting groups removed. The peptide is purified and characterized by LC-MS to determine complete methylation, then subjected to reduction using BH$_3$ THF to form tertiary amines in the peptide backbone and secondary amines from the Lys side chain ε amine. LMW methylated and reduced sulfhydryl cross-linking peptides form stable DNA co-condensates that, like PEI, enhance gene expression by buffering endosomes.

All of the compositions and methods disclosed and claimed herein can be made and executed without undue experimentation in light of the present disclosure. While the compositions and methods of this invention have been described in terms of certain preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abdallah, Hassan, Benoist, Goula, Behr, Demeneix, "A powerful nonviral vector for in vivo gene transfer into the adult mammalian brain: polyethylenimine," *Hum. Gene Ther.*, 7:1947–1954, 1996.

Adami and Rice, "Metabolic Stability of Glutaraldehyde Cross-linked Peptide DNA Condensates," *J. Pharm. Sci.*, 88(8):739–764, 1999.

Adami, Collard, Gupta, Kwok, Bonadio, Rice, "Stability of Peptide Condensed Plasmid DNA Formulations," *J. Pharm. Sci.*, 87:678–683, 1998.

Allison, Chang, Randolph, Carpenter, "Hydrogen bonding between sugar and protein is responsible for inhibition of dehydration-induced protein unfolding," *Arch. Biochem. Biophys.*, 365:289–298, 1999.

Anchordoquy, Carpenter, Kroll, "Maintenance of transfection rates and physical characterization of lipid/DNA complexes after freeze-drying and rehydration," *Arch. Biochem. Biophys.*, 348:199–206, 1997.

Anchordoquy, Girouard, Carpenter, Kroll, "Stability of lipid/DNA during agitation and freeze-thawing," *J. Pharm. Sci.*, 87:1046–1051, 1998.

Arnott, Shabanowitz, Hunt, "Mass spectrometry of proteins and peptides: Sensitive and accurate mass measurement and sequence analysis," *Clin. Chem.*, 39:2005–2010, 1993.

Batra, Wang-Johanning, Wagner, Garver Jr., Curiel, "Receptor-mediated gene delivery employing lectin-binding specificity," *Gene Ther.*, 1:255–260, 1994.

Bettinger, Remy, Erbacker, "Size reduction of galactosylated PEI/DNA complexes improves lectin-mediated gene transfer into hepatocytes," *Bioconj. Chem.*, 10:558–561, 1999.

Biessen, Noorman, van Teijlingen, Kuiper, Barrett-Bergshoeff, Bijsterbosch, Rijken, van Berkel, "Lysine-based cluster mannosides that inhibit ligand binding to the human mannose receptor at nanomolar concentration," *J. Biol. Chem.*, 271:28024–28030, 1996.

Blessing, Remy, Behr, "Monomolecular collapse of plasmid DNA into stable virus-like particles," *Proc. Natl. Acad. Sci. U.S.A.*, 95:1427–1431, 1998.

Boussif, Lezoualc'h, Zanta, Mergny, Scherman, Demeneix, Behr, "A versatile vector for gene and oligonucleotide transfer into cells in culture and in vivo: Polyethylenimine," *Proc. Natl. Acad. Sci. U.S.A.*, 92:7297–7301, 1995.

Bradford, "A Rapid and Sensitive Method for the Quantitation of Microgram Quantities of Protein Utilizing the Principle of Protein-Dye Binding," *Anal. Biochem.*, 72:248–254, 1976.

Burns, Butler, Moran, Whitesides, "Selective Reduction of Disulfides by Tris-(2-carboxyethyl)phosphine," *J. Org. Chem.*, 56:2648–2650, 1991.

Cherng, van de Wetering, Talsma, Crommelin, Hennink, "Effect of size and serum proteins on transfection efficiency of poly ((2-dimethylamino)ethyl methacrylate)-plasmid nanoparticles," *Pharm. Res.*, 13:1038–1042, 1996.

Cherng, Wetering, Talsma, Crommelin, Hennink, "Freeze-drying of poly((2-dimethylamino)ethyl methacrylate)-based gene delivery systems," *Pharm. Res.*, 14:1838–1841, 1997.

Chiou, Tangco, Levine, Robertson, Kormis, Wu, Wu, "Enhanced resistance to nuclease degradation of nucleic acids complexed to asialoglycoprotein-polylysine carriers," *Nucl. Acids Res.*, 22:5439–5446, 1994.

Chiu, Tamura, Wadhwa, Rice, "In Vivo Targeting Function of N-linked Oligosaccharides with Terminating Galactose and N-Acetyl-Galactosamine Residues," *J. Biol. Chem.*, 269:16195–16202, 1994.

Chiu, Thomas, Stubbs, Rice, "Tissue targeting of multivalent Le(x)-terminated N-linked oligosaccharides in mice," *J. Biol. Chem.*, 270:24024–24031, 1995.

Choi, Lee, Choi, Jeong, Park, "Poly(ethylene glycol)-block-poly(L-lysine) Dendrimer: Novel Linear Polymer/Dendrimer Block Copolymer Forming a Spherical Water-Soluble Polyionic Complex with DNA," *Bioconj. Chem.*, 10:62–65, 1999.

Choi, Liu, Kim, Choi, Park, Kim, "Polyethylene glycol-grafted poly-L-lysine as polymeric gene carrier," *J. Cont. Rel.*, 54:39–48, 1998.

Chowdhury, Wu, Wu, Yerneni, Bommineni, Chowdhury, "Fate of DNA targeted to the liver by asialoglycoprotein receptor-mediated endocytosis in vivo. Prolonged persistence in cytoplasmic vesicles after partial hepatectomy," *J. Biol. Chem.*, 268:11265–11271, 1993.

Christiano and Roth, *J. Mol. Med.*, 73:479–486, 1995.

Cohen, Fisch, Carey, *Hepatology*, 12:113–122, 1990.

Collard, Evers, McKenzie, Rice, "Synthesis of homogeneous glycopeptides and their utility as DNA condensing agents," *Carb. Res.*, 323:176–184, 2000a.

Collard, Yang, Kwok, Rice, "Biodistribution, metabolism, and in vitro gene expression of glycopeptide polyethylene glycol DNA co-condensates," *J. Pharm. Sci.,* 89(4):499–512, 2000b.

Connolly, Townsend, Kawaguchi, Hobish, Bell, Lee, *Biochem. J.,* 214:421–431, 1983.

Corradi da Silva, Tamura, Rice, "Derivatization and purification of bisecting tyrosinamide-oligosaccharides from ovotransferrin," *Arch. Biochem. Biophys.,* 315:460–466, 1994.

Corradi Da Silva, Stubbs, Tamura, Rice, "1H NMR characterization of a hen ovalbumin tyrosinamide N-linked oligosaccharide library," *Arch. Biochem. Biophys.* 318:465–475, 1995.

Crowe, Crowe, Chapman, "Interaction of carbohydrates with dry dipalmitoylphophatidylcholine," *Arch. Biochem. Biophys.,* 236:289–296, 1985.

Da Silva, Tamura, McBroom, Rice, "Tyrosine derivatization and preparative purification of the sialyl and asialy-N-linked oligosaccharides from porcine fibrinogen," *Arch. Biochem. Biophys.,* 312:151–157, 1994.

Daniel, Westling, Moss, Kanagy, "FastTag nucleic acid labeling system: a versatile method for incorporating haptens, fluorochromes, and affinity ligands into DNA, RNA and oligonucleotides," *BioTechniques,* 24:484–489, 1998.

De Jaeghere, Allemann, Leroux, Stevels, Feijen, Doelker, Gurny, "Formulation and lyoprotection of poly(lactic acid-co-ethylene oxide) nanoparticles: influence on physical stability and in vitro cell uptake," *Pharm. Res.,* 16:859–866, 1999.

Dingwall and Laskey, "Nuclear targeting sequences-a consensus?," *TIBS,* 16:478–481, 1991.

Dorner, Husar, Ostresch, Houghten, "The synthesis of petidomimetic combinatorial libraries through successive amide alkylations," *Bioorganic and Med. Chem.,* 4:709–715, 1996.

Drickamer, "Multiple subfamilies of carbohydrate recognition domains in animal lectins," *Ciba Foundation Symposium,* 145:45–58, 1989.

Drummer et al., "Reversibility of dislfide formation: comparison of chemical and enzyme-mediated reduction of penicillamine and captopril disulfides," *Biochem. Pharm.,* 36:1197–1201, 1987.

Duguid, Li, Shi, Logan, Alila, Rolland, Tomlinson, Sparrow, Smith, "A Physicochemical Approach for Predicting the Effectiveness of Peptide-Based Gene Delivery Systems for Use in Plasmid-Based Gene Therapy," *Biophysical J.,* 74:2802–2814, 1998.

Edwards, Carpenter, Minchin, "Uptake and intracellular trafficking of asialoglycoprotein-polylysine-DNA complexes in isolated rat hepatocytes," *Gene Ther.,* 3:937–940, 1996.

Ege, *Organic Chemistry: Structure and Reactivity*, D.C. Health and Company, Lexington, 1994.

Erbacher, Roche, Monsigny, Midoux, "Glycosylated polylysine/DNA complexes: gene transfer efficiency in relation with the size and the sugar substitution level of glycosylated polylysines and with the plasmid size," *Bioconj. Chem.,* 6:401–410, 1995.

Escriou, Ciolina, Lacroix, Byk, Scherman, Wils, "Cationic lipid-mediated gene transfer: effect of serum on cellular uptake and intracellular fate of lipopolyamine/DNA complexes," *Biochim. Biophys. Acta,* 1368:276–288, 1998.

Evers, Hung, Thomas, Rice, "Preparative purification of a high-mannose type N-glycan from soy bean agglutinin by hydrazinolysis and tyrosinamide derivatization," *Anal. Biochem.,* 265:313–316, 1998.

Fang, Zhu, Smiley, Bonadio, Rouleau, Goldstein, McCauley, Davidson, Roessler, "Stimulation of New Bone Formation by Direct Transfer of Osteogenic Plasmid Genes," *Proc. Natl. Acad. Sci. U.S.A.,* 93:5753–5758, 1996.

Feener, Shen, Ryser, *J. Biol. Chem.,* 265:18780–18785, 1990.

Ferkol, Perales, Mularo, Hanson, "Receptor-mediated gene transfer into macrophages," *Proc. Natl. Acad. Sci., U.S.A.,* 93:101–105, 1996.

Gasparovic, Barba, Born, Barton, Arlis, Mann, "A study of imidazole-based nuclear magnetic resonance probes of cellular pH," *Anal. Biochem.,* 261:64–72, 1998.

Geuze, Slot, Strous, Lodish, Schwartz, "Intracellular site of asialoglycoprotein receptor-ligand uncoupling: double-label immunoelectron microscopy during receptor-mediated endocytosis," *Cell,* 32:277–287, 1983.

Godbey, Wu, Hirasake, Mikos, "Improved packing of poly (ethylenimine)/DNA complexes increases transfection efficiency," *Gene Ther.,* 6:1380–1388, 1999.

Gottschalk, Sparrow, Hauer, Mims, Leland, Woo, Smith, "A novel DNA-peptide complex for efficient gene transfer and expression in mammalian cells," *Gene Ther.,* 3:448–457, 1996.

Gratzer, Pereira, Lee, "Solvent environment modulates effects of glutaraldehyde crosslinking on tissue-derived biomaterials," *J. Biomed. Mater. Res.,* 31:533–543, 1996.

Gupta and Hung, "Albumin microspheres I: physicochemical characteristics," *J. Microencapsulation,* 6:427–462, 1989.

Haensler and Szoka Jr., "Polyamidoamine cascade polymers mediate efficient transfection of cells in culture," *Bioconj. Chem.,* 4:372–379, 1993a.

Haensler and Szoka Jr., "Synthesis and characterization of a trigalactosylated bisacridine compound to target DNA to hepatocytes," *Bioconj. Chem.,* 4:85–93, 1993.

Haensler and Szoka Jr., "Synthesis and characterization of a trigalactosylated bisacridine compound to target DNA to hepatocytes," *Bioconj. Chem.,* 4:85–93, 1993b.

Hara, Tan, Huang, "In Vivo Gene Delivery to the Liver using Reconstituted Chylomicron Remnants as a Novel Nonviral Vector," *Proc. Natl. Acad. Sci. U.S.A.,* 94:14547–14552, 1997.

Harada and Kataoka, "Formation of Polyion Complex Micelles in an Aqueous Milieu from a Pair of Oppositely-Charged Block Copolymers with Poly(ethylene glycol) Segments," *Macromolecules,* 28:5294–5299, 1995.

Hardy, Townsend, Lee, "Monosaccharide Analysis of Glycoconjugates by Anion Exchange chromatography with Pulsed Amperometric Detection," *Anal. Biochem.,* 170:54–62, 1988.

Hashida, Takemura, Nishikawa, Takakura, "Targeted Delivery of Plasmid DNA Complexed with Galactosylated Poly(L)-Lysine," *J. Control. Release,* 53:301–310, 1998.

Hickman, Malone, Lehmann-Bruinsma, Sih, Knoell, Szoka, Walzem, Carlson, Powell, "Gene expression following direct injection of DNA into liver," *Hum. Gene Ther.,* 5:1477–1483, 1994.

Jayakrishnan and Jameela, "Glultaraldehyde as a Fixative in Bioprostheses and Drug Delivery Matrices," *Biomaterials,* 17:471–484, 1996.

Jones, Burton, Gray, "Albumin Microspheres as vehicles for the sustained and controlled release of doxorubicin," *J. Pharm. Pharmacol.,* 41:813–816, 1989.

Kabanov and Kabanov, "DNA complexes with polycations for the delivery of genetic material into cells," *Bioconj. Chem.,* 6:7–20, 1995.

Kabanov and Kabanov, "Interpolyelectrolyte and block ionomer complexes for gene delivery: physicochemical aspects," *Adv. Drug Del. Rev.,* 30:49–60, 1998.

Kabanov, Vinogradov, Suzdaltseva, Alakhov, "Water-soluble block polycations as carriers for oligonucleotide delivery," *Bioconj. Chem.,* 6:639–643, 1995.

Kaneda, Iwai, Uchida, "Increased expression of DNA cointroduced with nuclear protein in adult rat liver," *Science,* 242:375–378, 1989.

Katayose and Kataoka, "Water-soluble polyion complex associates of DNA and poly(ethylene glycol)-poly(L-lysine) block copolymer," *Bioconj. Chem.,* 8:702–707, 1997.

Katayose and Kataoka, "Remarkable Increase in Nuclease Resistance of Plasmid Supramolecular Assembly with Poly(ethylene glycol)-Poly(L-lysine) Block Copolymer," *J. Pharm. Sci.,* 87:160–163, 1998.

Kawabata, Takakura, Hashida, "The Fate of Plasmid DNA after Intravenous Injection in Mice: Involvement of Scavenger Receptors in its Hepatic Uptake," *Pharm. Res.,* 12:825–830, 1995.

Kawakami, Sato, Nishikawa, Yamashita, Hashida, "Mannose receptor-mediated gene transfer into macrophages using novel mannosylated cationic liposomes," *Gene Ther.,* 7:292–299, 2000.

Kay, Graham, Leland, Woo, "Therapeutic serum concentrations of human alpha-1-antitrypsin after adenoviral-mediated gene transfer into mouse hepatocytes." *Hepatology,* 21:815–819, 1995.

Kery, Krepinsky, Warren, Capek, Stahl, "Ligand recognition by purified human mannose receptor," *Arch. Biochem. Biophys.,* 298:49–55, 1992.

Krumlauf, "Northern blot analysis," *Meth. in Mol. Biol.,* 58:113–128, 1996.

Kwoh, Coffin, Lollo, Jovenal, Banaszczyk, Mullen, Phillips, Amini, Fabrycki, Bartholomew, Brostoff, Carlo, "Stabilization of poly-L-lysine/DNA polyplexes for in vivo gene delivery to the liver, *Biochim. Biophys. Acta,* 1444:71–190, 1999.

Kwok, McKenzie, Evers, Rice, "Formulation of highly soluble poly(ethylene glycol)-peptide DNA condensates," *J. Pharm. Sci.,* 88:996–1003, 1999.

Lane, "Reduction of organic compounds with diborane," *Chemical Reviews,* 76:773–799, 1976.

Laurent, Coninck, Mihaylova, Leontieva, Warnier-Pirotte, Wattiaux, Jadot, "Uptake by Rat liver and Intracellular Fate of Plasmid DNA Complexed with Poly-L-lysine or Poly-D-lysine," *FEBS Lett.,* 443:61–65, 1999.

Ledley, "Pharmaceutical Approach to Somatic Gene Therapy," *Pharm. Res.,* 13:1595–1614, 1996.

Lee, Townsend, Hardy, Lonngren, Arnarp, Haraldsson, Lonn, "Binding of synthetic oligosaccharides to the hepatic Gal/GalNAc lectin. Dependence on fine structural features," *J. Biol. Chem.,* 258:199–202, 1983.

Legendre and Szoka Jr., "Cyclic amphipathic peptide-DNA complexes mediate high-efficiency transfection of adherent mammalian cells," *Proc. Natl. Acad. Sci., U.S.A.,* 90:893–897, 1993.

Leong, Mao, Truong-Le, Roy, Walsh, August, "DNA-polycation nanospheres as non-viral gene delivery vehicles," *J. Cont. Rel.,* 53:183–193, 1998.

Lew, Parker, Latimer, Abai, Kuwahara-Rundell, Doh, Yang, Laface, Gromkowski, Nabel, Manthorpe, Norman, "Cancer Gene Therapy Using Plasmid DNA: Pharmacokinetic Study of DNA Following Injection in Mice," *Hum. Gene Ther.,* 6:553–564, 1995.

Lewis, Huang, Pecora, *Macromolec.,* 18:944–948, 1985.

Lin, Coombes, Garnett, Davies, Schact, Davis, Illum, "Preparation of sterically stabilized human serum albumin nanospheres using a novel dextranox-MPEG crosslinking agent," *Pharm. Res.,* 11:1588–1592, 1994.

Liu and Liu, "Serum independent liposome uptake by mouse liver," *Biochim. Biophys. Acta,* 1278:5–11, 1996.

Lodish, "Recognition of complex oligosaccharides by the multi-subunit asialoglycoprotein receptor," *TIBS,* 16:374–377, 1991.

Lukacs, Haggie, Seksek, Lechardeur, Freedman, Verkman, "Size-dependent DNA mobility in cytoplasm and nucleus," *J. Biol. Chem.,* 275:1625–1629, 2000.

Ma, Chen, Ying, D'Andrea, "Stable liquid and lyophilized formulations of polycation: DNA complexes," *Pharm. Sci. Supplement* 1:288, 1998.

Magnusson and Berg, "Extremely rapid endocytosis mediated by the mannose receptor of sinusoidal endothelial rat liver cells," *Biochem. J.,* 257:651–656, 1989.

Mahato, Rolland, Tomlinson, "Cationic Lipid-Based Gene Delivery Systems: Pharmaceutical Perspectives," *Pharm. Res.,* 14:853–859, 1997.

Marinez-Fong, Mullersamn, Purchio, Borunda, Martinez-Hernandez, *Hepatology,* 20:1602–1608, 1994.

Markley, "Observation of histidine residues in proteins by means of nuclear magnetic resonance spectroscopy," *Acc. Chem. Res.,* 8:70–80, 1975.

McKee, DeRome, Wu, Findeis, "Preparation of asialoorosomucoid-polylysine conjugates," *Bioconj. Chem.,* 5:306–311, 1994.

McKenzie, Collard, Rice, "Comparative Gene Transfer Efficiency of Low Molecular Weight Polylysine DNA Condensing Peptides," *J. Peptide Res.,* 54:1–9, 1999.

McKenzie, Kwok, Rice, "A potent new class of reductively activated peptide gene delivery agents, *J. Biol. Chem.,* 275:9970–9977, 2000.

Mellman, Fuchs, Helenius, *Annu. Rev. Biochem.,* 55:663–700, 1986.

Mendel, Ryser, Niaki, Ghani, Shen, "Isolation of variants of chinese hampster ovary cells with abnormally low levels of GSH: Decrease ability to cleave endocytosed disulfide bonds," *J. Cell Physiol.,* 149:60–65, 1991.

Merkel, Mandel, Ryser, McCoy, "Characterization of fibroblasts with a unique defect in processing antigens with disulfide bonds," *J. Immunol.,* 154:128–136, 1995.

Merwin, Noell, Thomas, Chiou, DeRome, McKee, Spitalny, Findeis, "Targeted Delivery of DNA using YEE (GalNAcAH)$_3$, a Synthetic Glycopeptide Ligand for the Asialoglycoprotein Receptor," *Bioconj. Chem.,* 5:612–620, 1994.

Michalski, McCombs, Sheth, McCarthy, deShazo, "A modified double antibody sandwich enzyme-linked immunosorbent assay for measurement of alpha-1-antitrypsin in biologic fluids," *J. Immun. Meth.,* 83:101–112., 1985.

Midoux and Monsigny, "Efficient gene transfer by histidylated polylysine/pDNA complexes," *Bioconj. Chem.,* 10:406–411, 1999.

Midoux, Mendes, Legrand, Raimond, Mayer, Monsigny, Roche, "Specific gene transfer mediated by lactosylated poly-L-lysine into hepatoma cells," *Nucl. Acids Res.,* 21:871–878, 1993.

Midoux, Kichler, Boutin, Maurizot, Monsigny, "Membrane permeabilization and efficient gene transfer by a peptide containing several histidines," *Bioconj. Chem.,* 9:260–267, 1998.

Morris, Vidal, Chaloin, Heitz, Divita, "A new peptide vector for efficient delivery of oligonucleotides into mammalian cells," *Nuc. Acids Res.,* 25:2730–2736, 1997.

Nicoli, McKenzie, Wu, "Application of dynamic light scattering to particle size analysis of macromolecules," *American Laboratory,* 1991.

Niidome, Ohmori, Ichinose, Wada, Mihara, Hirayama, Aoyagi, "Binding of Cationic α-Helical Peptides to Plasmid DNA and Their Gene Transfer Abilities into Cells," *J. Biol. Chem.,* 272:15307–15312, 1997.

Niidome, Takaji, Urakawa, Ohmori, Wada, Hirayama, Aoyagi, "Chain length of cationic α-helical peptide sufficient for gene delivery into cells," *Bioconj. Chem.,* 10:773–780, 1999.

Nishikawa, Takemura, Takakura, Hashida, "Targeted Delivery of Plasmid DNA to Hepatocytes In Vivo: Optimization of the Pharmacokinetics of Plasmid DNA/Galactosylated Poly (L-Lysine) Complexes by Controlling their Physicochemical Properties," *J. Pharm. and Exper. Therp.,* 287:408–415, 1998.

Nishikawa, Yamauchi, Morimoto, Ishida, Takakura, Hashida, "Heptocyte-targeted in vivo gene expression by intraveneous injection of plasmid DNA complexed with synthetic multi-functional gene delivery system," *Gene Ther.,* 7:548–555, 2000.

Niven, Pearlman, Wedeking, Mackeigan Noker, Simpson-Herren, Smith, "Biodistribution of Radiolabeled Lipid-DNA Complexes and DNA in Mice," *J. Pharm. Sci.,* 87:1292–1299, 1996.

Ogris, Steinlein, Kursa, Mechtler, Kircheis, Wagner, "The Size of DNA/Transferrin-PEI complexes is an Important Factor for Gene Expression in Cultured Cells," *Gene Ther.,* 5:425–1433, 1998.

Ogris, Brunner, Schuller, Kircheis, Wagner, "PEGylated DNA/transferrin-PEI complexes: reduced interaction with blood components, extended circulation in blood and potential for systemic gene delivery," *Gene Ther.,* 6:595–605, 1999.

Ouyang, Remy, Szoka Jr, "Controlled template-assisted assembly of plasmid DNA into nanometric particles with high DNA concentration," *Bioconj. Chem.,* 11:104–112, 2000.

Page and Roy, "Synthesis and biological properties of mannosylated starburst poly(amidoamine) dendrimers," *Bioconj. Chem.,* 8:714–723, 1997.

Perales, Ferkol, Molas, Hanson, "An evaluation of receptor-mediated gene transfer using synthetic DNA-ligand complexes," *Eur. J. Biochem.,* 226:255–266, 1994a.

Perales, Ferkol, Beegen, Ratnoff, Hanson, "Gene Transfer In Vivo: Sustained Expression and Regulation of Genes Introduced into the Liver by Receptor-Targeted Uptake," *Proc. Nat. Acad. Sci. U.S.A.,* 91:4086–4090, 1994b.

Perales, Grossmann, Molas, Liu, Ferkol, Harpst, Oda, Hanson, "Biochemical and functional characterization of DNA complexes capable of targeting genes to hepatocytes via the asialoglycoprotein receptor," *J. Biol. Chem.,* 272:7398–7407, 1997.

Plank, Zatloukal, Cotten, Mechtler, Wagner, "Gene transfer into hepatocytes using asialoglycoprotein receptor mediated endocytosis of DNA complexed with an artificial tetra-antennary galactose ligand," *Bioconj. Chem.,* 3:533–539, 1992.

Plank, Oberhauser, Mechtler, Koch, Wagner, "The influence of endosome-disruptive peptides on gene transfer using synthetic virus-like gene transfer systems," *J. Biol. Chem.,* 269:12918–12924, 1994.

Plank, Mechtler, Szoka Jr., Wagner, "Activation of the complement system by synthetic DNA complexes: a potential barrier for intravenous gene delivery," *Hum. Gene Ther.,* 7:1437–1446, 1996.

Plank, Tang, Wolfe, Szoka Jr., "Branched cationic peptides for gene delivery: role of type and number of cationic residues in formation and in vitro activity of DNA polyplexes," [published erratum appears in *Hum. Gene Ther.,* 10(13):2272, 1999]." *Hum. Gene Ther.,* 10, 319–332, 1999.

Pouton, "Nuclear import of polypeptides, polynucleotides and supramolecular complexes," *Adv. Drug Del. Rev.,* 34:51–64, 1998.

Pouton and Seymour, "Key Issues in Non-Viral Gene Delivery," *Adv. Drug Del. Rev.,* 34:3–19, 1998.

Pouton, Lucas, Thomas, Uduehi, Milroy, Moss, Polycation-DNA complexes for gene delivery: a comparison of the biopharmaceutical properties of cationic polypeptides and cationic lipids," *J. Cont. Release,* 53:289–299, 1998.

Rabenstein and Sayer, "Determination of microscopic acid dissociation constants by nuclear magnetic resonance spectrometry," *Anal. Chem.,* 48:1141–1146, 1976.

Rice, Weisz, Barthel, Lee, Lee, "Defined Geometry of Binding Between Triantennary Glycopeptide and the Asialoglycoprotein Receptor of Rat Hepatocytes," *J. Biol. Chem.,* 265:18429–18434, 1990.

Rice, Chiu, Wadhwa, Thomas, Stubbs, "In Vivo Targeting Function of N-linked Oligosaccharides," In: *Glycoimmunology,* A. Alavai and J. S. Axford (Eds), Plenum Press, 271–282, 1995.

Rice, Chiu, Wadhwa, Thomas, Stubbs, "In vivo targeting function of N-linked oligosaccharides. Pharmacokinetic and biodistribution of N-linked oligosaccharides," *Advances in Experimental Medicine and Biology,* 376:271–282, 1995.

Rogers and Kornfeld, "Hepatic uptake of proteins coupled to fetuin glycopeptide," *Biochem. and Biophys. Res. Comm.,* 45:622–629, 1971.

Royer and Lee, "Entrapment of bioactive compounds within native albumin beads," *J. Parenteral Science and Technology,* 37:34–37, 1983.

Schwartz, Geuze, Lodish, "Recycling of the asialoglycoprotein receptor: biochemical and immunocytochemical evidence," *Philosophical Transactions of the Royal Society of London—Series B: Biological Sciences,* 300:229–235, 1982a.

Schwartz, Fridovich, Lodish, "Kinetics of internalization and recycling of the asialoglycoprotein receptor in a hepatoma cell line," *J. Biol. Chem.,* 257:4230–4237, 1982b.

Shea, Smiley, Bonadio, Mooney, "DNA delivery from polymer matrices for tissue engineering," *Nature Biotechnol.,* 17:551–554, 1999.

Shorts, Merkel, Caffrey, McCoy, "Defective antigen processing correlates with a low level of intracellular glutathione," *Eur. J. Immunol.,* 26:3015–3020, 1996.

Smith, Loo, Edmonds, Barinaga, Udseth, "New developments in biochemical mass spectrometry: Electrospray ionization," *Anal. Chem.,* 62:882–899, 1990.

Stahl, "The macrophage mannose receptor: current status, *Am. J. Resp. Cell and Mole. Biol.,* 2:317–318, 1990.

Stang, Kindberg, Berg, Roos, "Endocytosis mediated by the mannose receptor in liver endothelial cells. An immunocytochemical study, *Euro. J. of Cell Biol.,* 2:7–76, 1990.

Stankovics, Crane, Andrews, Wu, Wu, Ledley, "Overexpression of Human Methylmalonyl CoA Mutase in Mice after In Vivo Gene Transfer with Asialoglycoprotein/Polylysine/DNA Complexes," *Hum. Gene Ther.,* 5:1095–1104, 1994.

Stubbs, Shia, Rice, "Preparative purification of tetraantennary oligosaccharides from human asialyl orosomucoid," *Anal. Biochem.,* 247:357–365, 1997.

Sugio, Kashima, Mochizuki, Noda, Kobayashi, "Crystal structure of human serum albumin at 2.5 Å resolution," *Protein Eng.,* 12:439–446, 1999.

Talsma, Cherng, Lehrmann, Kursa, Ogris, Hennink, Cotton, Wagner, "Stabilization of gene delivery systems by freeze-drying," *Int. J. Pharm.,* 157:233–238, 1997.

Tamura, Wadhwa, Rice, "Reducing-End Modification of N-linked Oligosaccharides With Tyrosine," *Anal. Biochem.,* 216:335–344, 1994.

Tang and Szoka, "The influence of polymer structure on the interactions of cationic polymers with DNA and morphology of the resulting complexes," *Gene Ther.,* 4:823–832, 1997.

Tang, Redemann, Szoka Jr., "In Vitro Gene Delivery by Degraded Polyamidoamine Dendrimers," *Bioconj. Chem.,* 7:703–714, 1996.

Taylor and Drickamer, "Structural requirements for high affinity binding of complex ligands by the macrophage mannose receptor," *J. Biol. Chem.,* 268:399–404, 1993.

Taylor, Leaning, Summerfield, "Uptake and processing of glycoproteins by rat hepatic mannose receptor," *Am. J. Phys.,* 252:E690–698, 1987.

Terebesi, Kwok, Rice, "Iodinated plasmid DNA as a tool for studying gene delivery," *Anal. Biochem.,* 263(1):120–123, 1998.

Thierry, Rabinovich, Peng, Mahan, Bryant, Gallo, "Characterization of liposome-mediated gene delivery: expression, stability and pharmacokinetics of plasmid DNA," *Gene Ther.,* 4:226–237, 1997.

Thomas, Yang, Rice, "In vivo ligand specificity of E-selectin binding to multivalent sialyl Lewisx N-linked oligosaccharides," *J. Biol. Chem.,* 274:19035–19040, 1999.

Toncheva, Wolfert, Dash, Oupicky Ulbrich, Seymour, Schacht, "Novel Vectors for Gene Delivery Formed by Self-Assembly of DNA with Poly(L-lysine) Grafted with Hydrophobic Polymers," *Biochim. Biophys. Acta,* 1380:354–368, 1998.

Torchilin, Omelyanenko, Papisov, Bogdanov, Trubetskoy, Herron, Gentry, "Poly(ethylene glycol) on the Liposome Surface: On the Mechanism of Polymer-Coated Liposome Longevity," *Biochim. Biophys. Acta,* 1195:11–20, 1994.

Torchilin, "Polymer-Coated Long-Circulating Microparticulate Pharmaceuticals," *J. Microencapsulation,* 15(1):1–19, 1998.

Trubetskoy, Budker, Hanson, Slattum, Wolff, Hagstrom, "Self-Assembly of DNA-Polymer Complexes Using Template Polymerization," *Nucl. Acid. Res.,* 26:4178–4185, 1998.

Trubetskoy, Loomis, Slattum, Hagstrom, Budker, Wolff, "Caged DNA does not aggregate in high ionic strength solutions," *Bioconj. Chem.,* 10:624–628, 1999.

Vinogradov, Suzdaltseva, Kabanov, "Block polycationic oligonucleotide derivative: synthesis and inhibition of herpes virus reproduction," *Bioconj. Chem.,* 7:3–6, 1996.

Wadhwa and Rice, *J. Drug Target.,* 3:111–127, 1995.

Wadhwa, Knoell, Young, Rice, "Targeted Gene Delivery with a Low Molecular Weight Glycopeptide," *Bioconj. Chem.,* 6:283–291, 1995.

Wadhwa, Collard, Adami, McKenzie, Rice, "Peptide-Mediated Gene Delivery: Influence of Peptide Structure on Gene Expression," *Bioconj. Chem.,* 8:81–88, 1997.

Wagner, "Fundamentals of Clinical Pharmacokinetics," In: *Drug Intelligence Publications,* Hamilton, Ill., 1975.

Wagner, "Effects of membrane-active agents in gene delivery," *J. Cont. Rel.,* 53:155–158, 1998.

Wagner, Zenke, Cotten, Beug, Birnstiel, "Transferrin-polycation conjugates as Carriers for DNA Uptake into Cells," *Proc. Natl. Acad. Sci. U.S.A.,* 87:3410–3414, 1990.

Wagner, Cotten, Mechtler, Kirlappos, Birnstiel, "DNA-binding transferrin conjugates as functional gene-delivery agents: synthesis by linkage of polylysine or ethidium homodimer to the transferrin carbohydrate moiety, *Bioconj. Chem.,* 2:226–231, 1991a.

Wagner, Cotten, Foisner, Birnstiel, "Transferrin-polycation-DNA complexes: the effect of polycations on the structure of the complex and DNA delivery to cells," *Proc. Natl. Acad. Sci. U.S.A.,* 88:4255–4259, 1991b.

Wagner, Plank, Zatloukal, Cotten, Birnstiel, "Influenza virus hemagglutinin HA-2 N-terminal fusogenic peptides augment gene transfer by transferrin-polylysine-DNA complexes: toward a synthetic virus-like gene-transfer vehicle," *Proc. Natl. Acad. Sci. U.S.A.,* 89:7934–7938, 1992.

Weigele, DeBernardo, Tengi, Leimgruber, "A novel reagent for the fluorometric assay of primary amines," *J. Amer. Chem. Soc.,* 94:5927–5928, 1972.

Wileman, Lennartz, Stahl, "Identification of the macrophage mannose receptor as a 175-kDa membrane protein," *Proc. Natl. Acad. Sci. U.S.A.,* 83:2501–2505, 1986.

Wilson, Grossman, Cabrera, Wu, Wu, "A novel mechanism for achieving transgene persistence in vivo after somatic gene transfer into hepatocytes," *J. Biol. Chem.,* 267:11483–11489, 1992a.

Wilson, Grossman, Wu, Chowdhury, Wu, Chowdhury, "Hepatocyte-directed gene transfer in vivo leads to transient improvement of hypercholesterolemia in low density lipoprotein receptor-deficient rabbits," *J. Biol. Chem.,* 267:963–967, 1992b.

Wilson, Dean, Wang, Dean, "Nuclear import of plasmid DNA in digitonin-permeabilized cells requires both cytoplasmic factors and specific DNA sequences," *J. Biol. Chem.,* 274:22025–22032, 1999.

Wolfert and Seymour, "Atomic force microscopic analysis of the influence of the molecular weight of poly(L)lysine on the size of polyelectrolyte complexes formed with DNA," *Gene Ther.,* 3:269–273, 1996.

Wolfert, Dash, Nazarova, Oupicky, Seymour, Smart, Strohalm, Ulbrich, "Polyelectrolyte vectors for gene delivery: influence of cationic polymer on biophysical properties of complexes formed with DNA," *Bioconj. Chem.,* 10:993–1004, 1999.

Wolfert, Schacht, Toncheva, Ulbrich, Nazarova, Seymour, "Characterization of vectors for gene therapy formed by self-assembly of DNA with synthetic block co-polymers," *Hum. Gene Ther.,* 7:2123–2133, 1996.

Woodle, "Controlling Liposome Blood Clearance by Surface-Grafted Polymers," *Adv. Drug Del. Rev.,* 32:139–152, 1998.

Wu and Wu, "Targeted inhibition of transferrin-mediated iron uptake in Hep G2 hepatoma cells," *J. Biol. Chem.,* 261:16834–16837, 1986.

Wu and Wu, "Evidence for targeted gene delivery to Hep G2 hepatoma cells in vitro," *Biochemistry,* 27:887–892, 1988a.

Wu and Wu, "Receptor-mediated gene delivery and expression in vivo," *J. Biol. Chem.,* 263:14621–14624, 1988b.

Wu, Wilson, Wu, "Receptor-mediated Gene Delivery and Expression in Vivo," *J. Biol. Chem.,* 264:16985–16987, 1989.

Wu, Wilson, Shalaby, Grossman, Shafritz, Wu, "Receptor-mediated gene delivery in vivo. Partial correction of genetic analbuminemia in Nagase rats," *J. Biol. Chem.,* 266:14338–14342, 1991.

Wyman, Nicol, Zelphati, Scaria, Plank, Szoka, Jr., "Design, synthesis, and characterization of a cationic peptide that binds to nucleic acids and permeabilizes bilayers," *Biochem.,* 36:3008–3017, 1997.

Yang and Huang, "Overcoming the inhibitory effect of serum on lipofection by increasing the charge ratio of cationic liposome to DNA," *Gene Ther.,* 4:950–960, 1997.

Yoshida, Akaji, Tatsumi, Iinuma, Fujiwara, Kimura, Kiso, "Synthesis of porcine brain natriuretic peptide-32 using silver tetrafluoroborate as a new deprotecting reagent of the S-trimethylacetamidomethyl group," *Chem. Pharm. Bull.,* 38:273275, 1990.

Zanta, Belguise-Valladier, Behr, x "Gene delivery: a single nuclear localization signal peptide is sufficient to carry DNA to the cell nucleus," *Proc. Natl. Acad. Sci. U.S.A.,* 96:91–96, 1999a.

Zanta, Belguise-Valladier, Berh, "Gene delivery: A single nuclear localization signal peptide is sufficient to carry DNA to the cell nucleus," *Proc. Natl. Acad. Sci. U.S.A.,* 96:91–96, 1999b.

Zhang, Reimer, Zhang, Lee, Bally, "Self Assembling DNA-Lipid Particles for Gene Transfer," *Pharm. Res.,* 14:190–196, 1997.

Zhang, Budker, Wolff, "High levels of foreign gene expression in hepatocytes after tail vein injections of naked plasmid DNA," *Hum. Gene Ther.,* 10:1735–1737, 1999.

---

What is claimed is:

1. A purified synthetic peptide, wherein said peptide is between 6 and about 20 amino acids in length; comprises a plurality of positively-charged residues that mediate binding of said peptide to a nucleic acid; and comprises at least two thiol groups, each located at each terminus of said peptide and wherein said thiol groups form disulfide-crosslinked peptides that induce nucleic acids to condense upon contact with a population of said peptides.

2. The peptide of claim 1, wherein said peptide is between 6 and about 10 amino acids in length.

3. The peptide of claim 1, wherein said peptide comprises between four and about eight positively-charged residues that mediate binding of said peptide to a nucleic acid.

4. The peptide of claim 1, wherein said peptide comprises between two and about four cysteine or Penicillamine (Pen) residues that provide said thiol groups, at least two of which are located at each terminus of said peptide.

5. The peptide of claim 1, wherein said peptide comprises between two and about six Histidine residues.

6. The peptide of claim 1, wherein said peptide is bound to a nucleic acid, associated with a biocompatible matrix or dispersed within a pharmaceutically acceptable medium.

7. The peptide of claim 1, wherein said peptide is operatively attached to at least a first stealthing agent that reduces non-specific cellular uptake or interaction with blood components or to at least a first targeting agent that binds to a receptor for cellular or sub-cellular delivery.

8. The peptide of claim 7, wherein said peptide is a glycopeptide.

9. The peptide of claim 7, wherein said peptide is a PEG-peptide.

10. A population of purified nucleic-acid condensing peptides, wherein said peptides are synthetic peptides of between 6 and about 20 amino acids in length; comprise a plurality of positively-charged residues that bind said peptide to nucleic acid; and comprise at least two thiol groups, each thiol group located at each terminus of said peptide, wherein said thiol groups spontaneously crosslink peptides within said population; wherein said population of peptides forms a nucleic acid-peptide condensate that is stable in an extracellular biological environment and that releases nucleic acids intracellularly and mediates expression of the released nucleic acids.

11. The population of claim 10, wherein at least a portion of said peptides are glycopeptides or PEG-peptides.

12. A kit comprising, in at least a first container:
(a) a plurality of synthetic peptides of between 6 and about 20 amino acids in length, which comprise a plurality of positively-charged residues that mediate binding of said peptides to a nucleic acid and comprise a glutaraldehyde group that crosslinks at least a portion of said peptides; or (b) a plurality of synthetic peptides of between 6 and about 20 amino acids in length, which comprise a plurality of positively-charged residues that mediate binding of said peptides to nucleic acids and comprise at least two thiol groups, wherein each thiol group is located at each terminus of said peptides and wherein said thiol groups form intermolecular disulfide-crosslinked peptides that induce nucleic acids to condense upon contact with a population of said peptides.

13. The peptide of claim 1, wherein said peptide is about 6 amino acids in length.

14. The peptide of claim 1, wherein said peptide is between about 10 and about 20 amino acids in length.

15. The peptide of claim 4, wherein said peptide comprises at least two Cysteine residues, each located at each terminus of said peptide, which Cysteine residues provide said thiol groups.

16. The peptide of claim 4, wherein said peptide comprises at least two Penicillamine residues, each located at each terminus of said peptide, which Penicillamine residues provide said thiol groups.

17. The peptide of claim 4, wherein said peptide comprises four Cysteine or Penicillamine residues, at least two of which are located at each terminus of said peptide.

18. The peptide of claim 1, wherein said peptide is alkylated.

19. The peptide of claim 1, wherein said peptide comprises the sequence Pen-Trp-$Lys_5$-Pen-$Lys_5$-Pen-$Lys_5$-Pen (SEQ ID NO:21) or Pen-His-$Lys_4$-Cys-$Lys_4$-His-Pen (SEQ ID NO:22).

20. The peptide of claim 19, wherein said peptide comprises the sequence Pen-Trp-$Lys_5$-Pen-$Lys_5$-Pen-$Lys_5$-Pen (SEQ ID NO:21).

21. The peptide of claim 1, wherein said peptide is about 10 amino acids in length.

22. The peptide of claim 1, wherein said peptide is about 12 amino acids in length.

23. The peptide of claim 1, wherein said peptide is about 14 amino acids in length.

24. The peptide of claim 1, wherein said peptide is about 20 amino acids in length.

25. The peptide of claim 1, wherein said peptide comprises about 10 positively-charged residues that mediate binding of said peptide to a nucleic acid.

26. The peptide of claim 1, wherein said peptide comprises about 15 positively-charged residues that mediate binding of said peptide to a nucleic acid.

27. The peptide of claim 3, wherein said peptide comprises between four and about eight Lysine residues that mediate binding of said peptide to a nucleic acid.

28. The peptide of claim 1, wherein said peptide comprises about 10 positively-charged Lysine residues that mediate binding of said peptide to a nucleic acid.

29. The peptide of claim 1, wherein said peptide comprises about 15 positively-charged Lysine residues that mediate binding of said peptide to a nucleic acid.

30. The peptide of claim 5, wherein said peptide comprises at least two Histidine residues that promote dissociation and release of bound nucleic acids from said peptide upon contact with an intracellular endosome after uptake into a cell.

31. The peptide of claim 7, wherein said targeting agent is an antibody, growth factor or a carbohydrate targeting agent or targeting peptide.

32. The peptide of claim 1, wherein said peptide comprises the sequence Cys-Trp-$Lys_{17}$Cys (SEQ ID NO:3), Cys-$Lys_4$-Cys (SEQ ID NO:9), Cys-$Lys_8$-Cys (SEQ ID NO:11) or Cys-His-$Lys_6$-His-Cys (SEQ ID NO:17).

33. A population of purified nucleic-acid condensing peptides, wherein said peptides are synthetic peptides of between 6 and about 20 amino acids in length; comprise a plurality of positively-charged residues that bind said peptide to nucleic acid; comprise at least two thiol groups, each thiol group located at each terminus of said peptide, wherein said thiol groups spontaneously crosslink peptides within said population; comprise an amount of secondary or tertiary amines that promote dissociation and release of nucleic acids from said peptides upon contact with an intracellular endosome; and wherein said population of peptides forms a nucleic acid-peptide condensate that is stable in an extracellular biological environment and that releases nucleic acids intracellularly and mediates expression of the released nucleic acids.

34. A purified synthetic peptide, wherein said peptide is between 6 and about 20 amino acids in length, comprises a plurality of positively-charged residues that mediate binding of said peptide to a nucleic acid and comprises at least two thiol groups, each located at each terminus of said peptide, wherein said peptide comprises the sequence Cys-Trp-$Lys_{17}$Cys (SEQ ID NO:3), Cys-$Lys_4$-Cys (SEQ ID NO:9), Cys-$Lys_8$-Cys (SEQ ID NO:11), Cys-His-$Lys_6$-His-Cys (SEQ ID NO:17), Pen-Trp-$Lys_5$-Pen-$Lys_5$-Pen-$Lys_5$-Pen (SEQ ID NO:21) or Pen-His-$Lys_4$-Cys-$Lys_4$-His-Pen (SEQ ID NO:22).

35. A purified synthetic peptide, wherein said peptide is between 6 and about 50 amino acids in length; comprises between 3 and about 45 positively-charged residues that mediate binding of said peptide to a nucleic acid; and comprises at least two thiol groups, each located at, or proximal to, each terminus of said peptide; wherein said thiol groups form interpeptide disulfide bonds, which crosslink adjacent peptides and induce nucleic acids to condense upon contact with a population of said peptides, and which release nucleic acids intracellularly.

* * * * *

UNITED STATES PATENT AND TRADEMARK OFFICE
CERTIFICATE OF CORRECTION

PATENT NO.     : 6,770,740 B1                                    Page 1 of 1
DATED          : August 3, 2004
INVENTOR(S)    : Rice et al.

It is certified that error appears in the above-identified patent and that said Letters Patent is hereby corrected as shown below:

<u>Title page,</u>
Item [54], delete "CONDESATE" and insert -- CONDENSATE -- therefor.

<u>Column 105,</u>
Delete "claim 1" and insert -- claim 4 -- therefor.

Signed and Sealed this

Twenty-eighth Day of September, 2004

JON W. DUDAS
*Director of the United States Patent and Trademark Office*

SEQUENCE LISTING

<160> NUMBER OF SEQ ID NOS: 22

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 1

Cys Trp Lys Lys Lys Lys Lys Lys Lys Lys Lys Lys Lys Lys Lys
  1               5                  10                  15

Lys Lys Lys Lys
            20

<210> SEQ ID NO 2
<211> LENGTH: 40
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 2

Lys Lys Lys Lys Lys Lys Lys Lys Lys Lys Lys Lys Lys Lys Lys
  1               5                  10                  15

Lys Lys Trp Cys Cys Trp Lys Lys Lys Lys Lys Lys Lys Lys Lys
                20                  25                  30

Lys Lys Lys Lys Lys Lys Lys Lys
            35                  40

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 3

Cys Trp Lys Lys Lys Lys Lys Lys Lys Lys Lys Lys Lys Lys Lys
  1               5                  10                  15

Lys Lys Lys Cys
            20

```
<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 4

Cys Trp Lys Lys Lys Lys Lys Lys Lys Cys Lys Lys Lys Lys Lys
 1               5                  10                  15

Lys Lys Lys Cys
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 5

Cys Trp Lys Lys Lys Lys Lys Cys Lys Lys Lys Lys Lys Cys Lys Lys
 1               5                  10                  15

Lys Lys Lys Cys
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 6

Cys Trp Lys Lys Lys Lys Cys Lys Lys Lys Cys Lys Lys Lys Cys Lys
 1               5                  10                  15

Lys Lys Lys Cys
            20

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 7

Cys Trp Lys Lys Lys Lys Lys Lys Lys Lys
 1               5                  10

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 8

Cys Lys Lys Cys
 1
```

```
<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 9

Cys Lys Lys Lys Lys Cys
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 10

Cys Lys Lys Lys Lys Lys Lys Cys
 1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 11

Cys Lys Lys Lys Lys Lys Lys Lys Lys Cys
 1               5                   10

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 12

Cys Lys Cys Lys Cys
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 13

Cys Lys Lys Cys Lys Lys Cys
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: SYNTHETIC
      PEPTIDE

<400> SEQUENCE: 14
```

```
Cys Lys Lys Cys Lys Lys Lys Cys
 1               5
```

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 15

```
Cys Lys Lys Lys Lys Cys Lys Lys Lys Cys
 1               5                  10
```

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 16

```
Cys Lys Lys Lys Lys His Lys Lys Lys Cys
 1               5                  10
```

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 17

```
Cys His Lys Lys Lys Lys Lys Lys His Cys
 1               5                  10
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 18

```
Cys His Lys Lys Lys His Lys Lys His Cys
 1               5                  10
```

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:  SYNTHETIC
      PEPTIDE

<400> SEQUENCE: 19

```
Cys His Lys His Lys His Lys His Lys Cys
 1               5                  10
```

<210> SEQ ID NO 20
<211> LENGTH: 10
<212> TYPE: PRT
<213> ORGANISM: Artificial Sequence -continued

```
<220> FEATURE:
<223> OTHER INFORMATION: Description of Artificial Sequence:   SYNTHETIC
      PEPTIDE

<400> SEQUENCE: 20

Cys His Lys His Lys His His Lys His Cys
 1               5                  10

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence:   SYNTHETIC
      PEPTIDE
<221> NAME/KEY: SITE
<222> LOCATION: (1)..(20)
<223> OTHER INFORMATION: WHERE Xaa = PENICILLAMINE

<400> SEQUENCE: 21

Xaa Trp Lys Lys Lys Lys Lys Xaa Lys Lys Lys Lys Lys Xaa Lys Lys
 1               5                  10                  15

Lys Lys Lys Xaa
            20

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence:   SYNTHETIC
      PEPTIDE
<221> NAME/KEY: SITE
<222> LOCATION: (1)..(13)
<223> OTHER INFORMATION: WHERE Xaa = PENICILLAMINE

<400> SEQUENCE: 22

Xaa His Lys Lys Lys Lys Cys Lys Lys Lys Lys His Xaa
 1               5                  10
```